US010618957B2

(12) United States Patent
Finney et al.

(10) Patent No.: US 10,618,957 B2
(45) Date of Patent: *Apr. 14, 2020

(54) ANTIBODY MOLECULES WHICH BIND CD79

(71) Applicant: UCB Biopharma SPRL, Brussels (BE)

(72) Inventors: Helene Margaret Finney, Slough (GB); Stephen Edward Rapecki, Slough (GB); Kerry Louise Tyson, Slough (GB); Michael John Wright, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/743,764

(22) PCT Filed: Jul. 15, 2016

(86) PCT No.: PCT/EP2016/066989
§ 371 (c)(1),
(2) Date: Jan. 11, 2018

(87) PCT Pub. No.: WO2017/009474
PCT Pub. Date: Jan. 19, 2017

(65) Prior Publication Data
US 2018/0201678 A1  Jul. 19, 2018

(30) Foreign Application Priority Data

Jul. 16, 2015 (EP) .................. PCT/EP2015/066368
Jul. 16, 2015 (EP) .................. PCT/EP2015/066369
Jan. 20, 2016 (GB) .................................. 1601075.3

(51) Int. Cl.
*C07K 16/18* (2006.01)
*C07K 16/28* (2006.01)
*A61K 47/68* (2017.01)

(52) U.S. Cl.
CPC ...... *C07K 16/2803* (2013.01); *A61K 47/6809* (2017.08); *A61K 47/6849* (2017.08); *A61K 47/6867* (2017.08); *C07K 16/18* (2013.01); *C07K 16/289* (2013.01); *C07K 16/2896* (2013.01); *C07K 2317/24* (2013.01); *C07K 2317/31* (2013.01); *C07K 2317/33* (2013.01); *C07K 2317/35* (2013.01); *C07K 2317/55* (2013.01); *C07K 2317/622* (2013.01); *C07K 2317/64* (2013.01); *C07K 2317/76* (2013.01)

(58) Field of Classification Search
CPC ............... C07K 16/18; C07K 16/2803; C07K 16/2896; C07K 2317/24; C07K 2317/31; C07K 2317/35; C07K 2317/64; C07K 2317/55; C07K 2317/56; C07K 2317/622; C07K 2317/624; C07K 2317/526; C07K 2317/76; C07K 2317/95; C07K 2309/505
See application file for complete search history.

(56) References Cited

U.S. PATENT DOCUMENTS

| | | |
|---|---|---|
| 4,741,900 A | 5/1988 | Alvarez et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,731,168 A | 3/1998 | Carter et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,798,229 A | 8/1998 | Strittmatter et al. |
| 5,821,047 A | 10/1998 | Garrard et al. |
| 5,969,108 A | 10/1999 | McCafferty et al. |
| 6,010,902 A | 1/2000 | Ledbetter et al. |
| 6,106,834 A | 8/2000 | Lazarovits et al. |
| 6,183,744 B1 | 2/2001 | Goldenberg |

(Continued)

FOREIGN PATENT DOCUMENTS

| | | |
|---|---|---|
| CN | 1326878 A | 12/2001 |
| CN | 103214578 A | 7/2013 |

(Continued)

OTHER PUBLICATIONS

Rudikoff et al., Proc. Natl. Acad. Sci. USA. 1982; 79: 1979-1983 (Year: 1982).*
Caldas et al., Mol. Immunol 39 (15):941-952 (Year: 2003).*
Wu et al., J. Mol. Biol. 294 (1): 151-162 (Year: 1999).*
International Search Report for PCT/EP2016/066989, dated Nov. 22, 2016.
Pfeifer et al., "Anti-CD22 and anti-CD79B antibody drug conjugates are active in different molecular diffuse large B-cell lymphoma subtypes," Leukemia 29(7):1578-1586 (2015).
Adair et al., "Therapeutic Antibodies," Drug Design Reviews Online 2(3):209-217 (2005).
Altschul et al., "Basic local alignment search tool," J Mol Biol 215(3):403-410 (1990).

(Continued)

*Primary Examiner* — Phuong Huynh
(74) *Attorney, Agent, or Firm* — Medler Ferro Woodhouse & Mills PLLC

(57) ABSTRACT

The present disclosure relates to antibody molecules comprising a binding domain specific to CD79, said binding domain comprising SEQ ID NO: 1, 2, 3 or 4, and/or SEQ ID NO: 5, 6 and 7. The disclosure also extends to pharmaceutical compositions comprising said antibody molecules and use of the antibody molecules/compositions in treatment.

12 Claims, 66 Drawing Sheets

Specification includes a Sequence Listing.

(56) References Cited

U.S. PATENT DOCUMENTS

| | | |
|---|---|---|
| 6,306,393 B1 | 10/2001 | Goldenberg |
| 6,368,596 B1 | 4/2002 | Ghetie et al. |
| 6,809,185 B1 | 10/2004 | Schoonjans et al. |
| 7,074,403 B1 | 7/2006 | Goldenberg et al. |
| 7,183,076 B2 | 2/2007 | Arathoon et al. |
| 7,321,026 B2 | 1/2008 | Leung |
| 7,338,659 B2 | 3/2008 | Leung |
| 7,355,012 B2 | 4/2008 | Pastan et al. |
| 7,491,514 B2 | 2/2009 | Leung |
| 7,495,081 B2 | 2/2009 | Leung |
| 7,541,034 B1 | 6/2009 | Fitzgerald et al. |
| 7,641,901 B2 | 1/2010 | Goldenberg et al. |
| 7,777,019 B2 | 8/2010 | Pastan et al. |
| 7,825,224 B2 | 11/2010 | Vilen et al. |
| 7,829,086 B2 | 11/2010 | Hilbert et al. |
| 7,837,995 B2 | 11/2010 | Goldenberg |
| 7,910,103 B2 | 3/2011 | Goldenberg |
| 7,939,073 B2 | 5/2011 | Goldenberg |
| 7,982,011 B2 | 7/2011 | Pastan et al. |
| 8,088,378 B2 | 1/2012 | Chen et al. |
| 8,153,768 B2 | 4/2012 | Kunz et al. |
| 8,226,945 B2 | 7/2012 | Ebens, Jr. et al. |
| 8,389,688 B2 | 3/2013 | Jones et al. |
| 8,409,577 B2 | 4/2013 | Thompson et al. |
| 8,420,086 B2 | 4/2013 | Govindan et al. |
| 8,481,683 B2 | 7/2013 | King et al. |
| 8,524,865 B2 | 9/2013 | Ebens et al. |
| 8,545,850 B2 | 10/2013 | Chen et al. |
| 8,591,889 B2 | 11/2013 | Dimitrov et al. |
| 8,658,168 B2 | 2/2014 | Ghetie et al. |
| 8,664,363 B2 | 3/2014 | Jones et al. |
| 8,669,349 B2 | 3/2014 | Johnson et al. |
| 8,691,531 B2 | 4/2014 | Chen et al. |
| 8,722,857 B2 | 5/2014 | Chen et al. |
| 8,747,857 B2 | 6/2014 | Kunz et al. |
| 8,809,502 B2 | 8/2014 | Pastan et al. |
| 8,835,611 B2 | 9/2014 | Kunz et al. |
| 8,852,599 B2 | 10/2014 | Zhang et al. |
| 8,871,201 B2 | 10/2014 | Kantor et al. |
| 8,968,741 B2 | 3/2015 | Ebens et al. |
| 9,138,485 B2 | 9/2015 | Govindan et al. |
| 9,139,649 B2 | 9/2015 | Chang et al. |
| 9,181,343 B2 | 11/2015 | Rabuka et al. |
| 9,192,664 B2 | 11/2015 | Chang et al. |
| 9,279,019 B2 | 3/2016 | Dimitrov et al. |
| 9,371,396 B2 | 6/2016 | Leung |
| 9,475,883 B2 | 10/2016 | Chang et al. |
| 9,499,632 B2 | 11/2016 | Tavares et al. |
| 9,518,115 B2 | 12/2016 | Chang et al. |
| 9,580,461 B2 | 2/2017 | Linke et al. |
| 9,592,304 B2 | 3/2017 | Fitzgerald et al. |
| 9,598,492 B2 | 3/2017 | Dimitrov et al. |
| 9,642,918 B2 | 5/2017 | Bruederle et al. |
| 9,663,576 B2 | 5/2017 | Chang et al. |
| 9,695,236 B2 | 7/2017 | Johnson et al. |
| 9,701,748 B2 | 7/2017 | Chang et al. |
| 9,845,355 B2 | 12/2017 | Chen et al. |
| 9,856,323 B2 | 1/2018 | Short et al. |
| 9,896,506 B2 | 2/2018 | Chen et al. |
| 9,944,703 B2 | 4/2018 | Chang et al. |
| 9,975,949 B2 | 5/2018 | Sun et al. |
| 10,358,493 B2 | 7/2019 | Finney et al. |
| 10,370,447 B2 | 8/2019 | Finney et al. |
| 2003/0027247 A1 | 2/2003 | Wang et al. |
| 2003/0202975 A1 | 10/2003 | Tedder |
| 2005/0033031 A1 | 2/2005 | Couto |
| 2005/0048578 A1 | 3/2005 | Zhang |
| 2006/0252130 A1 | 11/2006 | Boehm et al. |
| 2007/0141672 A1 | 6/2007 | Shin |
| 2011/0076270 A1 | 3/2011 | Aversa et al. |
| 2013/0142787 A1 | 6/2013 | Chang et al. |
| 2013/0209463 A1 | 8/2013 | Rotman et al. |
| 2013/0336977 A1 | 12/2013 | Thompson et al. |
| 2014/0099254 A1 | 4/2014 | Chang et al. |
| 2014/0212425 A1 | 7/2014 | Chang et al. |
| 2014/0248278 A1 | 9/2014 | Tuscano et al. |
| 2015/0239974 A1 | 8/2015 | Chang et al. |
| 2016/0229911 A1 | 8/2016 | Rabuka et al. |
| 2016/0304611 A1 | 10/2016 | Chevallier et al. |
| 2016/0363597 A1 | 12/2016 | Leung |
| 2017/0058031 A1 | 3/2017 | King et al. |
| 2017/0081404 A1 | 3/2017 | Finney et al. |
| 2017/0145097 A1 | 5/2017 | Dimitrov et al. |
| 2017/0151356 A1 | 6/2017 | Govindan et al. |
| 2017/0204178 A1 | 7/2017 | Finney et al. |
| 2017/0204183 A1 | 7/2017 | Finney et al. |
| 2017/0226207 A1 | 8/2017 | Yamajuku et al. |
| 2018/0086843 A1 | 3/2018 | Short et al. |
| 2018/0201679 A1 | 7/2018 | Chen et al. |
| 2018/0237521 A1 | 8/2018 | Finney |
| 2018/0273620 A1 | 9/2018 | Finney |
| 2018/0334513 A1 | 11/2018 | Wright |
| 2018/0334514 A1 | 11/2018 | Wright |
| 2018/0346603 A1 | 12/2018 | Bhatta et al. |
| 2018/0346604 A1 | 12/2018 | Rapecki |
| 2018/0355063 A1 | 12/2018 | Finney |
| 2019/0322739 A1 | 10/2019 | Finney et al. |

FOREIGN PATENT DOCUMENTS

| | | |
|---|---|---|
| EP | 0392745 A2 | 10/1990 |
| EP | 0438474 A1 | 7/1991 |
| EP | 0463151 A1 | 1/1992 |
| EP | 0546073 A1 | 6/1993 |
| EP | 1049787 A1 | 11/2000 |
| EP | 1156826 A1 | 11/2001 |
| EP | 1178826 A1 | 2/2002 |
| EP | 1242457 A1 | 9/2002 |
| EP | 1431311 A1 | 6/2004 |
| EP | 1442061 A1 | 8/2004 |
| EP | 1448584 A2 | 8/2004 |
| EP | 1543839 A1 | 6/2005 |
| EP | 1570267 A1 | 9/2005 |
| EP | 1689783 A1 | 8/2006 |
| EP | 1784219 A2 | 5/2007 |
| EP | 1998799 A2 | 12/2008 |
| EP | 1999148 A2 | 12/2008 |
| EP | 2032606 A2 | 3/2009 |
| EP | 2097097 A2 | 9/2009 |
| EP | 2176295 A1 | 4/2010 |
| EP | 2176296 A1 | 4/2010 |
| EP | 2247620 A1 | 11/2010 |
| EP | 2252631 A2 | 11/2010 |
| EP | 2295073 A1 | 3/2011 |
| EP | 2474557 A2 | 7/2012 |
| EP | 2502937 A2 | 9/2012 |
| EP | 2657253 A2 | 10/2013 |
| EP | 2706069 A1 | 3/2014 |
| EP | 2788020 A1 | 10/2014 |
| EP | 2841459 A1 | 3/2015 |
| EP | 2861622 A2 | 4/2015 |
| EP | 2869850 A1 | 5/2015 |
| EP | 2874650 A1 | 5/2015 |
| EP | 3045475 A1 | 7/2016 |
| EP | 3178929 A1 | 6/2017 |
| EP | 3110445 A1 | 9/2017 |
| EP | 3227336 A1 | 10/2017 |
| EP | 3269737 A1 | 1/2018 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A1 | 12/1992 |
| WO | WO93/06231 A1 | 4/1993 |
| WO | WO 93/11162 A1 | 6/1993 |
| WO | WO93/11236 A1 | 6/1993 |
| WO | WO95/15982 A1 | 6/1995 |
| WO | WO95/20401 A1 | 8/1995 |
| WO | WO 96/26964 A1 | 9/1996 |

(56) References Cited

FOREIGN PATENT DOCUMENTS

| WO | WO98/20734 A1 | 5/1998 |
|---|---|---|
| WO | WO 02/072832 A2 | 9/2002 |
| WO | WO 03/012069 A2 | 2/2003 |
| WO | WO03/031581 A2 | 4/2003 |
| WO | WO03/048327 A2 | 6/2003 |
| WO | WO 03/093320 A2 | 11/2003 |
| WO | WO2004/039840 A1 | 5/2004 |
| WO | WO2004/051268 A1 | 6/2004 |
| WO | WO 2004/081051 A1 | 9/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO 2005/026210 A2 | 3/2005 |
| WO | WO2005/113605 A1 | 12/2005 |
| WO | WO2005/117984 A2 | 12/2005 |
| WO | WO 2005/118642 A2 | 12/2005 |
| WO | WO2006/004910 A2 | 1/2006 |
| WO | WO 2006/119897 A2 | 11/2006 |
| WO | WO2007/060406 A1 | 5/2007 |
| WO | WO 2007/085837 A1 | 8/2007 |
| WO | WO2007/087453 A2 | 8/2007 |
| WO | WO 2007/146968 A2 | 12/2007 |
| WO | WO 2008/070569 A2 | 6/2008 |
| WO | WO 2008/119353 A1 | 10/2008 |
| WO | WO2009/012268 A1 | 1/2009 |
| WO | WO2009/040562 A1 | 4/2009 |
| WO | WO2010/035012 A1 | 4/2010 |
| WO | WO 2011/025904 A1 | 3/2011 |
| WO | WO2011/061492 A2 | 5/2011 |
| WO | WO2011/086091 A1 | 7/2011 |
| WO | WO2011/130305 A2 | 10/2011 |
| WO | WO2011/131746 A2 | 10/2011 |
| WO | WO2012/023053 A2 | 2/2012 |
| WO | WO 2012/116453 A1 | 9/2012 |
| WO | WO2012/151199 A1 | 11/2012 |
| WO | WO 2012/162561 A2 | 11/2012 |
| WO | WO2013/060867 A2 | 5/2013 |
| WO | WO 2013/078455 A2 | 5/2013 |
| WO | WO 2013/085893 A1 | 6/2013 |
| WO | WO 2014/001326 A1 | 1/2014 |
| WO | WO2014/011518 A1 | 1/2014 |
| WO | WO 2014/011519 A1 | 1/2014 |
| WO | WO2014/011520 A1 | 1/2014 |
| WO | WO 2014/011521 A1 | 1/2014 |
| WO | WO2014/096390 A1 | 6/2014 |
| WO | WO2014/131694 A1 | 9/2014 |
| WO | WO2015/021089 A1 | 2/2015 |
| WO | WO 2015/057834 A1 | 4/2015 |
| WO | WO 2015/181282 A1 | 12/2015 |
| WO | WO2015/197772 A1 | 12/2015 |
| WO | WO2015/197789 A1 | 12/2015 |
| WO | WO 2016/009029 A1 | 1/2016 |
| WO | WO 2016/009030 A2 | 1/2016 |
| WO | WO 2016/168773 A1 | 10/2016 |
| WO | WO 2017/009473 A1 | 1/2017 |
| WO | WO 2017/009476 A1 | 1/2017 |
| WO | WO2017/093402 A1 | 6/2017 |
| WO | WO2017/093404 A1 | 6/2017 |
| WO | WO2017/093406 A1 | 6/2017 |
| WO | WO2017/093408 A1 | 6/2017 |
| WO | WO2017/093410 A1 | 6/2017 |
| WO | WO2018/112407 A1 | 6/2018 |

OTHER PUBLICATIONS

Altschul et al., "Gapped BLAST and PSI-BLAST: a new generation of protein database search programs," Nucleic Acids Res 25(17):3389-3402 (1997).
Ames et al., "Conversion of murine Fabs isolated from a combinatorial phage display library to full length immunoglobulins," J Immunol Methods 184(2):177-186 (1995).
Angal et al., "A single amino acid substitution abolishes the heterogeneity of chimeric mouse/human (IgG4) antibody," Mol Immunol 30(1):105-108 (1993).
Armour et al., "Recombinant human IgG molecules lacking Fcgamma receptor I binding and monocyte triggering activities," Eur J Immunol 29(8):2613-2624 (1999).
Babcook et al., "A novel strategy for generating monoclonal antibodies from single, isolated lymphocytes producing antibodies of defined specificities," Proc Natl Acad Sci USA 93(15):7843-7848 (1996).
Bartalena et al., "Thyroid hormone transport proteins," Clin Lab Med 13(3):583-598 (1993).
Berger et al., "Antigen recognition by conformational selection," FEBS Lett 450:149-153 (1999).
Bradshaw et al., "Concurrent detection of secreted products from human lymphocytes by microengraving: cytokines and antigen-reactive antibodies," Clin Immunol 129(1):10-18 (2008).
Bree et al., "Pharmacokinetics of intravenously administered 125I-labelled human alpha 1-acid glycoprotein," Clin Pharmacokinet 11(4):336-342 (1986).
Brinkmann et al., "Phage display of disulfide-stabilized Fv fragments," J Immunol Methods 182(1):41-50 (1995).
Brosterhus et al., "Enrichment and detection of live antigen-specific CD4(+) and CD8(+) T cells based on cytokine secretion," Eur J Immunol 29(12):4053-4059 (1999).
Bruhns et al., "Specificity and affinity of human Fcgamma receptors and their polymorphic variants for human IgG subclasses," Blood 113(16):3716-3725 (2009).
Burton et al., "Human antibodies from combinatorial libraries," Adv Immunol 57:191-280 (1994).
Caldas et al., "Humanization of the anti-CD18 antibody 6.7: an unexpected effect of a framework residue in binding to antigen," Mol Immunol 39:941-952 (2003).
Casset et al., "A peptide mimetic of an anti-CD4 monoclonal antibody by rational design," Biochem Biophys Res Comm 307:198-205 (2003).
Chan et al., "Therapeutic antibodies for autoimmunity and inflammation," Nat Rev Immunol 10(5):301-316 (2010).
Chang et al., "Loop-Sequence Features and Stability Determinants in Antibody Variable Domains by High-Throughput Experiments," Structure 22:9-21 (2014).
Chien et al., "Significant structural and functional change of an antigen-binding site by a distant amino acid substitution: Proposal of a structural mechanism," Proc Natl Acad Sci USA 86:5532-5536 (1989).
Chothia et al., "Canonical structures for the hypervariable regions of immunoglobulins," J Mol Biol 196(4):901-917 (1987).
Chu et al., "Suppression of rheumatoid arthritis B cells by XmAb5871, an anti-CD19 antibody that coengages B cell antigen receptor complex and Fcγ receptor IIb inhibitory receptor," Arthritis Rheumatol 66:1153-1164 (2014).
Clargo et al., "The rapid generation of recombinant functional monoclonal antibodies from individual, antigen-specific bone marrow-derived plasma cells isolated using a novel fluorescence-based method," MAbs 6(1):143-159 (2014).
Crameri et al., "DNA shuffling of a family of genes from diverse species accelerates directed evolution," Nature 391:288-291 (1998).
Czerwinski et al., "Construction of dimeric F(ab) useful in blood group serology," Transfusion 42(2):257-264 (2002).
Datta-Mannan et al., "Humanized IgG1 variants with differential binding properties to the neonatal Fc receptor: relationship to pharmacokinetics in mice and primates," Drug Metab Dispos 35(1):86-94 (2007).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084 (2002).
Dennis et al., "Albumin Binding as a General Strategy for Improving the Pharmacokinetics of Proteins," J Biol Chem 277(38):35035-35043 (2002).
Dubowchik et al., "Receptor-mediated and enzyme-dependent targeting of cytotoxic anticancer drugs," Pharmacol Ther 83(2):67-123 (1999).
Dunkin et al., "Immune cell therapy in IBD," Dig Dis 32:61-66 (2014).

(56) References Cited

OTHER PUBLICATIONS

Feldman et al., "Adoptive Cell Therapy—Tumor-Infiltrating Lymphocytes, T-Cell Receptors, and Chimeric Antigen Receptors," Semin Oncol 42(4):626-639 (2015).
Finney et al., "Chimeric receptors providing both primary and costimulatory signaling in T cells from a single gene product," J Immunol 161:2791-2797 (1998).
Gish et al., "Identification of protein coding regions by database similarity search," Nat Genet 3(3):266-272 (1993).
Gitlin et al., "The selectivity of the human placenta in the transer of plasma proteins from mother to fetus," J Clin Invest 43:1938-1951 (1964).
Giusti et al., "Somatic diversification of S107 from an antiphosphocoline to an anti-DNA autoantibody is due to a single base change in its heavy chain variable region," Proc Natl Acad Sci USA 84:2926-2930 (1987).
Glockshuber et al., "A comparison of strategies to stabilize immunoglobulin Fv-fragments," Biochemistry 29(6):1362-1367 (1990).
Gussow et al., "Humanization of Monoclonal Antibodies," Meth Enzymol 203:99-121 (1991).
Harris, "Processing of C-terminal lysine and arginine residues of proteins isolated from mammalian cell culture," J Chromatogr A 705(1):129-134 (1995).
Hermiston et al., "CD45: A Critical Regulator of Signaling Thresholds in Immune Cells," Ann Rev Immunol 21:107-137 (2003).
Hinnebusch, "Evidence for translational regulation of the activator of general amino acid control in yeast," Proc Natl Acad Sci USA 81:6442-6446 (1984).
Hinton et al., "Engineered human IgG antibodies with longer serum half-lives in primates," J Biol Chem 279(8):6213-6216 (2004).
Hollinger et al., "Engineered antibody fragments and the rise of single domains," Nat Biotechnol 23(9):1126-1136 (2005).
Holm et al., "Functional mapping and single chain construction of the anti-cytokeratin 8 monoclonal antibody TSI1," Mol Immunol 44:1075-1084 (2007).
Holmes, "Buy buy bispecific antibodies," Nat Rev Drug Discov 10(11):798-800 (2011).
Holt et al., "Anti-serum albumin domain antibodies for extending the half-lives of short lived drugs," Protein Eng Des Sel 21(5):283-288 (2008).
Hope et al., "GCN4 protein, synthesized in vitro, binds HIS3 regulatory sequences: implications for general control of amino acid biosynthetic genes in yeast," Cell 43(1):177-188 (1985).
Idusogie et al., "Mapping of the C1q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 192(4):1480-1490 (2014).
Kashmiri et al., "SDR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).
Kohler et al., "Continuous cultures of fused cells secreting antibody of predefined specificity," Nature 256:495-497 (1975).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).
Labrijn et al., "Therapeutic IgG4 antibodies engage in Fab-arm exchange with endogenous human IgG4 in vivo," Nat Biotechnol 27(8):767-771 (2009).
Lazar et al., "Engineered antibody Fc variants with enhanced effector function," Proc Natl Acad Sci USA 103(11):4005-4010 (2006).
Love et al., "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "VI-linker-Vh orientation-dependent expression of single chain Fv-containing an engineered disulfide-stabilized bond in the framework regions," J Biochem 118(4):825-831 (1995).
MacCallum et al., "Antibody-antigen Interactions: Contact Analysis and Binding Site Topography," J Mol Biol 262:732-745 (1996).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Mariuzza et al., "The Structural Basis of Antigen-Antibody Recognition," Ann Rev Biophys Biophys Chem 16:139-159 (1987).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Patten et al., "Applications of DNA shuffling to pharmaceuticals and vaccines," Curr Opin Biotechnol 8(6):724-733 (1997).
Persic et al., "An integrated vector system for the eukaryotic expression of antibodies or their fragments after selection from phage display libraries," Gene 187(1):9-18 (1997).
Peters, "Serum albumin," Adv Protein Chem 37:161-245 (1985).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRIIa enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Ryan et al., "Antibody targeting of B-cell maturation antigen on malignant plasma cells," Mol Cancer Ther 6(11):3009-3018 (2007).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276(9):6591-6604 (2001).
Stavenhagen et al., "Enhancing the potency of therapeutic monoclonal antibodies via Fc optimization," Adv Enzyme Regul 48:152-164 (2008).

(56) References Cited

OTHER PUBLICATIONS

Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Steurer et al., "Ex vivo coating of islet cell allografts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable loop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Vajdos et al., "Comprehensive Functional Maps of the Antigen-binding Site of an Anti-ErbB2 Antibody Obtained with Shotgun Scanning Mutagenesis," J Mol Biol 320:415-428 (2002).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).
Wienands, "The B-cell antigen receptor: formation of signaling complexes and the function of adaptor proteins," Curr Top Microbiol Immunol 245:53-76 (2000).
Winkler et al., "Changing the Antigen Binding Specificity by Single Point Mutations of an Anti-p24 (HIV-1) Antibody," J Immunol 165:4505-4514 (2000).
Wu et al., "Humanization of a Murine Monoclonal Antibody by Simultaneous Optimization of Framework and CDR Residues," J Mol Biol 294:151-162 (1999).
Yang et al., "CDR walking mutagenesis for the affinity maturation of a potent human anti-HIV-1 antibodyinto the picomolar range," J Mol Biol 254(3):392-403 (1995).
Young et al., "Thermal stabilization of a single-chain Fv antibody fragment by introduction of a disulphide bond," FEBS Lett 377(2):135-139 (1995).
Yu et al., "Rationalization and Design of the Complementarity Determining Region Sequences in an Antibody-Antigen Recognition Surface," PLOS One 7(3):e33340 (2012).
Zhang et al., "PowerBLAST: a new network BLAST application for interactive or automated sequence analysis and annotation," Genome Res 7(6):649-656 (1997).
Zhu et al., "Remodeling domain interfaces to enhance heterodimer formation," Protein Sci 6(4):781-788 (1997).
Arndt et al., "Costimulation improves the killing capability of T cells redirected to tumor cells expressing low levels of CD33: description of a novel modular targeting system," Leukemia 28:59-69 (2014).
Campbell et al., "Rapid detection, enrichment and propagation of specific T cell subsets based on cytokine secretion," Clin Exp Immunol 163:1-10 (2010).
Carnahan et al., "Epratuzumab, a CD22-targeting recombinant humanized antibody with a different mode of action from rituximab," Mol Immunol 44:1331-1341 (2007).

Chen et al., "Enhancement and destruction of antibody function by somatic mutation: unequal occurrence is controlled by V gene combinatorial associations," EMBO J 14(12):2784-2794 (1995).
Dmitrova et al., "A new LexA-based genetic system for monitoring and analyzing protein heterodimerization in Escherichia coli," Mol Gen Genet 257:205-212 (1998).
Doerner et al., "Therapeutic antibody engineering by high efficiency cell screening," FEBS Lett 588:278-287 (2014).
Gold et al., "The B Cell Antigen Receptor Activates the Akt (Protein Kinase B)/Glycogen Synthase Kinase-3 Signaling Pathway via Phosphatidylinositol 3-Kinase," J Immunol 163:1894-1905 (1999).
Goldenberg et al., "Multifunctional Antibodies by the Dock-and-Lock Method for Improved Cancer Imaging and Therapy by Pretargeting," J Nuc Med 49(1):158-163 (2008).
Hanes et al., "Ribosome display efficiently selects and evolves high-affinity antibodies in vitro from immune libraries," Proc Natl Acad Sci USA 95:14130-14135 (1998).
Ko et al., "Engineering Antibodies for Dual Specificity and Enhanced Potency," Biotechnol Bioprocess Eng 20:201-210 (2015).
Konterman et al., "Dual targeting strategies with bispecific antibodies," mAbs, 4(2):182-197 (2012).
Luo et al., "Design and Applications of Bispecific Heterodimers: Molecular Imaging and Beyond," Mol Pharm 11:1750-1761 (2014).
Rodgers et al., "Switch-mediated activation and retargeting of CAR-T cells for B-cell malignancies," Proc Natl Acad Sci USA 113(4):E459-E468 (2016).
Rudikoff et al., "Single amino acid substitution altering antigen-binding specificity," Proc Natl Acad Sci USA 79:1979-1983 (1982).
Schoonjans et al., "A new model for intermediate molecular weight recombinant bispecific and trispecific antibodies by efficient heterodimerization of single chain variable domains through fusion to a Fab-chain," Biomol Eng 17:193-202 (2001).
Spang et al., "Heterodimeric Barnase-Barstar Vaccine Molecules: Influence of One versus Two Targeting Units Specific for Antigen Presenting Cells," PLoS One 7(9):e45393 (2012).
Veri et al., "Therapeutic Control of B Cell Activation via a Recruitment of Fcγ Receptor IIB (CD32B) Inhibitory Function with a Novel Bispecific Antibody Scaffold," Arthritis Rheum 62(7):1933-1943 (2010).
Wang et al., "Antibody Engineering Using Phage Display with a Coiled-Coil Heterodimeric Fv Antibody Fragment," PLoS One 6(4):e19023 (2011).
Willcox et al., "Production of soluble αβ T-cell receptor heterodimers suitable for biophysical analysis of ligand binding," Protein Sci 8:2418-2423 (1999).
Yu et al., "Interaction between Bevacizumab and Murine VEGF-A: A Reassessment," Invest Ophthalmol Vis Sci 49(2):522-527 (2008).
Zahnd et al., "Directed in Vitro Evolution and Crystallographic Analysis of a Peptide-binding Single Chain Antibody Fragment (scFv) with Low Picomolar Affinity," J Biol Chem 279(18):18870-18877 (2004).
Hernández-Molina et al., "The meaning of anti-Ro and anti-La antibodies in primary Sjögren's syndrome," Autoimmunity Reviews 10:123-125 (2011).
Non-Final Rejection issued in U.S. Appl. No. 15/326,501, dated May 16, 2018.
Final Rejection issued in U.S. Appl. No. 15/326,499, dated Mar. 7, 2019.
Notice of Allowance issued in U.S. Appl. No. 15/326,501, dated Apr. 10, 2019.
Non-Final Rejection issued in U.S. Appl. No. 15/326,499, dated Aug. 30, 2018.
Notice of Allowance issued in U.S. Appl. No. 15/326,499, dated Jun. 18, 2019.
Kussie et al., "A single engineered amino acid substitution changes antibody fine specificity" The Journal of Immunology 152:146-152 (1994).
Ward et al., "Binding activities of a repertoire of single immunoglobulin variable domains secreted from Escherichia coli," Nature 341:544-546 (1989).

(56) References Cited

OTHER PUBLICATIONS

Edwards, Bryan M., et al., "The remarkable flexibility of the human antibody repertoire; isolation of over one thousand different antibodies to a single protein, BLyS," The Journal of Molecular Biology 334: 103-118 (2003).

Lloyd, C., et al., "Modelling the human immune response: performance of a 10E11 human antibody repertoire against a broad panel of therapeutically relevant antigens," Protein Engineering, Design & Selection 22(3): 159-168 (2009).

* cited by examiner pAkt S473 on B cells pPLCγ2 Y759 on B cells

CD86 on B cells

Figure 9
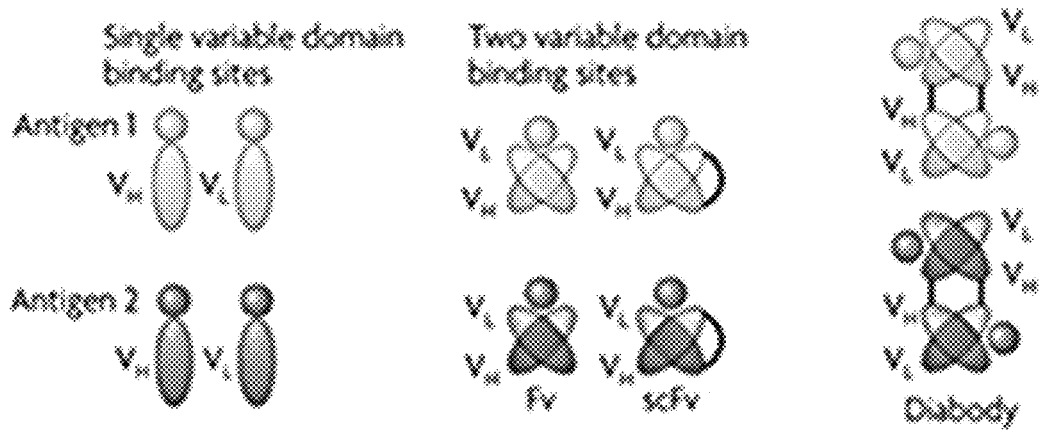
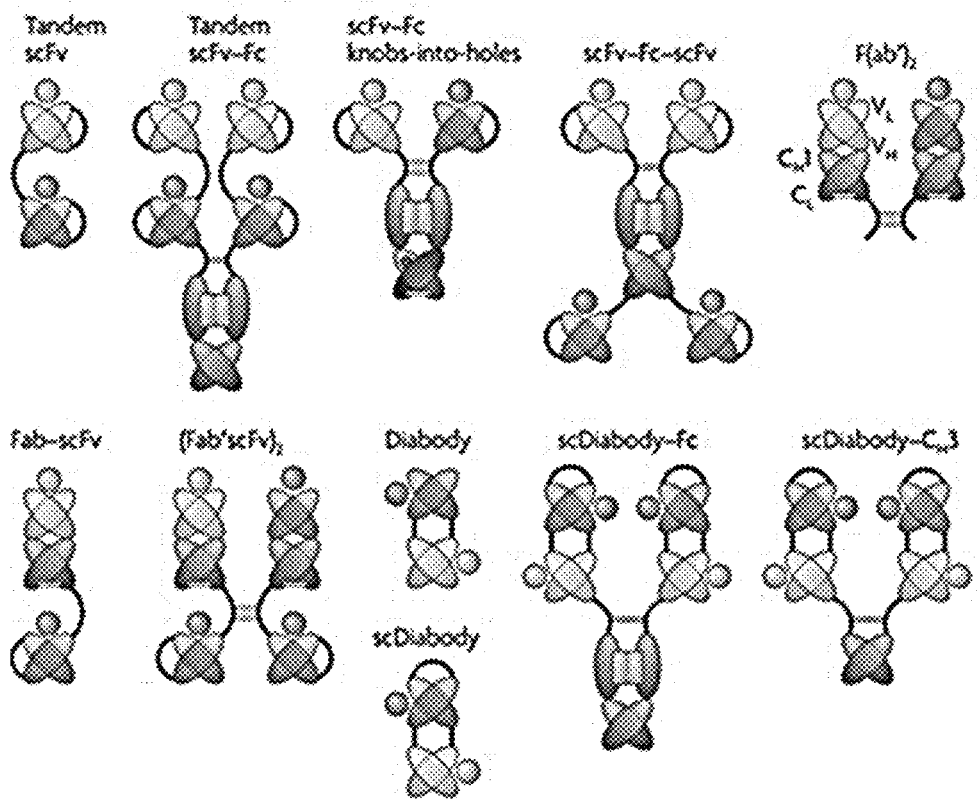

Figure 10

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -4.37 | 33.57 | 10.45 | 13.99 | 3.81 | 4.26 | 8.34 | 21.07 | 4.10 | 13.98 | 6.07 | 16.03 | 7.39 | 9.00 | 23.01 |
| 2 | 27.22 | 25.26 | 52.32 | 63.81 | 30.98 | 19.94 | 26.90 | 29.48 | 20.58 | 30.61 | 9.05 | 4.18 | 14.73 | 36.56 | 33.04 |
| 3 | 17.62 | 69.66 | 3.86 | 16.35 | 7.81 | -5.45 | 6.94 | 12.43 | 6.90 | 7.41 | 15.55 | 18.23 | 8.31 | 7.13 | 15.98 |
| 4 | 13.81 | 70.47 | -9.21 | 11.98 | 2.91 | -0.27 | 7.92 | 9.85 | 0.93 | 4.02 | 8.95 | 40.06 | 10.33 | 6.02 | 15.96 |
| 5 | 5.05 | 36.09 | -1.78 | -0.25 | 10.55 | -14.55 | 11.88 | 6.91 | -0.32 | -2.82 | 9.14 | 12.00 | 3.48 | 7.99 | 9.03 |
| 6 |  | 21.62 | 7.24 | 15.78 | 16.88 | 2.69 | 2.50 | 14.67 | 9.48 | 4.44 | 11.14 | 20.93 | 12.37 |  |  |
| 7 | 10.54 | 35.72 | 2.40 | 16.16 | 14.92 | 1.39 | 2.23 | 14.14 | 5.64 | 10.62 | 8.02 | 17.58 | 9.49 | 10.65 | 10.80 |
| 8 | 6.03 | 26.05 | -7.89 | 3.46 | 7.85 | -16.33 | 0.26 | -5.98 | -2.08 | 0.09 | 7.83 | 5.13 | 2.60 | 9.59 | 9.47 |
| 9 | 13.56 | 32.14 | -4.74 | 2.87 | 9.63 | -7.13 | 5.17 | 10.72 | 0.79 | 1.69 | 9.22 | 13.53 | 2.49 | 15.70 | 10.52 |
| 10 | 15.35 | 54.98 | 13.21 | 17.70 | -2.07 | 8.11 | 21.65 | 23.25 | 9.94 | 10.33 | 16.30 | 41.50 | 13.23 | 6.52 | 16.72 |
| 11 |  | -0.28 | -50.76 | -5.43 | -0.23 | -118.10 | -4.78 | -9.59 | 0.08 | -4.95 | 6.09 | 2.91 | -9.06 |  |  |
| 12 | 5.85 | 8.47 | 19.70 | 42.01 | 20.13 | 12.42 | 15.14 | 26.89 | 20.69 | 24.69 | 18.86 | 36.32 | 18.07 | 20.28 | 38.97 |
| 13 |  | 31.56 | 22.19 | 28.34 | 15.50 | 13.12 | 14.23 | 27.59 | 22.46 | 14.25 | 16.00 | 26.84 | 16.21 |  |  |
| 14 | 9.13 | 40.70 | 10.80 | 14.56 | 5.88 | 8.89 | 7.52 | 22.68 | 6.27 | 9.04 | 7.34 | 33.39 | 11.20 | 7.01 | 14.84 |
| 15 | 9.38 | 33.18 | 7.13 | 11.20 | 15.92 | 11.35 | 9.90 | 19.61 | 9.90 | 10.62 | 13.98 | 28.99 | 15.26 | 13.77 | 25.64 |
| 16 |  | 26.46 | -7.59 | 19.38 | 15.65 | -24.93 | 12.05 | 14.00 | 15.27 | 11.98 | 13.29 | 20.57 | 11.99 |  |  |
| 17 |  | 22.79 | -4.70 | 19.07 | 17.98 | -37.56 | 10.99 | 11.71 | 15.83 | 8.61 | 10.98 | 21.28 | 9.71 |  |  |
| 18 |  | 28.91 | 29.09 | 33.25 | 23.16 | 10.61 | 13.85 | 26.28 | 21.37 | 18.39 | 18.45 | 32.78 | 18.27 |  |  |
| 19 |  | 33.63 | -15.93 | 2.00 | 15.54 | -24.55 | 11.73 | 10.55 | 7.32 | 4.45 | 15.19 | 20.98 | 10.61 |  |  |
| 20 |  | 24.94 | -13.88 | 20.88 | 10.53 | -21.56 | 8.43 | 6.69 | 8.81 | 7.57 | 10.73 | 17.52 | 13.55 |  |  |
| 21 |  | 23.84 | 6.69 | 22.70 | 22.45 | -3.18 | 13.33 | 21.28 | 15.88 | 10.81 | 15.92 | 25.96 | 17.22 | 9.14 |  |
| 22 | 13.93 | 20.55 | -18.75 | -4.96 | 6.90 | -17.32 | 4.12 | -3.15 | -4.19 | -6.48 | 11.71 | 2.48 | -0.84 |  | 11.68 |
| 23 |  | 24.25 | -9.45 | 22.83 | 24.63 | -26.70 | 9.65 | 13.79 | 10.74 | 7.96 | 13.02 | 24.43 | 18.33 |  |  |

Fab-Y specificity antigen 1-23

% Inhibition Syk

Figure 11

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0.81 | 22.29 | 11.45 | 10.78 | 5.39 | 1.60 | 7.43 | 5.90 | 2.24 | 3.29 | -2.71 | 10.80 | 0.99 | 6.90 | -4.08 |
| 2 | 19.70 | 18.61 | 44.00 | 50.83 | 23.17 | 19.01 | 24.57 | 21.47 | 25.89 | 39.80 | 12.36 | 0.52 | 18.91 | 28.55 | 25.89 |
| 3 | 17.93 | 61.18 | 3.00 | 15.38 | 5.38 | -0.12 | 4.05 | 3.77 | 6.84 | 12.78 | 11.01 | 16.71 | 2.97 | 9.17 | 4.69 |
| 4 | 13.34 | 55.83 | -3.82 | 7.24 | 1.41 | -1.39 | 6.75 | 0.89 | 3.12 | 3.12 | 4.16 | 40.49 | 1.71 | 5.13 | 1.10 |
| 5 | 0.34 | 25.16 | 0.51 | -0.63 | 7.36 | -1.41 | 11.49 | 4.08 | 5.59 | 2.99 | 5.76 | 11.67 | 2.84 | 5.90 | -2.06 |
| 6 | ; | 20.71 | -0.85 | 6.04 | 0.40 | 3.49 | -2.80 | -0.87 | 3.41 | 0.22 | 1.34 | 12.34 | 3.36 | ; | ; |
| 7 | 10.95 | 27.95 | 1.38 | 15.66 | 11.27 | 2.40 | 2.48 | 4.45 | 6.13 | 16.07 | 3.18 | 12.77 | 3.92 | 5.85 | 0.37 |
| 8 | 7.73 | 24.86 | 4.02 | 5.23 | 3.56 | 0.49 | 2.68 | -1.16 | 2.39 | 1.45 | 4.10 | 8.50 | -0.64 | 3.01 | 0.97 |
| 9 | 7.37 | 28.27 | -0.02 | 3.22 | 6.39 | 1.35 | 4.75 | 4.08 | 4.92 | 4.09 | 3.10 | 10.50 | 0.62 | 5.62 | 1.50 |
| 10 | 17.08 | 47.69 | 7.72 | 5.65 | -5.55 | 1.40 | 21.89 | 6.66 | 5.90 | 5.11 | 7.61 | 35.77 | 1.50 | 4.32 | -0.06 |
| 11 | ; | 11.76 | -10.93 | 1.38 | -0.58 | -24.94 | -1.36 | 0.83 | 3.58 | 3.88 | 5.92 | 11.18 | -4.57 | ; | ; |
| 12 | 8.05 | -3.88 | 9.02 | 29.48 | 4.92 | 1.15 | 1.89 | 5.75 | 7.23 | 20.95 | 5.44 | 17.92 | 3.37 | 16.34 | 8.67 |
| 13 | ; | 23.78 | -0.99 | 7.30 | 0.43 | -1.40 | 1.83 | 6.41 | 8.91 | 3.25 | 2.76 | 11.64 | 5.41 | ; | ; |
| 14 | 4.40 | 28.11 | 1.77 | 5.61 | 4.01 | 1.73 | 5.96 | 2.45 | 4.05 | 6.85 | -0.60 | 20.60 | 5.45 | 4.11 | 0.05 |
| 15 | 4.96 | 25.60 | 0.87 | 3.43 | 5.41 | 1.77 | 1.89 | 1.80 | 3.72 | 1.98 | 2.29 | 14.57 | 5.26 | 2.36 | 0.11 |
| 16 | ; | 22.39 | -5.77 | 4.50 | 2.41 | -6.86 | 4.89 | 2.52 | 5.19 | 3.07 | 3.38 | 9.47 | 1.17 | ; | ; |
| 17 | ; | 19.53 | -6.98 | 6.73 | 2.99 | -10.27 | 2.35 | 2.13 | 6.02 | 2.08 | 3.10 | 10.86 | 2.03 | ; | ; |
| 18 | ; | 19.90 | 2.43 | 12.38 | 2.08 | -1.05 | 1.09 | 4.25 | 6.70 | 4.90 | 4.40 | 12.49 | 4.34 | ; | ; |
| 19 | ; | 35.50 | -12.22 | -2.38 | -1.61 | -9.05 | 5.97 | 1.78 | 5.27 | 4.63 | 5.92 | 15.60 | 3.16 | ; | ; |
| 20 | ; | 21.53 | -9.67 | 2.95 | -0.16 | -6.71 | -3.46 | -4.81 | 4.13 | 2.31 | 6.52 | 10.96 | 4.25 | ; | ; |
| 21 | ; | 19.03 | -6.66 | 2.36 | 1.10 | -6.49 | -0.95 | 5.09 | 4.96 | 3.55 | 3.97 | 10.89 | 3.63 | ; | 4.58 |
| 22 | 14.73 | 26.47 | -5.00 | 0.58 | 3.97 | -0.08 | 3.70 | -1.25 | 1.72 | 0.99 | 11.40 | 10.89 | 2.80 | 8.39 | ; |
| 23 | ; | 19.72 | -16.22 | 0.75 | -1.16 | -11.03 | -3.57 | 3.30 | 3.57 | 1.23 | 4.90 | 8.22 | 4.20 | ; | ; |

% Inhibition PLCg2

Fab-Y specificity antigen 1-23

Figure 12

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -11.06 | 53.06 | -1.56 | 6.02 | -8.08 | -12.41 | 3.84 | -12.93 | -8.22 | -8.88 | -11.49 | -3.34 | -17.29 | -4.43 | -8.28 |
| 2 | 40.41 | 37.15 | 48.29 | 48.35 | 39.50 | 30.66 | 40.36 | 25.61 | 42.23 | 42.64 | 32.59 | 37.11 | 26.58 | 35.70 | 38.11 |
| 3 | 13.19 | 70.81 | 2.37 | 15.53 | 8.68 | 7.93 | 12.32 | 3.78 | 10.56 | 14.18 | 8.76 | -1.58 | 6.61 | 10.75 | 10.83 |
| 4 | 8.35 | 55.50 | -6.07 | 17.80 | 7.97 | 7.14 | 8.49 | 6.54 | 6.98 | 9.67 | 12.96 | 41.04 | 5.99 | 9.28 | 7.89 |
| 5 | -3.80 | 40.21 | -0.85 | 13.54 | 2.05 | -2.13 | 3.01 | -6.86 | 0.91 | 2.02 | 0.76 | 4.48 | -3.42 | 4.06 | 0.15 |
| 6 | ;; | 40.39 | 6.67 | 19.26 | -4.86 | 12.95 | 3.52 | 2.59 | 6.73 | 5.65 | 5.28 | 4.77 | -1.03 | ;; | ;; |
| 7 | 0.53 | 45.36 | 4.87 | 18.76 | 4.08 | 0.72 | -1.43 | 5.07 | 4.69 | 11.49 | 6.48 | 5.72 | 4.78 | 0.73 | -3.71 |
| 8 | 6.61 | 37.54 | 5.72 | 16.25 | -1.45 | 2.38 | 0.64 | 0.17 | 1.10 | 2.08 | 6.50 | 7.58 | 2.18 | -4.37 | -4.53 |
| 9 | 0.51 | 42.34 | 0.95 | 9.41 | -0.30 | 1.07 | 2.86 | -2.56 | 0.51 | -0.55 | 2.07 | 2.49 | -2.84 | 4.54 | 0.16 |
| 10 | 11.13 | 52.32 | 3.75 | 12.67 | -4.41 | 3.82 | 15.78 | -3.15 | 5.70 | 4.26 | 1.77 | 22.73 | -4.88 | 7.65 | 8.05 |
| 11 | ;; | 33.40 | -3.95 | 18.04 | 7.48 | 6.00 | 3.13 | 4.24 | 5.66 | 13.11 | 9.85 | 11.24 | 2.04 | ;; | ;; |
| 12 | 0.89 | 29.50 | -7.93 | 38.94 | 2.68 | 4.95 | -0.13 | -2.53 | 2.52 | 15.03 | -0.82 | 3.63 | -5.61 | 25.99 | 12.57 |
| 13 | ;; | 35.33 | -4.80 | 10.35 | -4.98 | -7.45 | -7.91 | -6.47 | 3.78 | -0.83 | -4.88 | -3.84 | -9.54 | ;; | ;; |
| 14 | 1.62 | 44.02 | 0.91 | 16.05 | 1.80 | -2.56 | 1.09 | -4.49 | 3.94 | 5.30 | -0.19 | 8.15 | -5.85 | 5.21 | 0.66 |
| 15 | 2.25 | 36.02 | -2.44 | 10.00 | -0.22 | 0.37 | -2.20 | -2.11 | 2.41 | 1.84 | 3.23 | 2.78 | 2.51 | -2.19 | -4.62 |
| 16 | ;; | 33.56 | -3.12 | 15.33 | 0.19 | -5.48 | -0.71 | -5.67 | 1.83 | 1.35 | -0.24 | -1.99 | -8.53 | ;; | ;; |
| 17 | ;; | 35.02 | -4.92 | 16.87 | 1.78 | -2.20 | 0.34 | -2.12 | 3.07 | 1.17 | 0.98 | 0.80 | -2.14 | ;; | ;; |
| 18 | ;; | 31.31 | -1.77 | 19.71 | -6.19 | -4.39 | -3.72 | -3.91 | 2.70 | 3.44 | -0.42 | -1.65 | -5.72 | ;; | ;; |
| 19 | ;; | 50.00 | -2.93 | 9.92 | 2.01 | 9.54 | 10.19 | 2.60 | 11.44 | 9.84 | 7.98 | 9.17 | 3.37 | ;; | ;; |
| 20 | ;; | 38.56 | -1.83 | 18.96 | 1.40 | 5.57 | 0.37 | 1.23 | 4.23 | 6.85 | 10.48 | 6.54 | 2.60 | ;; | ;; |
| 21 | ;; | 36.74 | 1.67 | 11.59 | -5.60 | 6.23 | 0.59 | 6.00 | 6.99 | 5.11 | 3.12 | 3.73 | 3.44 | ;; | ;; |
| 22 | -2.71 | 40.50 | -2.45 | 12.91 | -1.39 | 6.77 | 1.56 | 4.97 | 1.68 | 2.93 | 19.10 | 8.41 | 6.06 | -2.35 | -4.93 |
| 23 | ;; | 33.54 | -1.68 | 5.45 | -2.46 | 7.13 | 0.05 | -3.14 | 2.99 | 3.34 | 6.02 | 4.97 | -4.12 | ;; | ;; |

Fab-Y specificity antigen 1-23

% Inhibition AKT

Figure 13
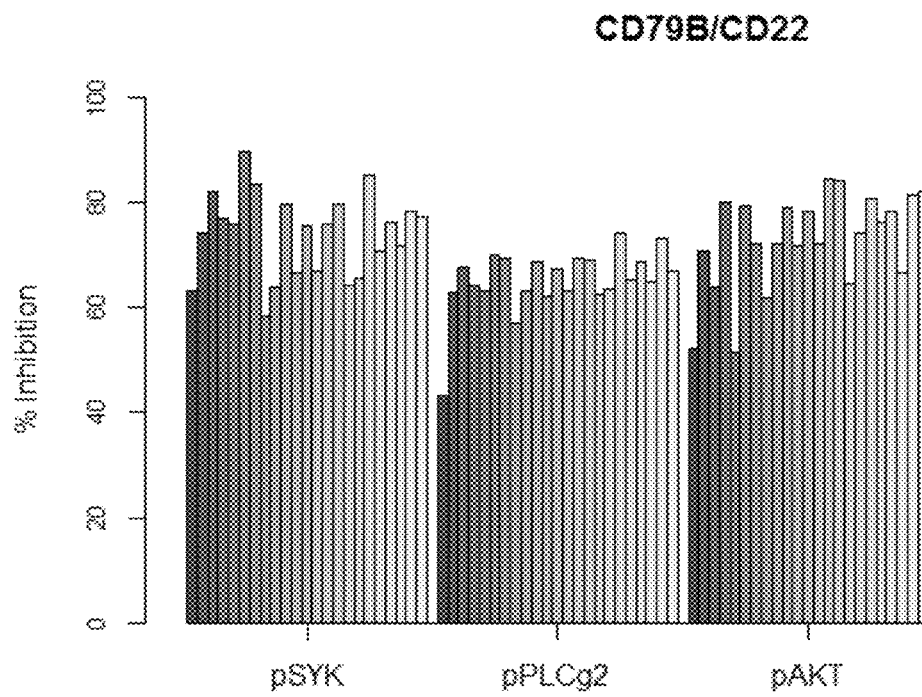
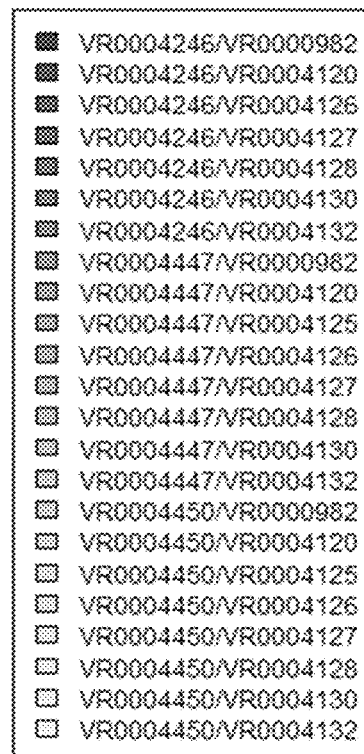

% Inhibition (+/- SD) of Phosphorylated P38 in Anti-IgM Stimulated B-cells, by CD79b and CD22 Specific Fab-Kd-Fab and BYbe.

% Inhibition of Anti-IgM Induced CD71 on B-cells, by CD79b and CD22 Specific Fab-Kd-Fab and BYbe

|  | IC50 (nM) |
|---|---|
| 4447 + 4130 Fab-Kd-Fab | 2.526 |
| 4447/4130 BYbe | 0.1715 |

Percentage inhibition of CD86 expression on total B cells stimulated with a goat anti human anti-IgM antibody Figure 27   Percentage inhibition of tetanus toxoid specific IgG production from human PBMCs
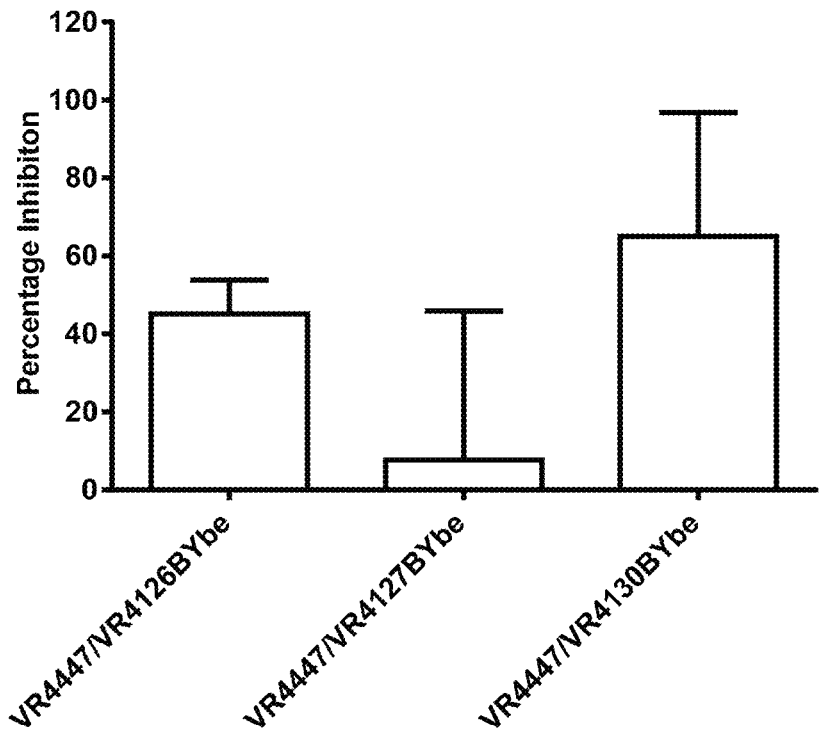
Figure 28   Percentage inhibition of tetanus toxoid specific IgG production from human B cells
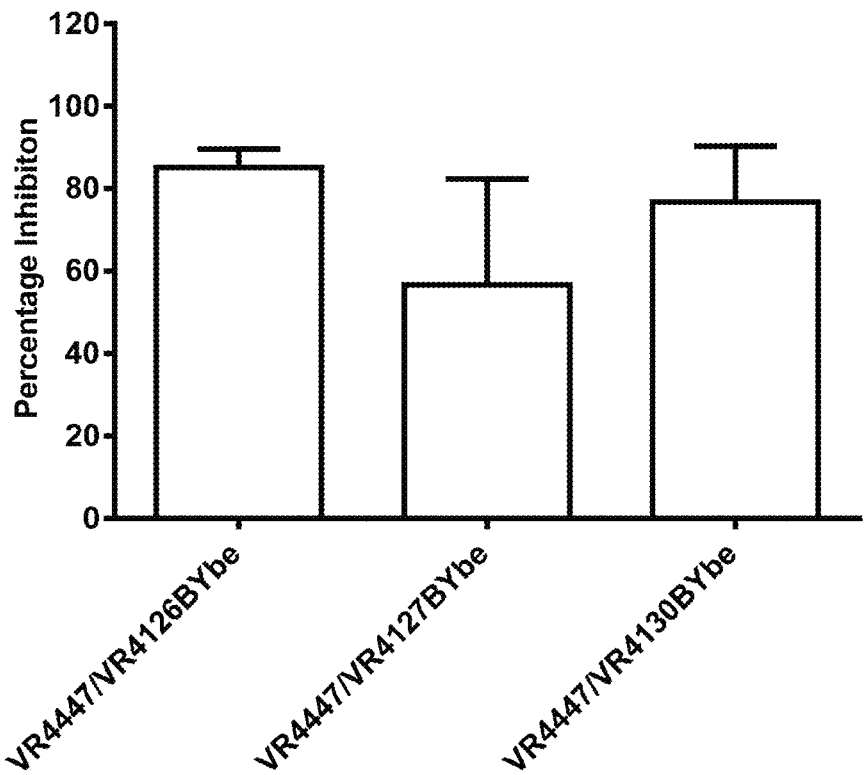

Figure 30 Baseline Levels of Phosphorylation in Unstimulated B-cells from 12 Healthy and 12 SLE Patient Samples Figure 31  Effect of CD79b & CD22 Specific VR4447/4130 BYbe on Anti-IgM Induced B cell NFκB Phosphorylation from 12 Healthy and 12 SLE Patient Samples Figure 32    Effect of CD79b & CD22 Specific VR4447/4130 BYbe on Anti-IgM Induced B cell Akt Phosphorylation from 12 Healthy and 12 SLE Patient Samples Figure 33  Effect of CD79b & CD22 Specific VR4447/4130 BYbe on Anti-IgM Induced B cell Syk Phosphorylation from 12 Healthy and 12 SLE Patient Samples Figure 34  Effect of CD79b & CD22 Specific VR4447/4130 BYbe on Anti-IgM Induced B cell ERK1 & 2 Phosphorylation from 12 Healthy and 12 SLE Patient Samples pAkt S473 on B cells

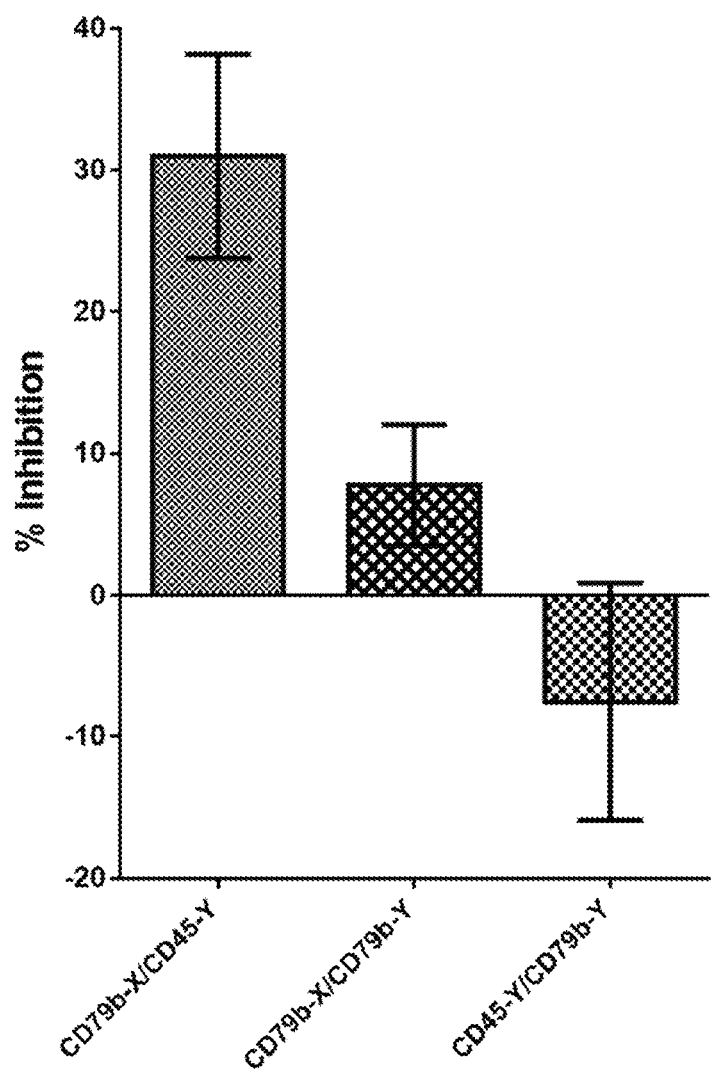
Figure 36 pPLCg2 Y759 on B cells

Figure 37 CD86 Titration –CD45/CD79b
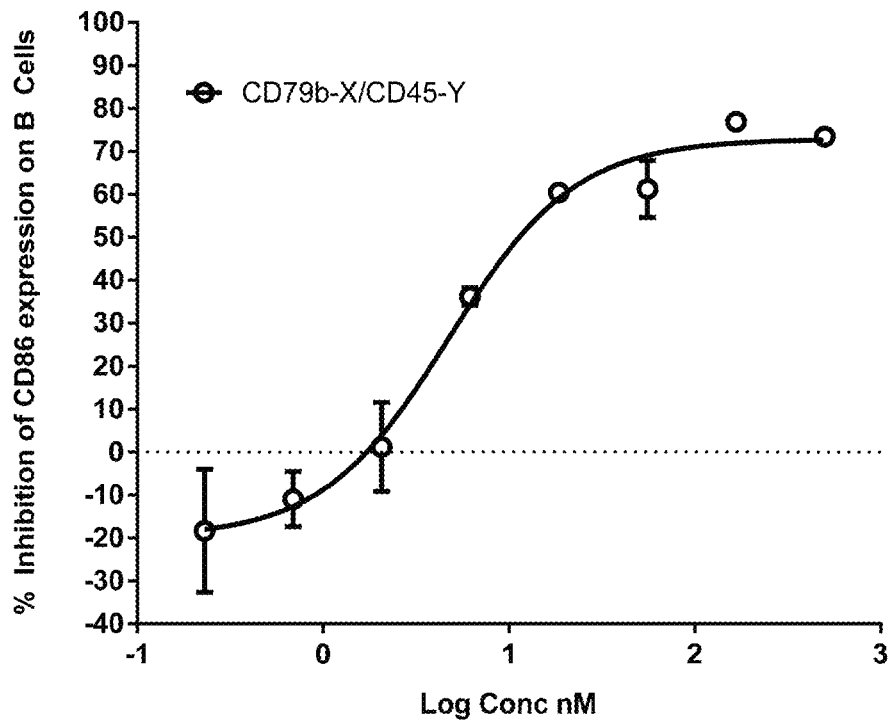
Figure 38 CD79b-Y Combination Inhibition of Anti-IgM Stimulation Induced by PLC-γ2 Phosphorylation
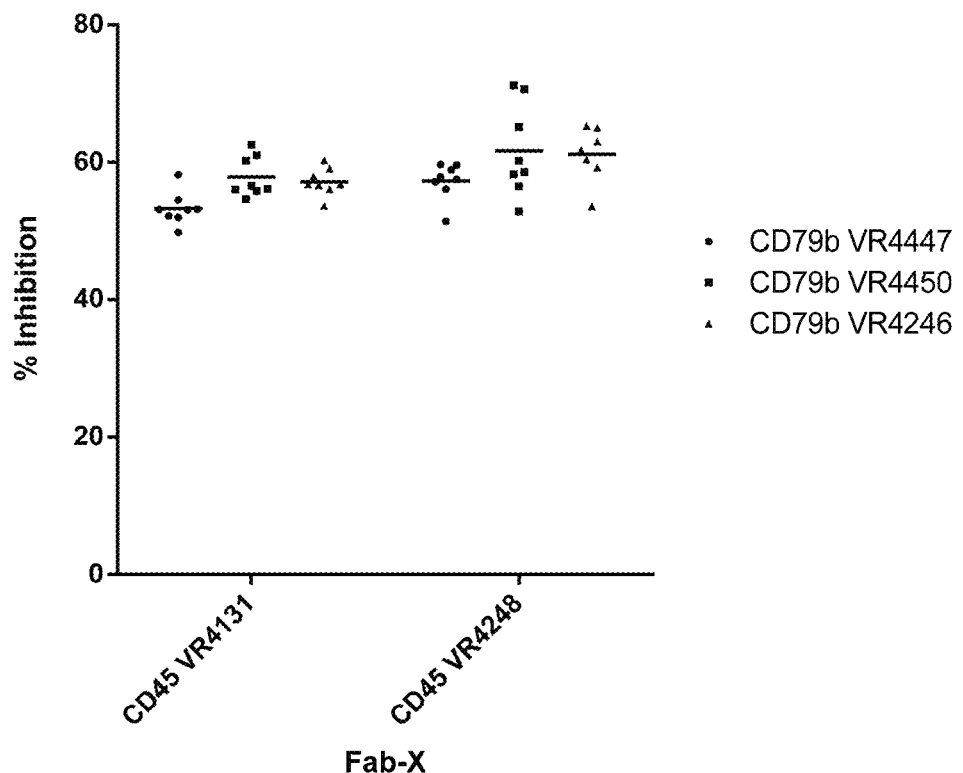

Figure 41  Inhibition of PLCγ2 (+/- SD) by purified CD79b-CD45 transient on IgM stimulated B-cells from donor 129

Figure 42 Inhibition of PLCγ2 (+/- SD) by purified CD79b-CD45 transient on IgM stimulated B-cells from donor 130

Figure 43 Inhibition of p38 (+/- SD) by purified CD79b-CD45 transient on IgM stimulated B-cells from donor 129

Figure 44 Inhibition of p38 (+/- SD) by purified CD79b-CD45 transient on IgM stimulated B-cells from donor 130

Figure 45 Inhibition of Akt (+/- SD) by purified CD79b-CD45 transient on IgM stimulated B-cells from donor 129

Figure 46 Inhibition of Akt (+/- SD) by purified CD79b-CD45 transient on IgM stimulated B-cells from donor 130

Figure 51

GCN4(7P14P) sequences

ASGGGRMKQLEPKVEELLPKNYHLENEVARLKKLVGERHHHHHH   SEQ ID NO:25
wherein the amino acids in bold are optional GCTAGCGGAGGCGGAAGAATGAAACAACTTGAACCCAAGGTTGAAGAATTGCTTCCGAAAAA
TTATCACTTGGAAAATGAGGTTGCCAGATTAAAGAAATTAGTTGGCGAACGCCATCACCATC
ACCATCAC SEQ ID NO: 26

52SR4 ds scFv sequence
DAVVTQESALTSSPGETVTLTCRSSTGAVTTSNYASWVQEKPDHLFTGLIGGTNNRAPGV
PARFSGSLIGDKAALTITGAQTEDEAIYFCVLWYSDHWVFGCGTKLTVLGGGGGSGGGGS
GGGGSGGGGSDVQLQQSGPGLVAPSQSLSITCTVSGFLLTDYGVNWVRQSPGKCLEWLGV
IWGDGITDYNSALKSRLSVTKDNSKSQVFLKMNSLQSGDSARYYCVTGLFDYWGQGTTLT
VSSAAAHHHHHHEQKLISEEDL- SEQ ID NO: 27

GATGCGGTGGTGACCCAGGAAAGCGCGCTGACCAGCAGCCCGGGCGAAACCGTGACCCTGAC
CTGCCGCAGCAGCACCGGCGCGGTGACCACCAGCAACTATGCGAGCTGGGTGCAGGAAAAAC
CGGATCATCTGTTTACCGGCCTGATTGGCGGCACCAACAACCGCGCGCCGGGCGTGCCGGCG
CGCTTTAGCGGCAGCCTGATTGGCGATAAAGCGGCGCTGACCATTACCGGCGCGCAGACCGA
AGATGAAGCGATTTATTTTTGCGTGCTGTGGTATAGCGACCATTGGGTGTTTGGCTGCGGCA
CCAAACTGACCGTGCTGGGTGGAGGCGGTGGCTCAGGCGGAGGTGGCTCAGGCGGTGGCGGG
TCTGGCGGCGGCGGCAGCGATGTGCAGCTGCAGCAGAGCGGCCCGGGCCTGGTGGCGCCGAG
CCAGAGCCTGAGCATTACCTGCACCGTGAGCGGCTTTCTCCTGACCGATTATGGCGTGAACT
GGGTGCGCCAGAGCCCGGGCAAATGCCTGGAATGGCTGGGCGTGATTTGGGGCGATGGCATT
ACCGATTATAACAGCGCGCTGAAAAGCCGCCTGAGCGTGACCAAAGATAACAGCAAAAGCCA
GGTGTTTCTGAAAATGAACAGCCTGCAGAGCGGCGATAGCGCGCGCTATTATTGCGTGACCG
GCCTGTTTGATTATTGGGGCCAGGGCACCACCCTGACCGTGAGCAGCGCGGCCGCCCATCAC
CATCACCATCACGAACAGAAACTGATTAGCGAAGAAGATCTGTAATAG    SEQ ID NO: 28

CD79b Antibodies

Ab 4447

| | | |
|---|---|---|
| SEQ ID NO: 11 | CDRH1 | GFSLSNYAVS |
| SEQ ID NO: 12 | CDRH2 | IIYIETGTTWYANWAKG |
| SEQ ID NO: 3 | CDRH3 | EPYEPYDDSNIYYGMDP |
| SEQ ID NO: 19 | CDRL1 | QASQSVVSGNYLA |
| SEQ ID NO: 20 | CDRL2 | SASTLAS |
| SEQ ID NO: 21 | CDRL3 | LGEFSCSSHDCNA |
| SEQ ID NO: 22 | CDRL3 variant 1 | LGEFSSSSHDSNA |
| SEQ ID NO: 23 | CDRL3 variant 2 | LGEFSCSSHDSNA |
| SEQ ID NO: 24 | CDRL3 variant 3 | LGEFSSSSHDCNA |

SEQ ID NO: 29   Rabbit Ab 4447 VL region
AQVLTQTPSP VSAPVGGTVT INCQASQSVV SGNYLAWLQQ KPGQPPKQLI HSASTLA
SGV SSRFSGSGSG TQFTLTISGV QCEDAATYYC LGEFSCSSHD CNAFGGGTEVVVK

Figure 51 continued

SEQ ID NO: 30 Rabbit Ab 4447 VL region
```
gcccaagtgc tgacccagac tccgtcccct gtgtctgcac ctgtgggagg cacagtcacc
atcaattgcc aggccagtca gagtgttgtt agtggcaatt acctagcctg gcttcagcag
aaaccagggc agcctcccaa gcaactgatc cattctgcat ccactctggc atctggggtc
tcatcgcggt tcagcggcag tggatctggg acacaattca ctctcaccat cagcggcgtg
cagtgtgaag atgctgccac ttactactgt ctaggcgaat ttagttgtag tagtcatgat
tgtaatgctt tcggcggagg gaccgaggtg gtggtcaaa
```

SEQ ID NO: 31 Rabbit Ab 4447 VH region
QSLEESGGRL VTPGTPLTLT CTVSGFSLSN YAVSWVRQAP GEGLEWIGII
YIETGTTWYA NWAKGRFTIS KTSTTVDLTI TSPSTEDTAT YFCAREPYEP
YDDSNIYYGM DPWGPGTLVT VSS

SEQ ID NO: 32 Rabbit Ab 4447 VH region
```
cagtcgctgg aggagtccgg gggtcgcctg gtcacgcctg gacacccct gacactcacc
tgcaccgtct ctggattctc cctcagtaac tatgcagtaa gctgggtccg ccaggctcca
ggggagggac tggaatggat cgggatcatt tatattgaaa ctggtaccac atggtacgcg
aactgggcga aaggccgatt caccatctcc aaaacctcga ccacggtgga tctgacaatc
accagtccgt caaccgagga cacggccacc tatttctgtg ccagagaacc ttatgaacct
tatgatgata gtaatattta ctacggcatg gacccctggg gccaggcac cctcgtcacc gtctcgagt
```

SEQ ID NO: 33 4447 gL1 V-region - IGKV1D-13 framework
AQVLTQSPSS LSASVGDRVT ITCQASQSVV SGNYLAWLQQ KPGKAPKQLI HSASTLASGV PSRFSGSGSG
TQFTLTISSL QPEDFATYYC LGEFSCSSHD CNAFGGGTKV EIK

SEQ ID NO: 250 4447 gL2 V-region - IGKV1D-13 framework
AQVLTQSPSS LSASVGDRVT ITCQASQSVV SGNYLAWLQQ KPGKAPKQLI HSASTLASGV PSRFSGSGSG TQFTLT
ISSL QPEDFATYYC LGEFSSSSHD SNAFGGGTKV EIK

SEQ ID NO: 34 4447 gH1 V-region – IGHV3-48 framework
EVQLVESGGG LVQPGGSLRL SCAVSGFSLS NYAVSWVRQA PGKGLEWIGI IYIETGTTWY ANWAKGRFTI
SKDSAKNSVY LQMNSLRDED TAVYYCAREP YEPYDDSNIY YGMDPWGQGT LVTVSS

SEQ ID NO: 35 4447 gH3 V-region – IGHV4-59 framework
EVQLQESGPG LVKPSETLSL TCTVSGFSLS NYAVSWVRQP PGKGLEWIGI IYIETGTTWY ANWAKGRFTI
SKDSSKNQVS LKLSSVTAAD TAVYYCAREP YEPYDDSNIY YGMDPWGQGT LVTVSS

Ab 4450

| | | |
|---|---|---|
| SEQ ID NO: 8 | CDRH1 | GFSLNNYVMV |
| SEQ ID NO: 9 | CDRH2 | IIYVSGNAYYASWAKG |
| SEQ ID NO: 4 | CDRH3 | DAGHSDVDVLDI |
| SEQ ID NO: 13 | CDRL1 | QSSQSIYNNNDLA |
| SEQ ID NO: 14 | CDRL2 | EASKLAS |
| SEQ ID NO: 15 | CDRL3 | QGGGSGGDGIA |
| SEQ ID NO: 16 | CDRL3 – variant 1 | QGGGSGGEGIA |
| SEQ ID NO: 17 | CDRL3 – variant 2 | QGGGSGGDAIA |
| SEQ ID NO: 18 | CDRL3 – variant 3 | QGGGSGGDSIA |

Figure 51 continued

SEQ ID NO: 36 Rabbit Ab 4450 VL region
AIDMTQTPSP VSAAVGGTVT INCQSSQSIY NNNDLAWYQQ KPGQPPKLLI YEASKLASGV
PSRFKGSGSG TQFTLTISGV QCDDAATYYC QGGGSGGDGI AFGGGTKVVV E

SEQ ID NO: 37 Rabbit Ab 4450 VL region
gccattgata tgacccagac tccatccccc gtgtctgcag ctgtgggagg cacagtcacc
atcaattgcc agtccagtca gagtatttat aataataatg acttagcctg tatcagcag
aaaccagggc agcctcccaa gctcctgatc tacgaagcat ccaaactggc atctggggtc
ccatcgcggt tcaaaggcag tggatctggg acacagttca ctctcaccat cagtggcgtg
cagtgtgatg atgctgccac ttactactgt cagggcggtg gtagtggtgg tgatggcatt
gctttcggcg gagggaccaa ggtggtcgtc gaa

SEQ ID NO: 38 Rabbit Ab 4450 VH region
QSVEESGGRL VTPGAPLTLT CTVSGFSLNN YVMVWVRQAP GKGLEWIGII YVSGNAYYAS
WAKGRFTISR TSTTVDLKVT SLTTEDTATY FCARDAGHSD VDVLDIWGPG TLVTVSS

SEQ ID NO: 39 Rabbit Ab 4450 VH region
cagtcggtgg aggagtccgg gggtcgcctg gtcacgcctg ggcacccct gacactcacc
tgcacagtct ctggattctc cctcaataac tatgtaatgg tctgggtccg ccaggctcca
gggaaggggc tggaatggat cggaatcatt tatgttagtg gtaatgcata ctacgcgagc
tgggcaaaag gccgattcac catctccaga acctcgacca cggtggatct gaaagtgacc
agtctgacaa ccgaggacac ggccacctat ttctgtgcca gagatgctgg tcatagtgat
gtcgatgttt tggatatttg ggggcccggc accctcgtca ccgtctcgag t

SEQ ID NO: 40 4450 gL1 V-region - IGKV1-6 framework
AI<u>D</u>MTQSPSS LSASVGDRVT ITCQSSQSIY NNNDLAWYQQ KPGKAPKLLI YEASKLASGV PSRFSGSGSG
T<u>Q</u>FTLTISSL QPEDFATYYC QGGGSGGDGI AFGGGTKVEI K

SEQ ID NO: 341 4450gL5 V-region – IGKV1-6 framework

AI<u>D</u>MTQSPSS LSASVGDRVT ITCQSSQSIY NNNDLAWYQQ KPGKAPKLLI YEASKLASGV PSRFSGSGSG
T<u>Q</u>FTLTISSL QPEDFATYYC QGGGSGGEGI AFGGGTKVEI K

SEQ ID NO: 342 4450gL6 V-region – IGKV1-6 framework

AI<u>D</u>MTQSPSS LSASVGDRVT ITCQSSQSIY NNNDLAWYQQ KPGKAPKLLI YEASKLASGV PSRFSGSGSG
T<u>Q</u>FTLTISSL QPEDFATYYC QGGGSGGDAI AFGGGTKVEI K

SEQ ID NO: 343 4450gL7 V-region – IGKV1-6 framework

AI<u>D</u>MTQSPSS LSASVGDRVT ITCQSSQSIY NNNDLAWYQQ KPGKAPKLLI YEASKLASGV PSRFSGSGSG
T<u>Q</u>FTLTISSL QPEDFATYYC QGGGSGGDSI AFGGGTKVEI K

SEQ ID NO: 41 4450 gH1 V-region - IGHV3-66 framework
EVQLVESGGG LVQPGGSLRL SCA<u>V</u>SGFSLN NYVMVWVRQA PGKGLEW<u>IGI</u> IYVSGNAYYA SWAKGRFTIS
RD<u>SS</u>KNT<u>VY</u>L QMNSLRAEDT AVYYCARDAG HSDVDVLDIW GQGTLVTVSS

SEQ ID NO: 42 4450 gH3 V-region – IGHV4-59 framework
<u>E</u>VQLQESGPG LVKPSETLSL TCTVSGFSLN NYVMVW<u>V</u>RQP PGKGLEWIGI IYVSGNAYYA SWAKGR<u>F</u>TIS
<u>R</u>D<u>SS</u>KNQ<u>V</u>SL KLSSVTAADT AVYYCARDAG HSDVDVLDIW GQGTLVTVSS

Figure 51 continued

CD22 Antibodies

Ab 4120

| | | |
|---|---|---|
| SEQ ID NO: 43 | CDRH1 | GFSFSSSYYMC |
| SEQ ID NO: 44 | CDRH1 variant | GFSFSSSYYMS |
| SEQ ID NO: 45 | CDRH2 | CIYTGSSGDTYYASWAKG |
| SEQ ID NO: 46 | CDRH2 variant | SIYTGSSGDTYYASWAKG |
| SEQ ID NO: 47 | CDRH3 | GPYVGYGYDLQYLYL |
| SEQ ID NO: 48 | CDRL1 | QASQSISTALA |
| SEQ ID NO: 49 | CDRL2 | GASTLAS |
| SEQ ID NO: 50 | CDRL3 | QSYYGTSSGGSWA |

SEQ ID NO: 51 Rabbit Ab 4120 VL region
AFELSQTPAS VEAAVGGTVT IKCQASQSIS TALAWYQQKP GQRPKLLIYG
ASTLASGVSS RFKGSGSGTE FTLTISDLEC ADAATYYCQS YYGTSSGGSW AFGGGTKVVV K

SEQ ID NO: 52 Rabbit Ab 4120 VL region
gcattcgaat tgagccagac tccagcctcc gtggaggcag ctgtgggagg cacagtcacc
atcaagtgcc aggccagtca gagcattagc actgcattag cctggtatca gcagaaacca
gggcagcgtc ccaagctcct gatctatggt gcatccactc tggcatctgg ggtctcatcg
cggttcaaag gcagtggatc tgggacagag ttcactctca ccatcagcga cctggagtgt
gccgatgctg ccacttacta ctgtcaaagc tattatggta cgagtagtgg tggttcttgg
gctttcggcg gagggaccaa ggtggtcgtc aaa

SEQ ID NO: 53 Rabbit Ab 4120 VH region
QSLEESGGDL VKPGASLTLT CTASGFSFSS SYYMCWVRQS PGKGLEWIAC IYTGSSGDTY
YASWAKGRFT ISKTSSTTVS LQMTSLTAAD TATYFCARGP YVGYGYDLQY LYLWGPGTLV TVSS

SEQ ID NO: 54 Rabbit Ab 4120 VH region
cagtcattgg aggagtccgg gggagacctg gtcaagcctg ggcatccct gacactcacc
tgcacagcct ctggattctc cttcagtagt agctactaca tgtgctgggt ccgccagtct
ccagggaagg ggctggagtg gatcgcatgc atttatactg gtagtagtgg tgacacttac
tacgcgagct gggcgaaagg ccgattcacc atctccaaaa cctcgtcgac cacggtgtct
ctgcaaatga ccagtctgac agccgcggac acggccactt atttctgtgc gagagggcct
tatgttggtt atggttatga tcttcaatac ttgtacttgt ggggcccggg gaccctcgtc
accgtctcga gt

SEQ ID NO: 55 4120 gL1 V-region IGKV1D-13 framework
A<u>FE</u>LTQSPSS LSASVGDRVT ITCQASQSIS TALAWYQQKP GKAPKLLIYG ASTLASGVPS RFSGSGSGTD
FTLTISSLQP EDFATYYCQS YYGTSSGGSW AFGGGTKVEI K

SEQ ID NO: 56 4120 gH1 V-region - IGHV3-33 framework
<u>E</u>VQLVESGGG <u>L</u>VQPGRSLRL SCAASGFSFS SSYYMCWVRQ APGKGLEW<u>I</u>A CIYTGSSGDT YYASWAKGRF
TIS<u>K</u>D<u>S</u>SK<u>TT</u> <u>V</u>YLQMNSLRA EDTAVYYCAR GPYVGYGYDL QYLYLWGQGT LVTVSS

Figure 51 continued

SEQ ID NO: 246 4120 gH2 V-region - IGHV3-33 framework
EVQLVESGGG LVQPGRSLRL SCAASGFSFS SSYYMSWVRQ APGKGLEWIA SIYTGSSGDT YYASWAKGRF
TISKDSSKTT VYLQMNSLRA EDTAVYYCAR GPYVGYGYDL QYLYLWGQGT LVTVSS

SEQ ID NO: 247 4120 gH5 V-region – IGHV4-38-2 framework
EVQLQESGPG LVKPSETLSL TCAASGFSFS SSYYMSWVRQ PPGKGLEWIA SIYTGSSGDT YYASWAKGRF
TISKDSSKTQ VSLKLSSVTA ADTAVYYCAR GPYVGYGYDL QYLYLWGQGT LVTVSS

SEQ ID NO: 248 4120 gH4 V-region – IGHV4-38-2 framework
EVQLQESGPG LVKPSETLSL TCAASGFSFS SSYYMCWVRQ PPGKGLEWIA CIYTGSSGDT YYASWAKGRF
TISKDSSKTQ VSLKLSSVTA ADTAVYYCAR GPYVGYGYDL QYLYLWGQGT LVTVSS

Ab 4126

SEQ ID NO: 249 Rabbit Ab 4126 VL region
DIVMTQTPAS VEAAVGGTVT IKCQASQNIG SGLAWYQQKP GQPPKLLIYY
ASTLASGVPS RFKGSGSGTQ FTLTISDLEC ADAATYYCQS HDYSSVRSYG NAFGGGTEVV VK

SEQ ID NO: 57 Rabbit Ab 4126 VL region
gacattgtga tgacccagac tccagcctcc gtggaggcag ctgtgggagg cacagtcacc
atcaagtgcc aggccagtca gaacattggt agtggtttag cctggtatca gcagaaacca
gggcagcctc ccaagctcct gatctattat gcatccactc tggcatctgg ggtcccatca
aggttcaaag gcagtggatc tgggacacag ttcactctca ccatcagcga cctggagtgt
gccgacgctg ccacttacta ctgtcaaagt catgattata gtagtgttcg gagttacggt
aatgctttcg gcggagggac cgaggtggtg gtcaaa

SEQ ID NO: 58 Rabbit Ab 4126 VH region
QQHLEESGGG LVKPGGTLTL TCKASGIDFS SYYYMCWVRQ APGKGLEWVA CIDPASSGTT
YYATWAKGRF TISKTSSTTV TLQMTSLTAA DTATYFCARA YGSGGSGYIG CYFDLWGQGT LVTVSS

SEQ ID NO: 59 Rabbit Ab 4126 VH region
cagcagcacc tggaggagtc cggggggaggc ctggtcaagc ctggaggaac cctgacactc
acctgcaaag cctctggaat cgacttcagt agctactact acatgtgctg ggtccgccag
gctccaggga aggggctgga gtgggtcgcg tgcattgatc ctgctagtag tggtactact
tactacgcga cctgggcgaa aggccgattc accatctcca aaacctcgtc gaccacggtg
actctgcaaa tgaccagtct gacagccgcg gacacggcca cctatttctg tgcgagggca
tatggtagtg ggggtagtgg ttatataggg tgctactttg acttgtgggg ccaaggcacc
ctcgtcaccg tctcgagt

SEQ ID NO: 60 CDRH1          GIDFSSYYYMC
SEQ ID NO: 61 CDRH1 variant  GIDFSSYYYMS
SEQ ID NO: 62 CDRH2          CIDPASSGTTYYATWAKG
SEQ ID NO: 63 CDRH2 variant  SIDPASSGTTYYATWAKG
SEQ ID NO: 64 CDRH3          AYGSGGSGYIGCYFDL
SEQ ID NO: 65 CDRH3 variant  AYGSGGSGYIGSYFDL
SEQ ID NO: 66 CDRL1          QASQNIGSGLA
SEQ ID NO: 67 CDRL2          YASTLAS
SEQ ID NO: 68 CDRL3          QSHDYSSVRSYGNA

Figure 51 continued

SEQ ID NO: 69  4126 gL3 V-region - IGKV1-5 framework
DI<u>V</u>MTQSPST LSASVGDRVT ITCQASQNIG SGLAWYQQKP GKAPKLLIYY ASTLASGVPS RFSGSGSGT<u>Q</u>
FTLTISSLQP DDFATYYCQS HDYSSVRSYG NAFGGGTKVE IK

SEQ ID NO: 70  4126 gH12 V-region - IGHV3-7 framework
EVQLVESGGG LVQPGGSLRL SCAASGIDFS SYYYMCWVRQ APGKGLEWVA CIDPASSGTT YYATWAKGRF
TIS<u>K</u>D<u>S</u>AK<u>T</u>S <u>V</u>YLQMNSLRA EDTAVYYCAR AYGSGGSGYI GCYFDLWGQG TLVTVSS

SEQ ID NO: 71  4126 gH3 V-region - IGHV3-7 framework
EVQLVESGGG LVQPGGSLRL SCAASGIDFS SYYYMCWVRQ APGKGLEWVA CIDPASSGTT YYATWAKGRF
TISKDSAKTS VYLQMNSLRA EDTAVYYCAR AYGSGGSGYI GSYFDLWGQG TLVTVSS

SEQ ID NO: 251  4126 gH4 V-region - IGHV3-7 framework
EVQLVESGGG LVQPGGSLRL SCAASGIDFS SYYYMSWVRQ APGKGLEWVA SIDPASSGTT YYATWAKGRF
TISKDSAKTS VYLQMNSLRA EDTAVYYCAR AYGSGGSGYI GSYFDLWGQG TLVTVSS

SEQ ID NO: 252  4126 gH13 V-region – IGHV4-4 framework
<u>E</u>VQLQESGPG LVKPSGTLSL TCA<u>A</u>SGIDFS SYYYMCWVRQ PPGKGLEW<u>VA</u> CIDPASSGTT YYATWAKGR<u>F</u>
TIS<u>K</u>D<u>S</u>SKT<u>Q</u> <u>V</u>SLKLSSVTA ADTAVYYCAR AYGSGGSGYI GCYFDLWGQG TLVTVSS

SEQ ID NO: 253  4126 gH6 V-region – IGHV4-4 framework
EVQLQESGPG LVKPSGTLSL TCAASGIDFS SYYYMCWVRQ PPGKGLEWVA CIDPASSGTT YYATWAKGRF TISKDS
SKTQ VSLKLSSVTA ADTAVYYCAR AYGSGGSGYI GSYFDLWGQG TLVTVSS

SEQ ID NO: 254  4126 gH7 V-region – IGHV4-4 framework
EVQLQESGPG LVKPSGTLSL TCAASGIDFS SYYYMSWVRQ PPGKGLEWVA SIDPASSGTT YYATWAKGRF TISKDS
SKTQ VSLKLSSVTA ADTAVYYCAR AYGSGGSGYI GSYFDLWGQG TLVTVSS

Ab 4127
| | | |
|---|---|---|
| SEQ ID NO: 72 | CDRH1 | GFSFSNLYYMC |
| SEQ ID NO: 73 | CDRH1 variant | GFSFSNLYYMS |
| SEQ ID NO: 74 | CDRH2 | CIDISSSGSTYYASWAKG |
| SEQ ID NO: 75 | CDRH2 variant | SIDISSSGSTYYASWAKG |
| SEQ ID NO: 76 | CDRH3 | DYYSSDWGVRFNL |
| SEQ ID NO: 77 | CDRL1 | QASQSVYGNNELS |
| SEQ ID NO: 78 | CDRL2 | LASRLAS |
| SEQ ID NO: 79 | CDRL3 | AGYKSDSDDGTT |
| SEQ ID NO: 80 | CDRL3 variant 1 | AGYKSESDDGTT |
| SEQ ID NO: 81 | CDRL3 variant 2 | AGYKSDADDGTT |
| SEQ ID NO: 82 | CDRL3 variant 3 | AGYKSDTDDGTT |
| SEQ ID NO: 83 | CDRL3 variant 4 | AGYKSDSDEGTT |
| SEQ ID NO: 84 | CDRL3 variant 5 | AGYKSDSDDATT |
| SEQ ID NO: 85 | CDRL3 variant 6 | AGYKSDSDDSTT |
| SEQ ID NO: 86 | CDRL3 variant 7 | AGYKSESDEGTT |
| SEQ ID NO: 87 | CDRL3 variant 8 | AGYKSESDDATT |
| SEQ ID NO: 88 | CDRL3 variant 9 | AGYKSESDDSTT |
| SEQ ID NO: 89 | CDRL3 variant 10 | AGYKSDADEGTT |
| SEQ ID NO: 90 | CDRL3 variant 11 | AGYKSDADDATT |

Figure 51 continued

SEQ ID NO: 91 CDRL3 variant 12     AGYKSDADDSTT
SEQ ID NO: 92 CDRL3 variant 13     AGYKSDTDEGTT
SEQ ID NO: 93 CDRL3 variant 14     AGYKSDTDDATT
SEQ ID NO: 94 CDRL3 variant 15     AGYKSDTDDSTT

SEQ ID NO: 95 Rabbit Ab 4127 VL region
AIVMTQTPSS KSVPMGGTVT INCQASQSVY GNNELSWYQQ KPGQPPKLLI YLASRLASGV
PSRFSGSGSG TQFTLTISGV QCDDAATYYC AGYKSDSDDG TTFGGGTKVV VE

SEQ ID NO: 96 Rabbit Ab 4127 VL region
gccatcgtga tgacccagac tccatcttcc aagtctgtcc ctatgggagg cacagtcacc
atcaactgcc aggccagtca gagtgtttat ggtaataacg aattatcctg gtatcagcag
aaaccaggc agcctcccaa gctcctgatc tatttggcat ccaggctggc atcggggtc
ccatcgcggt ttagcggcag tggatctggg acacagttca ctctcaccat cagcggcgtg
cagtgtgacg atgctgccac ttactactgt gcaggctata aaagtgatag tgatgatggc
actactttcg gcggagggac caaggtggtg gtcgaa

SEQ ID NO: 97 Rabbit Ab 4127 VH region
QQLEESGGDL VKPGASLTLT CTASGFSFSN LYYMCWVRQA PGKGLELIGC IDISSSGSTY
YASWAKGRFT ISKTSSTTVT LQMTSLTAAD TATYFCARDY YSSDWGVRFN LWGQGTLVTV SS

SEQ ID NO: 233 Rabbit Ab 4127 VH region
cagcagctgg aggagtccgg gggagacctg gtcaagcctg gggcatccct gacactcacc
tgcacagcct ctggattctc cttcagtaat ctctattaca tgtgttgggt ccgccaggct
ccagggaagg ggctggagtt gatcggatgc attgatatta gcagtagtgg tagcacttac
tacgcgagct gggcgaaagg ccgattcacc atctccaaaa cctcgtcgac acggtgact
ctgcagatga ccagtctgac agccgcggac acggccacct atttctgtgc gagagattac
tattctagtg actggggtgt tagatttaac ttgtggggcc agggcaccct cgtcaccgtc tcgagt

SEQ ID NO: 98 4127 gL3 V-region - IGKV1-5 framework
AIVMTQSPST LSASVGDRVT ITCQASQSVY GNNELSWYQQ KPGKAPKLLI YLASRLASGV PSRFSGSGSG
TQFTLTISSL QPDDFATYYC AGYKSDSDDG TTFGGGTKVE IK

SEQ ID NO: 99 4127 gH3 V-region - IGHV3-9 framework
EVQLVESGGG LVQPGRSLRL SCAASGFSFS NLYYMCWVRQ APGKGLELIG CIDISSSGST YYASWAKGRF
TISKDSAKTS VYLQMNSLRA EDTALYYCAR DYYSSDWGVR FNLWGQGTLV TVSS

SEQ ID NO: 100 4127 gH4 V-region - IGHV3-9 framework
EVQLVESGGG LVQPGRSLRL SCAASGFSFS NLYYMSWVRQ APGKGLELIG SIDISSSGST YYASWAKGRF TISKDS
AKTS VYLQMNSLRA EDTALYYCAR DYYSSDWGVR FNLWGQGTLV TVSS

SEQ ID NO: 255 4127 gH6 V-region – IGHV4-38-2 framework
EVQLQESGPG LVKPSETLSL TCAASGFSFS NLYYMCWVRQ PPGKGLELIG CIDISSSGST YYASWAKGRF
TISKDSSKTQ VSLKLSSVTA ADTAVYYCAR DYYSSDWGVR FNLWGQGTLV TVSS

SEQ ID NO: 256 4127 gH7 V-region – IGHV4-38-2 framework
EVQLQESGPG LVKPSETLSL TCAASGFSFS NLYYMSWVRQ PPGKGLELIG SIDISSSGST YYASWAKGRF TISKDS
SKTQ VSLKLSSVTA ADTAVYYCAR DYYSSDWGVR FNLWGQGTLV TVSS Figure 51 continued
Ab 4128

| | | | |
|---|---|---|---|
| SEQ ID NO: 101 | CDRH1 | | GLDFSSYWIC |
| SEQ ID NO: 102 | CDRH1 variant | | GLDFSSYWIS |
| SEQ ID NO: 103 | CDRH2 | | CIVTGSSDNTYYASWAKG |
| SEQ ID NO: 104 | CDRH2 variant | | SIVTGSSDNTYYASWAKG |
| SEQ ID NO: 105 | CDRH3 | | GGGAGYSGAFDL |
| SEQ ID NO: 106 | CDRL1 | | QASESISNYLS |
| SEQ ID NO: 107 | CDRL2 | | ASSKLSS |
| SEQ ID NO: 108 | CDRL3 | | QIYYSASGSRDWT |

SEQ ID NO: 109 Rabbit Ab 4128 VL region

```
DIVMTQTPAS VEAAVGGTVT IKCQASESIS NYLSWFQQKP GQPPKLLIYA
SSKLSSGVPS RFKGDRSGTE YTLTISDLEC ADAATYYCQI YYSASGSRDW TFGGGTKVVV E
```

SEQ ID NO: 110 Rabbit Ab 4128 VL region

```
gacattgtga tgacccagac tccagcctcc gtggaggcag ctgtgggagg cacagtcacc
atcaagtgcc aggccagtga aagcattagc aactactat cctggtttca gcagaaacca
gggcagcctc ccaagctcct gatctatgct tcatccaaac tgtcatctgg ggtcccatcg
cggttcaaag gcgatagatc tgggacagag tacactctca ccatcagcga cctgagtgt
gccgatgctg ccacttacta ctgtcaaatc tattattcgg ctagtggcag tcgtgattgg
actttcggcg gagggaccaa ggtggtcgtc gaa
```

SEQ ID NO: 111 Rabbit Ab 4128 VH region

```
QSLEESGGDL VQPEGSLTLT CKGSGLDFSS YWICWVRQAP GKGLEWIACI VTGSSDNTYY
ASWAKGRFTI SKTSSTTVTL QMTSLTAADT ATYFCARGGG AGYSGAFDLW GQGTLVTVSS
```

SEQ ID NO: 112 Rabbit Ab 4128 VH region

```
cagtcgttgg aggagtccgg gggagacctg gtccagcctg agggatccct gacactcacc
tgcaaaggct ccgggttaga cttcagtagc tactggatat gctgggtccg ccaggctcca
gggaaggggc tggagtggat cgcatgcatt gttactggta gtagtgataa cacttactac
gcgagctggg cgaaaggccg attcaccatc tccaaacct cgtcgaccac ggtgactctg
caaatgacca gtctgacagc cgcggacacg gccaccattt ctgtgcgag aggtggtggt
gctggttata gtggtgcctt tgacttgtgg ggccaaggga ccctcgtcac cgtctcgagt
```

SEQ ID NO: 113 4128 gL1 V-region – IGKV1-5 framework

```
DI<u>V</u>MTQSPST LSASVGDRVT ITCQASESIS NYLSW<u>F</u>QQKP GKAPKLLIYA SSKLSSGVPS RF<u>KGDR</u>SGTE
<u>Y</u>TLTISSLQP DDFATYYCQI YYSASGSRDW TFGGGTKVEI K
```

SEQ ID NO: 114 4128 gH1 V-region – IGHV3-33 framework

```
EVQLVESGGG <u>L</u>VQPGRSLRL SC<u>KG</u>SGLDFS SYWICWVRQA PGKGLEWI<u>A</u>C IVTGSSDNTY YASWAKGRFT
ISK<u>D</u>S<u>S</u>KT<u>TV</u> YLQMNSLRAE DTAVYYCARG GGAGYSGAFD LWGQGTLVTV SS
```

SEQ ID NO: 115 4128 gH2 V-region – IGHV3-33 framework

```
EVQLVESGGG LVQPGRSLRL SCKGSGLDFS SYWISWVRQA PGKGLEWIAS IVTGSSDNTY
YASWAKGRFT ISKDSSKTTV YLQMNSLRAE DTAVYYCARG GGAGYSGAFD LWGQGTLVTV SS
```

Figure 51 continued

SEQ ID NO: 257 4128 gH4 V-region - IGHV4-59 framework
EVQLQESGPG LVKPSETLSL TCKGSGLDFS SYWICWVRQP PGKGLEWIAC IVTGSSDNTY YASWAKGRFT
ISKDSSKTQV SLKLSSVTAA DTAVYYCARG GGAGYSGAFD LWGQGTLVTV SS

SEQ ID NO: 258 4128 gH5 V-region - IGHV4-59 framework
EVQLQESGPG LVKPSETLSL TCKGSGLDFS SYWISWVRQP PGKGLEWIAS IVTGSSDNTY YASWAKGRFT ISKDSS
KTQV SLKLSSVTAA DTAVYYCARG GGAGYSGAFD LWGQGTLVTV SS

Ab 4130

| | | |
|---|---|---|
| SEQ ID NO: 116 | CDRH1 | GFDFSGGYDIS |
| SEQ ID NO: 117 | CDRH2 | CIYGGINSVTDYASWAKG |
| SEQ ID NO: 118 | CDRH2 variant 1 | CIYGGINAVTDYASWAKG |
| SEQ ID NO: 119 | CDRH2 variant 2 | CIYGGINTVTDYASWAKG |
| SEQ ID NO: 120 | CDRH2 variant 3 | SIYGGINSVTDYASWAKG |
| SEQ ID NO: 121 | CDRH2 variant 4 | SIYGGINAVTDYASWAKG |
| SEQ ID NO: 122 | CDRH2 variant 5 | SIYGGINTVTDYASWAKG |
| SEQ ID NO: 123 | CDRH3 | DVSNSDHYTRLDL |
| SEQ ID NO: 124 | CDRH3 variant 1 | DVSNADHYTRLDL |
| SEQ ID NO: 125 | CDRH3 variant 2 | DVSNTDHYTRLDL |
| SEQ ID NO: 126 | CDRL1 | QSSQSVYNTKDLA |
| SEQ ID NO: 127 | CDRL2 | GTSTLAS |
| SEQ ID NO: 128 | CDRL3 | QGGFSSSDLNV |

SEQ ID NO: 129 Rabbit Ab 4130 VL region
AAVLTQTPSP VSAAVGGTVS ISCQSSQSVY NTKDLAWYQQ KPGQPPKLLI YGTSTLASGV
SSRFSGSGSG TEFTLTISDL ECDDAATYYC QGGFSSSDLN VFGGGTKVVV K

SEQ ID NO: 130 Rabbit Ab 4130 VL region
gccgccgtgc tgacccagac tccatctccc gtgtctgcag ctgtgggagg cacagtcagc
atcagttgcc agtccagtca gagtgtttat aatacaaagg acttagcctg gtatcagcag
aaaccagggc agcctcccaa gctcctgatc tatggtacat ccactctggc atctggggtc
tcatcacggt tcagcggcag tggatctggg acagagttca ctctcaccat cagcgacctg
gagtgtgacg atgctgccac ttattactgt caaggcggtt ttagtagtag tgatttgaat
gttttcggcg gagggaccaa ggtggtggtc aaa

SEQ ID NO: 131 Rabbit Ab 4130 VH region
QQQLEESGGD LVRPEGSLTL TCTASGFDFS GGYDISWVRQ APGKGLEWIG
CIYGGINSVT DYASWAKGRV TISKTSSTTV TLQMTSLTAA DTATYFCARD
VSNSDHYTRL DLWGQGTLVT VSS

SEQ ID NO: 132 Rabbit Ab 4130 VH region
cagcagcagc tggaggagtc cggggagac ctggtcaggc ctgagggatc cctgacactc
acctgcacag cctctggatt cgacttcagt ggcggctacg acatttcctg ggtccgccag
gctccaggga aggggctgga gtggatcgga tgcatttatg gtggtatcaa tagtgtcact
gactacgcga gctggcgaa aggccagtc accatctcca aaacctcgtc gaccacggtg
actctgcaga tgaccagtct gacagccgcg gacacggcca cctatttctg tgcgagagat
gttagtaata gcgatcatta tactcggttg gatctctggg gccaaggcac cctggtcacc gtctcgagt

Figure 51 continued

SEQ ID NO: 133 4130 gL3 V-region - IGKV1-9 framework
<u>AAV</u>LTQSPSF LSASVGDRVT ITCQSSQSVY NTKDLAWYQQ KPGKAPKLLI YGTSTLASGV PSRFSGSGSG
TEFTLTISSL QPEDFATYYC QGGFSSSDLN VFGGGTKVEI K

SEQ ID NO: 134 4130 gH8 V-region - IGHV3-66 framework
EVQLVESGGG LVQPGGSLRL SCAASGFDFS GGYDISWVRQ APGKGLEW<u>IG</u> CIYGGINSVT DYASWAKGR<u>V</u>
TIS<u>K</u>D<u>S</u>S<u>KT</u>T <u>V</u>YLQMNSLRA EDTAVYYCAR DVSNSDHYTR LDLWGQGTLV TVSS

SEQ ID NO: 135 4130 gH3 V-region - IGHV3-66 framework
EVQLVESGGG LVQPGGSLRL SCAASGFDFS GGYDISWVRQ APGKGLEWIG SIYGGINSVT DYASWAKGRV TISKDS
SKTT VYLQMNSLRA EDTAVYYCAR DVSNSDHYTR LDLWGQGTLV TVSS

SEQ ID NO: 259 4130 gH9 V-region - IGHV4-4 framework
<u>E</u>VQLQESGPG LVKPSGTLSL TCAASGFDFS GGYDISWVRQ PPGKGLEWIG CIYGGINSVT DYASWAKGRV
TIS<u>K</u>D<u>S</u>S<u>KT</u>Q <u>V</u>SLKLSSVTA ADTAVYYCAR DVSNSDHYTR LDLWGQGTLV TVSS

SEQ ID NO: 260 4130 gH5 V-region - IGHV4-4 framework
EVQLQESGPG LVKPSGTLSL TCAASGFDFS GGYDISWVRQ PPGKGLEWIG SIYGGINSVT DYASWAKGRV TISKDS
SKTQ VSLKLSSVTA ADTAVYYCAR DVSNSDHYTR LDLWGQGTLV TVSS

Ab 4132

| | | |
|---|---|---|
| SEQ ID NO: 136 | CDRH1 | GFSFSSSYWIC |
| SEQ ID NO: 137 | CDRH1 variant | GFSFSSSYWIS |
| SEQ ID NO: 138 | CDRH2 | CINSGTGGTAYASWAKG |
| SEQ ID NO: 139 | CDRH2 variant 1 | CINAGTGGTAYASWAKG |
| SEQ ID NO: 140 | CDRH2 variant 2 | CINTGTGGTAYASWAKG |
| SEQ ID NO: 141 | CDRH2 variant 3 | SINSGTGGTAYASWAKG |
| SEQ ID NO: 142 | CDRH2 variant 4 | SINAGTGGTAYASWAKG |
| SEQ ID NO: 143 | CDRH2 variant 5 | SINTGTGGTAYASWAKG |
| SEQ ID NO: 144 | CDRH3 | EWVSGYYKDAFDL |
| SEQ ID NO: 145 | CDRL1 | QASETISSRLA |
| SEQ ID NO: 146 | CDRL2 | SASTLAS |
| SEQ ID NO: 147 | CDRL3 | QGYYYSSGSDYG |

SEQ ID NO: 148 Rabbit Ab 4132 VL region
DIVMTQTPAS VEAAVGGTVT IKCQASETIS SRLAWYQQKL GQPPKLLIYS ASTLASGVPS
RFKGSGSGTE YTLTISGVQC ADAATYYCQG YYYSSGSDYG FGGGTKVVVK

SEQ ID NO: 149 Rabbit Ab 4132 VL region
gacattgtga tgacccagac tccagcctcc gtggaggcag ctgtgggagg cacagtcacc
atcaagtgcc aggccagtga gaccattagt agtagattag cctggtatca gcagaagcta
gggcagcctc ccaaactcct gatctattct gcatccactc tggcgtctgg ggtcccatcg
cggttcaaag gcagtggatc tgggacagag tacactctca ccatcagcgg cgtgcagtgt
gccgatgctg ccacttatta ctgtcaaggc tattattata gtagtggtag tgattatggt
ttcggcggag ggaccaaggt ggtcgtcaaa

Figure 51 continued

SEQ ID NO: 150  Rabbit Ab 4132 VH region
QSLEESGGDL VKPGASLTLT CTASGFSFSS SYWICWVRQA PGKGLEWSGC INSGTGGTAY
ASWAKGRFTI SNSSSTTVTL QMTSLTAADT ATYFCAREWV SGYYKDAFDL WGQGTLVTVS S

SEQ ID NO: 151  Rabbit Ab 4132 VH region
cagtcgttgg aggagtccgg gggagacctg gtcaagcctg ggcatccct gacactcacc
tgcacagcct ctggattctc cttcagtagc agctactgga tatgctgggt ccgccaggct
ccagggaagg ggctggagtg gagcggatgc attaatagtg gtactggtgg cactgcctac
gcgagctggg cgaaaggccg attcaccatc tccaattcct cgtcgaccac ggtgactctt
caaatgacca gtctgacagc cgcggacacg gccacctatt tctgtgcgag agaatgggtt
agtggttatt ataaagatgc ttttgatctc tggggccagg gcaccctggt caccgtctcg agt

SEQ ID NO: 152  4132 gL1 V-region – IGKV1-5 framework
DI<u>V</u>MTQSPST LSASVGDRVT ITCQASETIS SRLAWYQQKP GKAPKLLIYS ASTLASGVPS RFSGSGSGTE
<u>Y</u>TLTISSLQP DDFATYYCQG YYYSSGSDYG FGGGTKVEIK

SEQ ID NO: 153  4132 gH1 V-region – IGHV3-21 framework
EVQLVESGGG LVKPGGSLRL SCAASGFSFS SSYWICWVRQ APGKGLEW<u>SG</u> CINSGTGGTA YASWAKGRFT
IS<u>NDSAKTSV</u> YLQMNSLRAE DTAVYYCARE WVSGYYKDAF DLWGQGTLVT VSS

SEQ ID NO: 154  4132 gH2 V-region – IGHV3-21 framework
EVQLVESGGG LVKPGGSLRL SCAASGFSFS SSYWISWVRQ APGKGLEWSG SINSGTGGTA YASWAKGRFT ISNDSA
KTSV YLQMNSLRAE DTAVYYCARE WVSGYYKDAF DLWGQGTLVT VSS

SEQ ID NO: 261  4132 gH4 V-region – IGHV4-4 framework
<u>E</u>VQLQESGPG LVKPSGTLSL TCA<u>A</u>SGFSFS SSYWICWVRQ PPGKGLEW<u>SG</u> CINSGTGGTA YASWAKGR<u>F</u>T
IS<u>NDSSKTQV</u> SLKLSSVTAA DTAVYYCARE WVSGYYKDAF DLWGQGTLVT VSS

SEQ ID NO: 262  4132 gH5 V-region – IGHV4-4 framework
EVQLQESGPG LVKPSGTLSL TCAASGFSFS SSYWISWVRQ PPGKGLEWSG SINSGTGGTA YASWAKGRFT ISNDSS
KTQV SLKLSSVTAA DTAVYYCARE WVSGYYKDAF DLWGQGTLVT VSS

CD45 Antibodies
Ab 4122
| SEQ ID NO: 155 | CDRH1           | GFSFSAGYWIC      |
| SEQ ID NO: 156 | CDRH1 variant 1 | GFSFSAGYWIS      |
| SEQ ID NO: 157 | CDRH2           | CTYAGRSGSTYYANWVNG |
| SEQ ID NO: 158 | CDRH2 variant 1 | CTYAGRSGSTYYANWVNA |
| SEQ ID NO: 159 | CDRH2 variant 2 | CTYAGRSGSTYYANWVNS |
| SEQ ID NO: 160 | CDRH2 variant 3 | CTYAGRSGSTYYANWVNT |
| SEQ ID NO: 161 | CDRH2 variant 4 | STYAGRSGSTYYANWVNG |
| SEQ ID NO: 162 | CDRH2 variant 5 | STYAGRSGSTYYANWVNA |
| SEQ ID NO: 163 | CDRH2 variant 6 | STYAGRSGSTYYANWVNS |
| SEQ ID NO: 164 | CDRH2 variant 7 | STYAGRSGSTYYANWVNT |
| SEQ ID NO: 165 | CDRH3           | GNAGVAVGAL       |

Figure 51 continued

SEQ ID NO: 166 CDRL1          QASQSISNWLA
SEQ ID NO: 167 CDRL2          QASKLAS
SEQ ID NO: 168 CDRL3          QSYYDSGSNVFFA
SEQ ID NO: 169 CDRL3 variant 1    QSYYDAGSNVFFA
SEQ ID NO: 170 CDRL3 variant 2    QSYYDTGSNVFFA

SEQ ID NO: 171 Rabbit Ab 4122 VL region
DIVMTQTPAS VSEPVGGTVT IMCQASQSIS NWLAWYQQKP GQPPKLLIYQ ASKLASGVPS
RFKGSGSGTE YTLTISDLEC ADAATYYCQS YYDSGSNVFF AFGGGTKVVV E

SEQ ID NO: 172 Rabbit Ab 4122 VL region
gacattgtga tgacccagac tccagcctcc gtgtctgaac ctgtgggagg cacagtcacc
atcatgtgcc aggccagtca gagcattagc aattggttag cctggtatca acagaaacca
gggcagcctc ccaagctcct gatctaccag gcatccaaac tggcatctgg ggtcccatcg
cggttcaaag gcagtggatc tgggacagag tacactctca ccatcagcga cctggagtgt
gccgatgctg ccacttacta ctgtcaaagc tattatgata gtggtagtaa tgttttttt
gctttcggcg gagggaccaa ggtggtggtc gaa

SEQ ID NO: 173 Rabbit Ab 4122 VH region
LSLEESGGDL VKPGASLTLT CTASGFSFSA GYWICWVRQA PGKGLEWIAC TYAGRSGSTY
YANWVNGRFT IPKTSSTTVT LQMTSLSGAD TASYFCARGN AGVAVGALWG PGTLVTVSS

SEQ ID NO: 174 Rabbit Ab 4122 VH region
ctgtcgttgg aggagtccgg gggagacctg gtcaagcctg ggcatccct gacactcacc
tgcacagcct ctggattctc cttcagtgcc ggctattgga tatgttgggt ccgccaggct
ccagggaagg ggctggagtg gatcgcatgc acttatgctg gtcgtagtgg tagcacttac
tacgcgaact gggtgaatgg ccgattcacc atccccaaaa cctcgtcgac acggtgact
ctgcaaatga ccagtctgtc aggcgcggac acggccagct atttctgtgc gagaggtaat
gctggtgttg ctgttggtgc cttgtggggc ccaggcaccc tggtcaccgt ctcgagt

SEQ ID NO: 175 4122 gL1 V-region – IGKV1-5 framework
DIQMTQSPST LSASVGDRVT ITCQASQSIS NWLAWYQQKP GKAPKLLIYQ ASKLASGVPS RFSGSGSGTE
<u>Y</u>TLTISSLQP DDFATYYCQS YYDSGSNVFF AFGGGTKVEI K

SEQ ID NO: 176 4122 gH6 V-region - IGHV3-7 framework
EVQLVESGGG LVQPGGSLRL SCAASGFSFS AGYWICWVRQ APGKGLEW<u>IA</u> CTYAGRSGST YYANWVNGRF
TIS<u>KD</u>S<u>AKT</u>S <u>V</u>YLQMNSLRA EDTAVYYCAR GNAGVAVGAL WGRGTLVTVS S

SEQ ID NO: 177 4122 gH4 V-region - IGHV3-7 framework
EVQLVESGGG LVQPGGSLRL SCAASGFSFS AGYWISWVRQ APGKGLEWIA STYAGRSGST YYANWVNGRF TISKDS
AKTS VYLQMNSLRA EDTAVYYCAR GNAGVAVGAL WGRGTLVTVS S

SEQ ID NO: 263 4122 gH3 V-region – IGHV2-70 framework
<u>E</u>VTLKESGPA LVKPTQTLTL TCT<u>A</u>SGFSFS AGYWICW<u>V</u>RQ PPGK<u>GLEWIA</u> CTYAGRSGST YYANWVNGR<u>F</u>
TISKD<u>SS</u>K<u>T</u>Q VVLTMTNMDP VDTATYYCAR GNAGVAVGAL WGRGTLVTVS S

Figure 51 continued

SEQ ID NO: 264 4122 gH5 V-region – IGHV2-70 framework
EVTLKESGPA LVKPTQTLTL TCTASGFSFS AGYWISWVRQ PPGKGLEWIA STYAGRSGST YYANWVNGRF TISKDS
SKTQ VVLTMTNMDP VDTATYYCAR GNAGVAVGAL WGRGTLVTVS S

Ab 4129
| | | |
|---|---|---|
| SEQ ID NO: 178 | CDRH1 | GFSFSAGYWIC |
| SEQ ID NO: 179 | CDRH1 variant | GFSFSAGYWIS |
| SEQ ID NO: 180 | CDRH2 | CIYAGSSGSTYYASWAKG |
| SEQ ID NO: 181 | CDRH2 variant | SIYAGSSGSTYYASWAKG |
| SEQ ID NO: 182 | CDRH3 | GNAGVAVGAL |
| SEQ ID NO: 183 | CDRL1 | QASQSISSWLS |
| SEQ ID NO: 184 | CDRL2 | GASNLAS |
| SEQ ID NO: 185 | CDRL3 | QSYYDSGSSVFFN |
| SEQ ID NO: 186 | CDRL3 variant 1 | QSYYDAGSSVFFN |
| SEQ ID NO: 187 | CDRL3 variant 2 | QSYYDTGSSVFFN |

SEQ ID NO: 188 Rabbit Ab 4129 VL region
DIVMTQTPAS VEAAVGGTVT INCQASQSIS SWLSWYQQKP GQPPKLLIYG ASNLASGVPS
RFSGSGSGTQ FSLTISDLEC ADAATYYCQS YYDSGSSVFF NFGGGTKVVV K

SEQ ID NO: 189 Rabbit Ab 4129 VL region
gacattgtga tgacccagac tccagcctcc gtggaggcag ctgtgggagg cacagtcacc
atcaattgcc aagccagtca gagcattagc agttggttat cctggtatca gcagaaacca
gggcagcctc ccaagctcct gatctatggt gcatccaatc tggcatctgg ggtcccatca
cggttcagcg gcagtggatc tgggacacag ttcagtctca ccatcagcga cctggagtgt
gccgatgctg ccacttacta ctgtcaaagc tattatgata gtggtagtag tgttttttt
aatttcggcg agggaccaa ggtggtcgtc aaa

SEQ ID NO: 190 Rabbit Ab 4129 VH region
QSLEESGGDL VKPGASLTLT CTASGFSFSA GYWICWVRQA PGKGLEWIAC IYAGSSGSTY
YASWAKGRFT IPKTSSTTVT LQMTSLTGAD TATYFCARGN AGVAVGALWG PGTLVTVSS

SEQ ID NO: 191 Rabbit Ab 4129 VH region
cagtcgttgg aggagtccgg gggagacctg gttaagcctg ggcatcccg acactcacc
tgcacagcct ctggattctc cttcagtgcc ggctattgga tatgttgggt ccgccaggct
ccagggaagg ggctggagtg gatcgcatgc atttatgctg gtagtagtgg tagcacttac
tacgcgagct gggcgaaagg ccgattcacc atccccaaaa cctcgtcgac cacggtgact
ctgcaaatga ccagtctgac aggcgcggac acggccacct atttctgtgc gagaggtaat
gctggtgttg ctgttggtgc cttgtggggc ccaggcaccc tcgtcaccgt ctcgagt

SEQ ID NO: 192 4129 gL3 V-region - IGKV1-5 framework
DIQMTQSPST LSASVGDRVT ITCQASQSIS SWLSWYQQKP GKAPKLLIYG ASNLASGVPS RFSGSGSGTQ
FTLTISSLQP DDFATYYCQS YYDSGSSVFF NFGGGTKVEI K

SEQ ID NO: 193 4129 gH1 V-region – IGHV3-7 framework
EVQLVESGGG LVQPGGSLRL SCAASGFSFS AGYWICWVRQ APGKGLEWIA CIYAGSSGST YYASWAKGRF
TISKDSAKTS VYLQMNSLRA EDTAVYYCAR GNAGVAVGAL WGRGTLVTVS S

Figure 51 continued

SEQ ID NO: 194 4129 gH4 V-region – IGHV3-7 framework
EVQLVESGGG LVQPGGSLRL SCAASGFSFS AGYWISWVRQ APGKGLEWIA SIYAGSSGST YYASWAKGRF TISKDS
AKTS VYLQMNSLRA EDTAVYYCAR GNAGVAVGAL WGRGTLVTVS S

SEQ ID NO: 265 4129 gH3 V-region – IGHV2-70 framework
EVTLKESGPA LVKPTQTLTL TCTASGFSFS AGYWICWVRQ PPGKGLEWIA CIYAGSSGST YYASWAKGRF
TISKDSSKTQ VVLTMTNMDP VDTATYYCAR GNAGVAVGAL WGRGTLVTVS S

SEQ ID NO: 266 4129 gH5 V-region – IGHV2-70 framework
EVTLKESGPA LVKPTQTLTL TCTASGFSFS AGYWISWVRQ PPGKGLEWIA SIYAGSSGST YYASWAKGRF TISKDS
SKTQ VVLTMTNMDP VDTATYYCAR GNAGVAVGAL WGRGTLVTVS S

Ab 4131

| SEQ ID NO: 195 | CDRH1 | GVSFSSSYWIY |
| SEQ ID NO: 196 | CDRH2 | CIYTGSSGSTYYASWAKG |
| SEQ ID NO: 197 | CDRH2 variant | SIYTGSSGSTYYASWAKG |
| SEQ ID NO: 198 | CDRH3 | ASAWTYGMDL |
| SEQ ID NO: 199 | CDRL1 | QASQSFYNLLA |
| SEQ ID NO: 200 | CDRL2 | DASDLAS |
| SEQ ID NO: 201 | CDRL3 | QSADGSSYA |
| SEQ ID NO: 202 | CDRL3 variant 1 | QSADSSSYA |
| SEQ ID NO: 203 | CDRL3 variant 2 | QSADASSYA |
| SEQ ID NO: 204 | CDRL3 variant 3 | QSADTSSYA |

SEQ ID NO: 205 Rabbit Ab 4131 VL region
DIVMTQTPAS VSEPVGGSVT IKCQASQSFY NLLAWYQQKP GQPPKLLIYD ASDLASGVPS
RFKGSGSGTD FTLTISDLEC ADAAAYYCQS ADGSSYAFGG GTEVVVK

SEQ ID NO: 206 Rabbit Ab 4131 VL region
gacattgtga tgacccagac tccagcctcc gtgtctgaac ctgtgggagg ctcagtcacc
atcaagtgcc aggccagtca gagcttttac aacctcttag cctggtatca gcagaaacca
ggcagcctc ccaaactcct gatctatgat gcatccgatc tggcatctgg ggtcccatcg
cggttcaaag gcagtggatc tggactgat tcactctca ccatcagcga cctggagtgt
gccgatgctg ccgcttacta ctgtcaaagt gctgatggta gtagttacgc tttcggcgga
gggaccgagg tggtcgtcaa a

SEQ ID NO: 207 Rabbit Ab 4131 VH region
QEQLEESGGG LVKPEGSLTL TCTASGVSFS SSYWIYWVRQ APGKGLEWIA CIYTGSSGST
YYASWAKGRF TVSETSSTTV TLQMTSLTAA DTATYFCARA SAWTYGMDLW GPGTLVTVSS

Figure 51 continued

SEQ ID NO: 208 Rabbit Ab 4131 VH region
```
caggagcaat tggaggagtc cgggggaggc ctggtcaagc ctgagggatc cctgacactc
acctgcacag cctctggagt ctccttcagt agcagctatt ggatatactg ggtccgccag
gctccaggga aggggctgga gtggatcgca tgcatttata ctggtagtag tggtagcact
tactacgcga gctgggcgaa aggccgattc accgtctccg aaacctcgtc gaccacggtg
actctgcaaa tgaccagtct gacagccgcg gacacggcca cctatttctg tgcgagagca
agcgcttgga cctacggcat ggacctctgg ggcccgggca ccctcgtcac cgtctcgagt
```

SEQ ID NO: 209 4131 gL8 V-region - IGKV1-12 framework
DIVMTQSPSS VSASVGDRVT ITCQASQSFY NLLAWYQQKP GKAPKLLIYD ASDLASGVPS RFKGSGSGTD FTLTISSLQP EDFATYYCQS ADGSSYAFGG GTKVEIK

SEQ ID NO: 210 4131 gL3 V-region - IGKV1-12 framework
DIQMTQSPSS VSASVGDRVT ITCQASQSFY NLLAWYQQKP GKAPKLLIYD ASDLASGVPS RFSGSGSGTD FTLTISSLQP EDFATYYCQS ADGSSYAFGG GTKVEIK

SEQ ID NO: 211 4131 gH5 V-region - IGHV3-7 framework
EVQLVESGGG LVQPGGSLRL SCAASGVSFS SSYWIYWVRQ APGKGLEWIA CIYTGSSGST YYASWAKGRF TVSEDSAKTS VYLQMNSLRA EDTAVYYCAR ASAWTYGMDL WGRGTLVTVS S

SEQ ID NO: 267 4131 gH4 V-region - IGHV3-7 framework
EVQLVESGGG LVQPGGSLRL SCAASGVSFS SSYWIYWVRQ APGKGLEWIA SIYTGSSGST YYASWAKGRF TVSEDS AKTS VYLQMNSLRA EDTAVYYCAR ASAWTYGMDL WGRGTLVTVS S

SEQ ID NO: 268 4131 gH6 V-region - IGHV4-31 framework
EVQLQESGPG LVKPSQTLSL TCTASGVSFS SSYWIYWVRQ HPGKGLEWIA CIYTGSSGST YYASWAKGRF TVSEDSSKTQ VSLKLSSVTA ADTAVYYCAR ASAWTYGMDL WGRGTLVTVS S

SEQ ID NO: 269 4131 gH3 V-region - IGHV4-31 framework
EVQLQESGPG LVKPSQTLSL TCTASGVSFS SSYWIYWVRQ HPGKGLEWIA SIYTGSSGST YYASWAKGRF TVSEDS SKTQ VSLKLSSVTA ADTAVYYCAR ASAWTYGMDL WGRGTLVTVS S

Ab 4133
| | | |
|---|---|---|
| SEQ ID NO: 212 | CDRH1 | GFSFSGNYYMC |
| SEQ ID NO: 213 | CDRH1 variant | GFSFSGNYYMS |
| SEQ ID NO: 214 | CDRH2 | CLYTGSSGSTYYASWAKG |
| SEQ ID NO: 215 | CDRH2 variant | SLYTGSSGSTYYASWAKG |
| SEQ ID NO: 216 | CDRH3 | DLGYEIDGYGGL |
| SEQ ID NO: 217 | CDRH3 variant 1 | DLGYEIDSYGGL |
| SEQ ID NO: 218 | CDRH3 variant 2 | DLGYEIDAYGGL |
| SEQ ID NO: 219 | CDRH3 variant 3 | DLGYEIDTYGGL |
| SEQ ID NO: 220 | CDRL1 | QASQSVYNNNNLS |
| SEQ ID NO: 221 | CDRL1 variant 1 | QASQSVYNNNSLS |
| SEQ ID NO: 222 | CDRL1 variant 2 | QASQSVYNNNQLS |
| SEQ ID NO: 223 | CDRL1 variant 3 | QASQSVYNNNNLA |
| SEQ ID NO: 224 | CDRL2 | DASKLAS |

Figure 51 continued

SEQ ID NO: 225 CDRL3                     LGGYYSSGWYFA

SEQ ID NO: 226 Rabbit Ab 4133 VL region
AQVLTQTPSP VSAVVGGTVS ISCQASQSVY NNNNLSWYQQ KPGQPPKLLI YDASKLASGV
PSRFKGSGSG TQFTLTISGV QCDDAATYYC LGGYYSSGWY FAFGGGTKVV VK

SEQ ID NO: 227 Rabbit Ab 4133 VL region
gcgcaagtgc tgacccagac tccatctccc gtgtctgcag ttgtgggagg cacagtcagc
atcagttgcc aggccagtca gagtgtttat aataacaaca acttatcctg gtatcagcag
aaaccagggc agcctcccaa gctcttgatc tacgatgcat ccaaattggc atctggggtc
ccatcccgtt tcaaaggcag tggatctggg acacagttca ctctcaccat cagcggcgtg
cagtgtgacg atgctgccac ttactactgt ctaggcggtt attatagtag tggttggtat
tttgctttcg gcggagggac caaggtggtg gtcaaa

SEQ ID NO: 228 Rabbit Ab 4133 VH region
QEQLVESGGG LVQPEGSLTL TCTASGFSFS GNYYMCWVRQ APGKGLEWIG CLYTGSSGST
YYASWAKGRF TISKTSSTTV TLQMTSLTAA DTATYFCARD LGYEIDGYGG LWGQGTLVTV SS

SEQ ID NO: 229 Rabbit Ab 4133 VH region
caggagcagc tggtggagtc cgggggaggc ctggtccagc ctgagggatc cctgacacta
acctgcacag cttctggatt ctccttcagt ggcaactact acatgtgctg ggtccgccag
gctccaggga aggggctgga gtggatcgga tgcctttata ctggtagtag tggtagcaca
tattacgcga gctgggcgaa aggccgattc accatctcca aacctcgtc gaccacggtg
actctgcaaa tgaccagtct gacagccgcg gacacggcca cctatttctg tgcgagagat
ctaggttatg aaattgatgg ttatgggggc ttgtggggcc agggcaccct cgtcaccgtc tcgagt

SEQ ID NO: 230 4133 gL7 V-region – IGKV1D-13 framework
AQVLTQSPSS LSASVGDRVT ITCQASQSVY NNNNLSWYQQ KPGKAPKLLI YDASKLASGV PSRFSGSGSG
TQFTLTISSL QPEDFATYYC LGGYYSSGWY FAFGGGTKVE IK

SEQ ID NO: 231 4133 gL1 V-region – IGKV1D-13 framework
AQVLTQSPSS LSASVGDRVT ITCQASQSVY NNNNLAWYQQ KPGKAPKLLI YDASKLASGV PSRFSGSGSG
TQFTLTISSL QPEDFATYYC LGGYYSSGWY FAFGGGTKVE IK

SEQ ID NO: 232 4133 gH1 V-region – IGHV3-21 framework
EVQLVESGGG LVKPGGSLRL SCAASGFSFS GNYYMCWVRQ APGKGLEWIG CLYTGSSGST YYASWAKGRF
TISKDSAKTS VYLQMNSLRA EDTAVYYCAR DLGYEIDGYG GLWGQGTLVT VSS

SEQ ID NO: 270 4133 gH4 V-region – IGHV3-21 framework
EVQLVESGGG LVKPGGSLRL SCAASGFSFS GNYYMSWVRQ APGKGLEWIG SLYTGSSGST YYASWAKGRF
TISKDSAKTS VYLQMNSLRA EDTAVYYCAR DLGYEIDGYG GLWGQGTLVT VSS

SEQ ID NO: 271 4133 gH3 V-region – IGHV4-4 framework
EVQLQESGPG LVKPSGTLSL TCAASGFSFS GNYYMCWVRQ PPGKGLEWIG CLYTGSSGST YYASWAKGRV
TISKDSSKTQ VSLKLSSVTA ADTAVYYCAR DLGYEIDGYG GLWGQGTLVT VSS

SEQ ID NO: 272 4133 gH5 V-region – IGHV4-4 framework
EVQLQESGPG LVKPSGTLSL TCAASGFSFS GNYYMSWVRQ PPGKGLEWIG SLYTGSSGST YYASWAKGRV TISKDS
SKTQ VSLKLSSVTA ADTAVYYCAR DLGYEIDGYG GLWGQGTLVT VSS

Figure 51 continued

Serum Albumin Binding Antibodies

| | | |
|---|---|---|
| CDRH1 dAbH1 | SEQ ID NO: 234 | Gly Ile Asp Leu Ser Asn Tyr Ala Ile Asn |
| CDRH2 dAbH1 | SEQ ID NO: 235 | Ile Ile Trp Ala Ser Gly Thr Thr Phe Tyr Ala Thr Trp Ala Lys Gly |
| CDRH3 dAbH1 | SEQ ID NO: 236 | Thr Val Pro Gly Tyr Ser Thr Ala Pro Tyr Phe Asp Leu |
| CDRL1 dAbL1 | SEQ ID NO: 237 | Gln Ser Ser Pro Ser Val Trp Ser Asn Phe Leu Ser |
| CDRL2 dAbL1 | SEQ ID NO: 238 | Glu Ala Ser Lys Leu Thr Ser |
| CDRL3 dAbL1 | SEQ ID NO: 239 | Gly Gly Gly Tyr Ser Ser Ile Ser Asp Thr Thr |

Heavy chain variable domain of anti-albumin antibody (no ds)   SEQ ID NO: 240

Glu Val Gln Leu Leu Glu Ser Gly Gly Gly Leu Val Gln Pro Gly Gly Ser Leu Arg
Leu Ser Cys Ala Val Ser Gly Ile Asp Leu Ser Asn Tyr Ala Ile Asn Trp Val Arg
Gln Ala Pro Gly Lys Gly Leu Glu Trp Ile Gly Ile Ile Trp Ala Ser Gly Thr Thr
Phe Tyr Ala Thr Trp Ala Lys Gly Arg Phe Thr Ile Ser Arg Asp Asn Ser Lys Asn
Thr Val Tyr Leu Gln Met Asn Ser Leu Arg Ala Glu Asp Thr Ala Val Tyr Tyr Cys
Ala Arg Thr Val Pro Gly Tyr Ser Thr Ala Pro Tyr Phe Asp Leu Trp Gly Gln Gly
Thr Leu Val Thr Val Ser Ser

Heavy chain variable domain of anti-albumin antibody (ds) SEQ ID NO: 241

Glu Val Gln Leu Leu Glu Ser Gly Gly Gly Leu Val Gln Pro Gly Gly Ser Leu Arg
Leu Ser Cys Ala Val Ser Gly Ile Asp Leu Ser Asn Tyr Ala Ile Asn Trp Val Arg
Gln Ala Pro Gly Lys Cys Leu Glu Trp Ile Gly Ile Ile Trp Ala Ser Gly Thr Thr
Phe Tyr Ala Thr Trp Ala Lys Gly Arg Phe Thr Ile Ser Arg Asp Asn Ser Lys Asn
Thr Val Tyr Leu Gln Met Asn Ser Leu Arg Ala Glu Asp Thr Ala Val Tyr Tyr Cys
Ala Arg Thr Val Pro Gly Tyr Ser Thr Ala Pro Tyr Phe Asp Leu Trp Gly Gln Gly
Thr Leu Val Thr Val Ser Ser

Light chain variable domain of anti-albumin antibody (no ds)   SEQ ID NO: 242

Asp Ile Gln Met Thr Gln Ser Pro Ser Ser Val Ser Ala Ser Val Gly Asp Arg Val
Thr Ile Thr Cys Gln Ser Ser Pro Ser Val Trp Ser Asn Phe Leu Ser Trp Tyr Gln
Gln Lys Pro Gly Lys Ala Pro Lys Leu Leu Ile Tyr Glu Ala Ser Lys Leu Thr Ser
Gly Val Pro Ser Arg Phe Ser Gly Ser Gly Ser Gly Thr Asp Phe Thr Leu Thr Ile
Ser Ser Leu Gln Pro Glu Asp Phe Ala Thr Tyr Tyr Cys Gly Gly Gly Tyr Ser Ser
Ile Ser Asp Thr Thr Phe Gly Gly Gly Thr Lys Val Glu Ile Lys Arg Thr

Light chain variable domain of anti-albumin antibody (ds) SEQ ID NO: 243

Asp Ile Gln Met Thr Gln Ser Pro Ser Ser Val Ser Ala Ser Val Gly Asp Arg Val
Thr Ile Thr Cys Gln Ser Ser Pro Ser Val Trp Ser Asn Phe Leu Ser Trp Tyr Gln
Gln Lys Pro Gly Lys Ala Pro Lys Leu Leu Ile Tyr Glu Ala Ser Lys Leu Thr Ser
Gly Val Pro Ser Arg Phe Ser Gly Ser Gly Ser Gly Thr Asp Phe Thr Leu Thr Ile
Ser Ser Leu Gln Pro Glu Asp Phe Ala Thr Tyr Tyr Cys Gly Gly Gly Tyr Ser Ser
Ile Ser Asp Thr Thr Phe Gly Cys Gly Thr Lys Val Glu Ile Lys Arg Thr

Figure 51 continued

Human CD22     SEQ ID NO: 244
MHLLGPWLLL LVLEYLAFSD SSKWVFEHPE TLYAWEGACV WIPCTYRALD GDLESFILFH
NPEYNKNTSK FDGTRLYEST KDGKVPSEQK RVQFLGDKNK NCTLSIHPVH LNDSGQLGLR
MESKTEKWME RIHLNVSERP FPPHIQLPPE  IQESQEVTLT CLLNFSCYGY PIQLQWLLEG
VPMRQAAVTS TSLTIKSVFT RSELKFSPQW SHHGKIVTCQ LQDADGKFLS NDTVQLNVKH
TPKLEIKVTP SDAIVREGDS VTMTCEVSSS NPEYTTVSWL KDGTSLKKQN TFTLNLREVT
KDQSGKYCCQ VSNDVGPGRS EEVFLQVQYA PEPSTVQILH SPAVEGSQVE FLCMSLANPL
PTNYTWYHNG KEMQGRTEEK VHIPKILPWH AGTYSCVAEN ILGTGQRGPG AELDVQYPPK
KVTTVIQNPM PIREGDTVTL SCNYNSSNPS VTRYEWKPHG AWEEPSLGVL KIQNVGWDNT
TIACAACNSW CSWASPVALN VQYAPRDVRV RKIKPLSEIH SGNSVSLQCD FSSSHPKEVQ
FFWEKNGRLL GKESQLNFDS ISPEDAGSYS CWVNNSIGQT ASKAWTLEVL YAPRRLRVSM
SPGDQVMEGK SATLTCESDA NPPVSHYTWF DWNNQSLPYH SQKLRLEPVK VQHSGAYWCQ
GTNSVGKGRS PLSTLTVYYS PETIGRRVAV GLGSCLAILI LAICGLKLQR RWKRTQSQQG
LQENSSGQSF FVRNKKVRRA PLSEGPHSLG CYNPMMEDGI SYTTLRFPEM NIPRTGDAES
SEMQRPPPDC DDTVTYSALH KRQVGDYENV IPDFPEDEGI HYSELIQFGV GERPQAQENV DYVILKH Human CD79a    SEQ ID NO: 245
MPGGPGVLQA LPATIFLLFL LSAVYLGPGC QALWMHKVPA SLMVSLGEDA HFQCPHNSSN
NANVTWWRVL HGNYTWPPEF LGPGEDPNGT LIIQNVNKSH  GGIYVCRVQE GNESYQQSCG
TYLRVRQPPP RPFLDMGEGT KNRIITAEGI ILLFCAVVPG TLLLFRKRWQ NEKLGLDAGD
EYEDENLYEG LNLDDCSMYE DISRGLQGTY QDVGSLNIGD VQLEKP Human CD79b    SEQ ID NO: 298
MARLALSPVP SHWMVALLLL LSAEPVPAAR SEDRYRNPKG SACSRIWQSP
RFIARKRGFT VKMHCYMNSA SGNVSWLWKQ EMDENPQQLK LEKGRMEESQ
NESLATLTIQ GIRFEDNGIY FCQQKCNNTS EVYQGCGTEL RVMGFSTLAQ
LKQRNTLKDG IIMIQTLLII LFIIVPIFLL LDKDDSKAGM EEDHTYEGLD
IDQTATYEDI VTLRTGEVKW SVGEHPGQE

Figure 51 continued

Human CD45          SEQ ID NO: 10
MYLWLKLLAF GFAFLDTEVF VTGQSPTPSP TGLTTAKMPS VPLSSDPLPT HTTAFSPAST
FERENDFSET TTSLSPDNTS TQVSPDSLDN ASAFNTTGVS SVQTPHLPTH ADSQTPSAGT
DTQTFSGSAA NAKLNPTPGS NAISDVPGER STASTFPTDP VSPLTTTLSL AHHSSAALPA
RTSNTTITAN TSDAYLNASE TTTLSPSGSA VISTTTIATT PSKPTCDEKY ANITVDYLYN
KETKLFTAKL NVNENVECGN NTCTNNEVHN LTECKNASVS ISHNSCTAPD KTLILDVPPG
VEKFQLHDCT QVEKADTTIC LKWKNIETFT CDTQNITYRF QCGNMIFDNK EIKLENLEPE
HEYKCDSEIL YNNHKFTNAS KIIKTDFGSP GEPQIIFCRS EAAHQGVITW NPPQRSFHNF
TLCYIKETEK DCLNLDKNLI KYDLQNLKPY TKYVLSLHAY IIAKVQRNGS AAMCHFTTKS
APPSQVWNMT VSMTSDNSMH VKCRPPRDRN GPHERYHLEV EAGNTLVRNE SHKNCDFRVK
DLQYSTDYTF KAYFHNGDYP GEPFILHHST SYNSKALIAF LAFLIIVTSI ALLVVLYKIY
DLHKKRSCNL DEQQELVERD DEKQLMNVEP IHADILLETY KRKIADEGRL FLAEFQSIPR
VFSKFPIKEA RKPFNQNKNR YVDILPYDYN RVELSEINGD AGSNYINASY IDGFKEPRKY
IAAQGPRDET VDDFWRMIWE QKATVIVMVT RCEEGNRNKC AEYWPSMEEG TRAFGDVVVK
INQHKRCPDY IIQKLNIVNK KEKATGREVT HIQFTSWPDH GVPEDPHLLL KLRRRVNAFS
NFFSGPIVVH CSAGVGRTGT YIGIDAMLEG LEAENKVDVY GYVVKLRRQR CLMVQVEAQY
ILIHQALVEY NQFGETEVNL SELHPYLHNM KKRDPPSEPS PLEAEFQRLP SYRSWRTQHI
GNQEENKSKN RNSNVIPYDY NRVPLKHELE MSKESEHDSD ESSDDDSDSE EPSKYINASF
IMSYWKPEVM IAAQGPLKET IGDFWQMIFQ RKVKVIVMLT ELKHGDQEIC AQYWGEGKQT
YGDIEVDLKD TDKSSTYTLR VFELRHSKRK DSRTVYQYQY TNWSVEQLPA EPKELISMIQ
VVKQKLPQKN SSEGNKHHKS TPLLIHCRDG SQQTGIFCAL LNLLESAETE EVVDIFQVVK
ALRKARPGMV STFEQYQFLY DVIASTYPAQ NGQVKKNNHQ EDKIEFDNEV DKVKQDANCV
NPLGAPEKLP EAKEQAEGSE PTSGTEGPEH SVNGPASPAL NQGS

SEQUENCE LISTING

<160> NUMBER OF SEQ ID NOS: 343

<210> SEQ ID NO 1
<211> LENGTH: 10
<212> TYPE: PRT
<213> ORGANISM: Artificial Sequence
<220> FEATURE:
<223> OTHER INFORMATION: CDRH1 of formula (I)
<220> FEATURE:
<221> NAME/KEY: misc_feature
<222> LOCATION: (5)..(5)
<223> OTHER INFORMATION: Xaa is S or N
<220> FEATURE:
<221> NAME/KEY: misc_feature
<222> LOCATION: (8)..(8)
<223> OTHER INFORMATION: Xaa is V or A
<220> FEATURE:
<221> NAME/KEY: misc_feature
<222> LOCATION: (9)..(9)
<223> OTHER INFORMATION: Xaa is V or M
<220> FEATURE:
<221> NAME/KEY: misc_feature
<222> LOCATION: (10)..(10)
<223> OTHER INFORMATION: Xaa is S or V

<400> SEQUENCE: 1

Gly Phe Ser Leu Xaa Asn Tyr Xaa Xaa Xaa
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDRH2 of formula (II)
<220> FEATURE:
<221> NAME/KEY: misc_feature
<222> LOCATION: (4)..(4)
<223> OTHER INFORMATION: Xaa is V or I
<220> FEATURE:
<221> NAME/KEY: misc_feature
<222> LOCATION: (5)..(5)
<223> OTHER INFORMATION: Xaa is S or E
<220> FEATURE:
<221> NAME/KEY: misc_feature
<222> LOCATION: (6)..(6)
<223> OTHER INFORMATION: Xaa is T or G
<220> FEATURE:
<221> NAME/KEY: misc_feature
<222> LOCATION: (7)..(7)
<223> OTHER INFORMATION: Xaa is N or G
<220> FEATURE:
<221> NAME/KEY: misc_feature
<222> LOCATION: (8)..(8)
<223> OTHER INFORMATION: Xaa is T or A
<220> FEATURE:
<221> NAME/KEY: misc_feature
<222> LOCATION: (9)..(9)
<223> OTHER INFORMATION: Xaa is T or Y
<220> FEATURE:
<221> NAME/KEY: misc_feature
<222> LOCATION: (10)..(10)
<223> OTHER INFORMATION: Xaa is W or absent
<220> FEATURE:
<221> NAME/KEY: misc_feature
<222> LOCATION: (13)..(13)
<223> OTHER INFORMATION: Xaa is N or S

<400> SEQUENCE: 2

Ile Ile Tyr Xaa Xaa Xaa Xaa Xaa Xaa Xaa Tyr Ala Xaa Trp Ala Lys
1               5                   10                  15

Gly

```
<210> SEQ ID NO 3
<211> LENGTH: 17
<212> TYPE: PRT
<213> ORGANISM: Artificial Sequence
<220> FEATURE:
<223> OTHER INFORMATION: CDHR3

<400> SEQUENCE: 3

Glu Pro Tyr Glu Pro Tyr Asp Asp Ser Asn Ile Tyr Tyr Gly Met Asp
1               5                   10                  15

Pro

<210> SEQ ID NO 4
<211> LENGTH: 12
<212> TYPE: PRT
<213> ORGANISM: Artificial Sequence
<220> FEATURE:
<223> OTHER INFORMATION: CDRH3

<400> SEQUENCE: 4

Asp Ala Gly His Ser Asp Val Asp Val Leu Asp Ile
1               5                   10

<210> SEQ ID NO 5
<211> LENGTH: 13
<212> TYPE: PRT
<213> ORGANISM: Artificial Sequence
<220> FEATURE:
<223> OTHER INFORMATION: In one embodiment CDRL1 has a formula (III)
<220> FEATURE:
<221> NAME/KEY: misc_feature
<222> LOCATION: (2)..(2)
<223> OTHER INFORMATION: Xaa is A or S
<220> FEATURE:
<221> NAME/KEY: misc_feature
<222> LOCATION: (6)..(6)
<223> OTHER INFORMATION: Xaa is V or I
<220> FEATURE:
<221> NAME/KEY: misc_feature
<222> LOCATION: (7)..(7)
<223> OTHER INFORMATION: Xaa is V or Y
<220> FEATURE:
<221> NAME/KEY: misc_feature
<222> LOCATION: (8)..(8)
<223> OTHER INFORMATION: Xaa is N or S
<220> FEATURE:
<221> NAME/KEY: misc_feature
<222> LOCATION: (9)..(9)
<223> OTHER INFORMATION: Xaa is G or N
<220> FEATURE:
<221> NAME/KEY: misc_feature
<222> LOCATION: (11)..(11)
<223> OTHER INFORMATION: Xaa is L or D

<400> SEQUENCE: 5

Gln Xaa Ser Gln Ser Xaa Xaa Xaa Xaa Asn Xaa Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDRL2 has a formula (IV)
<220> FEATURE:
<221> NAME/KEY: misc_feature
<222> LOCATION: (1)..(1)
<223> OTHER INFORMATION: Xaa is S or E
<220> FEATURE:
<221> NAME/KEY: misc_feature
<222> LOCATION: (4)..(4)
<223> OTHER INFORMATION: Xaa is T or K
```

```
<400> SEQUENCE: 6

Xaa Ala Ser Xaa Leu Ala Ser
1               5

<210> SEQ ID NO 7
<211> LENGTH: 12
<212> TYPE: PRT
<213> ORGANISM: Artificial Sequence
<220> FEATURE:
<223> OTHER INFORMATION: CDRL3 has a formula (V)
<220> FEATURE:
<221> NAME/KEY: misc_feature
<222> LOCATION: (1)..(1)
<223> OTHER INFORMATION: Xaa is L or Q
<220> FEATURE:
<221> NAME/KEY: misc_feature
<222> LOCATION: (3)..(3)
<223> OTHER INFORMATION: Xaa is G or E
<220> FEATURE:
<221> NAME/KEY: misc_feature
<222> LOCATION: (4)..(4)
<223> OTHER INFORMATION: Xaa is G or F
<220> FEATURE:
<221> NAME/KEY: misc_feature
<222> LOCATION: (5)..(5)
<223> OTHER INFORMATION: Xaa is C, S or G (particularly S or G)
<220> FEATURE:
<221> NAME/KEY: misc_feature
<222> LOCATION: (6)..(6)
<223> OTHER INFORMATION: Xaa is S or G
<220> FEATURE:
<221> NAME/KEY: misc_feature
<222> LOCATION: (7)..(7)
<223> OTHER INFORMATION: Xaa is D, S or E
<220> FEATURE:
<221> NAME/KEY: misc_feature
<222> LOCATION: (8)..(8)
<223> OTHER INFORMATION: Xaa is H, G, A, S or C (particularly H, G, A or
      S)
<220> FEATURE:
<221> NAME/KEY: misc_feature
<222> LOCATION: (9)..(9)
<223> OTHER INFORMATION: Xaa is I or D
<220> FEATURE:
<221> NAME/KEY: misc_feature
<222> LOCATION: (10)..(10)
<223> OTHER INFORMATION: Xaa is C, S or absent
<220> FEATURE:
<221> NAME/KEY: misc_feature
<222> LOCATION: (11)..(11)
<223> OTHER INFORMATION: Xaa is N or absent

<400> SEQUENCE: 7

Xaa Gly Xaa Xaa Xaa Xaa Xaa Xaa Xaa Xaa Xaa Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: CDRH1

<400> SEQUENCE: 8

Gly Phe Ser Leu Asn Asn Tyr Val Met Val
1               5                   10

<210> SEQ ID NO 9
<211> LENGTH: 16
<212> TYPE: PRT
<213> ORGANISM: Artificial Sequence
<220> FEATURE:
```

-continued

<223> OTHER INFORMATION: CDRH2

<400> SEQUENCE: 9

Ile Ile Tyr Val Ser Gly Asn Ala Tyr Tyr Ala Ser Trp Ala Lys Gly
1               5                   10                  15

<210> SEQ ID NO 10
<211> LENGTH: 1304
<212> TYPE: PRT
<213> ORGANISM: Artificial Sequence
<220> FEATURE:
<223> OTHER INFORMATION: Human CD45

<400> SEQUENCE: 10

Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
                20                  25                  30

Leu Thr Thr Ala Lys Met Pro Ser Val Pro Leu Ser Ser Asp Pro Leu
            35                  40                  45

Pro Thr His Thr Thr Ala Phe Ser Pro Ala Ser Thr Phe Glu Arg Glu
50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
                85                  90                  95

Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
        115                 120                 125

Ala Ala Asn Ala Lys Leu Asn Pro Thr Pro Gly Ser Asn Ala Ile Ser
    130                 135                 140

Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
                165                 170                 175

Ala Leu Pro Ala Arg Thr Ser Asn Thr Thr Ile Thr Ala Asn Thr Ser
            180                 185                 190

Asp Ala Tyr Leu Asn Ala Ser Glu Thr Thr Thr Leu Ser Pro Ser Gly
        195                 200                 205

Ser Ala Val Ile Ser Thr Thr Thr Ile Ala Thr Thr Pro Ser Lys Pro
    210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
                245                 250                 255

Glu Cys Gly Asn Asn Thr Cys Thr Asn Asn Glu Val His Asn Leu Thr
            260                 265                 270

Glu Cys Lys Asn Ala Ser Val Ser Ile Ser His Asn Ser Cys Thr Ala
        275                 280                 285

Pro Asp Lys Thr Leu Ile Leu Asp Val Pro Pro Gly Val Glu Lys Phe
    290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
                325                 330                 335

```
Thr Tyr Arg Phe Gln Cys Gly Asn Met Ile Phe Asp Asn Lys Glu Ile
            340                 345                 350
Lys Leu Glu Asn Leu Glu Pro Glu His Glu Tyr Lys Cys Asp Ser Glu
            355                 360                 365
Ile Leu Tyr Asn Asn His Lys Phe Thr Asn Ala Ser Lys Ile Ile Lys
            370                 375                 380
Thr Asp Phe Gly Ser Pro Gly Glu Pro Gln Ile Ile Phe Cys Arg Ser
385                 390                 395                 400
Glu Ala Ala His Gln Gly Val Ile Thr Trp Asn Pro Pro Gln Arg Ser
                405                 410                 415
Phe His Asn Phe Thr Leu Cys Tyr Ile Lys Thr Glu Lys Asp Cys
            420                 425                 430
Leu Asn Leu Asp Lys Asn Leu Ile Lys Tyr Asp Leu Gln Asn Leu Lys
            435                 440                 445
Pro Tyr Thr Lys Tyr Val Leu Ser Leu His Ala Tyr Ile Ile Ala Lys
        450                 455                 460
Val Gln Arg Asn Gly Ser Ala Ala Met Cys His Phe Thr Thr Lys Ser
465                 470                 475                 480
Ala Pro Pro Ser Gln Val Trp Asn Met Thr Val Ser Met Thr Ser Asp
                485                 490                 495
Asn Ser Met His Val Lys Cys Arg Pro Pro Arg Asp Arg Asn Gly Pro
            500                 505                 510
His Glu Arg Tyr His Leu Glu Val Glu Ala Gly Asn Thr Leu Val Arg
            515                 520                 525
Asn Glu Ser His Lys Asn Cys Asp Phe Arg Val Lys Asp Leu Gln Tyr
            530                 535                 540
Ser Thr Asp Tyr Thr Phe Lys Ala Tyr Phe His Asn Gly Asp Tyr Pro
545                 550                 555                 560
Gly Glu Pro Phe Ile Leu His His Ser Thr Ser Tyr Asn Ser Lys Ala
                565                 570                 575
Leu Ile Ala Phe Leu Ala Phe Leu Ile Ile Val Thr Ser Ile Ala Leu
            580                 585                 590
Leu Val Val Leu Tyr Lys Ile Tyr Asp Leu His Lys Lys Arg Ser Cys
            595                 600                 605
Asn Leu Asp Glu Gln Gln Glu Leu Val Glu Arg Asp Asp Glu Lys Gln
            610                 615                 620
Leu Met Asn Val Glu Pro Ile His Ala Asp Ile Leu Leu Glu Thr Tyr
625                 630                 635                 640
Lys Arg Lys Ile Ala Asp Glu Gly Arg Leu Phe Leu Ala Glu Phe Gln
                645                 650                 655
Ser Ile Pro Arg Val Phe Ser Lys Phe Pro Ile Lys Glu Ala Arg Lys
            660                 665                 670
Pro Phe Asn Gln Asn Lys Asn Arg Tyr Val Asp Ile Leu Pro Tyr Asp
            675                 680                 685
Tyr Asn Arg Val Glu Leu Ser Glu Ile Asn Gly Asp Ala Gly Ser Asn
            690                 695                 700
Tyr Ile Asn Ala Ser Tyr Ile Asp Gly Phe Lys Glu Pro Arg Lys Tyr
705                 710                 715                 720
Ile Ala Ala Gln Gly Pro Arg Asp Glu Thr Val Asp Asp Phe Trp Arg
                725                 730                 735
Met Ile Trp Glu Gln Lys Ala Thr Val Ile Val Met Val Thr Arg Cys
            740                 745                 750
```

```
Glu Glu Gly Asn Arg Asn Lys Cys Ala Glu Tyr Trp Pro Ser Met Glu
            755                 760                 765
Glu Gly Thr Arg Ala Phe Gly Asp Val Val Lys Ile Asn Gln His
        770                 775                 780
Lys Arg Cys Pro Asp Tyr Ile Ile Gln Lys Leu Asn Ile Val Asn Lys
785                 790                 795                 800
Lys Glu Lys Ala Thr Gly Arg Glu Val Thr His Ile Gln Phe Thr Ser
                805                 810                 815
Trp Pro Asp His Gly Val Pro Glu Asp Pro His Leu Leu Leu Lys Leu
            820                 825                 830
Arg Arg Arg Val Asn Ala Phe Ser Asn Phe Phe Ser Gly Pro Ile Val
        835                 840                 845
Val His Cys Ser Ala Gly Val Gly Arg Thr Gly Thr Tyr Ile Gly Ile
    850                 855                 860
Asp Ala Met Leu Glu Gly Leu Glu Ala Glu Asn Lys Val Asp Val Tyr
865                 870                 875                 880
Gly Tyr Val Val Lys Leu Arg Arg Gln Arg Cys Leu Met Val Gln Val
                885                 890                 895
Glu Ala Gln Tyr Ile Leu Ile His Gln Ala Leu Val Glu Tyr Asn Gln
            900                 905                 910
Phe Gly Glu Thr Glu Val Asn Leu Ser Glu Leu His Pro Tyr Leu His
        915                 920                 925
Asn Met Lys Lys Arg Asp Pro Pro Ser Glu Pro Ser Pro Leu Glu Ala
930                 935                 940
Glu Phe Gln Arg Leu Pro Ser Tyr Arg Ser Trp Arg Thr Gln His Ile
945                 950                 955                 960
Gly Asn Gln Glu Glu Asn Lys Ser Lys Asn Arg Asn Ser Asn Val Ile
                965                 970                 975
Pro Tyr Asp Tyr Asn Arg Val Pro Leu Lys His Glu Leu Glu Met Ser
            980                 985                 990
Lys Glu Ser Glu His Asp Ser Asp Glu Ser Ser Asp Asp Ser Asp
            995                 1000                1005
Ser Glu Glu Pro Ser Lys Tyr Ile Asn Ala Ser Phe Ile Met Ser
    1010                1015                1020
Tyr Trp Lys Pro Glu Val Met Ile Ala Ala Gln Gly Pro Leu Lys
    1025                1030                1035
Glu Thr Ile Gly Asp Phe Trp Gln Met Ile Phe Gln Arg Lys Val
    1040                1045                1050
Lys Val Ile Val Met Leu Thr Glu Leu Lys His Gly Asp Gln Glu
    1055                1060                1065
Ile Cys Ala Gln Tyr Trp Gly Glu Gly Lys Gln Thr Tyr Gly Asp
    1070                1075                1080
Ile Glu Val Asp Leu Lys Asp Thr Asp Lys Ser Ser Thr Tyr Thr
    1085                1090                1095
Leu Arg Val Phe Glu Leu Arg His Ser Lys Arg Lys Asp Ser Arg
    1100                1105                1110
Thr Val Tyr Gln Tyr Gln Tyr Thr Asn Trp Ser Val Glu Gln Leu
    1115                1120                1125
Pro Ala Glu Pro Lys Glu Leu Ile Ser Met Ile Gln Val Val Lys
    1130                1135                1140
Gln Lys Leu Pro Gln Lys Asn Ser Ser Glu Gly Asn Lys His His
    1145                1150                1155
Lys Ser Thr Pro Leu Leu Ile His Cys Arg Asp Gly Ser Gln Gln
```

```
                1160                1165                1170

Thr Gly Ile Phe Cys Ala Leu Leu Asn Leu Leu Glu Ser Ala Glu
        1175                1180                1185

Thr Glu Glu Val Val Asp Ile Phe Gln Val Val Lys Ala Leu Arg
        1190                1195                1200

Lys Ala Arg Pro Gly Met Val Ser Thr Phe Glu Gln Tyr Gln Phe
        1205                1210                1215

Leu Tyr Asp Val Ile Ala Ser Thr Tyr Pro Ala Gln Asn Gly Gln
        1220                1225                1230

Val Lys Lys Asn Asn His Gln Glu Asp Lys Ile Glu Phe Asp Asn
        1235                1240                1245

Glu Val Asp Lys Val Lys Gln Asp Ala Asn Cys Val Asn Pro Leu
        1250                1255                1260

Gly Ala Pro Glu Lys Leu Pro Glu Ala Lys Glu Gln Ala Glu Gly
        1265                1270                1275

Ser Glu Pro Thr Ser Gly Thr Glu Gly Pro Glu His Ser Val Asn
        1280                1285                1290

Gly Pro Ala Ser Pro Ala Leu Asn Gln Gly Ser
        1295                1300

<210> SEQ ID NO 11
<211> LENGTH: 10
<212> TYPE: PRT
<213> ORGANISM: Artificial Sequence
<220> FEATURE:
<223> OTHER INFORMATION: CDRH1

<400> SEQUENCE: 11

Gly Phe Ser Leu Ser Asn Tyr Ala Val Ser
1               5                   10

<210> SEQ ID NO 12
<211> LENGTH: 17
<212> TYPE: PRT
<213> ORGANISM: Artificial Sequence
<220> FEATURE:
<223> OTHER INFORMATION: CDRH2

<400> SEQUENCE: 12

Ile Ile Tyr Ile Glu Thr Gly Thr Thr Trp Tyr Ala Asn Trp Ala Lys
1               5                   10                  15

Gly

<210> SEQ ID NO 13
<211> LENGTH: 13
<212> TYPE: PRT
<213> ORGANISM: Artificial Sequence
<220> FEATURE:
<223> OTHER INFORMATION: CDRL1

<400> SEQUENCE: 13

Gln Ser Ser Gln Ser Ile Tyr Asn Asn Asn Asp Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: CDRL2

<400> SEQUENCE: 14
```

Glu Ala Ser Lys Leu Ala Ser
1               5

<210> SEQ ID NO 15
<211> LENGTH: 11
<212> TYPE: PRT
<213> ORGANISM: Artificial Sequence
<220> FEATURE:
<223> OTHER INFORMATION: CDRL3

<400> SEQUENCE: 15

Gln Gly Gly Gly Ser Gly Gly Asp Gly Ile Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CDRL3 variant 1

<400> SEQUENCE: 16

Gln Gly Gly Gly Ser Gly Gly Glu Gly Ile Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: CDRL3 variant 2

<400> SEQUENCE: 17

Gln Gly Gly Gly Ser Gly Gly Asp Ala Ile Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: CDRL3 variant 3

<400> SEQUENCE: 18

Gln Gly Gly Gly Ser Gly Gly Asp Ser Ile Ala
1               5                   10

<210> SEQ ID NO 19
<211> LENGTH: 13
<212> TYPE: PRT
<213> ORGANISM: Artificial Sequence
<220> FEATURE:
<223> OTHER INFORMATION: CDRL1

<400> SEQUENCE: 19

Gln Ala Ser Gln Ser Val Val Ser Gly Asn Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: CDRL2

<400> SEQUENCE: 20

```
Ser Ala Ser Thr Leu Ala Ser
1               5

<210> SEQ ID NO 21
<211> LENGTH: 13
<212> TYPE: PRT
<213> ORGANISM: Artificial Sequence
<220> FEATURE:
<223> OTHER INFORMATION: CDRL3

<400> SEQUENCE: 21

Leu Gly Glu Phe Ser Cys Ser Ser His Asp Cys Asn Ala
1               5                   10

<210> SEQ ID NO 22
<211> LENGTH: 13
<212> TYPE: PRT
<213> ORGANISM: Artificial Sequence
<220> FEATURE:
<223> OTHER INFORMATION: CDRL3 variant 1

<400> SEQUENCE: 22

Leu Gly Glu Phe Ser Ser Ser Ser His Asp Ser Asn Ala
1               5                   10

<210> SEQ ID NO 23
<211> LENGTH: 13
<212> TYPE: PRT
<213> ORGANISM: Artificial Sequence
<220> FEATURE:
<223> OTHER INFORMATION: CDRL3 variant 2

<400> SEQUENCE: 23

Leu Gly Glu Phe Ser Cys Ser Ser His Asp Ser Asn Ala
1               5                   10

<210> SEQ ID NO 24
<211> LENGTH: 13
<212> TYPE: PRT
<213> ORGANISM: Artificial Sequence
<220> FEATURE:
<223> OTHER INFORMATION: CDRL3 variant 3

<400> SEQUENCE: 24

Leu Gly Glu Phe Ser Ser Ser Ser His Asp Cys Asn Ala
1               5                   10

<210> SEQ ID NO 25
<211> LENGTH: 44
<212> TYPE: PRT
<213> ORGANISM: Artificial Sequence
<220> FEATURE:
<223> OTHER INFORMATION: GCN4(7P14P) sequence

<400> SEQUENCE: 25

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His
        35                  40

<210> SEQ ID NO 26
<211> LENGTH: 132
<212> TYPE: PRT
<213> ORGANISM: Artificial Sequence
```

```
<220> FEATURE:
<223> OTHER INFORMATION: GCN4(7P14P) sequence

<400> SEQUENCE: 26

Gly Cys Thr Ala Gly Cys Gly Ala Gly Gly Cys Gly Gly Ala Ala
1               5                   10                  15

Gly Ala Ala Thr Gly Ala Ala Ala Cys Ala Ala Cys Thr Thr Gly Ala
            20                  25                  30

Ala Cys Cys Cys Ala Ala Gly Thr Thr Gly Ala Ala Gly Ala Ala
        35                  40                  45

Thr Thr Gly Cys Thr Thr Cys Cys Gly Ala Ala Ala Ala Thr Thr
    50                  55                  60

Ala Thr Cys Ala Cys Thr Thr Gly Gly Ala Ala Ala Thr Gly Ala
65                  70                  75                  80

Gly Gly Thr Thr Gly Cys Cys Ala Gly Ala Thr Ala Ala Ala Gly
                85                  90                  95

Ala Ala Ala Thr Thr Ala Gly Thr Thr Gly Gly Cys Gly Ala Ala Cys
            100                 105                 110

Gly Cys Cys Ala Thr Cys Ala Cys Cys Ala Thr Cys Ala Cys Cys Ala
        115                 120                 125

Thr Cys Ala Cys
    130

<210> SEQ ID NO 27
<211> LENGTH: 262
<212> TYPE: PRT
<213> ORGANISM: Artificial Sequence
<220> FEATURE:
<223> OTHER INFORMATION: 52SR4 ds scFv sequence

<400> SEQUENCE: 27

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
```

Phe Leu Lys Met Asn Ser Leu Gln Ser Gly Asp Ser Ala Arg Tyr Tyr
            210                 215                 220

Cys Val Thr Gly Leu Phe Asp Tyr Trp Gly Gln Gly Thr Thr Leu Thr
225                 230                 235                 240

Val Ser Ser Ala Ala Ala His His His His His His Glu Gln Lys Leu
                245                 250                 255

Ile Ser Glu Glu Asp Leu
            260

<210> SEQ ID NO 28
<211> LENGTH: 792
<212> TYPE: DNA
<213> ORGANISM: Artificial Sequence
<220> FEATURE:
<223> OTHER INFORMATION: 52SR4 ds scFv sequence

<400> SEQUENCE: 28

```
gatgcggtgg tgacccagga aagcgcgctg accagcagcc cgggcgaaac cgtgaccctg      60
acctgccgca gcagcaccgg cgcggtgacc accagcaact atgcgagctg ggtgcaggaa     120
aaaccggatc atctgtttac cggcctgatt ggcggcacca caaaccgcgc gccgggcgtg     180
ccggcgcgct tagcggcag cctgattggc gataaagcgg cgctgaccat taccggcgcg     240
cagaccgaag atgaagcgat ttattttgc gtgctgtggt atagcgacca ttgggtgttt     300
ggctgcggca ccaaactgac cgtgctgggt ggaggcggtg gctcaggcgg aggtggctca     360
ggcggtggcg gtctggcgg cggcggcagc gatgtgcagc tgcagcagag cggcccgggc     420
ctggtggcgc cgagccagag cctgagcatt acctgcaccg tgagcggctt tctcctgacc     480
gattatggc tgaactgggt cgccagagc ccgggcaaat gcctggaatg ctgggcgtg     540
atttggggcg atggcattac cgattataac agcgcgctga aaagccgcct gagcgtgacc     600
aaagataaca gcaaaagcca ggtgtttctg aaaatgaaca gcctgcagag cggcgatagc     660
gcgcgctatt attgcgtgac cggcctgttt gattattggg gccagggcac caccctgacc     720
gtgagcagcg cggccgccca tcaccatcac catcacgaac agaaactgat tagcgaagaa     780
gatctgtaat ag                                                        792
```

<210> SEQ ID NO 29
<211> LENGTH: 113
<212> TYPE: PRT
<213> ORGANISM: Artificial Sequence
<220> FEATURE:
<223> OTHER INFORMATION: Rabbit Ab 4447 VL region

<400> SEQUENCE: 29

Ala Gln Val Leu Thr Gln Thr Pro Ser Pro Val Ser Ala Pro Val Gly
1               5                   10                  15

Gly Thr Val Thr Ile Asn Cys Gln Ala Ser Gln Ser Val Val Ser Gly
            20                  25                  30

Asn Tyr Leu Ala Trp Leu Gln Gln Lys Pro Gly Gln Pro Pro Lys Gln
        35                  40                  45

Leu Ile His Ser Ala Ser Thr Leu Ala Ser Gly Val Ser Ser Arg Phe
    50                  55                  60

Ser Gly Ser Gly Ser Gly Thr Gln Phe Thr Leu Thr Ile Ser Gly Val
65                  70                  75                  80

Gln Cys Glu Asp Ala Ala Thr Tyr Tyr Cys Leu Gly Glu Phe Ser Cys
                85                  90                  95

Ser Ser His Asp Cys Asn Ala Phe Gly Gly Gly Thr Glu Val Val Val
                100                 105                 110

Lys

<210> SEQ ID NO 30
<211> LENGTH: 339
<212> TYPE: DNA
<213> ORGANISM: Artificial Sequence
<220> FEATURE:
<223> OTHER INFORMATION: Rabbit Ab 4447 VL region

<400> SEQUENCE: 30
gcccaagtgc tgacccagac tccgtcccct gtgtctgcac ctgtgggagg cacagtcacc      60
atcaattgcc aggccagtca gagtgttgtt agtggcaatt acctagcctg gcttcagcag     120
aaaccagggc agcctcccaa gcaactgatc cattctgcat ccactctggc atctggggtc     180
tcatcgcggt tcagcggcag tggatctggg acacaattca ctctcaccat cagcggcgtg     240
cagtgtgaag atgctgccac ttactactgt ctaggcgaat tagttgtag tagtcatgat      300 tgtaatgctt tcggcggagg gaccgaggtg gtggtcaaa                             339

<210> SEQ ID NO 31
<211> LENGTH: 123
<212> TYPE: PRT
<213> ORGANISM: Artificial Sequence
<220> FEATURE:
<223> OTHER INFORMATION: Rabbit Ab 4447 VH region

<400> SEQUENCE: 31

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
                20                  25                  30

Val Ser Trp Val Arg Gln Ala Pro Gly Glu Gly Leu Glu Trp Ile Gly
            35                  40                  45

Ile Ile Tyr Ile Glu Thr Gly Thr Thr Trp Tyr Ala Asn Trp Ala Lys
        50                  55                  60

Gly Arg Phe Thr Ile Ser Lys Thr Ser Thr Thr Val Asp Leu Thr Ile
65                  70                  75                  80

Thr Ser Pro Ser Thr Glu Asp Thr Ala Thr Tyr Phe Cys Ala Arg Glu
                85                  90                  95

Pro Tyr Glu Pro Tyr Asp Asp Ser Asn Ile Tyr Tyr Gly Met Asp Pro
            100                 105                 110

Trp Gly Pro Gly Thr Leu Val Thr Val Ser Ser
        115                 120

<210> SEQ ID NO 32
<211> LENGTH: 369
<212> TYPE: DNA
<213> ORGANISM: Artificial Sequence
<220> FEATURE:
<223> OTHER INFORMATION: Rabbit Ab 4447 VH region

<400> SEQUENCE: 32
cagtcgctgg aggagtccgg gggtcgcctg gtcacgcctg gacacccct gacactcacc       60 tgcaccgtct ctggattctc cctcagtaac tatgcagtaa gctgggtccg ccaggctcca    120
ggggagggac tggaatggat cgggatcatt tatattgaaa ctggtaccac atggtacgcg    180
aactgggcga aggccgatt caccatctcc aaaacctcga ccacggtgga tctgacaatc    240

```
accagtccgt caaccgagga cacggccacc tatttctgtg ccagagaacc ttatgaacct    300
tatgatgata gtaatattta ctacggcatg gaccccotggg gcccaggcac cctcgtcacc    360
gtctcgagt                                                              369
```

```
<210> SEQ ID NO 33
<211> LENGTH: 113
<212> TYPE: PRT
<213> ORGANISM: Artificial Sequence
<220> FEATURE:
<223> OTHER INFORMATION: 4447 gL1 V-region - IGKV1D-13 framework

<400> SEQUENCE: 33
```

Ala Gln Val Leu Thr Gln Ser Pro Ser Ser Leu Ser Ala Ser Val Gly
1               5                   10                  15

Asp Arg Val Thr Ile Thr Cys Gln Ala Ser Gln Ser Val Val Ser Gly
            20                  25                  30

Asn Tyr Leu Ala Trp Leu Gln Gln Lys Pro Gly Lys Ala Pro Lys Gln
        35                  40                  45

Leu Ile His Ser Ala Ser Thr Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Leu Gly Glu Phe Ser Cys
                85                  90                  95

Ser Ser His Asp Cys Asn Ala Phe Gly Gly Gly Thr Lys Val Glu Ile
            100                 105                 110

Lys

```
<210> SEQ ID NO 34
<211> LENGTH: 126
<212> TYPE: PRT
<213> ORGANISM: Artificial Sequence
<220> FEATURE:
<223> OTHER INFORMATION: 4447 gH1 V-region - IGHV3-48 framework

<400> SEQUENCE: 34
```

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Asn Tyr
            20                  25                  30

Ala Val Ser Trp Val Arg Gln Ala Pro Gly Lys Gly Leu Glu Trp Ile
        35                  40                  45

Gly Ile Ile Tyr Ile Glu Thr Gly Thr Thr Trp Tyr Ala Asn Trp Ala
    50                  55                  60

Lys Gly Arg Phe Thr Ile Ser Lys Asp Ser Ala Lys Asn Ser Val Tyr
65                  70                  75                  80

Leu Gln Met Asn Ser Leu Arg Asp Glu Asp Thr Ala Val Tyr Tyr Cys
                85                  90                  95

Ala Arg Glu Pro Tyr Glu Pro Tyr Asp Asp Ser Asn Ile Tyr Tyr Gly
            100                 105                 110

Met Asp Pro Trp Gly Gln Gly Thr Leu Val Thr Val Ser Ser
        115                 120                 125

```
<210> SEQ ID NO 35
<211> LENGTH: 126
<212> TYPE: PRT
<213> ORGANISM: Artificial Sequence
```

<220> FEATURE:
<223> OTHER INFORMATION: 4447 gH3 V-region - IGHV4-59 framework

<400> SEQUENCE: 35

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Ala Val Ser Trp Val Arg Gln Pro Pro Gly Lys Gly Leu Glu Trp Ile
        35                  40                  45

Gly Ile Ile Tyr Ile Glu Thr Gly Thr Thr Trp Tyr Ala Asn Trp Ala
    50                  55                  60

Lys Gly Arg Phe Thr Ile Ser Lys Asp Ser Ser Lys Asn Gln Val Ser
65                  70                  75                  80

Leu Lys Leu Ser Ser Val Thr Ala Ala Asp Thr Ala Val Tyr Tyr Cys
                85                  90                  95

Ala Arg Glu Pro Tyr Glu Pro Tyr Asp Asp Ser Asn Ile Tyr Tyr Gly
            100                 105                 110

Met Asp Pro Trp Gly Gln Gly Thr Leu Val Thr Val Ser Ser
        115                 120                 125

<210> SEQ ID NO 36
<211> LENGTH: 111
<212> TYPE: PRT
<213> ORGANISM: Artificial Sequence
<220> FEATURE:
<223> OTHER INFORMATION: Rabbit Ab 4450 VL region

<400> SEQUENCE: 36

Ala Ile Asp Met Thr Gln Thr Pro Ser Pro Val Ser Ala Ala Val Gly
1               5                   10                  15

Gly Thr Val Thr Ile Asn Cys Gln Ser Ser Gln Ser Ile Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Gly Gly Ser Gly
                85                  90                  95

Gly Asp Gly Ile Ala Phe Gly Gly Gly Thr Lys Val Val Val Glu
            100                 105                 110

<210> SEQ ID NO 37
<211> LENGTH: 333
<212> TYPE: DNA
<213> ORGANISM: Artificial Sequence
<220> FEATURE:
<223> OTHER INFORMATION: Rabbit Ab 4450 VL region

<400> SEQUENCE: 37
gccattgata tgacccagac tccatccccc gtgtctgcag ctgtgggagg cacagtcacc        60
atcaattgcc agtccagtca gagtatttat aataataatg acttagcctg gtatcagcag       120
aaaccagggc agcctcccaa gctcctgatc tacgaagcat ccaaactggc atctggggtc       180
ccatcgcggt tcaaaggcag tggatctggg acacagttca ctctcaccat cagtggcgtg       240
cagtgtgatg atgctgccac ttactactgt cagggcggtg gtagtggtgg tgatggcatt       300
gctttcggcg agggaccaa ggtggtcgtc gaa        333

<210> SEQ ID NO 38
<211> LENGTH: 117
<212> TYPE: PRT
<213> ORGANISM: Artificial Sequence
<220> FEATURE:
<223> OTHER INFORMATION: Rabbit Ab 4450 VH region

<400> SEQUENCE: 38

Gln Ser Val Glu Glu Ser Gly Gly Arg Leu Val Thr Pro Gly Ala Pro
1               5                   10                  15

Leu Thr Leu Thr Cys Thr Val Ser Gly Phe Ser Leu Asn Asn Tyr Val
            20                  25                  30

Met Val Trp Val Arg Gln Ala Pro Gly Lys Gly Leu Glu Trp Ile Gly
        35                  40                  45

Ile Ile Tyr Val Ser Gly Asn Ala Tyr Tyr Ala Ser Trp Ala Lys Gly
    50                  55                  60

Arg Phe Thr Ile Ser Arg Thr Ser Thr Thr Val Asp Leu Lys Val Thr
65                  70                  75                  80

Ser Leu Thr Thr Glu Asp Thr Ala Thr Tyr Phe Cys Ala Arg Asp Ala
                85                  90                  95

Gly His Ser Asp Val Asp Val Leu Asp Ile Trp Gly Pro Gly Thr Leu
            100                 105                 110

Val Thr Val Ser Ser
        115

<210> SEQ ID NO 39
<211> LENGTH: 351
<212> TYPE: DNA
<213> ORGANISM: Artificial Sequence
<220> FEATURE:
<223> OTHER INFORMATION: Rabbit Ab 4450 VH region

<400> SEQUENCE: 39
cagtcggtgg aggagtccgg gggtcgcctg gtcacgcctg ggcacccct gacactcacc        60 tgcacagtct ctggattctc cctcaataac tatgtaatgg tctgggtccg ccaggctcca       120
gggaaggggc tggaatggat cggaatcatt tatgttagtg gtaatgcata ctacgcgagc       180
tgggcaaaag gccgattcac catctccaga acctcgacca cggtggatct gaaagtgacc       240
agtctgacaa ccgaggacac ggccacctat ttctgtgcca gagatgctgg tcatagtgat       300
gtcgatgttt tggatatttg gggcccgggc accctcgtca ccgtctcgag t               351

<210> SEQ ID NO 40
<211> LENGTH: 111
<212> TYPE: PRT
<213> ORGANISM: Artificial Sequence
<220> FEATURE:
<223> OTHER INFORMATION: 4450 gL1 V-region - IGKV1-6 framework

<400> SEQUENCE: 40

Ala Ile Asp Met Thr Gln Ser Pro Ser Ser Leu Ser Ala Ser Val Gly
1               5                   10                  15

Asp Arg Val Thr Ile Thr Cys Gln Ser Ser Gln Ser Ile Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Glu Ala Ser Lys Leu Ala Ser Gly Val Pro Ser Arg Phe

```
                50             55              60
Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Gln Gly Gly Ser Gly
                85                  90                  95

Gly Asp Gly Ile Ala Phe Gly Gly Gly Thr Lys Val Glu Ile Lys
            100                 105                 110
```

<210> SEQ ID NO 41
<211> LENGTH: 120
<212> TYPE: PRT
<213> ORGANISM: Artificial Sequence
<220> FEATURE:
<223> OTHER INFORMATION: 4450 gH1 V-region - IGHV3-66 framework

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asn Tyr
            20                  25                  30

Val Met Val Trp Val Arg Gln Ala Pro Gly Lys Gly Leu Glu Trp Ile
        35                  40                  45

Gly Ile Ile Tyr Val Ser Gly Asn Ala Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Ala Gly His Ser Asp Val Asp Val Leu Asp Ile Trp Gly Gln
            100                 105                 110

Gly Thr Leu Val Thr Val Ser Ser
        115                 120
```

<210> SEQ ID NO 42
<211> LENGTH: 120
<212> TYPE: PRT
<213> ORGANISM: Artificial Sequence
<220> FEATURE:
<223> OTHER INFORMATION: 4450 gH3 V-region - IGHV4-59 framework

<400> SEQUENCE: 42

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Asn Asn Tyr
            20                  25                  30

Val Met Val Trp Val Arg Gln Pro Pro Gly Lys Gly Leu Glu Trp Ile
        35                  40                  45

Gly Ile Ile Tyr Val Ser Gly Asn Ala Tyr Tyr Ala Ser Trp Ala Lys
    50                  55                  60

Gly Arg Phe Thr Ile Ser Arg Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Ala Gly His Ser Asp Val Asp Val Leu Asp Ile Trp Gly Gln
            100                 105                 110

Gly Thr Leu Val Thr Val Ser Ser
        115                 120
```

<210> SEQ ID NO 43
<211> LENGTH: 11
<212> TYPE: PRT
<213> ORGANISM: Artificial Sequence
<220> FEATURE:
<223> OTHER INFORMATION: Ab 4120 CDRH1

<400> SEQUENCE: 43

Gly Phe Ser Phe Ser Ser Ser Tyr Tyr Met Cys
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Ab 4120 CDRH1 variant

<400> SEQUENCE: 44

Gly Phe Ser Phe Ser Ser Ser Tyr Tyr Met Ser
1               5                   10

<210> SEQ ID NO 45
<211> LENGTH: 18
<212> TYPE: PRT
<213> ORGANISM: Artificial Sequence
<220> FEATURE:
<223> OTHER INFORMATION: Ab 4120 CDRH2

<400> SEQUENCE: 45

Cys Ile Tyr Thr Gly Ser Ser Gly Asp Thr Tyr Tyr Ala Ser Trp Ala
1               5                   10                  15

Lys Gly

<210> SEQ ID NO 46
<211> LENGTH: 18
<212> TYPE: PRT
<213> ORGANISM: Artificial Sequence
<220> FEATURE:
<223> OTHER INFORMATION: Ab 4120 CDRH2 variant

<400> SEQUENCE: 46

Ser Ile Tyr Thr Gly Ser Ser Gly Asp Thr Tyr Tyr Ala Ser Trp Ala
1               5                   10                  15

Lys Gly

<210> SEQ ID NO 47
<211> LENGTH: 15
<212> TYPE: PRT
<213> ORGANISM: Artificial Sequence
<220> FEATURE:
<223> OTHER INFORMATION: Ab 4120 CDRH3

<400> SEQUENCE: 47

Gly Pro Tyr Val Gly Tyr Gly Tyr Asp Leu Gln Tyr Leu Tyr Leu
1               5                   10                  15

<210> SEQ ID NO 48
<211> LENGTH: 11
<212> TYPE: PRT
<213> ORGANISM: Artificial Sequence
<220> FEATURE:
<223> OTHER INFORMATION: Ab 4120 CDRL1

<400> SEQUENCE: 48

Gln Ala Ser Gln Ser Ile Ser Thr Ala Leu Ala
1               5                  10

<210> SEQ ID NO 49
<211> LENGTH: 7
<212> TYPE: PRT
<213> ORGANISM: Artificial Sequence
<220> FEATURE:
<223> OTHER INFORMATION: Ab 4120 CDRL2

<400> SEQUENCE: 49

Gly Ala Ser Thr Leu Ala Ser
1               5

<210> SEQ ID NO 50
<211> LENGTH: 13
<212> TYPE: PRT
<213> ORGANISM: Artificial Sequence
<220> FEATURE:
<223> OTHER INFORMATION: Ab 4120 CDRL3

<400> SEQUENCE: 50

Gln Ser Tyr Tyr Gly Thr Ser Ser Gly Gly Ser Trp Ala
1               5                   10

<210> SEQ ID NO 51
<211> LENGTH: 111
<212> TYPE: PRT
<213> ORGANISM: Artificial Sequence
<220> FEATURE:
<223> OTHER INFORMATION: Rabbit Ab 4120 VL region

<400> SEQUENCE: 51

Ala Phe Glu Leu Ser Gln Thr Pro Ala Ser Val Glu Ala Ala Val Gly
1               5                   10                  15

Gly Thr Val Thr Ile Lys Cys Gln Ala Ser Gln Ser Ile Ser Thr Ala
            20                  25                  30

Leu Ala Trp Tyr Gln Gln Lys Pro Gly Gln Arg Pro Lys Leu Leu Ile
        35                  40                  45

Tyr Gly Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Gly Thr Ser Ser
                85                  90                  95

Gly Gly Ser Trp Ala Phe Gly Gly Thr Lys Val Val Val Lys
            100                 105                 110

<210> SEQ ID NO 52
<211> LENGTH: 333
<212> TYPE: DNA
<213> ORGANISM: Artificial Sequence
<220> FEATURE:
<223> OTHER INFORMATION: Rabbit Ab 4120 VL region

<400> SEQUENCE: 52
gcattcgaat tgagccagac tccagcctcc gtggaggcag ctgtgggagg cacagtcacc      60
atcaagtgcc aggccagtca gagcattagc actgcattag cctggtatca gcagaaacca    120
gggcagcgtc ccaagctcct gatctatggt gcatccactc tggcatctgg ggtctcatcg    180
cggttcaaag gcagtggatc tgggacagag ttcactctca ccatcagcga cctggagtgt    240
gccgatgctg ccacttacta ctgtcaaagc tattatggta cgagtagtgg tggttcttgg    300
gctttcggcg agggaccaa ggtggtcgtc aaa    333

<210> SEQ ID NO 53
<211> LENGTH: 124
<212> TYPE: PRT
<213> ORGANISM: Artificial Sequence
<220> FEATURE:
<223> OTHER INFORMATION: Rabbit Ab 4120 VH region

<400> SEQUENCE: 53

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ser Pro Gly Lys Gly Leu Glu Trp Ile
        35                  40                  45

Ala Cys Ile Tyr Thr Gly Ser Ser Gly Asp Thr Tyr Tyr Ala Ser Trp
    50                  55                  60

Ala Lys Gly Arg Phe Thr Ile Ser Lys Thr Ser Ser Thr Thr Val Ser
65                  70                  75                  80

Leu Gln Met Thr Ser Leu Thr Ala Ala Asp Thr Ala Thr Tyr Phe Cys
                85                  90                  95

Ala Arg Gly Pro Tyr Val Gly Tyr Gly Tyr Asp Leu Gln Tyr Leu Tyr
            100                 105                 110

Leu Trp Gly Pro Gly Thr Leu Val Thr Val Ser Ser
        115                 120
```

<210> SEQ ID NO 54
<211> LENGTH: 372
<212> TYPE: DNA
<213> ORGANISM: Artificial Sequence
<220> FEATURE:
<223> OTHER INFORMATION: Rabbit Ab 4120 VH region

<400> SEQUENCE: 54
cagtcattgg aggagtccgg gggagacctg gtcaagcctg gggcatccct gacactcacc    60
tgcacagcct ctggattctc cttcagtagt agctactaca tgtgctgggt ccgccagtct    120
ccagggaagg gctggagtg gatcgcatgc atttatactg gtagtagtgg tgacacttac     180
tacgcgagct gggcgaaagg ccgattcacc atctccaaaa cctcgtcgac cacggtgtct    240
ctgcaaatga ccagtctgac agccgcggac acggccactt atttctgtgc gagagggcct    300
tatgttggtt atggttatga tcttcaatac ttgtacttgt ggggcccggg gaccctcgtc    360
accgtctcga gt    372

<210> SEQ ID NO 55
<211> LENGTH: 111
<212> TYPE: PRT
<213> ORGANISM: Artificial Sequence
<220> FEATURE:
<223> OTHER INFORMATION: 4120 gL1 V-region IGKV1D-13 framework

<400> SEQUENCE: 55

```
Ala Phe Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45
```

```
Tyr Gly Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Tyr Gly Thr Ser Ser
                85                  90                  95

Gly Gly Ser Trp Ala Phe Gly Gly Gly Thr Lys Val Glu Ile Lys
            100                 105                 110
```

<210> SEQ ID NO 56
<211> LENGTH: 126
<212> TYPE: PRT
<213> ORGANISM: Artificial Sequence
<220> FEATURE:
<223> OTHER INFORMATION: 4120 gH1 V-region - IGHV3-33 framework

<400> SEQUENCE: 56

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Ser Ser Ser
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Ser Gly Asp Thr Tyr Tyr Ala Ser
    50                  55                  60

Trp Ala Lys Gly Arg Phe Thr Ile Ser Lys Asp Ser Ser Lys Thr Thr
65                  70                  75                  80

Val Tyr Leu Gln Met Asn Ser Leu Arg Ala Glu Asp Thr Ala Val Tyr
                85                  90                  95

Tyr Cys Ala Arg Gly Pro Tyr Val Gly Tyr Gly Tyr Asp Leu Gln Tyr
            100                 105                 110

Leu Tyr Leu Trp Gly Gln Gly Thr Leu Val Thr Val Ser Ser
        115                 120                 125
```

<210> SEQ ID NO 57
<211> LENGTH: 336
<212> TYPE: DNA
<213> ORGANISM: Artificial Sequence
<220> FEATURE:
<223> OTHER INFORMATION: Rabbit Ab 4126 VL region

<400> SEQUENCE: 57

```
gacattgtga tgacccagac tccagcctcc gtggaggcag ctgtgggagg cacagtcacc      60
atcaagtgcc aggccagtca gaacattggt agtggtttag cctggtatca gcagaaacca     120
gggcagcctc ccaagctcct gatctattat gcatccactc tggcatctgg ggtcccatca     180
aggttcaaag gcagtggatc tgggacacag ttcactctca ccatcagcga cctggagtgt     240
gccgacgctg ccacttacta ctgtcaaagt catgattata gtagtgttcg gagttacggt     300
aatgctttcg gcggagggac cgaggtggtg gtcaaa                               336
```

<210> SEQ ID NO 58
<211> LENGTH: 126
<212> TYPE: PRT
<213> ORGANISM: Artificial Sequence
<220> FEATURE:
<223> OTHER INFORMATION: Rabbit Ab 4126 VH region

<400> SEQUENCE: 58

```
Gln Gln His Leu Glu Glu Ser Gly Gly Gly Leu Val Lys Pro Gly Gly
1               5                   10                  15

Thr Leu Thr Leu Thr Cys Lys Ala Ser Gly Ile Asp Phe Ser Ser Tyr
            20                  25                  30

Tyr Tyr Met Cys Trp Val Arg Gln Ala Pro Gly Lys Gly Leu Glu Trp
        35                  40                  45

Val Ala Cys Ile Asp Pro Ala Ser Ser Gly Thr Thr Tyr Tyr Ala Thr
    50                  55                  60

Trp Ala Lys Gly Arg Phe Thr Ile Ser Lys Thr Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ala Tyr Gly Ser Gly Gly Ser Gly Tyr Ile Gly Cys Tyr
            100                 105                 110

Phe Asp Leu Trp Gly Gln Gly Thr Leu Val Thr Val Ser Ser
            115                 120                 125

<210> SEQ ID NO 59
<211> LENGTH: 378
<212> TYPE: DNA
<213> ORGANISM: Artificial Sequence
<220> FEATURE:
<223> OTHER INFORMATION: Rabbit Ab 4126 VH region

<400> SEQUENCE: 59
cagcagcacc tggaggagtc cggggaggc ctggtcaagc ctggaggaac cctgacactc    60
acctgcaaag cctctggaat cgacttcagt agctactact acatgtgctg ggtccgccag   120
gctccaggga aggggctgga gtgggtcgcg tgcattgatc ctgctagtag tggtactact   180
tactacgcga cctgggcgaa aggccgattc accatctcca aaacctcgtc gaccacggtg   240
actctgcaaa tgaccagtct gacagccgcg gacacggcca cctatttctg tgcgagggca   300
tatggtagtg ggggtagtgg ttatataggg tgctactttg acttgtgggg ccaaggcacc   360
ctcgtcaccg tctcgagt                                                 378

<210> SEQ ID NO 60
<211> LENGTH: 11
<212> TYPE: PRT
<213> ORGANISM: Artificial Sequence
<220> FEATURE:
<223> OTHER INFORMATION: CDRH1

<400> SEQUENCE: 60

Gly Ile Asp Phe Ser Ser Tyr Tyr Tyr Met Cys
1               5                   10

<210> SEQ ID NO 61
<211> LENGTH: 11
<212> TYPE: PRT
<213> ORGANISM: Artificial Sequence
<220> FEATURE:
<223> OTHER INFORMATION: CDRH1 variant

<400> SEQUENCE: 61

Gly Ile Asp Phe Ser Ser Tyr Tyr Tyr Met Ser
1               5                   10

<210> SEQ ID NO 62
<211> LENGTH: 18
<212> TYPE: PRT
<213> ORGANISM: Artificial Sequence
```

-continued

```
<220> FEATURE:
<223> OTHER INFORMATION: CDRH2

<400> SEQUENCE: 62

Cys Ile Asp Pro Ala Ser Ser Gly Thr Thr Tyr Tyr Ala Thr Trp Ala
1               5                   10                  15

Lys Gly

<210> SEQ ID NO 63
<211> LENGTH: 18
<212> TYPE: PRT
<213> ORGANISM: Artificial Sequence
<220> FEATURE:
<223> OTHER INFORMATION: CDRH2 variant

<400> SEQUENCE: 63

Ser Ile Asp Pro Ala Ser Ser Gly Thr Thr Tyr Tyr Ala Thr Trp Ala
1               5                   10                  15

Lys Gly

<210> SEQ ID NO 64
<211> LENGTH: 16
<212> TYPE: PRT
<213> ORGANISM: Artificial Sequence
<220> FEATURE:
<223> OTHER INFORMATION: CDRH3

<400> SEQUENCE: 64

Ala Tyr Gly Ser Gly Gly Ser Gly Tyr Ile Gly Cys Tyr Phe Asp Leu
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: CDRH3 variant

<400> SEQUENCE: 65

Ala Tyr Gly Ser Gly Gly Ser Gly Tyr Ile Gly Ser Tyr Phe Asp Leu
1               5                   10                  15

<210> SEQ ID NO 66
<211> LENGTH: 11
<212> TYPE: PRT
<213> ORGANISM: Artificial Sequence
<220> FEATURE:
<223> OTHER INFORMATION: CDRL1

<400> SEQUENCE: 66

Gln Ala Ser Gln Asn Ile Gly Ser Gly Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: CDRL2

<400> SEQUENCE: 67

Tyr Ala Ser Thr Leu Ala Ser
1               5

<210> SEQ ID NO 68
```

```
<211> LENGTH: 14
<212> TYPE: PRT
<213> ORGANISM: Artificial Sequence
<220> FEATURE:
<223> OTHER INFORMATION: CDRL3

<400> SEQUENCE: 68

Gln Ser His Asp Tyr Ser Ser Val Arg Ser Tyr Gly Asn Ala
1               5                   10

<210> SEQ ID NO 69
<211> LENGTH: 112
<212> TYPE: PRT
<213> ORGANISM: Artificial Sequence
<220> FEATURE:
<223> OTHER INFORMATION: 4126 gL3 V-region - IGKV1-5 framework

<400> SEQUENCE: 69

Asp Ile Val Met Thr Gln Ser Pro Ser Thr Leu Ser Ala Ser Val Gly
1               5                   10                  15

Asp Arg Val Thr Ile Thr Cys Gln Ala Ser Gln Asn Ile Gly Ser Gly
                20                  25                  30

Leu Ala Trp Tyr Gln Gln Lys Pro Gly Lys Ala Pro Lys Leu Leu Ile
            35                  40                  45

Tyr Tyr Ala Ser Thr Leu Ala Ser Gly Val Pro Ser Arg Phe Ser Gly
        50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Ser His Asp Tyr Ser Ser Val
                85                  90                  95

Arg Ser Tyr Gly Asn Ala Phe Gly Gly Gly Thr Lys Val Glu Ile Lys
            100                 105                 110

<210> SEQ ID NO 70
<211> LENGTH: 127
<212> TYPE: PRT
<213> ORGANISM: Artificial Sequence
<220> FEATURE:
<223> OTHER INFORMATION: 4126 gH12 V-region - IGHV3-7 framework

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Ser Tyr
                20                  25                  30

Tyr Tyr Met Cys Trp Val Arg Gln Ala Pro Gly Lys Gly Leu Glu Trp
            35                  40                  45

Val Ala Cys Ile Asp Pro Ala Ser Ser Gly Thr Thr Tyr Tyr Ala Thr
        50                  55                  60

Trp Ala Lys Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Ala Tyr Gly Ser Gly Gly Ser Gly Tyr Ile Gly Cys
            100                 105                 110

Tyr Phe Asp Leu Trp Gly Gln Gly Thr Leu Val Thr Val Ser Ser
        115                 120                 125

<210> SEQ ID NO 71
<211> LENGTH: 127
```

```
<212> TYPE: PRT
<213> ORGANISM: Artificial Sequence
<220> FEATURE:
<223> OTHER INFORMATION: 4126 gH3 V-region - IGHV3-7 framework

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Ser Tyr
            20                  25                  30

Tyr Tyr Met Cys Trp Val Arg Gln Ala Pro Gly Lys Gly Leu Glu Trp
        35                  40                  45

Val Ala Cys Ile Asp Pro Ala Ser Ser Gly Thr Thr Tyr Tyr Ala Thr
    50                  55                  60

Trp Ala Lys Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Ala Tyr Gly Ser Gly Ser Gly Tyr Ile Gly Ser
            100                 105                 110

Tyr Phe Asp Leu Trp Gly Gln Gly Thr Leu Val Thr Val Ser Ser
        115                 120                 125

<210> SEQ ID NO 72
<211> LENGTH: 11
<212> TYPE: PRT
<213> ORGANISM: Artificial Sequence
<220> FEATURE:
<223> OTHER INFORMATION: Ab 4127 CDRH1

<400> SEQUENCE: 72

Gly Phe Ser Phe Ser Asn Leu Tyr Tyr Met Cys
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Ab 4127 CDRH1 variant

<400> SEQUENCE: 73

Gly Phe Ser Phe Ser Asn Leu Tyr Tyr Met Ser
1               5                   10

<210> SEQ ID NO 74
<211> LENGTH: 18
<212> TYPE: PRT
<213> ORGANISM: Artificial Sequence
<220> FEATURE:
<223> OTHER INFORMATION: Ab 4127 CDRH2

<400> SEQUENCE: 74

Cys Ile Asp Ile Ser Ser Ser Gly Ser Thr Tyr Tyr Ala Ser Trp Ala
1               5                   10                  15

Lys Gly

<210> SEQ ID NO 75
<211> LENGTH: 18
<212> TYPE: PRT
<213> ORGANISM: Artificial Sequence
<220> FEATURE:
<223> OTHER INFORMATION: Ab 4127 CDRH2 variant
```

```
<400> SEQUENCE: 75

Ser Ile Asp Ile Ser Ser Ser Gly Ser Thr Tyr Tyr Ala Ser Trp Ala
1               5                   10                  15

Lys Gly

<210> SEQ ID NO 76
<211> LENGTH: 13
<212> TYPE: PRT
<213> ORGANISM: Artificial Sequence
<220> FEATURE:
<223> OTHER INFORMATION: Ab 4127 CDRH3

<400> SEQUENCE: 76

Asp Tyr Tyr Ser Ser Asp Trp Gly Val Arg Phe Asn Leu
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Ab 4127 CDRL1

<400> SEQUENCE: 77

Gln Ala Ser Gln Ser Val Tyr Gly Asn Asn Glu Leu Ser
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Ab 4127 CDRL2

<400> SEQUENCE: 78

Leu Ala Ser Arg Leu Ala Ser
1               5

<210> SEQ ID NO 79
<211> LENGTH: 12
<212> TYPE: PRT
<213> ORGANISM: Artificial Sequence
<220> FEATURE:
<223> OTHER INFORMATION: Ab 4127 CDRL3

<400> SEQUENCE: 79

Ala Gly Tyr Lys Ser Asp Ser Asp Asp Gly Thr Thr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Ab 4127 CDRL3 variant 1

<400> SEQUENCE: 80

Ala Gly Tyr Lys Ser Glu Ser Asp Asp Gly Thr Thr
1               5                   10

<210> SEQ ID NO 81
<211> LENGTH: 12
<212> TYPE: PRT
<213> ORGANISM: Artificial Sequence
<220> FEATURE:
```

<223> OTHER INFORMATION: Ab 4127 CDRL3 variant 2 Ab 4127

<400> SEQUENCE: 81

Ala Gly Tyr Lys Ser Asp Ala Asp Asp Gly Thr Thr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Ab 4127 CDRL3 variant 3

<400> SEQUENCE: 82

Ala Gly Tyr Lys Ser Asp Thr Asp Asp Gly Thr Thr
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Ab 4127 CDRL3 variant 4

<400> SEQUENCE: 83

Ala Gly Tyr Lys Ser Asp Ser Asp Glu Gly Thr Thr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Ab 4127 CDRL3 variant 5

<400> SEQUENCE: 84

Ala Gly Tyr Lys Ser Asp Ser Asp Asp Ala Thr Thr
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Ab 4127CDRL3 variant 6

<400> SEQUENCE: 85

Ala Gly Tyr Lys Ser Asp Ser Asp Asp Ser Thr Thr
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Ab 4127 CDRL3 variant 7

<400> SEQUENCE: 86

Ala Gly Tyr Lys Ser Glu Ser Asp Glu Gly Thr Thr
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Ab 4127 CDRL3 variant 8

```
<400> SEQUENCE: 87

Ala Gly Tyr Lys Ser Glu Ser Asp Asp Ala Thr Thr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Ab 4127 CDRL3 variant 9

<400> SEQUENCE: 88

Ala Gly Tyr Lys Ser Glu Ser Asp Asp Ser Thr Thr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Ab 4127 CDRL3 variant 10

<400> SEQUENCE: 89

Ala Gly Tyr Lys Ser Asp Ala Asp Glu Gly Thr Thr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Ab 4127 CDRL3 variant 11

<400> SEQUENCE: 90

Ala Gly Tyr Lys Ser Asp Ala Asp Asp Ala Thr Thr
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Ab 4127 CDRL3 variant 12

<400> SEQUENCE: 91

Ala Gly Tyr Lys Ser Asp Ala Asp Asp Ser Thr Thr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Ab 4127 CDRL3 variant 13

<400> SEQUENCE: 92

Ala Gly Tyr Lys Ser Asp Thr Asp Glu Gly Thr Thr
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Ab 4127 CDRL3 variant 14
```

<400> SEQUENCE: 93

Ala Gly Tyr Lys Ser Asp Thr Asp Asp Ala Thr Thr
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Ab 4127 CDRL3 variant 15

<400> SEQUENCE: 94

Ala Gly Tyr Lys Ser Asp Thr Asp Asp Ser Thr Thr
1               5                   10

<210> SEQ ID NO 95
<211> LENGTH: 112
<212> TYPE: PRT
<213> ORGANISM: Artificial Sequence
<220> FEATURE:
<223> OTHER INFORMATION: Rabbit Ab 4127 VL region

<400> SEQUENCE: 95

Ala Ile Val Met Thr Gln Thr Pro Ser Ser Lys Ser Val Pro Met Gly
1               5                   10                  15

Gly Thr Val Thr Ile Asn Cys Gln Ala Ser Gln Ser Val Tyr Gly Asn
            20                  25                  30

Asn Glu Leu Ser Trp Tyr Gln Gln Lys Pro Gly Gln Pro Pro Lys Leu
        35                  40                  45

Leu Ile Tyr Leu Ala Ser Arg Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Tyr Lys Ser Asp
                85                  90                  95

Ser Asp Asp Gly Thr Thr Phe Gly Gly Gly Thr Lys Val Val Val Glu
            100                 105                 110

<210> SEQ ID NO 96
<211> LENGTH: 336
<212> TYPE: DNA
<213> ORGANISM: Artificial Sequence
<220> FEATURE:
<223> OTHER INFORMATION: Rabbit Ab 4127 VL region

<400> SEQUENCE: 96
gccatcgtga tgacccagac tccatcttcc aagtctgtcc ctatgggagg cacagtcacc        60
atcaactgcc aggccagtca gagtgtttat ggtaataacg aattatcctg gtatcagcag       120
aaaccagggc agcctcccaa gctcctgatc tatttggcat ccaggctggc atcgggggtc       180
ccatcgcggt ttagcggcag tggatctggg acacagttca ctctcaccat cagcggcgtg       240
cagtgtgacg atgctgccac ttactactgt gcaggctata aaagtgatag tgatgatggc       300
actactttcg gcggagggac caaggtggtg gtcgaa                                 336

<210> SEQ ID NO 97
<211> LENGTH: 122
<212> TYPE: PRT
<213> ORGANISM: Artificial Sequence
<220> FEATURE:
<223> OTHER INFORMATION: Rabbit Ab 4127 VH region

```
<400> SEQUENCE: 97

Gln Gln Leu Glu Glu Ser Gly Gly Asp Leu Val Lys Pro Ala Ser
1               5                   10                  15

Leu Thr Leu Thr Cys Thr Ala Ser Gly Phe Ser Phe Ser Asn Leu Tyr
                20                  25                  30

Tyr Met Cys Trp Val Arg Gln Ala Pro Gly Lys Gly Leu Glu Leu Ile
            35                  40                  45

Gly Cys Ile Asp Ile Ser Ser Gly Ser Thr Tyr Tyr Ala Ser Trp
50                  55                  60

Ala Lys Gly Arg Phe Thr Ile Ser Lys Thr Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Tyr Tyr Ser Ser Asp Trp Gly Val Arg Phe Asn Leu Trp
            100                 105                 110

Gly Gln Gly Thr Leu Val Thr Val Ser Ser
            115                 120

<210> SEQ ID NO 98
<211> LENGTH: 112
<212> TYPE: PRT
<213> ORGANISM: Artificial Sequence
<220> FEATURE:
<223> OTHER INFORMATION: 4127 gL3 V-region - IGKV1-5 framework

<400> SEQUENCE: 98

Ala Ile Val Met Thr Gln Ser Pro Ser Thr Leu Ser Ala Ser Val Gly
1               5                   10                  15

Asp Arg Val Thr Ile Thr Cys Gln Ala Ser Gln Ser Val Tyr Gly Asn
                20                  25                  30

Asn Glu Leu Ser Trp Tyr Gln Gln Lys Pro Gly Lys Ala Pro Lys Leu
            35                  40                  45

Leu Ile Tyr Leu Ala Ser Arg Leu Ala Ser Gly Val Pro Ser Arg Phe
50                  55                  60

Ser Gly Ser Gly Ser Gly Thr Gln Phe Thr Leu Thr Ile Ser Ser Leu
65                  70                  75                  80

Gln Pro Asp Asp Phe Ala Thr Tyr Tyr Cys Ala Gly Tyr Lys Ser Asp
                85                  90                  95

Ser Asp Asp Gly Thr Thr Phe Gly Gly Gly Thr Lys Val Glu Ile Lys
            100                 105                 110

<210> SEQ ID NO 99
<211> LENGTH: 124
<212> TYPE: PRT
<213> ORGANISM: Artificial Sequence
<220> FEATURE:
<223> OTHER INFORMATION: 4127 gH3 V-region - IGHV3-9 framework

<400> SEQUENCE: 99

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Ser Asn Leu
                20                  25                  30

Tyr Tyr Met Cys Trp Val Arg Gln Ala Pro Gly Lys Gly Leu Glu Leu
            35                  40                  45

Ile Gly Cys Ile Asp Ile Ser Ser Gly Ser Thr Tyr Tyr Ala Ser
50                  55                  60
```

```
Trp Ala Lys Gly Arg Phe Thr Ile Ser Lys Asp Ser Ala Lys Thr Ser
 65                  70                  75                  80

Val Tyr Leu Gln Met Asn Ser Leu Arg Ala Glu Asp Thr Ala Leu Tyr
                 85                  90                  95

Tyr Cys Ala Arg Asp Tyr Tyr Ser Ser Asp Trp Gly Val Arg Phe Asn
            100                 105                 110

Leu Trp Gly Gln Gly Thr Leu Val Thr Val Ser Ser
        115                 120

<210> SEQ ID NO 100
<211> LENGTH: 124
<212> TYPE: PRT
<213> ORGANISM: Artificial Sequence
<220> FEATURE:
<223> OTHER INFORMATION: 4127 gH4 V-region - IGHV3-9 framework

<400> SEQUENCE: 100

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Ser Asn Leu
             20                  25                  30

Tyr Tyr Met Ser Trp Val Arg Gln Ala Pro Gly Lys Gly Leu Glu Leu
         35                  40                  45

Ile Gly Ser Ile Asp Ile Ser Ser Gly Ser Thr Tyr Tyr Ala Ser
     50                  55                  60

Trp Ala Lys Gly Arg Phe Thr Ile Ser Lys Asp Ser Ala Lys Thr Ser
 65                  70                  75                  80

Val Tyr Leu Gln Met Asn Ser Leu Arg Ala Glu Asp Thr Ala Leu Tyr
                 85                  90                  95

Tyr Cys Ala Arg Asp Tyr Tyr Ser Ser Asp Trp Gly Val Arg Phe Asn
            100                 105                 110

Leu Trp Gly Gln Gly Thr Leu Val Thr Val Ser Ser
        115                 120

<210> SEQ ID NO 101
<211> LENGTH: 10
<212> TYPE: PRT
<213> ORGANISM: Artificial Sequence
<220> FEATURE:
<223> OTHER INFORMATION: Ab 4128 CDRH1

<400> SEQUENCE: 101

Gly Leu Asp Phe Ser Ser Tyr Trp Ile Cys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Ab 4128 CDRH1 variant

<400> SEQUENCE: 102

Gly Leu Asp Phe Ser Ser Tyr Trp Ile Ser
1               5                   10

<210> SEQ ID NO 103
<211> LENGTH: 18
<212> TYPE: PRT
<213> ORGANISM: Artificial Sequence
<220> FEATURE:
<223> OTHER INFORMATION: Ab 4128 CDRH2
```

<400> SEQUENCE: 103

Cys Ile Val Thr Gly Ser Ser Asp Asn Thr Tyr Tyr Ala Ser Trp Ala
1               5                   10                  15

Lys Gly

<210> SEQ ID NO 104
<211> LENGTH: 18
<212> TYPE: PRT
<213> ORGANISM: Artificial Sequence
<220> FEATURE:
<223> OTHER INFORMATION: Ab 4128 CDRH2 variant

<400> SEQUENCE: 104

Ser Ile Val Thr Gly Ser Ser Asp Asn Thr Tyr Tyr Ala Ser Trp Ala
1               5                   10                  15

Lys Gly

<210> SEQ ID NO 105
<211> LENGTH: 12
<212> TYPE: PRT
<213> ORGANISM: Artificial Sequence
<220> FEATURE:
<223> OTHER INFORMATION: Ab 4128 CDRH3

<400> SEQUENCE: 105

Gly Gly Gly Ala Gly Tyr Ser Gly Ala Phe Asp Leu
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Ab 4128 CDRL1

<400> SEQUENCE: 106

Gln Ala Ser Glu Ser Ile Ser Asn Tyr Leu Ser
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Ab 4128 CDRL2

<400> SEQUENCE: 107

Ala Ser Ser Lys Leu Ser Ser
1               5

<210> SEQ ID NO 108
<211> LENGTH: 13
<212> TYPE: PRT
<213> ORGANISM: Artificial Sequence
<220> FEATURE:
<223> OTHER INFORMATION: Ab 4128 CDRL3

<400> SEQUENCE: 108

Gln Ile Tyr Tyr Ser Ala Ser Gly Ser Arg Asp Trp Thr
1               5                   10

<210> SEQ ID NO 109
<211> LENGTH: 111
<212> TYPE: PRT

<213> ORGANISM: Artificial Sequence
<220> FEATURE:
<223> OTHER INFORMATION: Rabbit Ab 4128 VL region

<400> SEQUENCE: 109

```
Asp Ile Val Met Thr Gln Thr Pro Ala Ser Val Glu Ala Ala Val Gly
 1               5                  10                  15

Gly Thr Val Thr Ile Lys Cys Gln Ala Ser Glu Ser Ile Ser Asn Tyr
                20                  25                  30

Leu Ser Trp Phe Gln Gln Lys Pro Gly Gln Pro Pro Lys Leu Leu Ile
            35                  40                  45

Tyr Ala Ser Ser Lys Leu Ser Ser Gly Val Pro Ser Arg Phe Lys Gly
50                  55                  60

Asp Arg Ser Gly Thr Glu Tyr Thr Leu Thr Ile Ser Asp Leu Glu Cys
65                  70                  75                  80

Ala Asp Ala Ala Thr Tyr Tyr Cys Gln Ile Tyr Tyr Ser Ala Ser Gly
                85                  90                  95

Ser Arg Asp Trp Thr Phe Gly Gly Gly Thr Lys Val Val Val Glu
            100                 105                 110
```

<210> SEQ ID NO 110
<211> LENGTH: 333
<212> TYPE: DNA
<213> ORGANISM: Artificial Sequence
<220> FEATURE:
<223> OTHER INFORMATION: Rabbit Ab 4128 VL region

<400> SEQUENCE: 110

```
gacattgtga tgacccagac tccagcctcc gtggaggcag ctgtgggagg cacagtcacc       60
atcaagtgcc aggccagtga aagcattagc aactacttat cctggtttca gcagaaacca      120
gggcagcctc ccaagctcct gatctatgct tcatccaaac tgtcatctgg ggtcccatcg      180
cggttcaaag gcgatagatc tgggacagag tacactctca ccatcagcga cctggagtgt      240
gccgatgctg ccacttacta ctgtcaaatc tattattcgg ctagtggcag tcgtgattgg      300
actttcggcg gagggaccaa ggtggtcgtc gaa                                   333
```

<210> SEQ ID NO 111
<211> LENGTH: 120
<212> TYPE: PRT
<213> ORGANISM: Artificial Sequence
<220> FEATURE:
<223> OTHER INFORMATION: Rabbit Ab 4128 VH region

<400> SEQUENCE: 111

```
Gln Ser Leu Glu Glu Ser Gly Gly Asp Leu Val Gln Pro Glu Gly Ser
 1               5                  10                  15

Leu Thr Leu Thr Cys Lys Gly Ser Gly Leu Asp Phe Ser Ser Tyr Trp
                20                  25                  30

Ile Cys Trp Val Arg Gln Ala Pro Gly Lys Gly Leu Glu Trp Ile Ala
            35                  40                  45

Cys Ile Val Thr Gly Ser Ser Asp Asn Thr Tyr Tyr Ala Ser Trp Ala
50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Gly Gly Ala Gly Tyr Ser Gly Ala Phe Asp Leu Trp Gly Gln
            100                 105                 110
```

Gly Thr Leu Val Thr Val Ser Ser
        115                 120

<210> SEQ ID NO 112
<211> LENGTH: 360
<212> TYPE: DNA
<213> ORGANISM: Artificial Sequence
<220> FEATURE:
<223> OTHER INFORMATION: Rabbit Ab 4128 VH region

<400> SEQUENCE: 112
cagtcgttgg aggagtccgg gggagacctg gtccagcctg agggatccct gacactcacc    60
tgcaaaggct ccgggttaga cttcagtagc tactggatat gctgggtccg ccaggctcca   120
gggaaggggc tggagtggat cgcatgcatt gttactggta gtagtgataa cacttactac   180
gcgagctggg cgaaaggccg attcaccatc tccaaaacct cgtcgaccac ggtgactctg   240
caaatgacca gtctgacagc cgcggacacg gccacctatt tctgtgcgag aggtggtggt   300
gctggttata gtggtgcctt tgacttgtgg ggccaaggga ccctcgtcac cgtctcgagt   360

<210> SEQ ID NO 113
<211> LENGTH: 111
<212> TYPE: PRT
<213> ORGANISM: Artificial Sequence
<220> FEATURE:
<223> OTHER INFORMATION: 4128 gL1 V-region - IGKV1-5 framework

<400> SEQUENCE: 113

Asp Ile Val Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Asn Tyr
            20                  25                  30

Leu Ser Trp Phe Gln Gln Lys Pro Gly Lys Ala Pro Lys Leu Leu Ile
        35                  40                  45

Tyr Ala Ser Ser Lys Leu Ser Ser Gly Val Pro Ser Arg Phe Lys Gly
    50                  55                  60

Asp Arg Ser Gly Thr Glu Tyr Thr Leu Thr Ile Ser Ser Leu Gln Pro
65                  70                  75                  80

Asp Asp Phe Ala Thr Tyr Tyr Cys Gln Ile Tyr Tyr Ser Ala Ser Gly
                85                  90                  95

Ser Arg Asp Trp Thr Phe Gly Gly Gly Thr Lys Val Glu Ile Lys
            100                 105                 110

<210> SEQ ID NO 114
<211> LENGTH: 122
<212> TYPE: PRT
<213> ORGANISM: Artificial Sequence
<220> FEATURE:
<223> OTHER INFORMATION: 4128 gH1 V-region - IGHV3-33 framework

<400> SEQUENCE: 114

Glu Val Gln Leu Val Glu Ser Gly Gly Gly Leu Val Gln Pro Gly Arg
1               5                   10                  15

Ser Leu Arg Leu Ser Cys Lys Gly Ser Gly Leu Asp Phe Ser Ser Tyr
            20                  25                  30

Trp Ile Cys Trp Val Arg Gln Ala Pro Gly Lys Gly Leu Glu Trp Ile
        35                  40                  45

Ala Cys Ile Val Thr Gly Ser Ser Asp Asn Thr Tyr Tyr Ala Ser Trp
    50                  55                  60

```
Ala Lys Gly Arg Phe Thr Ile Ser Lys Asp Ser Ser Lys Thr Thr Val
 65                  70                  75                  80

Tyr Leu Gln Met Asn Ser Leu Arg Ala Glu Asp Thr Ala Val Tyr Tyr
                 85                  90                  95

Cys Ala Arg Gly Gly Gly Ala Gly Tyr Ser Gly Ala Phe Asp Leu Trp
            100                 105                 110

Gly Gln Gly Thr Leu Val Thr Val Ser Ser
        115                 120
```

<210> SEQ ID NO 115
<211> LENGTH: 122
<212> TYPE: PRT
<213> ORGANISM: Artificial Sequence
<220> FEATURE:
<223> OTHER INFORMATION: 4128 gH2 V-region - IGHV3-33 framework

<400> SEQUENCE: 115

```
Glu Val Gln Leu Val Glu Ser Gly Gly Gly Leu Val Gln Pro Gly Arg
1               5                   10                  15

Ser Leu Arg Leu Ser Cys Lys Gly Ser Gly Leu Asp Phe Ser Ser Tyr
             20                  25                  30

Trp Ile Ser Trp Val Arg Gln Ala Pro Gly Lys Gly Leu Glu Trp Ile
         35                  40                  45

Ala Ser Ile Val Thr Gly Ser Ser Asp Asn Thr Tyr Tyr Ala Ser Trp
 50                  55                  60

Ala Lys Gly Arg Phe Thr Ile Ser Lys Asp Ser Ser Lys Thr Thr Val
 65                  70                  75                  80

Tyr Leu Gln Met Asn Ser Leu Arg Ala Glu Asp Thr Ala Val Tyr Tyr
                 85                  90                  95

Cys Ala Arg Gly Gly Gly Ala Gly Tyr Ser Gly Ala Phe Asp Leu Trp
            100                 105                 110

Gly Gln Gly Thr Leu Val Thr Val Ser Ser
        115                 120
```

<210> SEQ ID NO 116
<211> LENGTH: 11
<212> TYPE: PRT
<213> ORGANISM: Artificial Sequence
<220> FEATURE:
<223> OTHER INFORMATION: Ab 4130 CDRH1

<400> SEQUENCE: 116

```
Gly Phe Asp Phe Ser Gly Gly Tyr Asp Ile Ser
1               5                   10
```

<210> SEQ ID NO 117
<211> LENGTH: 18
<212> TYPE: PRT
<213> ORGANISM: Artificial Sequence
<220> FEATURE:
<223> OTHER INFORMATION: Ab 4130 CDRH2

<400> SEQUENCE: 117

```
Cys Ile Tyr Gly Gly Ile Asn Ser Val Thr Asp Tyr Ala Ser Trp Ala
1               5                   10                  15

Lys Gly
```

<210> SEQ ID NO 118
<211> LENGTH: 18
<212> TYPE: PRT
<213> ORGANISM: Artificial Sequence

```
<220> FEATURE:
<223> OTHER INFORMATION: Ab 4130 CDRH2 variant 1

<400> SEQUENCE: 118

Cys Ile Tyr Gly Gly Ile Asn Ala Val Thr Asp Tyr Ala Ser Trp Ala
1               5                   10                  15

Lys Gly

<210> SEQ ID NO 119
<211> LENGTH: 18
<212> TYPE: PRT
<213> ORGANISM: Artificial Sequence
<220> FEATURE:
<223> OTHER INFORMATION: Ab 4130 CDRH2 variant 2

<400> SEQUENCE: 119

Cys Ile Tyr Gly Gly Ile Asn Thr Val Thr Asp Tyr Ala Ser Trp Ala
1               5                   10                  15

Lys Gly

<210> SEQ ID NO 120
<211> LENGTH: 18
<212> TYPE: PRT
<213> ORGANISM: Artificial Sequence
<220> FEATURE:
<223> OTHER INFORMATION: Ab 4130 CDRH2 variant 3

<400> SEQUENCE: 120

Ser Ile Tyr Gly Gly Ile Asn Ser Val Thr Asp Tyr Ala Ser Trp Ala
1               5                   10                  15

Lys Gly

<210> SEQ ID NO 121
<211> LENGTH: 18
<212> TYPE: PRT
<213> ORGANISM: Artificial Sequence
<220> FEATURE:
<223> OTHER INFORMATION: Ab 4130 CDRH2 variant 4

<400> SEQUENCE: 121

Ser Ile Tyr Gly Gly Ile Asn Ala Val Thr Asp Tyr Ala Ser Trp Ala
1               5                   10                  15

Lys Gly

<210> SEQ ID NO 122
<211> LENGTH: 18
<212> TYPE: PRT
<213> ORGANISM: Artificial Sequence
<220> FEATURE:
<223> OTHER INFORMATION: Ab 4130 CDRH2 variant 5

<400> SEQUENCE: 122

Ser Ile Tyr Gly Gly Ile Asn Thr Val Thr Asp Tyr Ala Ser Trp Ala
1               5                   10                  15

Lys Gly

<210> SEQ ID NO 123
<211> LENGTH: 13
<212> TYPE: PRT
<213> ORGANISM: Artificial Sequence
<220> FEATURE:
<223> OTHER INFORMATION: Ab 4130 CDRH3

<400> SEQUENCE: 123
```

```
Asp Val Ser Asn Ser Asp His Tyr Thr Arg Leu Asp Leu
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Ab 4130 CDRH3 variant 1

<400> SEQUENCE: 124

Asp Val Ser Asn Ala Asp His Tyr Thr Arg Leu Asp Leu
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Ab 4130 CDRH3 variant 2

<400> SEQUENCE: 125

Asp Val Ser Asn Thr Asp His Tyr Thr Arg Leu Asp Leu
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Ab 4130 CDRL1

<400> SEQUENCE: 126

Gln Ser Ser Gln Ser Val Tyr Asn Thr Lys Asp Leu Ala
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Ab 4130 CDRL2

<400> SEQUENCE: 127

Gly Thr Ser Thr Leu Ala Ser
1               5

<210> SEQ ID NO 128
<211> LENGTH: 11
<212> TYPE: PRT
<213> ORGANISM: Artificial Sequence
<220> FEATURE:
<223> OTHER INFORMATION: Ab 4130 CDRL3

<400> SEQUENCE: 128

Gln Gly Gly Phe Ser Ser Ser Asp Leu Asn Val
1               5                   10

<210> SEQ ID NO 129
<211> LENGTH: 111
<212> TYPE: PRT
<213> ORGANISM: Artificial Sequence
<220> FEATURE:
<223> OTHER INFORMATION: Rabbit Ab 4130 VL region

<400> SEQUENCE: 129
```

Ala Ala Val Leu Thr Gln Thr Pro Ser Pro Val Ser Ala Val Gly
1               5                   10                  15

Gly Thr Val Ser Ile Ser Cys Gln Ser Ser Gln Ser Val Tyr Asn Thr
            20                  25                  30

Lys Asp Leu Ala Trp Tyr Gln Gln Lys Pro Gly Gln Pro Pro Lys Leu
            35                  40                  45

Leu Ile Tyr Gly Thr Ser Thr Leu Ala Ser Gly Val Ser Ser Arg Phe
        50                  55                  60

Ser Gly Ser Gly Ser Gly Thr Glu Phe Thr Leu Thr Ile Ser Asp Leu
65                  70                  75                  80

Glu Cys Asp Asp Ala Ala Thr Tyr Tyr Cys Gln Gly Gly Phe Ser Ser
                85                  90                  95

Ser Asp Leu Asn Val Phe Gly Gly Gly Thr Lys Val Val Val Lys
            100                 105                 110

<210> SEQ ID NO 130
<211> LENGTH: 333
<212> TYPE: DNA
<213> ORGANISM: Artificial Sequence
<220> FEATURE:
<223> OTHER INFORMATION: Rabbit Ab 4130 VL region

<400> SEQUENCE: 130
gccgccgtgc tgacccagac tccatctccc gtgtctgcag ctgtgggagg cacagtcagc       60
atcagttgcc agtccagtca gagtgtttat aatacaaagg acttagcctg gtatcagcag      120
aaaccagggc agcctcccaa gctcctgatc tatggtacat ccactctggc atctggggtc      180
tcatcacggt tcagcggcag tggatctggg acagagttca ctctcaccat cagcgacctg      240
gagtgtgacg atgctgccac ttattactgt caaggcggtt ttagtagtag tgatttgaat      300
gttttcggcg agggaccaa ggtggtggtc aaa                                    333

<210> SEQ ID NO 131
<211> LENGTH: 123
<212> TYPE: PRT
<213> ORGANISM: Artificial Sequence
<220> FEATURE:
<223> OTHER INFORMATION: Rabbit Ab 4130 VH region

<400> SEQUENCE: 131

Gln Gln Gln Leu Glu Glu Ser Gly Gly Asp Leu Val Arg Pro Glu Gly
1               5                   10                  15

Ser Leu Thr Leu Thr Cys Thr Ala Ser Gly Phe Asp Phe Ser Gly Gly
            20                  25                  30

Tyr Asp Ile Ser Trp Val Arg Gln Ala Pro Gly Lys Gly Leu Glu Trp
            35                  40                  45

Ile Gly Cys Ile Tyr Gly Gly Ile Asn Ser Val Thr Asp Tyr Ala Ser
        50                  55                  60

Trp Ala Lys Gly Arg Val Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Val Ser Asn Ser Asp His Tyr Thr Arg Leu Asp Leu
            100                 105                 110

Trp Gly Gln Gly Thr Leu Val Thr Val Ser Ser
        115                 120

<210> SEQ ID NO 132

<211> LENGTH: 369
<212> TYPE: DNA
<213> ORGANISM: Artificial Sequence
<220> FEATURE:
<223> OTHER INFORMATION: Rabbit Ab 4130 VH region

<400> SEQUENCE: 132

```
cagcagcagc tggaggagtc cggggggagac ctggtcaggc ctgagggatc cctgacactc      60
acctgcacag cctctggatt cgacttcagt ggcggctacg acatttcctg ggtccgccag     120
gctccaggga aggggctgga gtggatcgga tgcatttatg gtggtatcaa tagtgtcact     180
gactacgcga gctgggcgaa aggccgagtc accatctcca aaacctcgtc gaccacggtg     240
actctgcaga tgaccagtct gacagccgcg gacacggcca cctatttctg tgcgagagat     300
gttagtaata gcgatcatta tactcggttg gatctctggg gccaaggcac cctggtcacc     360
gtctcgagt                                                             369
```

<210> SEQ ID NO 133
<211> LENGTH: 111
<212> TYPE: PRT
<213> ORGANISM: Artificial Sequence
<220> FEATURE:
<223> OTHER INFORMATION: 4130 gL3 V-region - IGKV1-9 framework

<400> SEQUENCE: 133

Ala Ala Val Leu Thr Gln Ser Pro Ser Phe Leu Ser Ala Ser Val Gly
1               5                   10                  15

Asp Arg Val Thr Ile Thr Cys Gln Ser Ser Gln Ser Val Tyr Asn Thr
            20                  25                  30

Lys Asp Leu Ala Trp Tyr Gln Gln Lys Pro Gly Lys Ala Pro Lys Leu
        35                  40                  45

Leu Ile Tyr Gly Thr Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gly Gly Phe Ser Ser
                85                  90                  95

Ser Asp Leu Asn Val Phe Gly Gly Gly Thr Lys Val Glu Ile Lys
            100                 105                 110

<210> SEQ ID NO 134
<211> LENGTH: 124
<212> TYPE: PRT
<213> ORGANISM: Artificial Sequence
<220> FEATURE:
<223> OTHER INFORMATION: 4130 gH8 V-region - IGHV3-66 framework

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Gly Gly
            20                  25                  30

Tyr Asp Ile Ser Trp Val Arg Gln Ala Pro Gly Lys Gly Leu Glu Trp
        35                  40                  45

Ile Gly Cys Ile Tyr Gly Gly Ile Asn Ser Val Thr Asp Tyr Ala Ser
    50                  55                  60

Trp Ala Lys Gly Arg Val Thr Ile Ser Lys Asp Ser Ser Lys Thr Thr
65                  70                  75                  80

Val Tyr Leu Gln Met Asn Ser Leu Arg Ala Glu Asp Thr Ala Val Tyr

```
                    85                  90                  95

Tyr Cys Ala Arg Asp Val Ser Asn Ser Asp His Tyr Thr Arg Leu Asp
                100                 105                 110

Leu Trp Gly Gln Gly Thr Leu Val Thr Val Ser Ser
        115                 120

<210> SEQ ID NO 135
<211> LENGTH: 124
<212> TYPE: PRT
<213> ORGANISM: Artificial Sequence
<220> FEATURE:
<223> OTHER INFORMATION: 4130 gH3 V-region - IGHV3-66 framework

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Gly Gly
            20                  25                  30

Tyr Asp Ile Ser Trp Val Arg Gln Ala Pro Gly Lys Gly Leu Glu Trp
        35                  40                  45

Ile Gly Ser Ile Tyr Gly Gly Ile Asn Ser Val Thr Asp Tyr Ala Ser
    50                  55                  60

Trp Ala Lys Gly Arg Val Thr Ile Ser Lys Asp Ser Ser Lys Thr Thr
65                  70                  75                  80

Val Tyr Leu Gln Met Asn Ser Leu Arg Ala Glu Asp Thr Ala Val Tyr
                85                  90                  95

Tyr Cys Ala Arg Asp Val Ser Asn Ser Asp His Tyr Thr Arg Leu Asp
                100                 105                 110

Leu Trp Gly Gln Gly Thr Leu Val Thr Val Ser Ser
        115                 120

<210> SEQ ID NO 136
<211> LENGTH: 11
<212> TYPE: PRT
<213> ORGANISM: Artificial Sequence
<220> FEATURE:
<223> OTHER INFORMATION: Ab 4132 CDRH1

<400> SEQUENCE: 136

Gly Phe Ser Phe Ser Ser Ser Tyr Trp Ile Cys
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Ab 4132 CDRH1 variant

<400> SEQUENCE: 137

Gly Phe Ser Phe Ser Ser Ser Tyr Trp Ile Ser
1               5                   10

<210> SEQ ID NO 138
<211> LENGTH: 17
<212> TYPE: PRT
<213> ORGANISM: Artificial Sequence
<220> FEATURE:
<223> OTHER INFORMATION: Ab 4132 CDRH2

<400> SEQUENCE: 138

Cys Ile Asn Ser Gly Thr Gly Gly Thr Ala Tyr Ala Ser Trp Ala Lys
```

```
1               5                   10                  15
Gly

<210> SEQ ID NO 139
<211> LENGTH: 17
<212> TYPE: PRT
<213> ORGANISM: Artificial Sequence
<220> FEATURE:
<223> OTHER INFORMATION: Ab 4132 CDRH2 variant 1

<400> SEQUENCE: 139

Cys Ile Asn Ala Gly Thr Gly Gly Thr Ala Tyr Ala Ser Trp Ala Lys
1               5                   10                  15

Gly

<210> SEQ ID NO 140
<211> LENGTH: 17
<212> TYPE: PRT
<213> ORGANISM: Artificial Sequence
<220> FEATURE:
<223> OTHER INFORMATION: Ab 4132 CDRH2 variant 2

<400> SEQUENCE: 140

Cys Ile Asn Thr Gly Thr Gly Gly Thr Ala Tyr Ala Ser Trp Ala Lys
1               5                   10                  15

Gly

<210> SEQ ID NO 141
<211> LENGTH: 17
<212> TYPE: PRT
<213> ORGANISM: Artificial Sequence
<220> FEATURE:
<223> OTHER INFORMATION: Ab 4132 CDRH2 variant 3

<400> SEQUENCE: 141

Ser Ile Asn Ser Gly Thr Gly Gly Thr Ala Tyr Ala Ser Trp Ala Lys
1               5                   10                  15

Gly

<210> SEQ ID NO 142
<211> LENGTH: 17
<212> TYPE: PRT
<213> ORGANISM: Artificial Sequence
<220> FEATURE:
<223> OTHER INFORMATION: Ab 4132 CDRH2 variant 4

<400> SEQUENCE: 142

Ser Ile Asn Ala Gly Thr Gly Gly Thr Ala Tyr Ala Ser Trp Ala Lys
1               5                   10                  15

Gly

<210> SEQ ID NO 143
<211> LENGTH: 17
<212> TYPE: PRT
<213> ORGANISM: Artificial Sequence
<220> FEATURE:
<223> OTHER INFORMATION: Ab 4132 CDRH2 variant 5

<400> SEQUENCE: 143

Ser Ile Asn Thr Gly Thr Gly Gly Thr Ala Tyr Ala Ser Trp Ala Lys
1               5                   10                  15

Gly
```

<210> SEQ ID NO 144
<211> LENGTH: 13
<212> TYPE: PRT
<213> ORGANISM: Artificial Sequence
<220> FEATURE:
<223> OTHER INFORMATION: Ab 4132 CDRH3

<400> SEQUENCE: 144

Glu Trp Val Ser Gly Tyr Tyr Lys Asp Ala Phe Asp Leu
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Ab 4132 CDRL1

<400> SEQUENCE: 145

Gln Ala Ser Glu Thr Ile Ser Ser Arg Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Ab 4132 CDRL2

<400> SEQUENCE: 146

Ser Ala Ser Thr Leu Ala Ser
1               5

<210> SEQ ID NO 147
<211> LENGTH: 12
<212> TYPE: PRT
<213> ORGANISM: Artificial Sequence
<220> FEATURE:
<223> OTHER INFORMATION: Ab 4132 CDRL3

<400> SEQUENCE: 147

Gln Gly Tyr Tyr Tyr Ser Ser Gly Ser Asp Tyr Gly
1               5                   10

<210> SEQ ID NO 148
<211> LENGTH: 110
<212> TYPE: PRT
<213> ORGANISM: Artificial Sequence
<220> FEATURE:
<223> OTHER INFORMATION: Rabbit Ab 4132 VL region

<400> SEQUENCE: 148

Asp Ile Val Met Thr Gln Thr Pro Ala Ser Val Glu Ala Ala Val Gly
1               5                   10                  15

Gly Thr Val Thr Ile Lys Cys Gln Ala Ser Glu Thr Ile Ser Ser Arg
            20                  25                  30

Leu Ala Trp Tyr Gln Gln Lys Leu Gly Gln Pro Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Gly Tyr Tyr Tyr Ser Ser Gly
                85                  90                  95

Ser Asp Tyr Gly Phe Gly Gly Gly Thr Lys Val Val Val Lys
        100                 105                 110

<210> SEQ ID NO 149
<211> LENGTH: 330
<212> TYPE: DNA
<213> ORGANISM: Artificial Sequence
<220> FEATURE:
<223> OTHER INFORMATION: Rabbit Ab 4132 VL region

<400> SEQUENCE: 149
gacattgtga tgacccagac tccagcctcc gtggaggcag ctgtgggagg cacagtcacc     60
atcaagtgcc aggccagtga gaccattagt agtagattag cctggtatca gcagaagcta    120
gggcagcctc ccaaactcct gatctattct gcatccactc tggcgtctgg ggtcccatcg    180
cggttcaaag gcagtggatc tgggacagag tacactctca ccatcagcgg cgtgcagtgt    240
gccgatgctg ccacttatta ctgtcaaggc tattattata gtagtggtag tgattatggt    300
ttcggcggag ggaccaaggt ggtcgtcaaa                                     330

<210> SEQ ID NO 150
<211> LENGTH: 121
<212> TYPE: PRT
<213> ORGANISM: Artificial Sequence
<220> FEATURE:
<223> OTHER INFORMATION: Rabbit Ab 4132 VH region

<400> SEQUENCE: 150

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Ser
        35                  40                  45

Gly Cys Ile Asn Ser Gly Thr Gly Gly Thr Ala Tyr Ala Ser Trp Ala
    50                  55                  60

Lys Gly Arg Phe Thr Ile Ser Asn Ser Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Glu Trp Val Ser Gly Tyr Tyr Lys Asp Ala Phe Asp Leu Trp Gly
            100                 105                 110

Gln Gly Thr Leu Val Thr Val Ser Ser
        115                 120

<210> SEQ ID NO 151
<211> LENGTH: 363
<212> TYPE: DNA
<213> ORGANISM: Artificial Sequence
<220> FEATURE:
<223> OTHER INFORMATION: Rabbit Ab 4132 VH region

<400> SEQUENCE: 151
cagtcgttgg aggagtccgg gggagacctg gtcaagcctg ggcatccct gacactcacc      60 tgcacagcct ctggattctc cttcagtagc agctactgga tatgctgggt ccgccaggct    120
ccagggaagg ggctggagtg gagcggatgc attaatagtg gtactggtgg cactgcctac    180
gcgagctggg cgaaaggccg attcaccatc tccaattcct cgtcgaccac ggtgactctt    240
caaatgacca gtctgacagc cgcggacacg gccacctatt tctgtgcgag agaatgggtt    300

```
agtggttatt ataaagatgc ttttgatctc tggggccagg gcaccctggt caccgtctcg    360
agt                                                                  363
```

<210> SEQ ID NO 152
<211> LENGTH: 110
<212> TYPE: PRT
<213> ORGANISM: Artificial Sequence
<220> FEATURE:
<223> OTHER INFORMATION: 4132 gL1 V-region - IGKV1-5 framework

<400> SEQUENCE: 152

```
Asp Ile Val Met Thr Gln Ser Pro Ser Thr Leu Ser Ala Ser Val Gly
1               5                   10                  15

Asp Arg Val Thr Ile Thr Cys Gln Ala Ser Glu Thr Ile Ser Ser Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gly Tyr Tyr Ser Ser Ser Gly
                85                  90                  95

Ser Asp Tyr Gly Phe Gly Gly Gly Thr Lys Val Glu Ile Lys
            100                 105                 110
```

<210> SEQ ID NO 153
<211> LENGTH: 123
<212> TYPE: PRT
<213> ORGANISM: Artificial Sequence
<220> FEATURE:
<223> OTHER INFORMATION: 4132 gH1 V-region - IGHV3-21 framework

<400> SEQUENCE: 153

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ser Gly Cys Ile Asn Ser Gly Thr Gly Gly Thr Ala Tyr Ala Ser Trp
    50                  55                  60

Ala Lys Gly Arg Phe Thr Ile Ser Asn Asp Ser Ala Lys Thr Ser Val
65                  70                  75                  80

Tyr Leu Gln Met Asn Ser Leu Arg Ala Glu Asp Thr Ala Val Tyr Tyr
                85                  90                  95

Cys Ala Arg Glu Trp Val Ser Gly Tyr Tyr Lys Asp Ala Phe Asp Leu
            100                 105                 110

Trp Gly Gln Gly Thr Leu Val Thr Val Ser Ser
        115                 120
```

<210> SEQ ID NO 154
<211> LENGTH: 123
<212> TYPE: PRT
<213> ORGANISM: Artificial Sequence
<220> FEATURE:
<223> OTHER INFORMATION: 4132 gH2 V-region - IGHV3-21 framework

<400> SEQUENCE: 154

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Ser Ser
            20                  25                  30

Tyr Trp Ile Ser Trp Val Arg Gln Ala Pro Lys Gly Leu Glu Trp
        35                  40                  45

Ser Gly Ser Ile Asn Ser Gly Thr Gly Thr Ala Tyr Ala Ser Trp
    50                  55                  60

Ala Lys Gly Arg Phe Thr Ile Ser Asn Asp Ser Ala Lys Thr Ser Val
65                  70                  75                  80

Tyr Leu Gln Met Asn Ser Leu Arg Ala Glu Asp Thr Ala Val Tyr Tyr
                85                  90                  95

Cys Ala Arg Glu Trp Val Ser Gly Tyr Tyr Lys Asp Ala Phe Asp Leu
                100                 105                 110

Trp Gly Gln Gly Thr Leu Val Thr Val Ser Ser
        115                 120

<210> SEQ ID NO 155
<211> LENGTH: 11
<212> TYPE: PRT
<213> ORGANISM: Artificial Sequence
<220> FEATURE:
<223> OTHER INFORMATION: Ab 4122 CDRH1

<400> SEQUENCE: 155

Gly Phe Ser Phe Ser Ala Gly Tyr Trp Ile Cys
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Ab 4122 CDRH1 variant 1

<400> SEQUENCE: 156

Gly Phe Ser Phe Ser Ala Gly Tyr Trp Ile Ser
1               5                   10

<210> SEQ ID NO 157
<211> LENGTH: 18
<212> TYPE: PRT
<213> ORGANISM: Artificial Sequence
<220> FEATURE:
<223> OTHER INFORMATION: Ab 4122 CDRH2

<400> SEQUENCE: 157

Cys Thr Tyr Ala Gly Arg Ser Gly Ser Thr Tyr Tyr Ala Asn Trp Val
1               5                   10                  15

Asn Gly

<210> SEQ ID NO 158
<211> LENGTH: 18
<212> TYPE: PRT
<213> ORGANISM: Artificial Sequence
<220> FEATURE:
<223> OTHER INFORMATION: Ab 4122 CDRH2 variant 1

<400> SEQUENCE: 158

Cys Thr Tyr Ala Gly Arg Ser Gly Ser Thr Tyr Tyr Ala Asn Trp Val
1               5                   10                  15

Asn Ala

<210> SEQ ID NO 159
<211> LENGTH: 18
<212> TYPE: PRT
<213> ORGANISM: Artificial Sequence
<220> FEATURE:
<223> OTHER INFORMATION: Ab 4122 CDRH2 variant 2

<400> SEQUENCE: 159

Cys Thr Tyr Ala Gly Arg Ser Gly Ser Thr Tyr Tyr Ala Asn Trp Val
1               5                   10                  15

Asn Ser

<210> SEQ ID NO 160
<211> LENGTH: 18
<212> TYPE: PRT
<213> ORGANISM: Artificial Sequence
<220> FEATURE:
<223> OTHER INFORMATION: Ab 4122 CDRH2 variant 3

<400> SEQUENCE: 160

Cys Thr Tyr Ala Gly Arg Ser Gly Ser Thr Tyr Tyr Ala Asn Trp Val
1               5                   10                  15

Asn Thr

<210> SEQ ID NO 161
<211> LENGTH: 18
<212> TYPE: PRT
<213> ORGANISM: Artificial Sequence
<220> FEATURE:
<223> OTHER INFORMATION: Ab 4122 CDRH2 variant 4

<400> SEQUENCE: 161

Ser Thr Tyr Ala Gly Arg Ser Gly Ser Thr Tyr Tyr Ala Asn Trp Val
1               5                   10                  15

Asn Gly

<210> SEQ ID NO 162
<211> LENGTH: 18
<212> TYPE: PRT
<213> ORGANISM: Artificial Sequence
<220> FEATURE:
<223> OTHER INFORMATION: Ab 4122 CDRH2 variant 5

<400> SEQUENCE: 162

Ser Thr Tyr Ala Gly Arg Ser Gly Ser Thr Tyr Tyr Ala Asn Trp Val
1               5                   10                  15

Asn Ala

<210> SEQ ID NO 163
<211> LENGTH: 18
<212> TYPE: PRT
<213> ORGANISM: Artificial Sequence
<220> FEATURE:
<223> OTHER INFORMATION: Ab 4122 CDRH2 variant 6

<400> SEQUENCE: 163

Ser Thr Tyr Ala Gly Arg Ser Gly Ser Thr Tyr Tyr Ala Asn Trp Val
1               5                   10                  15

Asn Ser

<210> SEQ ID NO 164

```
<211> LENGTH: 18
<212> TYPE: PRT
<213> ORGANISM: Artificial Sequence
<220> FEATURE:
<223> OTHER INFORMATION: Ab 4122 CDRH2 variant 7

<400> SEQUENCE: 164

Ser Thr Tyr Ala Gly Arg Ser Gly Ser Thr Tyr Tyr Ala Asn Trp Val
1               5                   10                  15
Asn Thr

<210> SEQ ID NO 165
<211> LENGTH: 10
<212> TYPE: PRT
<213> ORGANISM: Artificial Sequence
<220> FEATURE:
<223> OTHER INFORMATION: Ab 4122 CDRH3

<400> SEQUENCE: 165

Gly Asn Ala Gly Val Ala Val Gly Ala Leu
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Ab 4122 CDRL1

<400> SEQUENCE: 166

Gln Ala Ser Gln Ser Ile Ser Asn Trp Leu Ala
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Ab 4122 CDRL2

<400> SEQUENCE: 167

Gln Ala Ser Lys Leu Ala Ser
1               5

<210> SEQ ID NO 168
<211> LENGTH: 13
<212> TYPE: PRT
<213> ORGANISM: Artificial Sequence
<220> FEATURE:
<223> OTHER INFORMATION: Ab 4122 CDRL3

<400> SEQUENCE: 168

Gln Ser Tyr Tyr Asp Ser Gly Ser Asn Val Phe Phe Ala
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Ab 4122 CDRL3 variant 1

<400> SEQUENCE: 169

Gln Ser Tyr Tyr Asp Ala Gly Ser Asn Val Phe Phe Ala
1               5                   10
```

```
<210> SEQ ID NO 170
<211> LENGTH: 13
<212> TYPE: PRT
<213> ORGANISM: Artificial Sequence
<220> FEATURE:
<223> OTHER INFORMATION: Ab 4122 CDRL3 variant 2

<400> SEQUENCE: 170

Gln Ser Tyr Tyr Asp Thr Gly Ser Asn Val Phe Phe Ala
1               5                   10

<210> SEQ ID NO 171
<211> LENGTH: 111
<212> TYPE: PRT
<213> ORGANISM: Artificial Sequence
<220> FEATURE:
<223> OTHER INFORMATION: Rabbit Ab 4122 VL region

<400> SEQUENCE: 171

Asp Ile Val Met Thr Gln Thr Pro Ala Ser Val Ser Glu Pro Val Gly
1               5                   10                  15

Gly Thr Val Thr Ile Met Cys Gln Ala Ser Gln Ser Ile Ser Asn Trp
            20                  25                  30

Leu Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Tyr Asp Ser Gly Ser
                85                  90                  95

Asn Val Phe Phe Ala Phe Gly Gly Gly Thr Lys Val Val Val Glu
            100                 105                 110

<210> SEQ ID NO 172
<211> LENGTH: 333
<212> TYPE: DNA
<213> ORGANISM: Artificial Sequence
<220> FEATURE:
<223> OTHER INFORMATION: Rabbit Ab 4122 VL region

<400> SEQUENCE: 172
gacattgtga tgacccagac tccagcctcc gtgtctgaac ctgtgggagg cacagtcacc      60
atcatgtgcc aggccagtca gagcattagc aattggttag cctggtatca acagaaacca    120
gggcagcctc ccaagctcct gatctaccag gcatccaaac tggcatctgg ggtcccatcg    180
cggttcaaag gcagtggatc tgggacagag tacactctca ccatcagcga cctggagtgt    240
gccgatgctg ccacttacta ctgtcaaagc tattatgata gtggtagtaa tgttttttt    300 gctttcggcg agggaccaa ggtggtggtc gaa                                  333

<210> SEQ ID NO 173
<211> LENGTH: 119
<212> TYPE: PRT
<213> ORGANISM: Artificial Sequence
<220> FEATURE:
<223> OTHER INFORMATION: Rabbit Ab 4122 VH region

<400> SEQUENCE: 173

Leu Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ala Gly Tyr
```

```
                20                  25                  30
Trp Ile Cys Trp Val Arg Gln Ala Pro Gly Lys Gly Leu Glu Trp Ile
         35                  40                  45
Ala Cys Thr Tyr Ala Gly Arg Ser Gly Ser Thr Tyr Tyr Ala Asn Trp
     50                  55                  60
Val Asn Gly Arg Phe Thr Ile Pro Lys Thr Ser Thr Thr Val Thr
 65                  70                  75                  80
Leu Gln Met Thr Ser Leu Ser Gly Ala Asp Thr Ala Ser Tyr Phe Cys
                 85                  90                  95
Ala Arg Gly Asn Ala Gly Val Ala Val Gly Ala Leu Trp Gly Pro Gly
            100                 105                 110
Thr Leu Val Thr Val Ser Ser
            115

<210> SEQ ID NO 174
<211> LENGTH: 357
<212> TYPE: DNA
<213> ORGANISM: Artificial Sequence
<220> FEATURE:
<223> OTHER INFORMATION: Rabbit Ab 4122 VH region

<400> SEQUENCE: 174
ctgtcgttgg aggagtccgg gggagacctg gtcaagcctg ggcatccct gacactcacc      60 tgcacagcct ctggattctc cttcagtgcc ggctattgga tatgttgggt ccgccaggct    120
ccagggaagg ggctggagtg gatcgcatgc acttatgctg gtcgtagtgg tagcacttac    180
tacgcgaact gggtgaatgg ccgattcacc atccccaaaa cctcgtcgac cacggtgact    240
ctgcaaatga ccagtctgtc aggcgcggac acggccagct atttctgtgc gagaggtaat    300
gctggtgttg ctgttggtgc cttgtgggggc ccaggcaccc tggtcaccgt ctcgagt      357

<210> SEQ ID NO 175
<211> LENGTH: 111
<212> TYPE: PRT
<213> ORGANISM: Artificial Sequence
<220> FEATURE:
<223> OTHER INFORMATION: 4122 gL1 V-region - IGKV1-5 framework

<400> SEQUENCE: 175

Asp Ile Gln Met Thr Gln Ser Pro Ser Thr Leu Ser Ala Ser Val Gly
 1               5                  10                  15
Asp Arg Val Thr Ile Thr Cys Gln Ala Ser Gln Ser Ile Ser Asn Trp
             20                  25                  30
Leu Ala Trp Tyr Gln Gln Lys Pro Gly Lys Ala Pro Lys Leu Leu Ile
         35                  40                  45
Tyr Gln Ala Ser Lys Leu Ala Ser Gly Val Pro Ser Arg Phe Ser Gly
     50                  55                  60
Ser Gly Ser Gly Thr Glu Tyr Thr Leu Thr Ile Ser Ser Leu Gln Pro
 65                  70                  75                  80
Asp Asp Phe Ala Thr Tyr Tyr Cys Gln Ser Tyr Tyr Asp Ser Gly Ser
                 85                  90                  95
Asn Val Phe Phe Ala Phe Gly Gly Gly Thr Lys Val Glu Ile Lys
            100                 105                 110

<210> SEQ ID NO 176
<211> LENGTH: 121
<212> TYPE: PRT
<213> ORGANISM: Artificial Sequence
<220> FEATURE:
```

<223> OTHER INFORMATION: 4122 gH6 V-region - IGHV3-7 framework

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Gly
            20                  25                  30

Tyr Trp Ile Cys Trp Val Arg Gln Ala Pro Gly Lys Gly Leu Glu Trp
        35                  40                  45

Ile Ala Cys Thr Tyr Ala Gly Arg Ser Gly Ser Thr Tyr Tyr Ala Asn
    50                  55                  60

Trp Val Asn Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Gly Asn Ala Gly Val Ala Val Gly Ala Leu Trp Gly
            100                 105                 110

Arg Gly Thr Leu Val Thr Val Ser Ser
        115                 120

<210> SEQ ID NO 177
<211> LENGTH: 121
<212> TYPE: PRT
<213> ORGANISM: Artificial Sequence
<220> FEATURE:
<223> OTHER INFORMATION: 4122 gH4 V-region - IGHV3-7 framework

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Gly
            20                  25                  30

Tyr Trp Ile Ser Trp Val Arg Gln Ala Pro Gly Lys Gly Leu Glu Trp
        35                  40                  45

Ile Ala Ser Thr Tyr Ala Gly Arg Ser Gly Ser Thr Tyr Tyr Ala Asn
    50                  55                  60

Trp Val Asn Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Gly Asn Ala Gly Val Ala Val Gly Ala Leu Trp Gly
            100                 105                 110

Arg Gly Thr Leu Val Thr Val Ser Ser
        115                 120

<210> SEQ ID NO 178
<211> LENGTH: 11
<212> TYPE: PRT
<213> ORGANISM: Artificial Sequence
<220> FEATURE:
<223> OTHER INFORMATION: Ab 4129 CDRH1

<400> SEQUENCE: 178

Gly Phe Ser Phe Ser Ala Gly Tyr Trp Ile Cys
1               5                   10

<210> SEQ ID NO 179
<211> LENGTH: 11
<212> TYPE: PRT

```
<213> ORGANISM: Artificial Sequence
<220> FEATURE:
<223> OTHER INFORMATION: Ab 4129 CDRH1 variant

<400> SEQUENCE: 179

Gly Phe Ser Phe Ser Ala Gly Tyr Trp Ile Ser
1               5                   10

<210> SEQ ID NO 180
<211> LENGTH: 18
<212> TYPE: PRT
<213> ORGANISM: Artificial Sequence
<220> FEATURE:
<223> OTHER INFORMATION: Ab 4129 CDRH2

<400> SEQUENCE: 180

Cys Ile Tyr Ala Gly Ser Ser Gly Ser Thr Tyr Tyr Ala Ser Trp Ala
1               5                   10                  15

Lys Gly

<210> SEQ ID NO 181
<211> LENGTH: 18
<212> TYPE: PRT
<213> ORGANISM: Artificial Sequence
<220> FEATURE:
<223> OTHER INFORMATION: Ab 4129 CDRH2 variant

<400> SEQUENCE: 181

Ser Ile Tyr Ala Gly Ser Ser Gly Ser Thr Tyr Tyr Ala Ser Trp Ala
1               5                   10                  15

Lys Gly

<210> SEQ ID NO 182
<211> LENGTH: 10
<212> TYPE: PRT
<213> ORGANISM: Artificial Sequence
<220> FEATURE:
<223> OTHER INFORMATION: Ab 4129 CDRH3

<400> SEQUENCE: 182

Gly Asn Ala Gly Val Ala Val Gly Ala Leu
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Ab 4129 CDRL1

<400> SEQUENCE: 183

Gln Ala Ser Gln Ser Ile Ser Ser Trp Leu Ser
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Ab 4129 CDRL2

<400> SEQUENCE: 184

Gly Ala Ser Asn Leu Ala Ser
1               5
```

```
<210> SEQ ID NO 185
<211> LENGTH: 13
<212> TYPE: PRT
<213> ORGANISM: Artificial Sequence
<220> FEATURE:
<223> OTHER INFORMATION: Ab 4129 CDRL3

<400> SEQUENCE: 185

Gln Ser Tyr Tyr Asp Ser Gly Ser Ser Val Phe Phe Asn
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Ab 4129 CDRL3 variant 1

<400> SEQUENCE: 186

Gln Ser Tyr Tyr Asp Ala Gly Ser Ser Val Phe Phe Asn
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Ab 4129 CDRL3 variant 2

<400> SEQUENCE: 187

Gln Ser Tyr Tyr Asp Thr Gly Ser Ser Val Phe Phe Asn
1               5                   10

<210> SEQ ID NO 188
<211> LENGTH: 111
<212> TYPE: PRT
<213> ORGANISM: Artificial Sequence
<220> FEATURE:
<223> OTHER INFORMATION: Rabbit Ab 4129 VL region

<400> SEQUENCE: 188

Asp Ile Val Met Thr Gln Thr Pro Ala Ser Val Glu Ala Ala Val Gly
1               5                   10                  15

Gly Thr Val Thr Ile Asn Cys Gln Ala Ser Gln Ser Ile Ser Ser Trp
            20                  25                  30

Leu Ser Trp Tyr Gln Gln Lys Pro Gly Gln Pro Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Gln Phe Ser Leu Thr Ile Ser Asp Leu Glu Cys
65                  70                  75                  80

Ala Asp Ala Ala Thr Tyr Tyr Cys Gln Ser Tyr Tyr Asp Ser Gly Ser
                85                  90                  95

Ser Val Phe Phe Asn Phe Gly Gly Gly Thr Lys Val Val Val Lys
            100                 105                 110

<210> SEQ ID NO 189
<211> LENGTH: 333
<212> TYPE: DNA
<213> ORGANISM: Artificial Sequence
<220> FEATURE:
<223> OTHER INFORMATION: Rabbit Ab 4129 VL region

<400> SEQUENCE: 189
```

-continued

```
gacattgtga tgacccagac tccagcctcc gtggaggcag ctgtgggagg cacagtcacc    60
atcaattgcc aagccagtca gagcattagc agttggttat cctggtatca gcagaaacca   120
gggcagcctc ccaagctcct gatctatggt gcatccaatc tggcatctgg ggtcccatca   180
cggttcagcg gcagtggatc tgggacacag ttcagtctca ccatcagcga cctggagtgt   240
gccgatgctg ccacttacta ctgtcaaagc tattatgata gtggtagtag tgttttttt    300 aatttcggcg agggaccaa ggtggtcgtc aaa                                 333
```

<210> SEQ ID NO 190
<211> LENGTH: 119
<212> TYPE: PRT
<213> ORGANISM: Artificial Sequence
<220> FEATURE:
<223> OTHER INFORMATION: Rabbit Ab 4129 VH region

<400> SEQUENCE: 190

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ala Gly Tyr
                20                  25                  30

Trp Ile Cys Trp Val Arg Gln Ala Pro Gly Lys Gly Leu Glu Trp Ile
            35                  40                  45

Ala Cys Ile Tyr Ala Gly Ser Ser Gly Ser Thr Tyr Tyr Ala Ser Trp
        50                  55                  60

Ala Lys Gly Arg Phe Thr Ile Pro Lys Thr Ser Ser Thr Val Thr
65                  70                  75                  80

Leu Gln Met Thr Ser Leu Thr Gly Ala Asp Thr Ala Thr Tyr Phe Cys
                85                  90                  95

Ala Arg Gly Asn Ala Gly Val Ala Val Gly Ala Leu Trp Gly Pro Gly
            100                 105                 110

Thr Leu Val Thr Val Ser Ser
        115

<210> SEQ ID NO 191
<211> LENGTH: 357
<212> TYPE: DNA
<213> ORGANISM: Artificial Sequence
<220> FEATURE:
<223> OTHER INFORMATION: Rabbit Ab 4129 VH region

<400> SEQUENCE: 191

```
cagtcgttgg aggagtccgg gggagacctg gttaagcctg ggcatccct gacactcacc     60 tgcacagcct ctggattctc cttcagtgcc ggctattgga tatgttgggt ccgccaggct   120
ccagggaagg gctggagtg gatcgcatgc atttatgctg gtagtagtgg tagcacttac   180
tacgcgagct gggcgaaagg ccgattcacc atccccaaaa cctcgtcgac cacggtgact   240
ctgcaaatga ccagtctgac aggcgcggac acggccacct atttctgtgc gagaggtaat   300
gctggtgttg ctgttggtgc cttgtggggc ccaggcaccc tcgtcaccgt ctcgagt      357
```

<210> SEQ ID NO 192
<211> LENGTH: 111
<212> TYPE: PRT
<213> ORGANISM: Artificial Sequence
<220> FEATURE:
<223> OTHER INFORMATION: 4129 gL3 V-region - IGKV1-5 framework

<400> SEQUENCE: 192

Asp Ile Gln Met Thr Gln Ser Pro Ser Thr Leu Ser Ala Ser Val Gly

-continued

```
                1               5              10                 15
Asp Arg Val Thr Ile Thr Cys Gln Ala Ser Gln Ser Ile Ser Ser Trp
                        20                  25                 30

Leu Ser Trp Tyr Gln Gln Lys Pro Gly Lys Ala Pro Lys Leu Leu Ile
            35                  40                  45

Tyr Gly Ala Ser Asn Leu Ala Ser Gly Val Pro Ser Arg Phe Ser Gly
        50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Ser Tyr Tyr Asp Ser Gly Ser
                85                  90                  95

Ser Val Phe Phe Asn Phe Gly Gly Gly Thr Lys Val Glu Ile Lys
                100                 105                 110
```

<210> SEQ ID NO 193
<211> LENGTH: 121
<212> TYPE: PRT
<213> ORGANISM: Artificial Sequence
<220> FEATURE:
<223> OTHER INFORMATION: 4129 gH1 V-region - IGHV3-7 framework

<400> SEQUENCE: 193

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Ser Phe Ser Ala Gly
            20                  25                  30

Tyr Trp Ile Cys Trp Val Arg Gln Ala Pro Gly Lys Gly Leu Glu Trp
            35                  40                  45

Ile Ala Cys Ile Tyr Ala Gly Ser Ser Gly Ser Thr Tyr Tyr Ala Ser
        50                  55                  60

Trp Ala Lys Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Gly Asn Ala Gly Val Ala Val Gly Ala Leu Trp Gly
                100                 105                 110

Arg Gly Thr Leu Val Thr Val Ser Ser
        115                 120
```

<210> SEQ ID NO 194
<211> LENGTH: 121
<212> TYPE: PRT
<213> ORGANISM: Artificial Sequence
<220> FEATURE:
<223> OTHER INFORMATION: 4129 gH4 V-region - IGHV3-7 framework

<400> SEQUENCE: 194

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Ser Phe Ser Ala Gly
            20                  25                  30

Tyr Trp Ile Ser Trp Val Arg Gln Ala Pro Gly Lys Gly Leu Glu Trp
            35                  40                  45

Ile Ala Ser Ile Tyr Ala Gly Ser Ser Gly Ser Thr Tyr Tyr Ala Ser
        50                  55                  60

Trp Ala Lys Gly Arg Phe Thr Ile Ser Lys Asp Ser Ala Lys Thr Ser
65                  70                  75                  80
```

Val Tyr Leu Gln Met Asn Ser Leu Arg Ala Glu Asp Thr Ala Val Tyr
                85                  90                  95

Tyr Cys Ala Arg Gly Asn Ala Gly Val Ala Val Gly Ala Leu Trp Gly
            100                 105                 110

Arg Gly Thr Leu Val Thr Val Ser Ser
        115                 120

<210> SEQ ID NO 195
<211> LENGTH: 11
<212> TYPE: PRT
<213> ORGANISM: Artificial Sequence
<220> FEATURE:
<223> OTHER INFORMATION: Ab 4131 CDRH1

<400> SEQUENCE: 195

Gly Val Ser Phe Ser Ser Ser Tyr Trp Ile Tyr
1               5                   10

<210> SEQ ID NO 196
<211> LENGTH: 18
<212> TYPE: PRT
<213> ORGANISM: Artificial Sequence
<220> FEATURE:
<223> OTHER INFORMATION: Ab 4131 CDRH2

<400> SEQUENCE: 196

Cys Ile Tyr Thr Gly Ser Ser Gly Ser Thr Tyr Tyr Ala Ser Trp Ala
1               5                   10                  15

Lys Gly

<210> SEQ ID NO 197
<211> LENGTH: 18
<212> TYPE: PRT
<213> ORGANISM: Artificial Sequence
<220> FEATURE:
<223> OTHER INFORMATION: Ab 4131 CDRH2 variant

<400> SEQUENCE: 197

Ser Ile Tyr Thr Gly Ser Ser Gly Ser Thr Tyr Tyr Ala Ser Trp Ala
1               5                   10                  15

Lys Gly

<210> SEQ ID NO 198
<211> LENGTH: 10
<212> TYPE: PRT
<213> ORGANISM: Artificial Sequence
<220> FEATURE:
<223> OTHER INFORMATION: Ab 4131 CDRH3

<400> SEQUENCE: 198

Ala Ser Ala Trp Thr Tyr Gly Met Asp Leu
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Ab 4131 CDRL1

<400> SEQUENCE: 199

Gln Ala Ser Gln Ser Phe Tyr Asn Leu Leu Ala
1               5                   10

```
<210> SEQ ID NO 200
<211> LENGTH: 7
<212> TYPE: PRT
<213> ORGANISM: Artificial Sequence
<220> FEATURE:
<223> OTHER INFORMATION: Ab 4131 CDRL2

<400> SEQUENCE: 200

Asp Ala Ser Asp Leu Ala Ser
1               5

<210> SEQ ID NO 201
<211> LENGTH: 9
<212> TYPE: PRT
<213> ORGANISM: Artificial Sequence
<220> FEATURE:
<223> OTHER INFORMATION: Ab 4131 CDRL3

<400> SEQUENCE: 201

Gln Ser Ala Asp Gly Ser Ser Tyr Ala
1               5

<210> SEQ ID NO 202
<211> LENGTH: 9
<212> TYPE: PRT
<213> ORGANISM: Artificial Sequence
<220> FEATURE:
<223> OTHER INFORMATION: Ab 4131 CDRL3 variant 1

<400> SEQUENCE: 202

Gln Ser Ala Asp Ser Ser Ser Tyr Ala
1               5

<210> SEQ ID NO 203
<211> LENGTH: 9
<212> TYPE: PRT
<213> ORGANISM: Artificial Sequence
<220> FEATURE:
<223> OTHER INFORMATION: Ab 4131 CDRL3 variant 2

<400> SEQUENCE: 203

Gln Ser Ala Asp Ala Ser Ser Tyr Ala
1               5

<210> SEQ ID NO 204
<211> LENGTH: 9
<212> TYPE: PRT
<213> ORGANISM: Artificial Sequence
<220> FEATURE:
<223> OTHER INFORMATION: Ab 4131 CDRL3 variant 3

<400> SEQUENCE: 204

Gln Ser Ala Asp Thr Ser Ser Tyr Ala
1               5

<210> SEQ ID NO 205
<211> LENGTH: 107
<212> TYPE: PRT
<213> ORGANISM: Artificial Sequence
<220> FEATURE:
<223> OTHER INFORMATION: Rabbit Ab 4131 VL region

<400> SEQUENCE: 205

Asp Ile Val Met Thr Gln Thr Pro Ala Ser Val Ser Glu Pro Val Gly
1               5                   10                  15

Gly Ser Val Thr Ile Lys Cys Gln Ala Ser Gln Ser Phe Tyr Asn Leu
            20                  25                  30
```

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Lys Gly
 50                  55                  60

Ser Gly Ser Gly Thr Asp Phe Thr Leu Thr Ile Ser Asp Leu Glu Cys
 65                  70                  75                  80

Ala Asp Ala Ala Ala Tyr Tyr Cys Gln Ser Ala Asp Gly Ser Ser Tyr
                 85                  90                  95

Ala Phe Gly Gly Gly Thr Glu Val Val Val Lys
            100                 105

<210> SEQ ID NO 206
<211> LENGTH: 321
<212> TYPE: DNA
<213> ORGANISM: Artificial Sequence
<220> FEATURE:
<223> OTHER INFORMATION: Rabbit Ab 4131 VL region

<400> SEQUENCE: 206
gacattgtga tgacccagac tccagcctcc gtgtctgaac ctgtgggagg ctcagtcacc    60
atcaagtgcc aggccagtca gagcttttac aacctcttag cctggtatca gcagaaacca   120
gggcagcctc ccaaactcct gatctatgat gcatccgatc tggcatctgg ggtcccatcg   180
cggttcaaag gcagtggatc tgggactgat ttcactctca ccatcagcga cctggagtgt   240
gccgatgctg ccgcttacta ctgtcaaagt gctgatggta gtagttacgc tttcggcgga   300
gggaccgagg tggtcgtcaa a                                             321

<210> SEQ ID NO 207
<211> LENGTH: 120
<212> TYPE: PRT
<213> ORGANISM: Artificial Sequence
<220> FEATURE:
<223> OTHER INFORMATION: Rabbit Ab 4131 VH region

<400> SEQUENCE: 207

Gln Glu Gln Leu Glu Glu Ser Gly Gly Gly Leu Val Lys Pro Glu Gly
 1               5                   10                  15

Ser Leu Thr Leu Thr Cys Thr Ala Ser Gly Val Ser Phe Ser Ser Ser
             20                  25                  30

Tyr Trp Ile Tyr Trp Val Arg Gln Ala Pro Gly Lys Gly Leu Glu Trp
         35                  40                  45

Ile Ala Cys Ile Tyr Thr Gly Ser Ser Gly Ser Thr Tyr Tyr Ala Ser
 50                  55                  60

Trp Ala Lys Gly Arg Phe Thr Val Ser Glu Thr Ser Ser Thr Thr Val
 65                  70                  75                  80

Thr Leu Gln Met Thr Ser Leu Thr Ala Ala Asp Thr Ala Thr Tyr Phe
                 85                  90                  95

Cys Ala Arg Ala Ser Ala Trp Thr Tyr Gly Met Asp Leu Trp Gly Pro
            100                 105                 110

Gly Thr Leu Val Thr Val Ser Ser
        115                 120

<210> SEQ ID NO 208
<211> LENGTH: 360
<212> TYPE: DNA
<213> ORGANISM: Artificial Sequence
<220> FEATURE:
<223> OTHER INFORMATION: Rabbit Ab 4131 VH region

<400> SEQUENCE: 208

```
caggagcaat tggaggagtc cgggggaggc ctggtcaagc ctgagggatc cctgacactc    60
acctgcacag cctctggagt ctccttcagt agcagctatt ggatatactg ggtccgccag   120
gctccaggga aggggctgga gtggatcgca tgcatttata ctggtagtag tggtagcact   180
tactacgcga gctgggcgaa aggccgattc accgtctccg aaacctcgtc gaccacggtg   240
actctgcaaa tgaccagtct gacagccgcg gacacggcca cctatttctg tgcgagagca   300
agcgcttgga cctacggcat ggacctctgg ggcccgggca ccctcgtcac cgtctcgagt   360
```

<210> SEQ ID NO 209
<211> LENGTH: 107
<212> TYPE: PRT
<213> ORGANISM: Artificial Sequence
<220> FEATURE:
<223> OTHER INFORMATION: 4131 gL8 V-region - IGKV1-12 framework

<400> SEQUENCE: 209

Asp Ile Val Met Thr Gln Ser Pro Ser Ser Val Ser Ala Ser Val Gly
1               5                   10                  15

Asp Arg Val Thr Ile Thr Cys Gln Ala Ser Gln Ser Phe Tyr Asn Leu
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ala Asp Gly Ser Ser Tyr
                85                  90                  95

Ala Phe Gly Gly Gly Thr Lys Val Glu Ile Lys
            100                 105

<210> SEQ ID NO 210
<211> LENGTH: 107
<212> TYPE: PRT
<213> ORGANISM: Artificial Sequence
<220> FEATURE:
<223> OTHER INFORMATION: 4131 gL3 V-region - IGKV1-12 framework

<400> SEQUENCE: 210

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Ser Phe Tyr Asn Leu
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ala Asp Gly Ser Ser Tyr
                85                  90                  95

Ala Phe Gly Gly Gly Thr Lys Val Glu Ile Lys
            100                 105

<210> SEQ ID NO 211

```
<211> LENGTH: 121
<212> TYPE: PRT
<213> ORGANISM: Artificial Sequence
<220> FEATURE:
<223> OTHER INFORMATION: 4131 gH5 V-region - IGHV3-7 framework

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Ser Phe Ser Ser Ser
            20                  25                  30

Tyr Trp Ile Tyr Trp Val Arg Gln Ala Pro Gly Lys Gly Leu Glu Trp
        35                  40                  45

Ile Ala Cys Ile Tyr Thr Gly Ser Ser Gly Ser Thr Tyr Tyr Ala Ser
50                  55                  60

Trp Ala Lys Gly Arg Phe Thr Val Ser Glu Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Ala Ser Ala Trp Thr Tyr Gly Met Asp Leu Trp Gly
            100                 105                 110

Arg Gly Thr Leu Val Thr Val Ser Ser
        115                 120

<210> SEQ ID NO 212
<211> LENGTH: 11
<212> TYPE: PRT
<213> ORGANISM: Artificial Sequence
<220> FEATURE:
<223> OTHER INFORMATION: Ab 4133 CDRH1

<400> SEQUENCE: 212

Gly Phe Ser Phe Ser Gly Asn Tyr Tyr Met Cys
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Ab 4133 CDRH1 variant

<400> SEQUENCE: 213

Gly Phe Ser Phe Ser Gly Asn Tyr Tyr Met Ser
1               5                   10

<210> SEQ ID NO 214
<211> LENGTH: 18
<212> TYPE: PRT
<213> ORGANISM: Artificial Sequence
<220> FEATURE:
<223> OTHER INFORMATION: Ab 4133 CDRH2

<400> SEQUENCE: 214

Cys Leu Tyr Thr Gly Ser Ser Gly Ser Thr Tyr Tyr Ala Ser Trp Ala
1               5                   10                  15

Lys Gly

<210> SEQ ID NO 215
<211> LENGTH: 18
<212> TYPE: PRT
<213> ORGANISM: Artificial Sequence
<220> FEATURE:
```

```
<223> OTHER INFORMATION: Ab 4133 CDRH2 variant

<400> SEQUENCE: 215

Ser Leu Tyr Thr Gly Ser Ser Gly Ser Thr Tyr Tyr Ala Ser Trp Ala
1               5                   10                  15
Lys Gly

<210> SEQ ID NO 216
<211> LENGTH: 12
<212> TYPE: PRT
<213> ORGANISM: Artificial Sequence
<220> FEATURE:
<223> OTHER INFORMATION: Ab 4133 CDRH3

<400> SEQUENCE: 216

Asp Leu Gly Tyr Glu Ile Asp Gly Tyr Gly Gly Leu
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Ab 4133 CDRH3 variant 1

<400> SEQUENCE: 217

Asp Leu Gly Tyr Glu Ile Asp Ser Tyr Gly Gly Leu
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Ab 4133 CDRH3 variant 2

<400> SEQUENCE: 218

Asp Leu Gly Tyr Glu Ile Asp Ala Tyr Gly Gly Leu
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Ab 4133 CDRH3 variant 3

<400> SEQUENCE: 219

Asp Leu Gly Tyr Glu Ile Asp Thr Tyr Gly Gly Leu
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Ab 4133 CDRL1

<400> SEQUENCE: 220

Gln Ala Ser Gln Ser Val Tyr Asn Asn Asn Leu Ser
1               5                   10

<210> SEQ ID NO 221
<211> LENGTH: 13
<212> TYPE: PRT
<213> ORGANISM: Artificial Sequence
```

<220> FEATURE:
<223> OTHER INFORMATION: Ab 4133 CDRL1 variant 1

<400> SEQUENCE: 221

Gln Ala Ser Gln Ser Val Tyr Asn Asn Asn Ser Leu Ser
1               5                   10

<210> SEQ ID NO 222
<211> LENGTH: 13
<212> TYPE: PRT
<213> ORGANISM: Artificial Sequence
<220> FEATURE:
<223> OTHER INFORMATION: Ab 4133 CDRL1 variant 2

<400> SEQUENCE: 222

Gln Ala Ser Gln Ser Val Tyr Asn Asn Asn Gln Leu Ser
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Ab 4133 CDRL1 variant 3

<400> SEQUENCE: 223

Gln Ala Ser Gln Ser Val Tyr Asn Asn Asn Asn Leu Ala
1               5                   10

<210> SEQ ID NO 224
<211> LENGTH: 7
<212> TYPE: PRT
<213> ORGANISM: Artificial Sequence
<220> FEATURE:
<223> OTHER INFORMATION: Ab 4133 CDRL2

<400> SEQUENCE: 224

Asp Ala Ser Lys Leu Ala Ser
1               5

<210> SEQ ID NO 225
<211> LENGTH: 12
<212> TYPE: PRT
<213> ORGANISM: Artificial Sequence
<220> FEATURE:
<223> OTHER INFORMATION: Ab 4133 CDRL3

<400> SEQUENCE: 225

Leu Gly Gly Tyr Tyr Ser Ser Gly Trp Tyr Phe Ala
1               5                   10

<210> SEQ ID NO 226
<211> LENGTH: 112
<212> TYPE: PRT
<213> ORGANISM: Artificial Sequence
<220> FEATURE:
<223> OTHER INFORMATION: Rabbit Ab 4133 VL region

<400> SEQUENCE: 226

Ala Gln Val Leu Thr Gln Thr Pro Ser Pro Val Ser Ala Val Val Gly
1               5                   10                  15

Gly Thr Val Ser Ile Ser Cys Gln Ala Ser Gln Ser Val Tyr Asn Asn
            20                  25                  30

Asn Asn Leu Ser Trp Tyr Gln Gln Lys Pro Gly Gln Pro Pro Lys Leu
        35                  40                  45

```
Leu Ile Tyr Asp Ala Ser Lys Leu Ala Ser Gly Val Pro Ser Arg Phe
    50                  55                  60
Lys Gly Ser Gly Ser Gly Thr Gln Phe Thr Leu Thr Ile Ser Gly Val
 65                  70                  75                  80
Gln Cys Asp Asp Ala Ala Thr Tyr Tyr Cys Leu Gly Gly Tyr Tyr Ser
                 85                  90                  95
Ser Gly Trp Tyr Phe Ala Phe Gly Gly Gly Thr Lys Val Val Val Lys
            100                 105                 110
```

<210> SEQ ID NO 227
<211> LENGTH: 336
<212> TYPE: DNA
<213> ORGANISM: Artificial Sequence
<220> FEATURE:
<223> OTHER INFORMATION: Rabbit Ab 4133 VL region

<400> SEQUENCE: 227

```
gcgcaagtgc tgacccagac tccatctccc gtgtctgcag ttgtgggagg cacagtcagc      60
atcagttgcc aggccagtca gagtgtttat aataacaaca acttatcctg gtatcagcag     120
aaaccagggc agcctcccaa gctcttgatc tacgatgcat ccaaattggc atctggggtc     180
ccatcccggt tcaaaggcag tggatctggg acacagttca ctctcaccat cagcggcgtg     240
cagtgtgacg atgctgccac ttactactgt ctaggcggtt attatagtag tggttggtat     300
tttgctttcg gcggagggac caaggtggtg gtcaaa                               336
```

<210> SEQ ID NO 228
<211> LENGTH: 122
<212> TYPE: PRT
<213> ORGANISM: Artificial Sequence
<220> FEATURE:
<223> OTHER INFORMATION: Rabbit Ab 4133 VH region

<400> SEQUENCE: 228

```
Gln Glu Gln Leu Val Glu Ser Gly Gly Gly Leu Val Gln Pro Glu Gly
  1               5                  10                  15
Ser Leu Thr Leu Thr Cys Thr Ala Ser Gly Phe Ser Phe Ser Gly Asn
                 20                  25                  30
Tyr Tyr Met Cys Trp Val Arg Gln Ala Pro Gly Lys Gly Leu Glu Trp
             35                  40                  45
Ile Gly Cys Leu Tyr Thr Gly Ser Ser Gly Ser Thr Tyr Tyr Ala Ser
         50                  55                  60
Trp Ala Lys Gly Arg Phe Thr Ile Ser Lys Thr Ser Ser Thr Thr Val
 65                  70                  75                  80
Thr Leu Gln Met Thr Ser Leu Thr Ala Ala Asp Thr Ala Thr Tyr Phe
                 85                  90                  95
Cys Ala Arg Asp Leu Gly Tyr Glu Ile Asp Gly Tyr Gly Gly Leu Trp
            100                 105                 110
Gly Gln Gly Thr Leu Val Thr Val Ser Ser
        115                 120
```

<210> SEQ ID NO 229
<211> LENGTH: 366
<212> TYPE: DNA
<213> ORGANISM: Artificial Sequence
<220> FEATURE:
<223> OTHER INFORMATION: Rabbit Ab 4133 VH region

<400> SEQUENCE: 229

```
caggagcagc tggtggagtc cggggggaggc ctggtccagc ctgagggatc cctgacacta     60
```

```
acctgcacag cttctggatt ctccttcagt ggcaactact acatgtgctg ggtccgccag    120
gctccaggga aggggctgga gtggatcgga tgcctttata ctggtagtag tggtagcaca    180
tattacgcga gctgggcgaa aggccgattc accatctcca aaacctcgtc gaccacggtg    240
actctgcaaa tgaccagtct gacagccgcg gacacggcca cctatttctg tgcgagagat    300
ctaggttatg aaattgatgg ttatgggggc ttgtggggcc agggcaccct cgtcaccgtc    360
tcgagt                                                              366
```

<210> SEQ ID NO 230
<211> LENGTH: 112
<212> TYPE: PRT
<213> ORGANISM: Artificial Sequence
<220> FEATURE:
<223> OTHER INFORMATION: 4133 gL7 V-region - IGKV1D-13 framework

<400> SEQUENCE: 230

```
Ala Gln Val Leu Thr Gln Ser Pro Ser Ser Leu Ser Ala Ser Val Gly
1               5                   10                  15

Asp Arg Val Thr Ile Thr Cys Gln Ala Ser Gln Ser Val Tyr Asn Asn
            20                  25                  30

Asn Asn Leu Ser Trp Tyr Gln Gln Lys Pro Gly Lys Ala Pro Lys Leu
        35                  40                  45

Leu Ile Tyr Asp Ala Ser Lys Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Leu Gly Gly Tyr Tyr Ser
                85                  90                  95

Ser Gly Trp Tyr Phe Ala Phe Gly Gly Gly Thr Lys Val Glu Ile Lys
            100                 105                 110
```

<210> SEQ ID NO 231
<211> LENGTH: 112
<212> TYPE: PRT
<213> ORGANISM: Artificial Sequence
<220> FEATURE:
<223> OTHER INFORMATION: 4133 gL1 V-region - IGKV1D-13 framework

<400> SEQUENCE: 231

```
Ala Gln Val Leu Thr Gln Ser Pro Ser Ser Leu Ser Ala Ser Val Gly
1               5                   10                  15

Asp Arg Val Thr Ile Thr Cys Gln Ala Ser Gln Ser Val Tyr Asn Asn
            20                  25                  30

Asn Asn Leu Ala Trp Tyr Gln Gln Lys Pro Gly Lys Ala Pro Lys Leu
        35                  40                  45

Leu Ile Tyr Asp Ala Ser Lys Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Leu Gly Gly Tyr Tyr Ser
                85                  90                  95

Ser Gly Trp Tyr Phe Ala Phe Gly Gly Gly Thr Lys Val Glu Ile Lys
            100                 105                 110
```

<210> SEQ ID NO 232
<211> LENGTH: 123
<212> TYPE: PRT

<213> ORGANISM: Artificial Sequence
<220> FEATURE:
<223> OTHER INFORMATION: 4133 gH1 V-region - IGHV3-21 framework

<400> SEQUENCE: 232

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Gly Asn
            20                  25                  30

Tyr Tyr Met Cys Trp Val Arg Gln Ala Pro Gly Lys Gly Leu Glu Trp
        35                  40                  45

Ile Gly Cys Leu Tyr Thr Gly Ser Ser Gly Ser Thr Tyr Tyr Ala Ser
    50                  55                  60

Trp Ala Lys Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Asp Leu Gly Tyr Glu Ile Asp Gly Tyr Gly Gly Leu
            100                 105                 110

Trp Gly Gln Gly Thr Leu Val Thr Val Ser Ser
        115                 120

<210> SEQ ID NO 233
<211> LENGTH: 366
<212> TYPE: DNA
<213> ORGANISM: Artificial Sequence
<220> FEATURE:
<223> OTHER INFORMATION: Rabbit Ab 4127 VH region

<400> SEQUENCE: 233
cagcagctgg aggagtccgg gggagacctg gtcaagcctg ggcatccct gacactcacc      60
tgcacagcct ctggattctc cttcagtaat ctctattaca tgtgttgggt ccgccaggct    120
ccagggaagg gctggagtt gatcggatgc attgatatta gcagtagtgg tagcacttac    180
tacgcgagct gggcgaaagg ccgattcacc atctccaaaa cctcgtcgac cacggtgact    240
ctgcagatga ccagtctgac agccgcggac acggccacct atttctgtgc gagagattac    300
tattctagtg actggggtgt tagatttaac ttgtgggggcc agggcacccct cgtcaccgtc    360
tcgagt                                                                366

<210> SEQ ID NO 234
<211> LENGTH: 10
<212> TYPE: PRT
<213> ORGANISM: Artificial Sequence
<220> FEATURE:
<223> OTHER INFORMATION: CDRH1 dAbH1

<400> SEQUENCE: 234

Gly Ile Asp Leu Ser Asn Tyr Ala Ile Asn
1               5                   10

<210> SEQ ID NO 235
<211> LENGTH: 16
<212> TYPE: PRT
<213> ORGANISM: Artificial Sequence
<220> FEATURE:
<223> OTHER INFORMATION: CDRH2 dAbH1

<400> SEQUENCE: 235

Ile Ile Trp Ala Ser Gly Thr Thr Phe Tyr Ala Thr Trp Ala Lys Gly
1               5                   10                  15

<210> SEQ ID NO 236
<211> LENGTH: 13
<212> TYPE: PRT
<213> ORGANISM: Artificial Sequence
<220> FEATURE:
<223> OTHER INFORMATION: CDRH3 dAbH1

<400> SEQUENCE: 236

Thr Val Pro Gly Tyr Ser Thr Ala Pro Tyr Phe Asp Leu
1               5                   10

<210> SEQ ID NO 237
<211> LENGTH: 12
<212> TYPE: PRT
<213> ORGANISM: Artificial Sequence
<220> FEATURE:
<223> OTHER INFORMATION: CDRL1 dAbL1

<400> SEQUENCE: 237

Gln Ser Ser Pro Ser Val Trp Ser Asn Phe Leu Ser
1               5                   10

<210> SEQ ID NO 238
<211> LENGTH: 7
<212> TYPE: PRT
<213> ORGANISM: Artificial Sequence
<220> FEATURE:
<223> OTHER INFORMATION: CDRL2 dAbL1

<400> SEQUENCE: 238

Glu Ala Ser Lys Leu Thr Ser
1               5

<210> SEQ ID NO 239
<211> LENGTH: 11
<212> TYPE: PRT
<213> ORGANISM: Artificial Sequence
<220> FEATURE:
<223> OTHER INFORMATION: CDRL3 dAbL1

<400> SEQUENCE: 239

Gly Gly Gly Tyr Ser Ser Ile Ser Asp Thr Thr
1               5                   10

<210> SEQ ID NO 240
<211> LENGTH: 121
<212> TYPE: PRT
<213> ORGANISM: Artificial Sequence
<220> FEATURE:
<223> OTHER INFORMATION: Heavy chain variable domain of anti-albumin
      antibody (no ds)

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

-continued

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 241
<211> LENGTH: 121
<212> TYPE: PRT
<213> ORGANISM: Artificial Sequence
<220> FEATURE:
<223> OTHER INFORMATION: Heavy chain variable domain of anti-albumin
      antibody (ds)

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 242
<211> LENGTH: 112
<212> TYPE: PRT
<213> ORGANISM: Artificial Sequence
<220> FEATURE:
<223> OTHER INFORMATION: Light chain variable domain of anti-albumin
      antibody (no ds)

<400> SEQUENCE: 242

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110

<210> SEQ ID NO 243
<211> LENGTH: 112

<212> TYPE: PRT
<213> ORGANISM: Artificial Sequence
<220> FEATURE:
<223> OTHER INFORMATION: Light chain variable domain of anti-albumin
      antibody (ds)

<400> SEQUENCE: 243

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Cys Gly Thr Lys Val Glu Ile Lys Arg Thr
                100                 105                 110

<210> SEQ ID NO 244
<211> LENGTH: 847
<212> TYPE: PRT
<213> ORGANISM: Artificial Sequence
<220> FEATURE:
<223> OTHER INFORMATION: Human CD22

<400> SEQUENCE: 244

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala

-continued

```
            210                 215                 220
Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                    245                 250                 255

Glu Gly Asp Ser Val Thr Met Thr Cys Glu Val Ser Ser Asn Pro
                260                 265                 270

Glu Tyr Thr Thr Val Ser Trp Leu Lys Asp Gly Thr Ser Leu Lys Lys
                275                 280                 285

Gln Asn Thr Phe Thr Leu Asn Leu Arg Glu Val Thr Lys Asp Gln Ser
            290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                    325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
            355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                    405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
                435                 440                 445

Pro Ser Val Thr Arg Tyr Glu Trp Lys Pro His Gly Ala Trp Glu Glu
            450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
                500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
            530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu
            595                 600                 605

Gly Lys Ser Ala Thr Leu Thr Cys Glu Ser Asp Ala Asn Pro Pro Val
            610                 615                 620

Ser His Tyr Thr Trp Phe Asp Trp Asn Asn Gln Ser Leu Pro Tyr His
625                 630                 635                 640
```

-continued

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845

<210> SEQ ID NO 245
<211> LENGTH: 226
<212> TYPE: PRT
<213> ORGANISM: Artificial Sequence
<220> FEATURE:
<223> OTHER INFORMATION: Human CD79a

<400> SEQUENCE: 245

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

```
Thr Leu Leu Leu Phe Arg Lys Arg Trp Gln Asn Glu Lys Leu Gly Leu
            165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Asp Ile Ser Arg Gly Leu Gln Gly
            195                 200                 205

Thr Tyr Gln Asp Val Gly Ser Leu Asn Ile Gly Asp Val Gln Leu Glu
            210                 215                 220

Lys Pro
225

<210> SEQ ID NO 246
<211> LENGTH: 126
<212> TYPE: PRT
<213> ORGANISM: Artificial Sequence
<220> FEATURE:
<223> OTHER INFORMATION: 4120 gH2 V-region - IGHV3-33 framework

<400> SEQUENCE: 246

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Ser Ser Ser
            20                  25                  30

Tyr Tyr Met Ser Trp Val Arg Gln Ala Pro Gly Lys Gly Leu Glu Trp
        35                  40                  45

Ile Ala Ser Ile Tyr Thr Gly Ser Ser Gly Asp Thr Tyr Tyr Ala Ser
    50                  55                  60

Trp Ala Lys Gly Arg Phe Thr Ile Ser Lys Asp Ser Ser Lys Thr Thr
65                  70                  75                  80

Val Tyr Leu Gln Met Asn Ser Leu Arg Ala Glu Asp Thr Ala Val Tyr
                85                  90                  95

Tyr Cys Ala Arg Gly Pro Tyr Val Gly Tyr Gly Tyr Asp Leu Gln Tyr
            100                 105                 110

Leu Tyr Leu Trp Gly Gln Gly Thr Leu Val Thr Val Ser Ser
        115                 120                 125

<210> SEQ ID NO 247
<211> LENGTH: 126
<212> TYPE: PRT
<213> ORGANISM: Artificial Sequence
<220> FEATURE:
<223> OTHER INFORMATION: 4120 gH5 V-region - IGHV4-38-2 framework

<400> SEQUENCE: 247

Glu Val Gln Leu Gln Glu Ser Gly Pro Gly Leu Val Lys Pro Ser Glu
1               5                   10                  15

Thr Leu Ser Leu Thr Cys Ala Ala Ser Gly Phe Ser Phe Ser Ser Ser
            20                  25                  30

Tyr Tyr Met Ser Trp Val Arg Gln Pro Pro Gly Lys Gly Leu Glu Trp
        35                  40                  45

Ile Ala Ser Ile Tyr Thr Gly Ser Ser Gly Asp Thr Tyr Tyr Ala Ser
    50                  55                  60

Trp Ala Lys Gly Arg Phe Thr Ile Ser Lys Asp Ser Ser Lys Thr Gln
65                  70                  75                  80

Val Ser Leu Lys Leu Ser Ser Val Thr Ala Ala Asp Thr Ala Val Tyr
                85                  90                  95

Tyr Cys Ala Arg Gly Pro Tyr Val Gly Tyr Gly Tyr Asp Leu Gln Tyr
```

Leu Tyr Leu Trp Gly Gln Gly Thr Leu Val Thr Val Ser Ser
          115                 120                 125

<210> SEQ ID NO 248
<211> LENGTH: 126
<212> TYPE: PRT
<213> ORGANISM: Artificial Sequence
<220> FEATURE:
<223> OTHER INFORMATION: 4120 gH4 V-region - IGHV4-38-2 framework

<400> SEQUENCE: 248

Glu Val Gln Leu Gln Glu Ser Gly Pro Gly Leu Val Lys Pro Ser Glu
1               5                   10                  15

Thr Leu Ser Leu Thr Cys Ala Ala Ser Gly Phe Ser Phe Ser Ser Ser
            20                  25                  30

Tyr Tyr Met Cys Trp Val Arg Gln Pro Pro Gly Lys Gly Leu Glu Trp
        35                  40                  45

Ile Ala Cys Ile Tyr Thr Gly Ser Ser Gly Asp Thr Tyr Tyr Ala Ser
    50                  55                  60

Trp Ala Lys Gly Arg Phe Thr Ile Ser Lys Asp Ser Ser Lys Thr Gln
65                  70                  75                  80

Val Ser Leu Lys Leu Ser Ser Val Thr Ala Ala Asp Thr Ala Val Tyr
                85                  90                  95

Tyr Cys Ala Arg Gly Pro Tyr Val Gly Tyr Gly Tyr Asp Leu Gln Tyr
            100                 105                 110

Leu Tyr Leu Trp Gly Gln Gly Thr Leu Val Thr Val Ser Ser
        115                 120                 125

<210> SEQ ID NO 249
<211> LENGTH: 112
<212> TYPE: PRT
<213> ORGANISM: Artificial Sequence
<220> FEATURE:
<223> OTHER INFORMATION: Rabbit Ab 4126 VL region

<400> SEQUENCE: 249

Asp Ile Val Met Thr Gln Thr Pro Ala Ser Val Glu Ala Ala Val Gly
1               5                   10                  15

Gly Thr Val Thr Ile Lys Cys Gln Ala Ser Gln Asn Ile Gly Ser Gly
            20                  25                  30

Leu Ala Trp Tyr Gln Gln Lys Pro Gly Gln Pro Pro Lys Leu Leu Ile
        35                  40                  45

Tyr Tyr Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser His Asp Tyr Ser Ser Val
                85                  90                  95

Arg Ser Tyr Gly Asn Ala Phe Gly Gly Gly Thr Glu Val Val Val Lys
            100                 105                 110

<210> SEQ ID NO 250
<211> LENGTH: 113
<212> TYPE: PRT
<213> ORGANISM: Artificial Sequence
<220> FEATURE:
<223> OTHER INFORMATION: 4447 gL2 V-region - IGKV1D-13 framework

<400> SEQUENCE: 250

```
Ala Gln Val Leu Thr Gln Ser Pro Ser Ser Leu Ser Ala Ser Val Gly
1               5                   10                  15

Asp Arg Val Thr Ile Thr Cys Gln Ala Ser Gln Ser Val Val Ser Gly
                20                  25                  30

Asn Tyr Leu Ala Trp Leu Gln Gln Lys Pro Gly Lys Ala Pro Lys Gln
            35                  40                  45

Leu Ile His Ser Ala Ser Thr Leu Ala Ser Gly Val Pro Ser Arg Phe
        50                  55                  60

Ser Gly Ser Gly Ser Gly Thr Gln Phe Thr Leu Thr Ile Ser Ser Leu
65              70                  75                  80

Gln Pro Glu Asp Phe Ala Thr Tyr Tyr Cys Leu Gly Glu Phe Ser Ser
                85                  90                  95

Ser Ser His Asp Ser Asn Ala Phe Gly Gly Gly Thr Lys Val Glu Ile
            100                 105                 110

Lys

<210> SEQ ID NO 251
<211> LENGTH: 127
<212> TYPE: PRT
<213> ORGANISM: Artificial Sequence
<220> FEATURE:
<223> OTHER INFORMATION: 4126 gH4 V-region - IGHV3-7 framework

<400> SEQUENCE: 251

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Ser Tyr
                20                  25                  30

Tyr Tyr Met Ser Trp Val Arg Gln Ala Pro Gly Lys Gly Leu Glu Trp
            35                  40                  45

Val Ala Ser Ile Asp Pro Ala Ser Ser Gly Thr Thr Tyr Tyr Ala Thr
        50                  55                  60

Trp Ala Lys Gly Arg Phe Thr Ile Ser Lys Asp Ser Ala Lys Thr Ser
65              70                  75                  80

Val Tyr Leu Gln Met Asn Ser Leu Arg Ala Glu Asp Thr Ala Val Tyr
                85                  90                  95

Tyr Cys Ala Arg Ala Tyr Gly Ser Gly Gly Ser Gly Tyr Ile Gly Ser
            100                 105                 110

Tyr Phe Asp Leu Trp Gly Gln Gly Thr Leu Val Thr Val Ser Ser
        115                 120                 125

<210> SEQ ID NO 252
<211> LENGTH: 127
<212> TYPE: PRT
<213> ORGANISM: Artificial Sequence
<220> FEATURE:
<223> OTHER INFORMATION: 4126 gH13 V-region - IGHV4-4 framework

<400> SEQUENCE: 252

Glu Val Gln Leu Gln Glu Ser Gly Pro Gly Leu Val Lys Pro Ser Gly
1               5                   10                  15

Thr Leu Ser Leu Thr Cys Ala Ala Ser Gly Ile Asp Phe Ser Ser Tyr
                20                  25                  30

Tyr Tyr Met Cys Trp Val Arg Gln Pro Pro Gly Lys Gly Leu Glu Trp
            35                  40                  45

Val Ala Cys Ile Asp Pro Ala Ser Ser Gly Thr Thr Tyr Tyr Ala Thr
        50                  55                  60
```

```
Trp Ala Lys Gly Arg Phe Thr Ile Ser Lys Asp Ser Ser Lys Thr Gln
 65                  70                  75                  80

Val Ser Leu Lys Leu Ser Ser Val Thr Ala Ala Asp Thr Ala Val Tyr
                 85                  90                  95

Tyr Cys Ala Arg Ala Tyr Gly Ser Gly Gly Ser Gly Tyr Ile Gly Cys
            100                 105                 110

Tyr Phe Asp Leu Trp Gly Gln Gly Thr Leu Val Thr Val Ser Ser
        115                 120                 125
```

<210> SEQ ID NO 253
<211> LENGTH: 127
<212> TYPE: PRT
<213> ORGANISM: Artificial Sequence
<220> FEATURE:
<223> OTHER INFORMATION: 4126 gH6 V-region - IGHV4-4 framework

<400> SEQUENCE: 253

```
Glu Val Gln Leu Gln Glu Ser Gly Pro Gly Leu Val Lys Pro Ser Gly
 1               5                  10                  15

Thr Leu Ser Leu Thr Cys Ala Ala Ser Gly Ile Asp Phe Ser Ser Tyr
                 20                  25                  30

Tyr Tyr Met Cys Trp Val Arg Gln Pro Pro Gly Lys Gly Leu Glu Trp
            35                  40                  45

Val Ala Cys Ile Asp Pro Ala Ser Ser Gly Thr Thr Tyr Tyr Ala Thr
 50                  55                  60

Trp Ala Lys Gly Arg Phe Thr Ile Ser Lys Asp Ser Ser Lys Thr Gln
 65                  70                  75                  80

Val Ser Leu Lys Leu Ser Ser Val Thr Ala Ala Asp Thr Ala Val Tyr
                 85                  90                  95

Tyr Cys Ala Arg Ala Tyr Gly Ser Gly Gly Ser Gly Tyr Ile Gly Ser
            100                 105                 110

Tyr Phe Asp Leu Trp Gly Gln Gly Thr Leu Val Thr Val Ser Ser
        115                 120                 125
```

<210> SEQ ID NO 254
<211> LENGTH: 127
<212> TYPE: PRT
<213> ORGANISM: Artificial Sequence
<220> FEATURE:
<223> OTHER INFORMATION: 4126 gH7 V-region - IGHV4-4 framework

<400> SEQUENCE: 254

```
Glu Val Gln Leu Gln Glu Ser Gly Pro Gly Leu Val Lys Pro Ser Gly
 1               5                  10                  15

Thr Leu Ser Leu Thr Cys Ala Ala Ser Gly Ile Asp Phe Ser Ser Tyr
                 20                  25                  30

Tyr Tyr Met Ser Trp Val Arg Gln Pro Pro Gly Lys Gly Leu Glu Trp
            35                  40                  45

Val Ala Ser Ile Asp Pro Ala Ser Ser Gly Thr Thr Tyr Tyr Ala Thr
 50                  55                  60

Trp Ala Lys Gly Arg Phe Thr Ile Ser Lys Asp Ser Ser Lys Thr Gln
 65                  70                  75                  80

Val Ser Leu Lys Leu Ser Ser Val Thr Ala Ala Asp Thr Ala Val Tyr
                 85                  90                  95

Tyr Cys Ala Arg Ala Tyr Gly Ser Gly Gly Ser Gly Tyr Ile Gly Ser
            100                 105                 110

Tyr Phe Asp Leu Trp Gly Gln Gly Thr Leu Val Thr Val Ser Ser
```

<210> SEQ ID NO 255
<211> LENGTH: 124
<212> TYPE: PRT
<213> ORGANISM: Artificial Sequence
<220> FEATURE:
<223> OTHER INFORMATION: 4127 gH6 V-region - IGHV4-38-2 framework

<400> SEQUENCE: 255

Glu Val Gln Leu Gln Glu Ser Gly Pro Gly Leu Val Lys Pro Ser Glu
1               5                   10                  15

Thr Leu Ser Leu Thr Cys Ala Ala Ser Gly Phe Ser Phe Ser Asn Leu
            20                  25                  30

Tyr Tyr Met Cys Trp Val Arg Gln Pro Pro Gly Lys Gly Leu Glu Leu
        35                  40                  45

Ile Gly Cys Ile Asp Ile Ser Ser Ser Gly Ser Thr Tyr Tyr Ala Ser
    50                  55                  60

Trp Ala Lys Gly Arg Phe Thr Ile Ser Lys Asp Ser Ser Lys Thr Gln
65                  70                  75                  80

Val Ser Leu Lys Leu Ser Ser Val Thr Ala Ala Asp Thr Ala Val Tyr
                85                  90                  95

Tyr Cys Ala Arg Asp Tyr Tyr Ser Ser Asp Trp Gly Val Arg Phe Asn
            100                 105                 110

Leu Trp Gly Gln Gly Thr Leu Val Thr Val Ser Ser
        115                 120

<210> SEQ ID NO 256
<211> LENGTH: 124
<212> TYPE: PRT
<213> ORGANISM: Artificial Sequence
<220> FEATURE:
<223> OTHER INFORMATION: 4127 gH7 V-region - IGHV4-38-2 framework

<400> SEQUENCE: 256

Glu Val Gln Leu Gln Glu Ser Gly Pro Gly Leu Val Lys Pro Ser Glu
1               5                   10                  15

Thr Leu Ser Leu Thr Cys Ala Ala Ser Gly Phe Ser Phe Ser Asn Leu
            20                  25                  30

Tyr Tyr Met Ser Trp Val Arg Gln Pro Pro Gly Lys Gly Leu Glu Leu
        35                  40                  45

Ile Gly Ser Ile Asp Ile Ser Ser Ser Gly Ser Thr Tyr Tyr Ala Ser
    50                  55                  60

Trp Ala Lys Gly Arg Phe Thr Ile Ser Lys Asp Ser Ser Lys Thr Gln
65                  70                  75                  80

Val Ser Leu Lys Leu Ser Ser Val Thr Ala Ala Asp Thr Ala Val Tyr
                85                  90                  95

Tyr Cys Ala Arg Asp Tyr Tyr Ser Ser Asp Trp Gly Val Arg Phe Asn
            100                 105                 110

Leu Trp Gly Gln Gly Thr Leu Val Thr Val Ser Ser
        115                 120

<210> SEQ ID NO 257
<211> LENGTH: 122
<212> TYPE: PRT
<213> ORGANISM: Artificial Sequence
<220> FEATURE:
<223> OTHER INFORMATION: 4128 gH4 V-region - IGHV4-59 framework

<400> SEQUENCE: 257

```
Glu Val Gln Leu Gln Glu Ser Gly Pro Gly Leu Val Lys Pro Ser Glu
1               5                   10                  15

Thr Leu Ser Leu Thr Cys Lys Gly Ser Gly Leu Asp Phe Ser Ser Tyr
            20                  25                  30

Trp Ile Cys Trp Val Arg Gln Pro Pro Gly Lys Gly Leu Glu Trp Ile
        35                  40                  45

Ala Cys Ile Val Thr Gly Ser Ser Asp Asn Thr Tyr Tyr Ala Ser Trp
50                      55                  60

Ala Lys Gly Arg Phe Thr Ile Ser Lys Asp Ser Ser Lys Thr Gln Val
65                  70                  75                  80

Ser Leu Lys Leu Ser Ser Val Thr Ala Ala Asp Thr Ala Val Tyr Tyr
                85                  90                  95

Cys Ala Arg Gly Gly Gly Ala Gly Tyr Ser Gly Ala Phe Asp Leu Trp
            100                 105                 110

Gly Gln Gly Thr Leu Val Thr Val Ser Ser
            115                 120
```

<210> SEQ ID NO 258
<211> LENGTH: 122
<212> TYPE: PRT
<213> ORGANISM: Artificial Sequence
<220> FEATURE:
<223> OTHER INFORMATION: 4128 gH5 V-region - IGHV4-59 framework

<400> SEQUENCE: 258

```
Glu Val Gln Leu Gln Glu Ser Gly Pro Gly Leu Val Lys Pro Ser Glu
1               5                   10                  15

Thr Leu Ser Leu Thr Cys Lys Gly Ser Gly Leu Asp Phe Ser Ser Tyr
            20                  25                  30

Trp Ile Ser Trp Val Arg Gln Pro Pro Gly Lys Gly Leu Glu Trp Ile
        35                  40                  45

Ala Ser Ile Val Thr Gly Ser Ser Asp Asn Thr Tyr Tyr Ala Ser Trp
50                      55                  60

Ala Lys Gly Arg Phe Thr Ile Ser Lys Asp Ser Ser Lys Thr Gln Val
65                  70                  75                  80

Ser Leu Lys Leu Ser Ser Val Thr Ala Ala Asp Thr Ala Val Tyr Tyr
                85                  90                  95

Cys Ala Arg Gly Gly Gly Ala Gly Tyr Ser Gly Ala Phe Asp Leu Trp
            100                 105                 110

Gly Gln Gly Thr Leu Val Thr Val Ser Ser
            115                 120
```

<210> SEQ ID NO 259
<211> LENGTH: 124
<212> TYPE: PRT
<213> ORGANISM: Artificial Sequence
<220> FEATURE:
<223> OTHER INFORMATION: 4130 gH9 V-region - IGHV4-4 framework

<400> SEQUENCE: 259

```
Glu Val Gln Leu Gln Glu Ser Gly Pro Gly Leu Val Lys Pro Ser Gly
1               5                   10                  15

Thr Leu Ser Leu Thr Cys Ala Ala Ser Gly Phe Asp Phe Ser Gly Gly
            20                  25                  30

Tyr Asp Ile Ser Trp Val Arg Gln Pro Pro Gly Lys Gly Leu Glu Trp
        35                  40                  45

Ile Gly Cys Ile Tyr Gly Gly Ile Asn Ser Val Thr Asp Tyr Ala Ser
```

```
                 50                  55                  60
Trp Ala Lys Gly Arg Val Thr Ile Ser Lys Asp Ser Ser Lys Thr Gln
 65                  70                  75                  80

Val Ser Leu Lys Leu Ser Ser Val Thr Ala Ala Asp Thr Ala Val Tyr
                 85                  90                  95

Tyr Cys Ala Arg Asp Val Ser Asn Ser Asp His Tyr Thr Arg Leu Asp
                100                 105                 110

Leu Trp Gly Gln Gly Thr Leu Val Thr Val Ser Ser
                115                 120

<210> SEQ ID NO 260
<211> LENGTH: 124
<212> TYPE: PRT
<213> ORGANISM: Artificial Sequence
<220> FEATURE:
<223> OTHER INFORMATION: 4130 gH5 V-region - IGHV4-4 framework

<400> SEQUENCE: 260

Glu Val Gln Leu Gln Glu Ser Gly Pro Gly Leu Val Lys Pro Ser Gly
  1               5                  10                  15

Thr Leu Ser Leu Thr Cys Ala Ala Ser Gly Phe Asp Phe Ser Gly Gly
                 20                  25                  30

Tyr Asp Ile Ser Trp Val Arg Gln Pro Pro Gly Lys Gly Leu Glu Trp
                 35                  40                  45

Ile Gly Ser Ile Tyr Gly Gly Ile Asn Ser Val Thr Asp Tyr Ala Ser
                 50                  55                  60

Trp Ala Lys Gly Arg Val Thr Ile Ser Lys Asp Ser Ser Lys Thr Gln
 65                  70                  75                  80

Val Ser Leu Lys Leu Ser Ser Val Thr Ala Ala Asp Thr Ala Val Tyr
                 85                  90                  95

Tyr Cys Ala Arg Asp Val Ser Asn Ser Asp His Tyr Thr Arg Leu Asp
                100                 105                 110

Leu Trp Gly Gln Gly Thr Leu Val Thr Val Ser Ser
                115                 120

<210> SEQ ID NO 261
<211> LENGTH: 123
<212> TYPE: PRT
<213> ORGANISM: Artificial Sequence
<220> FEATURE:
<223> OTHER INFORMATION: 4132 gH4 V-region - IGHV4-4 framework

<400> SEQUENCE: 261

Glu Val Gln Leu Gln Glu Ser Gly Pro Gly Leu Val Lys Pro Ser Gly
  1               5                  10                  15

Thr Leu Ser Leu Thr Cys Ala Ala Ser Gly Phe Ser Phe Ser Ser Ser
                 20                  25                  30

Tyr Trp Ile Cys Trp Val Arg Gln Pro Pro Gly Lys Gly Leu Glu Trp
                 35                  40                  45

Ser Gly Cys Ile Asn Ser Gly Thr Gly Thr Ala Tyr Ala Ser Trp
                 50                  55                  60

Ala Lys Gly Arg Phe Thr Ile Ser Asn Asp Ser Ser Lys Thr Gln Val
 65                  70                  75                  80

Ser Leu Lys Leu Ser Ser Val Thr Ala Ala Asp Thr Ala Val Tyr Tyr
                 85                  90                  95

Cys Ala Arg Glu Trp Val Ser Gly Tyr Tyr Lys Asp Ala Phe Asp Leu
                100                 105                 110
```

Trp Gly Gln Gly Thr Leu Val Thr Val Ser Ser
        115                 120

<210> SEQ ID NO 262
<211> LENGTH: 123
<212> TYPE: PRT
<213> ORGANISM: Artificial Sequence
<220> FEATURE:
<223> OTHER INFORMATION: 4132 gH5 V-region - IGHV4-4 framework

<400> SEQUENCE: 262

Glu Val Gln Leu Gln Glu Ser Gly Pro Gly Leu Val Lys Pro Ser Gly
1               5                   10                  15

Thr Leu Ser Leu Thr Cys Ala Ala Ser Gly Phe Ser Phe Ser Ser Ser
            20                  25                  30

Tyr Trp Ile Ser Trp Val Arg Gln Pro Pro Gly Lys Gly Leu Glu Trp
        35                  40                  45

Ser Gly Ser Ile Asn Ser Gly Thr Gly Gly Thr Ala Tyr Ala Ser Trp
    50                  55                  60

Ala Lys Gly Arg Phe Thr Ile Ser Asn Asp Ser Ser Lys Thr Gln Val
65                  70                  75                  80

Ser Leu Lys Leu Ser Ser Val Thr Ala Ala Asp Thr Ala Val Tyr Tyr
                85                  90                  95

Cys Ala Arg Glu Trp Val Ser Gly Tyr Tyr Lys Asp Ala Phe Asp Leu
            100                 105                 110

Trp Gly Gln Gly Thr Leu Val Thr Val Ser Ser
        115                 120

<210> SEQ ID NO 263
<211> LENGTH: 121
<212> TYPE: PRT
<213> ORGANISM: Artificial Sequence
<220> FEATURE:
<223> OTHER INFORMATION: 4122 gH3 V-region - IGHV2-70 framework

<400> SEQUENCE: 263

Glu Val Thr Leu Lys Glu Ser Gly Pro Ala Leu Val Lys Pro Thr Gln
1               5                   10                  15

Thr Leu Thr Leu Thr Cys Thr Ala Ser Gly Phe Ser Phe Ser Ala Gly
            20                  25                  30

Tyr Trp Ile Cys Trp Val Arg Gln Pro Pro Gly Lys Gly Leu Glu Trp
        35                  40                  45

Ile Ala Cys Thr Tyr Ala Gly Arg Ser Gly Ser Thr Tyr Tyr Ala Asn
    50                  55                  60

Trp Val Asn Gly Arg Phe Thr Ile Ser Lys Asp Ser Ser Lys Thr Gln
65                  70                  75                  80

Val Val Leu Thr Met Thr Asn Met Asp Pro Val Asp Thr Ala Thr Tyr
                85                  90                  95

Tyr Cys Ala Arg Gly Asn Ala Gly Val Ala Val Gly Ala Leu Trp Gly
            100                 105                 110

Arg Gly Thr Leu Val Thr Val Ser Ser
        115                 120

<210> SEQ ID NO 264
<211> LENGTH: 121
<212> TYPE: PRT
<213> ORGANISM: Artificial Sequence
<220> FEATURE:
<223> OTHER INFORMATION: 4122 gH5 V-region - IGHV2-70 framework

```
<400> SEQUENCE: 264

Glu Val Thr Leu Lys Glu Ser Gly Pro Ala Leu Val Lys Pro Thr Gln
1               5                   10                  15

Thr Leu Thr Leu Thr Cys Thr Ala Ser Gly Phe Ser Phe Ser Ala Gly
            20                  25                  30

Tyr Trp Ile Ser Trp Val Arg Gln Pro Pro Gly Lys Gly Leu Glu Trp
        35                  40                  45

Ile Ala Ser Thr Tyr Ala Gly Arg Ser Gly Ser Thr Tyr Tyr Ala Asn
    50                  55                  60

Trp Val Asn Gly Arg Phe Thr Ile Ser Lys Asp Ser Ser Lys Thr Gln
65                  70                  75                  80

Val Val Leu Thr Met Thr Asn Met Asp Pro Val Asp Thr Ala Thr Tyr
                85                  90                  95

Tyr Cys Ala Arg Gly Asn Ala Gly Val Ala Val Gly Ala Leu Trp Gly
            100                 105                 110

Arg Gly Thr Leu Val Thr Val Ser Ser
            115                 120

<210> SEQ ID NO 265
<211> LENGTH: 121
<212> TYPE: PRT
<213> ORGANISM: Artificial Sequence
<220> FEATURE:
<223> OTHER INFORMATION: 4129 gH3 V-region - IGHV2-70 framework

<400> SEQUENCE: 265

Glu Val Thr Leu Lys Glu Ser Gly Pro Ala Leu Val Lys Pro Thr Gln
1               5                   10                  15

Thr Leu Thr Leu Thr Cys Thr Ala Ser Gly Phe Ser Phe Ser Ala Gly
            20                  25                  30

Tyr Trp Ile Cys Trp Val Arg Gln Pro Pro Gly Lys Gly Leu Glu Trp
        35                  40                  45

Ile Ala Cys Ile Tyr Ala Gly Ser Ser Gly Ser Thr Tyr Tyr Ala Ser
    50                  55                  60

Trp Ala Lys Gly Arg Phe Thr Ile Ser Lys Asp Ser Ser Lys Thr Gln
65                  70                  75                  80

Val Val Leu Thr Met Thr Asn Met Asp Pro Val Asp Thr Ala Thr Tyr
                85                  90                  95

Tyr Cys Ala Arg Gly Asn Ala Gly Val Ala Val Gly Ala Leu Trp Gly
            100                 105                 110

Arg Gly Thr Leu Val Thr Val Ser Ser
            115                 120

<210> SEQ ID NO 266
<211> LENGTH: 121
<212> TYPE: PRT
<213> ORGANISM: Artificial Sequence
<220> FEATURE:
<223> OTHER INFORMATION: 4129 gH5 V-region - IGHV2-70 framework

<400> SEQUENCE: 266

Glu Val Thr Leu Lys Glu Ser Gly Pro Ala Leu Val Lys Pro Thr Gln
1               5                   10                  15

Thr Leu Thr Leu Thr Cys Thr Ala Ser Gly Phe Ser Phe Ser Ala Gly
            20                  25                  30

Tyr Trp Ile Ser Trp Val Arg Gln Pro Pro Gly Lys Gly Leu Glu Trp
        35                  40                  45
```

```
Ile Ala Ser Ile Tyr Ala Gly Ser Ser Gly Ser Thr Tyr Tyr Ala Ser
    50                  55                  60

Trp Ala Lys Gly Arg Phe Thr Ile Ser Lys Asp Ser Lys Thr Gln
65                  70                  75                  80

Val Val Leu Thr Met Thr Asn Met Asp Pro Val Asp Thr Ala Thr Tyr
                85                  90                  95

Tyr Cys Ala Arg Gly Asn Ala Gly Val Ala Val Gly Ala Leu Trp Gly
                100                 105                 110

Arg Gly Thr Leu Val Thr Val Ser Ser
            115                 120
```

<210> SEQ ID NO 267
<211> LENGTH: 121
<212> TYPE: PRT
<213> ORGANISM: Artificial Sequence
<220> FEATURE:
<223> OTHER INFORMATION: 4131 gH4 V-region - IGHV3-7 framework

<400> SEQUENCE: 267

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Ser Phe Ser Ser Ser
                20                  25                  30

Tyr Trp Ile Tyr Trp Val Arg Gln Ala Pro Gly Lys Gly Leu Glu Trp
                35                  40                  45

Ile Ala Ser Ile Tyr Thr Gly Ser Ser Gly Ser Thr Tyr Tyr Ala Ser
    50                  55                  60

Trp Ala Lys Gly Arg Phe Thr Val Ser Glu Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Ala Ser Ala Trp Thr Tyr Gly Met Asp Leu Trp Gly
                100                 105                 110

Arg Gly Thr Leu Val Thr Val Ser Ser
            115                 120
```

<210> SEQ ID NO 268
<211> LENGTH: 121
<212> TYPE: PRT
<213> ORGANISM: Artificial Sequence
<220> FEATURE:
<223> OTHER INFORMATION: 4131 gH6 V-region - IGHV4-31 framework

<400> SEQUENCE: 268

```
Glu Val Gln Leu Gln Glu Ser Gly Pro Gly Leu Val Lys Pro Ser Gln
1               5                   10                  15

Thr Leu Ser Leu Thr Cys Thr Ala Ser Gly Val Ser Phe Ser Ser Ser
                20                  25                  30

Tyr Trp Ile Tyr Trp Val Arg Gln His Pro Gly Lys Gly Leu Glu Trp
                35                  40                  45

Ile Ala Cys Ile Tyr Thr Gly Ser Ser Gly Ser Thr Tyr Tyr Ala Ser
    50                  55                  60

Trp Ala Lys Gly Arg Phe Thr Val Ser Glu Asp Ser Lys Thr Gln
65                  70                  75                  80

Val Ser Leu Lys Leu Ser Ser Val Thr Ala Ala Asp Thr Ala Val Tyr
                85                  90                  95

Tyr Cys Ala Arg Ala Ser Ala Trp Thr Tyr Gly Met Asp Leu Trp Gly
                100                 105                 110
```

Arg Gly Thr Leu Val Thr Val Ser Ser
        115                 120

<210> SEQ ID NO 269
<211> LENGTH: 121
<212> TYPE: PRT
<213> ORGANISM: Artificial Sequence
<220> FEATURE:
<223> OTHER INFORMATION: 4131 gH3 V-region - IGHV4-31 framework

<400> SEQUENCE: 269

Glu Val Gln Leu Gln Glu Ser Gly Pro Gly Leu Val Lys Pro Ser Gln
1               5                   10                  15

Thr Leu Ser Leu Thr Cys Thr Ala Ser Gly Val Ser Phe Ser Ser Ser
            20                  25                  30

Tyr Trp Ile Tyr Trp Val Arg Gln His Pro Gly Lys Gly Leu Glu Trp
        35                  40                  45

Ile Ala Ser Ile Tyr Thr Gly Ser Ser Gly Ser Thr Tyr Tyr Ala Ser
    50                  55                  60

Trp Ala Lys Gly Arg Phe Thr Val Ser Glu Asp Ser Ser Lys Thr Gln
65                  70                  75                  80

Val Ser Leu Lys Leu Ser Ser Val Thr Ala Ala Asp Thr Ala Val Tyr
                85                  90                  95

Tyr Cys Ala Arg Ala Ser Ala Trp Thr Tyr Gly Met Asp Leu Trp Gly
            100                 105                 110

Arg Gly Thr Leu Val Thr Val Ser Ser
        115                 120

<210> SEQ ID NO 270
<211> LENGTH: 123
<212> TYPE: PRT
<213> ORGANISM: Artificial Sequence
<220> FEATURE:
<223> OTHER INFORMATION: 4133 gH4 V-region - IGHV3-21 framework

<400> SEQUENCE: 270

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Gly Asn
            20                  25                  30

Tyr Tyr Met Ser Trp Val Arg Gln Ala Pro Gly Lys Gly Leu Glu Trp
        35                  40                  45

Ile Gly Ser Leu Tyr Thr Gly Ser Ser Gly Ser Thr Tyr Tyr Ala Ser
    50                  55                  60

Trp Ala Lys Gly Arg Phe Thr Ile Ser Lys Asp Ser Ala Lys Thr Ser
65                  70                  75                  80

Val Tyr Leu Gln Met Asn Ser Leu Arg Ala Glu Asp Thr Ala Val Tyr
                85                  90                  95

Tyr Cys Ala Arg Asp Leu Gly Tyr Glu Ile Asp Gly Tyr Gly Gly Leu
            100                 105                 110

Trp Gly Gln Gly Thr Leu Val Thr Val Ser Ser
        115                 120

<210> SEQ ID NO 271
<211> LENGTH: 123
<212> TYPE: PRT
<213> ORGANISM: Artificial Sequence
<220> FEATURE:
<223> OTHER INFORMATION: 4133 gH3 V-region - IGHV4-4 framework

<400> SEQUENCE: 271

```
Glu Val Gln Leu Gln Glu Ser Gly Pro Gly Leu Val Lys Pro Ser Gly
1               5                   10                  15
Thr Leu Ser Leu Thr Cys Ala Ala Ser Gly Phe Ser Phe Ser Gly Asn
            20                  25                  30
Tyr Tyr Met Cys Trp Val Arg Gln Pro Pro Gly Lys Gly Leu Glu Trp
        35                  40                  45
Ile Gly Cys Leu Tyr Thr Gly Ser Ser Gly Ser Thr Tyr Tyr Ala Ser
    50                  55                  60
Trp Ala Lys Gly Arg Val Thr Ile Ser Lys Asp Ser Ser Lys Thr Gln
65                  70                  75                  80
Val Ser Leu Lys Leu Ser Ser Val Thr Ala Ala Asp Thr Ala Val Tyr
                85                  90                  95
Tyr Cys Ala Arg Asp Leu Gly Tyr Glu Ile Asp Gly Tyr Gly Gly Leu
            100                 105                 110
Trp Gly Gln Gly Thr Leu Val Thr Val Ser Ser
        115                 120
```

<210> SEQ ID NO 272
<211> LENGTH: 123
<212> TYPE: PRT
<213> ORGANISM: Artificial Sequence
<220> FEATURE:
<223> OTHER INFORMATION: 4133 gH5 V-region - IGHV4-4 framework

<400> SEQUENCE: 272

```
Glu Val Gln Leu Gln Glu Ser Gly Pro Gly Leu Val Lys Pro Ser Gly
1               5                   10                  15
Thr Leu Ser Leu Thr Cys Ala Ala Ser Gly Phe Ser Phe Ser Gly Asn
            20                  25                  30
Tyr Tyr Met Ser Trp Val Arg Gln Pro Pro Gly Lys Gly Leu Glu Trp
        35                  40                  45
Ile Gly Ser Leu Tyr Thr Gly Ser Ser Gly Ser Thr Tyr Tyr Ala Ser
    50                  55                  60
Trp Ala Lys Gly Arg Val Thr Ile Ser Lys Asp Ser Ser Lys Thr Gln
65                  70                  75                  80
Val Ser Leu Lys Leu Ser Ser Val Thr Ala Ala Asp Thr Ala Val Tyr
                85                  90                  95
Tyr Cys Ala Arg Asp Leu Gly Tyr Glu Ile Asp Gly Tyr Gly Gly Leu
            100                 105                 110
Trp Gly Gln Gly Thr Leu Val Thr Val Ser Ser
        115                 120
```

<210> SEQ ID NO 273
<211> LENGTH: 8
<212> TYPE: PRT
<213> ORGANISM: Artificial Sequence
<220> FEATURE:
<223> OTHER INFORMATION: Hinge linker sequence

<400> SEQUENCE: 273

```
Asp Lys Thr His Thr Cys Ala Ala
1               5
```

<210> SEQ ID NO 274
<211> LENGTH: 11
<212> TYPE: PRT
<213> ORGANISM: Artificial Sequence
<220> FEATURE:
<223> OTHER INFORMATION: Hinge linker sequence

<400> SEQUENCE: 274

Asp Lys Thr His Thr Cys Pro Pro Cys Pro Ala
1               5                   10

<210> SEQ ID NO 275
<211> LENGTH: 18
<212> TYPE: PRT
<213> ORGANISM: Artificial Sequence
<220> FEATURE:
<223> OTHER INFORMATION: Hinge linker sequence

<400> SEQUENCE: 275

Asp Lys Thr His Thr Cys Pro Pro Cys Pro Ala Thr Cys Pro Pro Cys
1               5                   10                  15

Pro Ala

<210> SEQ ID NO 276
<211> LENGTH: 25
<212> TYPE: PRT
<213> ORGANISM: Artificial Sequence
<220> FEATURE:
<223> OTHER INFORMATION: Hinge linker sequence

<400> SEQUENCE: 276

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 277
<211> LENGTH: 30
<212> TYPE: PRT
<213> ORGANISM: Artificial Sequence
<220> FEATURE:
<223> OTHER INFORMATION: Hinge linker sequence

<400> SEQUENCE: 277

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 278
<211> LENGTH: 31
<212> TYPE: PRT
<213> ORGANISM: Artificial Sequence
<220> FEATURE:
<223> OTHER INFORMATION: Hinge linker sequence

<400> SEQUENCE: 278

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 279
<211> LENGTH: 15
<212> TYPE: PRT
<213> ORGANISM: Artificial Sequence
<220> FEATURE:
<223> OTHER INFORMATION: Hinge linker sequence

```
<400> SEQUENCE: 279

Asp Lys Thr His Thr Cys Cys Val Glu Cys Pro Pro Cys Pro Ala
1               5                   10                  15

<210> SEQ ID NO 280
<211> LENGTH: 26
<212> TYPE: PRT
<213> ORGANISM: Artificial Sequence
<220> FEATURE:
<223> OTHER INFORMATION: Hinge linker sequence

<400> SEQUENCE: 280

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 281
<211> LENGTH: 11
<212> TYPE: PRT
<213> ORGANISM: Artificial Sequence
<220> FEATURE:
<223> OTHER INFORMATION: Hinge linker sequence

<400> SEQUENCE: 281

Asp Lys Thr His Thr Cys Pro Ser Cys Pro Ala
1               5                   10

<210> SEQ ID NO 282
<211> LENGTH: 7
<212> TYPE: PRT
<213> ORGANISM: Artificial Sequence
<220> FEATURE:
<223> OTHER INFORMATION: Flexible linker sequence

<400> SEQUENCE: 282

Ser Gly Gly Gly Gly Ser Glu
1               5

<210> SEQ ID NO 283
<211> LENGTH: 6
<212> TYPE: PRT
<213> ORGANISM: Artificial Sequence
<220> FEATURE:
<223> OTHER INFORMATION: Flexible linker sequence

<400> SEQUENCE: 283

Asp Lys Thr His Thr Ser
1               5

<210> SEQ ID NO 284
<211> LENGTH: 6
<212> TYPE: PRT
<213> ORGANISM: Artificial Sequence
<220> FEATURE:
<223> OTHER INFORMATION: Flexible linker sequence

<400> SEQUENCE: 284

Ser Gly Gly Gly Gly Ser
1               5

<210> SEQ ID NO 285
<211> LENGTH: 11
<212> TYPE: PRT
<213> ORGANISM: Artificial Sequence
<220> FEATURE:
```

<223> OTHER INFORMATION: Flexible linker sequence

<400> SEQUENCE: 285

Ser Gly Gly Gly Gly Ser Gly Gly Gly Gly Ser
1               5                   10

<210> SEQ ID NO 286
<211> LENGTH: 16
<212> TYPE: PRT
<213> ORGANISM: Artificial Sequence
<220> FEATURE:
<223> OTHER INFORMATION: Flexible linker sequence

<400> SEQUENCE: 286

Ser Gly Gly Gly Gly Ser Gly Gly Gly Gly Ser Gly Gly Gly Gly Ser
1               5                   10                  15

<210> SEQ ID NO 287
<211> LENGTH: 21
<212> TYPE: PRT
<213> ORGANISM: Artificial Sequence
<220> FEATURE:
<223> OTHER INFORMATION: Flexible linker sequence

<400> SEQUENCE: 287

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 288
<211> LENGTH: 26
<212> TYPE: PRT
<213> ORGANISM: Artificial Sequence
<220> FEATURE:
<223> OTHER INFORMATION: Flexible linker sequence

<400> SEQUENCE: 288

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 289
<211> LENGTH: 11
<212> TYPE: PRT
<213> ORGANISM: Artificial Sequence
<220> FEATURE:
<223> OTHER INFORMATION: Flexible linker sequence

<400> SEQUENCE: 289

Ala Ala Ala Gly Ser Gly Gly Ala Ser Ala Ser
1               5                   10

<210> SEQ ID NO 290
<211> LENGTH: 16
<212> TYPE: PRT
<213> ORGANISM: Artificial Sequence
<220> FEATURE:
<223> OTHER INFORMATION: Flexible linker sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 290

```
Ala Ala Ala Gly Ser Gly Xaa Gly Gly Gly Ser Gly Ala Ser Ala Ser
1               5                   10                  15
```

<210> SEQ ID NO 291
<211> LENGTH: 21
<212> TYPE: PRT
<213> ORGANISM: Artificial Sequence
<220> FEATURE:
<223> OTHER INFORMATION: Flexible linker sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 291

```
Ala Ala Ala Gly Ser Gly Xaa Gly Gly Gly Ser Xaa Gly Gly Gly Ser
1               5                   10                  15

Gly Ala Ser Ala Ser
            20
```

<210> SEQ ID NO 292
<211> LENGTH: 26
<212> TYPE: PRT
<213> ORGANISM: Artificial Sequence
<220> FEATURE:
<223> OTHER INFORMATION: Flexible linker sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 292

```
Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25
```

<210> SEQ ID NO 293
<211> LENGTH: 31
<212> TYPE: PRT
<213> ORGANISM: Artificial Sequence
<220> FEATURE:
<223> OTHER INFORMATION: Flexible linker sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

```
<400> SEQUENCE: 293

Ala Ala Ala Gly Ser Gly Xaa Gly Gly Ser Xaa Gly Gly Ser
1               5                   10                  15

Xaa Gly Gly Gly Ser Xaa Gly Gly Gly Ser Gly Ala Ser Ala Ser
                20                  25                  30

<210> SEQ ID NO 294
<211> LENGTH: 13
<212> TYPE: PRT
<213> ORGANISM: Artificial Sequence
<220> FEATURE:
<223> OTHER INFORMATION: Flexible linker sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 294

Ala Ala Ala Gly Ser Gly Xaa Ser Gly Ala Ser Ala Ser
1               5                   10

<210> SEQ ID NO 295
<211> LENGTH: 28
<212> TYPE: PRT
<213> ORGANISM: Artificial Sequence
<220> FEATURE:
<223> OTHER INFORMATION: Flexible linker sequence

<400> SEQUENCE: 295

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
                20                  25

<210> SEQ ID NO 296
<211> LENGTH: 11
<212> TYPE: PRT
<213> ORGANISM: Artificial Sequence
<220> FEATURE:
<223> OTHER INFORMATION: Flexible linker sequence

<400> SEQUENCE: 296

Ala Thr Thr Thr Gly Ser Ser Pro Gly Pro Thr
1               5                   10

<210> SEQ ID NO 297
<211> LENGTH: 6
<212> TYPE: PRT
<213> ORGANISM: Artificial Sequence
<220> FEATURE:
<223> OTHER INFORMATION: Flexible linker sequence

<400> SEQUENCE: 297

Ala Thr Thr Thr Gly Ser
1               5

<210> SEQ ID NO 298
<211> LENGTH: 229
<212> TYPE: PRT
<213> ORGANISM: Artificial Sequence
<220> FEATURE:
<223> OTHER INFORMATION: Human CD79b

<400> SEQUENCE: 298

Met Ala Arg Leu Ala Leu Ser Pro Val Pro Ser His Trp Met Val Ala
1               5                   10                  15
```

```
Leu Leu Leu Leu Leu Ser Ala Glu Pro Val Pro Ala Ala Arg Ser Glu
            20                  25                  30

Asp Arg Tyr Arg Asn Pro Lys Gly Ser Ala Cys Ser Arg Ile Trp Gln
        35                  40                  45

Ser Pro Arg Phe Ile Ala Arg Lys Arg Gly Phe Thr Val Lys Met His
50                  55                  60

Cys Tyr Met Asn Ser Ala Ser Gly Asn Val Ser Trp Leu Trp Lys Gln
65                  70                  75                  80

Glu Met Asp Glu Asn Pro Gln Gln Leu Lys Leu Glu Lys Gly Arg Met
                85                  90                  95

Glu Glu Ser Gln Asn Glu Ser Leu Ala Thr Leu Thr Ile Gln Gly Ile
            100                 105                 110

Arg Phe Glu Asp Asn Gly Ile Tyr Phe Cys Gln Gln Lys Cys Asn Asn
        115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
            180                 185                 190

Asp His Thr Tyr Glu Gly Leu Asp Ile Asp Gln Thr Ala Thr Tyr Glu
        195                 200                 205

Asp Ile Val Thr Leu Arg Thr Gly Glu Val Lys Trp Ser Val Gly Glu
210                 215                 220

His Pro Gly Gln Glu
225

<210> SEQ ID NO 299
<211> LENGTH: 21
<212> TYPE: PRT
<213> ORGANISM: Artificial Sequence
<220> FEATURE:
<223> OTHER INFORMATION: Flexible linker sequence

<400> SEQUENCE: 299

Glu Pro Ser Gly Pro Ile Ser Thr Ile Asn Ser Pro Pro Ser Lys Glu
1               5                   10                  15

Ser His Lys Ser Pro
            20

<210> SEQ ID NO 300
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 300

Gly Thr Val Ala Ala Pro Ser Val Phe Ile Phe Pro Pro Ser Asp
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Flexible linker sequence
```

<400> SEQUENCE: 301

Gly Gly Gly Gly Ile Ala Pro Ser Met Val Gly Gly Gly Gly Ser
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 302

Gly Gly Gly Gly Lys Val Glu Gly Ala Gly Gly Gly Gly Gly Ser
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 303

Gly Gly Gly Gly Ser Met Lys Ser His Asp Gly Gly Gly Gly Ser
1               5                   10                  15

<210> SEQ ID NO 304
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 304

Gly Gly Gly Gly Asn Leu Ile Thr Ile Val Gly Gly Gly Gly Ser
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 305

Gly Gly Gly Gly Val Val Pro Ser Leu Pro Gly Gly Gly Gly Ser
1               5                   10                  15

<210> SEQ ID NO 306
<211> LENGTH: 12
<212> TYPE: PRT
<213> ORGANISM: Artificial Sequence
<220> FEATURE:
<223> OTHER INFORMATION: Flexible linker sequence

<400> SEQUENCE: 306

Gly Gly Glu Lys Ser Ile Pro Gly Gly Gly Gly Ser
1               5                   10

<210> SEQ ID NO 307
<211> LENGTH: 18
<212> TYPE: PRT
<213> ORGANISM: Artificial Sequence
<220> FEATURE:
<223> OTHER INFORMATION: Flexible linker sequence

```
<400> SEQUENCE: 307

Arg Pro Leu Ser Tyr Arg Pro Pro Phe Pro Phe Gly Phe Pro Ser Val
1               5                   10                  15

Arg Pro

<210> SEQ ID NO 308
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 308

Tyr Pro Arg Ser Ile Tyr Ile Arg Arg His Pro Ser Pro Ser Leu
1               5                   10                  15

Thr Thr

<210> SEQ ID NO 309
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 309

Thr Pro Ser His Leu Ser His Ile Leu Pro Ser Phe Gly Leu Pro Thr
1               5                   10                  15

Phe Asn

<210> SEQ ID NO 310
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 310

Arg Pro Val Ser Pro Phe Thr Phe Pro Arg Leu Ser Asn Ser Trp Leu
1               5                   10                  15

Pro Ala

<210> SEQ ID NO 311
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 311

Ser Pro Ala Ala His Phe Pro Arg Ser Ile Pro Arg Pro Gly Pro Ile
1               5                   10                  15

Arg Thr

<210> SEQ ID NO 312
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 312

Ala Pro Gly Pro Ser Ala Pro Ser His Arg Ser Leu Pro Ser Arg Ala
1               5                   10                  15
```

Phe Gly

<210> SEQ ID NO 313
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 313

Pro Arg Asn Ser Ile His Phe Leu His Pro Leu Leu Val Ala Pro Leu
1               5                   10                  15

Gly Ala

<210> SEQ ID NO 314
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 314

Met Pro Ser Leu Ser Gly Val Leu Gln Val Arg Tyr Leu Ser Pro Pro
1               5                   10                  15

Asp Leu

<210> SEQ ID NO 315
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 315

Ser Pro Gln Tyr Pro Ser Pro Leu Thr Leu Thr Leu Pro Pro His Pro
1               5                   10                  15

Ser Leu

<210> SEQ ID NO 316
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 316

Asn Pro Ser Leu Asn Pro Pro Ser Tyr Leu His Arg Ala Pro Ser Arg
1               5                   10                  15

Ile Ser

<210> SEQ ID NO 317
<211> LENGTH: 17
<212> TYPE: PRT
<213> ORGANISM: Artificial Sequence
<220> FEATURE:
<223> OTHER INFORMATION: Flexible linker sequence

<400> SEQUENCE: 317

Leu Pro Trp Arg Thr Ser Leu Leu Pro Ser Leu Pro Leu Arg Arg Arg
1               5                   10                  15

Pro

<210> SEQ ID NO 318
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 318

Pro Pro Leu Phe Ala Lys Gly Pro Val Gly Leu Leu Ser Arg Ser Phe
1               5                   10                  15

Pro Pro

<210> SEQ ID NO 319
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 319

Val Pro Pro Ala Pro Val Val Ser Leu Arg Ser Ala His Ala Arg Pro
1               5                   10                  15

Pro Tyr

<210> SEQ ID NO 320
<211> LENGTH: 17
<212> TYPE: PRT
<213> ORGANISM: Artificial Sequence
<220> FEATURE:
<223> OTHER INFORMATION: Flexible linker sequence

<400> SEQUENCE: 320

Leu Arg Pro Thr Pro Pro Arg Val Arg Ser Tyr Thr Cys Cys Pro Thr
1               5                   10                  15

Pro

<210> SEQ ID NO 321
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 321

Pro Asn Val Ala His Val Leu Pro Leu Leu Thr Val Pro Trp Asp Asn
1               5                   10                  15

Leu Arg

<210> SEQ ID NO 322
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 322

Cys Asn Pro Leu Leu Pro Leu Cys Ala Arg Ser Pro Ala Val Arg Thr
1               5                   10                  15

Phe Pro

<210> SEQ ID NO 323
<211> LENGTH: 11
<212> TYPE: PRT
<213> ORGANISM: Artificial Sequence

```
<220> FEATURE:
<223> OTHER INFORMATION: Other linker

<400> SEQUENCE: 323

Asp Leu Cys Leu Arg Asp Trp Gly Cys Leu Trp
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Other linker

<400> SEQUENCE: 324

Asp Ile Cys Leu Pro Arg Trp Gly Cys Leu Trp
1               5                   10

<210> SEQ ID NO 325
<211> LENGTH: 15
<212> TYPE: PRT
<213> ORGANISM: Artificial Sequence
<220> FEATURE:
<223> OTHER INFORMATION: Other linker

<400> SEQUENCE: 325

Met Glu Asp Ile Cys Leu Pro Arg Trp Gly Cys Leu Trp Gly Asp
1               5                   10                  15

<210> SEQ ID NO 326
<211> LENGTH: 20
<212> TYPE: PRT
<213> ORGANISM: Artificial Sequence
<220> FEATURE:
<223> OTHER INFORMATION: Other linker

<400> SEQUENCE: 326

Gln Arg Leu Met Glu Asp Ile Cys Leu Pro Arg Trp Gly Cys Leu Trp
1               5                   10                  15

Glu Asp Asp Glu
            20

<210> SEQ ID NO 327
<211> LENGTH: 20
<212> TYPE: PRT
<213> ORGANISM: Artificial Sequence
<220> FEATURE:
<223> OTHER INFORMATION: Other linker

<400> SEQUENCE: 327

Gln Gly Leu Ile Gly Asp Ile Cys Leu Pro Arg Trp Gly Cys Leu Trp
1               5                   10                  15

Gly Arg Ser Val
            20

<210> SEQ ID NO 328
<211> LENGTH: 21
<212> TYPE: PRT
<213> ORGANISM: Artificial Sequence
<220> FEATURE:
<223> OTHER INFORMATION: Other linker

<400> SEQUENCE: 328

Gln Gly Leu Ile Gly Asp Ile Cys Leu Pro Arg Trp Gly Cys Leu Trp
1               5                   10                  15
```

Gly Arg Ser Val Lys
            20

<210> SEQ ID NO 329
<211> LENGTH: 15
<212> TYPE: PRT
<213> ORGANISM: Artificial Sequence
<220> FEATURE:
<223> OTHER INFORMATION: Other linker

<400> SEQUENCE: 329

Glu Asp Ile Cys Leu Pro Arg Trp Gly Cys Leu Trp Glu Asp Asp
1               5                   10                  15

<210> SEQ ID NO 330
<211> LENGTH: 18
<212> TYPE: PRT
<213> ORGANISM: Artificial Sequence
<220> FEATURE:
<223> OTHER INFORMATION: Other linker

<400> SEQUENCE: 330

Arg Leu Met Glu Asp Ile Cys Leu Pro Arg Trp Gly Cys Leu Trp Glu
1               5                   10                  15

Asp Asp

<210> SEQ ID NO 331
<211> LENGTH: 16
<212> TYPE: PRT
<213> ORGANISM: Artificial Sequence
<220> FEATURE:
<223> OTHER INFORMATION: Other linker

<400> SEQUENCE: 331

Met Glu Asp Ile Cys Leu Pro Arg Trp Gly Cys Leu Trp Glu Asp Asp
1               5                   10                  15

<210> SEQ ID NO 332
<211> LENGTH: 15
<212> TYPE: PRT
<213> ORGANISM: Artificial Sequence
<220> FEATURE:
<223> OTHER INFORMATION: Other linker

<400> SEQUENCE: 332

Met Glu Asp Ile Cys Leu Pro Arg Trp Gly Cys Leu Trp Glu Asp
1               5                   10                  15

<210> SEQ ID NO 333
<211> LENGTH: 18
<212> TYPE: PRT
<213> ORGANISM: Artificial Sequence
<220> FEATURE:
<223> OTHER INFORMATION: Other linker

<400> SEQUENCE: 333

Arg Leu Met Glu Asp Ile Cys Leu Ala Arg Trp Gly Cys Leu Trp Glu
1               5                   10                  15

Asp Asp

<210> SEQ ID NO 334
<211> LENGTH: 20
<212> TYPE: PRT
<213> ORGANISM: Artificial Sequence
<220> FEATURE:
<223> OTHER INFORMATION: Other linker

```
<400> SEQUENCE: 334

Glu Val Arg Ser Phe Cys Thr Arg Trp Pro Ala Glu Lys Ser Cys Lys
1               5                   10                  15

Pro Leu Arg Gly
            20

<210> SEQ ID NO 335
<211> LENGTH: 20
<212> TYPE: PRT
<213> ORGANISM: Artificial Sequence
<220> FEATURE:
<223> OTHER INFORMATION: Other linker

<400> SEQUENCE: 335

Arg Ala Pro Glu Ser Phe Val Cys Tyr Trp Glu Thr Ile Cys Phe Glu
1               5                   10                  15

Arg Ser Glu Gln
            20

<210> SEQ ID NO 336
<211> LENGTH: 11
<212> TYPE: PRT
<213> ORGANISM: Artificial Sequence
<220> FEATURE:
<223> OTHER INFORMATION: Other linker

<400> SEQUENCE: 336

Glu Met Cys Tyr Phe Pro Gly Ile Cys Trp Met
1               5                   10

<210> SEQ ID NO 337
<211> LENGTH: 11
<212> TYPE: PRT
<213> ORGANISM: Artificial Sequence
<220> FEATURE:
<223> OTHER INFORMATION: peptide sequence

<400> SEQUENCE: 337

Gly Ala Pro Ala Pro Ala Ala Pro Ala Pro Ala
1               5                   10

<210> SEQ ID NO 338
<211> LENGTH: 4
<212> TYPE: PRT
<213> ORGANISM: Artificial Sequence
<220> FEATURE:
<223> OTHER INFORMATION: peptide sequence

<400> SEQUENCE: 338

Pro Pro Pro Pro
1

<210> SEQ ID NO 339
<211> LENGTH: 11
<212> TYPE: PRT
<213> ORGANISM: Artificial Sequence
<220> FEATURE:
<223> OTHER INFORMATION: linker

<400> SEQUENCE: 339

Ser Gly Gly Gly Gly Ser Gly Gly Gly Gly Ser
1               5                   10

<210> SEQ ID NO 340
```

```
<211> LENGTH: 11
<212> TYPE: PRT
<213> ORGANISM: Artificial Sequence
<220> FEATURE:
<223> OTHER INFORMATION: linker

<400> SEQUENCE: 340

Ser Gly Gly Gly Gly Thr Gly Gly Gly Gly Ser
1               5                   10

<210> SEQ ID NO 341
<211> LENGTH: 111
<212> TYPE: PRT
<213> ORGANISM: Artificial Sequence
<220> FEATURE:
<223> OTHER INFORMATION: 4450gL5 V-region - IGKV1-6 framework

<400> SEQUENCE: 341

Ala Ile Asp Met Thr Gln Ser Pro Ser Ser Leu Ser Ala Ser Val Gly
1               5                   10                  15

Asp Arg Val Thr Ile Thr Cys Gln Ser Ser Gln Ser Ile Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Gln Gly Gly Ser Gly
                85                  90                  95

Gly Glu Gly Ile Ala Phe Gly Gly Gly Thr Lys Val Glu Ile Lys
            100                 105                 110

<210> SEQ ID NO 342
<211> LENGTH: 111
<212> TYPE: PRT
<213> ORGANISM: Artificial Sequence
<220> FEATURE:
<223> OTHER INFORMATION: 4450gL6 V-region - IGKV1-6 framework

<400> SEQUENCE: 342

Ala Ile Asp Met Thr Gln Ser Pro Ser Ser Leu Ser Ala Ser Val Gly
1               5                   10                  15

Asp Arg Val Thr Ile Thr Cys Gln Ser Ser Gln Ser Ile Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Gln Gly Gly Ser Gly
                85                  90                  95

Gly Asp Ala Ile Ala Phe Gly Gly Gly Thr Lys Val Glu Ile Lys
            100                 105                 110

<210> SEQ ID NO 343
<211> LENGTH: 111
<212> TYPE: PRT
<213> ORGANISM: Artificial Sequence
<220> FEATURE:
```

```
<223> OTHER INFORMATION: 4450gL7 V-region - IGKV1-6 framework

<400> SEQUENCE: 343

Ala Ile Asp Met Thr Gln Ser Pro Ser Ser Leu Ser Ala Ser Val Gly
 1               5                  10                  15

Asp Arg Val Thr Ile Thr Cys Gln Ser Ser Gln Ser Ile Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Gln Gly Gly Gly Ser Gly
                85                  90                  95

Gly Asp Ser Ile Ala Phe Gly Gly Gly Thr Lys Val Glu Ile Lys
            100                 105                 110
```

ANTIBODY MOLECULES WHICH BIND CD79

REFERENCE TO AN ELECTRONIC SEQUENCE LISTING

The contents of the electronic sequence listing (00890010US1seqlist.txt; Size: 203,219 bytes; and Date of Creation Dec. 14, 2017) is herein incorporated by reference in its entirety.

The present disclosure claims priority from PCT/EP2015/066368, PCT/EP2015/066369 and GB1601075.3 each of which are incorporated herein by reference.

FIELD OF INVENTION

The present disclosure relates to antibody molecules which are at least specific to the antigen CD79, formulations comprising said antibody molecules and use of any one of the same, in treatment. The present disclosure also extends to methods of preparing said antibody molecules and said formulations.

BACKGROUND OF INVENTION

Biological mechanisms in vivo are extremely complicated cascades of signals, which are difficult to deconvolute and understand. An example of such signalling is that required to activate B-cells. The B cell antigen receptor (BCR) is composed of membrane immunoglobulin (mIg) molecules and associated Igα/Igβ (CD79a/CD79b) heterodimers (α/β). The mIg subunits bind antigen, resulting in receptor aggregation, while the α/β subunits transduce signals to the cell interior. BCR aggregation rapidly activates the Src family kinases Lyn, Blk, and Fyn as well as the Syk and Btk tyrosine kinases. This initiates the formation of a 'signalosome' composed of the BCR, the aforementioned tyrosine kinases, adaptor proteins such as CD19 and BLNK, and signaling enzymes such as PLCγ2, PI3K, and Vav.

Signals emanating from the signalosome activate multiple signaling cascades that involve kinases, GTPases, and transcription factors. This results in changes in cell metabolism, gene expression, and cytoskeletal organization. The complexity of BCR signaling permits many distinct outcomes, including survival, tolerance (anergy) or apoptosis, proliferation, and differentiation into antibody-producing cells or memory B cells. The outcome of the response is determined by the maturation state of the cell, the nature of the antigen, the magnitude and duration of BCR signaling, and signals from other receptors such as CD40, the IL-21 receptor, and BAFF-R. Many other transmembrane proteins, some of which are receptors, modulate specific elements of BCR signaling. A few of these, including CD45, CD19, CD22, PIR-B, and FcγRIIB1 (CD32). The magnitude and duration of BCR signaling are limited by negative feedback loops including those involving the Lyn/CD22/SHP-1 pathway, the Cbp/Csk pathway, SHIP, Cbl, Dok-1, Dok-3, FcγRIIB1, PIR-B, and internalization of the BCR. In vivo, B cells are often activated by antigen-presenting cells that capture antigens and display them on their cell surface. Activation of B cells by such membrane-associated antigens requires BCR-induced cytoskeletal reorganization.

Autoreactive B cells are responsible for the production of pathogenic autoantibodies which can either directly or indirectly cause or exacerbate autoimmune conditions. Depletion of CD20 positive B cells has been used to successfully treat a number of autoimmune conditions and thus established conclusively that B cells play an important role in causing or maintaining a number of autoimmune diseases, such as rheumatoid arthritis, systemic lupus erythematosus, multiple sclerosis and type I diabetes mellitus. Although B cell depletion has been a successful therapeutic option evidence also exists that control of B cell growth and activation status can also be an effective way to modulate B cell function. Alternative strategies that do not deplete B cells and offer the flexibility of controlling B cells without long term suppression of B cell immunity, which has been shown to be associated with some side effects would therefore be desirable. In addition not all B cell responses or activities are harmful and evidence suggests that maintenance of regulatory B cell populations can be protective. Such an approach should be effective in diseases which have abnormal B cell function caused by inappropriate or excessive BcR signalling. Examples of such diseases include, but are not limited to, inflammation, autoimmunity and cancer. Of particular interest are diseases that either have a direct requirement for BcR signalling or require inhibition or stimulation of humoral immune responses.

CD79a along with CD79b (formerly known as Ig-alpha and Ig-beta) form a heterodimer on the surface of a B cell stabilized by disulfide bonding. This complex is the heterodimerc signal transducing molecule of the BCR which regulates B cell signalling and all stages of B cell development, activation and tolerance. CD79 is expressed almost exclusively on B cells and B cell neoplasms. Modulation of differential signals delivered through this molecule by antibodies can cause B cell activation, B cell anergy or B cell death and therefore can have therapeutic benefit in many different diseases which depend upon B cell activation including autoimmuninty, immunodeficiency, and malignancy (See for example, The B-Cell Antigen Receptor: Formation of Signaling Complexes and the Function of Adaptor Proteins. Current Topics in Microbiology & Immunology. 2000. Vol 245(1):53-76).

The present disclosure provides a number of antibody molecules specific to CD79, which may be employed alone or in combination with an entity, such as an antibody or binding fragment thereof specific to a further antigen, such as a B cell surface receptor (such as CD22 or CD45), useful in controlling aberrant B cell functions, for example associated with certain diseases such as autoimmunity and cancer.

SUMMARY OF THE DISCLOSURE

Thus provided is an antibody molecule comprising a:
CDRH1 of formula (I):

$$GFSLX_1NYX_2X_3X_4 \quad \text{(SEQ ID NO: 1)}$$

wherein $X_1$ is S or N, $X_2$ is V or A, $X_3$ is V or M and $X_4$ is S or V,

CDRH2 of formula (II):

$$IIYX_5X_6X_7X_8X_9X_{10}X_{11}YAX_{12}WAKG \quad \text{(SEQ ID NO: 2)}$$

wherein $X_5$ is V or I, $X_6$ is S or E, $X_7$ is T or G and $X_8$ is N or G, $X_9$ is T or A, $X_{10}$ is T or Y, $X_{11}$ is W or absent, $X_{12}$ is N or S, CDHR3 is

```
                                              (SEQ ID NO: 3)
EPYEPYDDSNIYYGMDP
or
                                              (SEQ ID NO: 4)
DAGHSDVDVLDI,
``` and a light chain variable domain (VL). In one example the light chain variable domain comprises CDRL1, CDRL2 and CDRL3 from a lagomorph, in particular a light chain variable domain comprising a human framework and CDRL1, CDRL2 and CDRL3 from a rabbit or variants thereof.

In one embodiment CDRL1 has a formula (III):

```
                                              (SEQ ID NO: 5)
QX13SQSX14X15X16X17NX18LA
``` wherein $X_{13}$ is A or S, $X_{14}$ is V or I, $X_{15}$ is V or Y and $X_{16}$ is N or S, $X_{17}$ is G or N, and $X_{18}$ is Y or D;

CDRL2 has a formula (IV):

```
                                              (SEQ ID NO: 6)
X19ASX20LAS
``` wherein $X_{19}$ is S or E, and $X_{20}$ T or K;

CDRL3 has a formula (V):

```
                                              (SEQ ID NO: 7)
X21GX22X23SX24X25X26X27X28X29X30A
``` wherein $X_{21}$ is L or Q, $X_{22}$ is G or E, $X_{23}$ is G or F, $X_{24}$ is C, S or G (particularly S or G), $X_{25}$ is S or G, $X_{26}$ is D, S or E, $X_{27}$ is H, G, A, S or C (particularly H, G, A or S), $X_{28}$ is I or D, $X_{29}$ is C, S or absent and $X_{30}$ is N or absent.

Examples of CDRs falling with the definition of formula (I) and (II) are provided as follows:

```
                                              SEQ ID NO: 8
GFSLNNYVMV
(for example as CDRH1)

SEQ ID NO: 9
IIYVSGNAYYASWAKG
(for example as CDRH2)

SEQ ID NO: 11
GFSLSNYAVS
(for example as CDRH1)

SEQ ID NO: 12
IIYIETGTTWYANWAKG
(for example as CDRH2)
```

Examples of CDRs falling with the definition of formula (III), (IV) and (V) are provided as follows:

```
                                              SEQ ID NO: 13
QSSQSIYNNNDLA
(for example as CDRL1)

SEQ ID NO: 14
EASKLAS
(for example as CDRL2)

SEQ ID NO: 15
QGGGSGGDGIA
(for example as CDRL3)

SEQ ID NO: 16
QGGGSGGEGIA
(for example as CDRL3 variant 1)

SEQ ID NO: 17
QGGGSGGDAIA
(for example as CDRL3 variant 2)

SEQ ID NO: 18
QGGGSGGDSIA
(for example as CDRL3 variant 3)

SEQ ID NO: 19
QASQSVVSGNYLA
(for example as CDRL1)

SEQ ID NO: 20
SASTLAS
(for example as CDRL2)

SEQ ID NO: 21
LGEFSCSSHDCNA
(for example as CDRL3)

SEQ ID NO: 22
LGEFSSSSHDSNA
(for example as CDRL3 variant 1)

SEQ ID NO: 23
LGEFSCSSHDSNA
(for example as CDRL3 variant 2)

SEQ ID NO: 24
LGEFSSSSHDCNA
(for example as CDRL3 variant 3)
```

In one example the present inventon provides the CD79 antibodies described herein in any suitable antibody format. Accordingly provided are anti-CD79 antibodies or fragments thereof containing one or more of the binding domains described herein and in FIG. 51, comprising the CDRs provided herein and in SEQ ID NOS 11, 12, 3, 19, 20 and 21 (antibody 4447) or SEQ ID NOs 8, 9, 4, 13, 14 and 15 (antibody 4450). Said CDRs may be incorporated into any suitable antibody framework and into any suitable antibody format. Such antibodies include whole antibodies and functionally active fragments or derivatives thereof which may be, but are not limited to, monoclonal, humanised, fully human or chimeric antibodies. Accordingly, such antibodies may comprise a complete antibody molecule having full length heavy and light chains or a fragment thereof and may be, but are not limited to Fab, modified Fab, Fab', F(ab')$_2$, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Multivalent antibodies may comprise multiple specificities or may be monospecific (see for example WO 92/22853 and WO05/113605). It will be appreciated that this aspect of the invention also extends to variants of these CD79 antibodies including humanised versions and modified versions, including those in which amino acids have been mutated in the CDRs to remove one or more isomerisation, deamidation, glycosylation site or cysteine residue as described herein.

Thus in one example there is provided an anti-CD79 antibody or binding fragment thereof comprising a heavy chain or heavy chain fragment having a variable region, wherein said variable region comprises one, two or three CDRs independently selected from SEQ ID NO: 1, SEQ ID NO: 2 and SEQ ID NO: 3 or SEQ ID NO: 4, for example wherein CDR H1 is SEQ ID NO: 1, CDR H2 is SEQ ID NO: 2 and CDR H3 is SEQ ID NO: 3 or SEQ ID NO: 4.

Thus one embodiment CDR H1 is SEQ ID NO: 1 and CDR H2 is SEQ ID NO: 2, or CDR H1 is SEQ ID NO: 1 and CDR H3 is SEQ ID NO: 3 or CDR H1 is SEQ ID NO: 1 and CDR H3 is SEQ ID NO: 4, or CDR H2 is SEQ ID NO: 2 and CDR H3 is SEQ ID NO: 3 or CDR H2 is SEQ ID NO: 2 and CDR H3 is SEQ ID NO: 4.

Thus in one example there is provided an anti-CD79 antibody or binding fragment thereof comprising a heavy chain or heavy chain fragment having a variable region, wherein said variable region comprises one, two or three CDRs independently selected from SEQ ID NO: 8, SEQ ID NO: 9 and SEQ ID NO: 4, for example wherein CDR H1 is SEQ ID NO: 8, CDR H2 is SEQ ID NO: 9 and CDR H3 is SEQ ID NO: 4.

Thus one embodiment CDR H1 is SEQ ID NO: 8 and CDR H2 is SEQ ID NO: 9, or CDR H1 is SEQ ID NO: 8 and CDR H3 is SEQ ID NO: 4, or CDR H2 is SEQ ID NO: 9 and CDR H3 is SEQ ID NO: 4.

Thus in one example there is provided an anti-CD79 antibody or binding fragment thereof comprising a heavy chain or heavy chain fragment having a variable region, wherein said variable region comprises one, two or three CDRs independently selected from SEQ ID NO: 11, SEQ ID NO: 12 and SEQ ID NO: 3, for example wherein CDR H1 is SEQ ID NO: 11, CDR H2 is SEQ ID NO: 12 and CDR H3 is SEQ ID NO: 3.

Thus one embodiment CDR H1 is SEQ ID NO: 11 and CDR H2 is SEQ ID NO: 12, or CDR H1 is SEQ ID NO: 11 and CDR H3 is SEQ ID NO: 3, or CDR H2 is SEQ ID NO: 12 and CDR H3 is SEQ ID NO: 3.

In one embodiment the antibody molecule according to the present disclosure comprises a light chain or light chain fragment having a variable region, for example comprising one, two or three CDRs independently selected from SEQ ID NO: 5, 6 and 7, in particular wherein CDR L1 has the sequence given in SEQ ID NO: 5, CDR L2 has the sequence given in SEQ ID NO: 6 and CDR L3 has the sequence given in SEQ ID NO: 7.

Thus in one embodiment CDR L1 is SEQ ID NO: 5 and CDR L2 is SEQ ID NO: 6, or CDR L1 is SEQ ID NO: 5 and CDR L3 is SEQ ID NO: 7; or CDR L2 is SEQ ID NO: 6 and CDR L3 is SEQ ID NO: 7.

In one embodiment the antibody molecule according to the present disclosure comprises a light chain or light chain fragment having a variable region, for example comprising one, two or three CDRs independently selected from SEQ ID NO: 13 to 24, in particular wherein CDR L1 has the sequence given in SEQ ID NO: 13 or 19, CDR L2 has the sequence given in SEQ ID NO: 14 or 20 and CDR L3 has the sequence independently selected from SEQ ID NO: 15, 16, 17, 18, 21, 22, 23 and 24.

Thus in one embodiment CDR L1 is SEQ ID NO: 13 and CDR L2 is SEQ ID NO: 14; or CDR L1 is SEQ ID NO: 13 and CDR L3 is SEQ ID NO: 15, 16, 17 or 18; or CDR L2 is SEQ ID NO: 14 and CDR L3 is SEQ ID NO: 15, 16, 17 or 18; or CDR L1 is SEQ ID NO: 13, CDR L2 is SEQ ID NO: 14 and CDR L3 is SEQ ID NO: 15, 16, 17 or 18.

Thus in one embodiment CDR L1 is SEQ ID NO: 19 and CDR L2 is SEQ ID NO: 20, or CDR L1 is SEQ ID NO: 19 and CDR L3 is SEQ ID NO: 21, 22, 23 or 24; or CDR L2 is SEQ ID NO: 20 and CDR L3 is SEQ ID NO: 21, 22, 23 or 24; or CDR L1 is SEQ ID NO: 19, CDRL2 is SEQ ID NO: 20 and CDR L3 is SEQ ID NO: 21, 22, 23 or 24 (such as SEQ ID NO: 22).

In one embodiment the antibodies or binding fragments according to the present disclosure comprise CDR sequences selected from SEQ ID NOs: 1 to 24, for example wherein CDR H1 is SEQ ID NO: 1, CDR H2 is SEQ ID NO: 2, CDR H3 is SEQ ID NO: 3 or 4, CDR L1 is SEQ ID NO: 5, CDR L2 is SEQ ID NO: 6 and CDR L3 is SEQ ID NO: 7.

In one embodiment CDR H1 is SEQ ID NO: 8 or 11, CDR H2 is SEQ ID NO: 9 or 12, CDR H3 is SEQ ID NO: 3 or 4, CDR L1 is SEQ ID NO: 5, CDR L2 is SEQ ID NO: 6 and CDR L3 is SEQ ID NO: 7.

In one embodiment CDR H1 is SEQ ID NO: 8 or 11, CDR H2 is SEQ ID NO: 9 or 12, CDR H3 is SEQ ID NO: 3 or 4, CDR L1 is SEQ ID NO: 13 or 19, CDR L2 is SEQ ID NO: 14 or 20 and CDR L3 is SEQ ID NO: 15, 16, 17, 18, 21, 22, 23 or 24.

In one embodiment CDR H1 is SEQ ID NO: 1, CDR H2 is SEQ ID NO: 2, CDR H3 is SEQ ID NO: 3 or 4, CDR L1 is SEQ ID NO: 13 or 19, CDR L2 is SEQ ID NO: 14 or 20 and CDR L3 is SEQ ID NO: 15, 16, 17, 18, 21, 22, 23 or 24.

In one embodiment CDR H1 is SEQ ID NO: 8, CDR H2 is SEQ ID NO: 9, CDR H3 is SEQ ID NO: 4, CDR L1 is SEQ ID NO: 13, CDR L2 is SEQ ID NO: 14 and CDR L3 is SEQ ID NO: 15, 16, 17 or 18.

In one embodiment CDR H1 is SEQ ID NO: 11, CDR H2 is SEQ ID NO: 12, CDR H3 is SEQ ID NO: 3, CDR L1 is SEQ ID NO: 19, CDR L2 is SEQ ID NO: 20 and CDR L3 is SEQ ID NO: 21, 22, 23 or 24.

Kabat numbering is employed herein unless the context indicates otherwise.

In one embodiment an antibody molecule according to the present disclosure is humanised and incorporates CDRs described herein or variants therof.

In one embodiment the heavy chain variable region human framework employed in the antibody molecule of the present disclosure is selected from the group comprising IGHV3-48, IGHV4-59, IGHV3-66 and a variant of any one of the same wherein one, two, three, four, five, six, seven, eight, nine, ten or more amino acids are substituted with an amino acid other than cysteine, for example substituted with a residue in the corresponding location in the original donor antibody, for example from the donor VH sequences provided in SEQ ID NO:31 or 38. Typically the human framework further comprises a suitable J region sequence, such as the JH4 or JH2 J region.

In one embodiment substitutions in the VH framework (particularly for use with heavy chain anti-CD79 CDRs described herein above) may be made in one or more, such as at 1, 2, 3, 4, 5, 6, 7 or 8 positions selected from 24, 37, 48, 49, 67, 71, 73 and 78 (such as at least substitution at position 73 and 78), for example substitution in all of the positions 24, 48, 49, 73, and 78 (particularly suitable for IGHV3-66) or all of the positions 24, 48, 49, 71, 73, and 78 (particularly suitable for IGHV3-48) or all the positions 37, 49, 67, 71, 73, 76 and 78 or all of the positions 37, 67, 71, 73, 76 and 78 (particularly suitable for IGHV4-59).

In one embodiment after substitution position 24 of the VH framework is valine.

In one embodiment after substitution position 37 of the VH framework is valine.

In one embodiment after substitution position 48 of the VH framework is isoleucine.

In one embodiment after substitution position 49 of the VH framework is glycine.

In one embodiment after substitution position 67 of the VH framework is phenylalanine.

In one embodiment after substitution position 71 of the VH framework is lysine.

In one embodiment after substitution position 71 of the VH framework is arginine.

In one embodiment after susbstitution position 73 of the VH framework is serine.

In one embodiment after substitution position 78 of the VH framework is valine.

It will be appreciated that one or more of these substitutions may be combined to generate a humanised VH region for use in an antibody molecule of the invention.

In one embodiment the humanised VH variable domain comprises a sequence independently selected from SEQ ID NO: 34, 35, 41 and 42.

In one embodiment residue 1 of the VH is changed to glutamic acid to facilitate processing of the sequence.

In one embodiment the light chain variable region human framework employed in the humanised antibody molecule of the present disclosure is selected from the group comprising IGKV1-6, IGKV1D-13 and a variant of any one of the same wherein one, two, three, four, five or six amino acids are substituted with an amino acid other than cysteine, for example substituted with a donor residue in the corresponding location in the original donor antibody for example from the donor VL sequences provided in SEQ ID NO:29 or 36. Typically the human framework further comprises a suitable J region such as a JK4 J region.

In one embodiment a human VL framework employed (for example to accept light chain anti-CD79 CDRs) in an antibody molecule of the present disclosure comprises an amino acid substituted in at least one position, such as 1, 2, 3, 4, 5 or 6 selected from the group comprising 2, 3, 36, 46, 49 and 70, for example wherein the original amino acid in the framework is substituted for another amino acid other than cysteine, in particular substituted for a residue in the corresponding location in the framework of the donor antibody.

In one embodiment the human VL framework employed is an IGKV1 framework and has substitutions in at least positions 3 and 70.

In one embodiment the human VL framework employed (such as an IGKV1 framework) has substitutions in positions 2, 3, 36, 46, 49 and 70 (particularly suitable for IGKV1D-13) or positions 3 and 70 (particularly suitable for IGKV1-6).

In one embodiment after susbstitution position 2 of the VL framework is glutamine.

In one embodiment after susbstitution position 3 of the VL framework is valine or aspartic acid.

In one embodiment after substitution position 36 of the VL framework is leucine.

In one embodiment after substitution position 46 of the VL framework is glutamine.

In one embodiment after substitution position 49 of the VL framework is histidine.

In one embodiment after substitution position 70 of the VL framework is glutamine.

It will be appreciated that one or more of these substitutions may be combined to generate a humanised VL region for use in an antibody of the invention.

In one embodiment the humanised VL variable domain comprises a sequence independently selected from SEQ ID NO: 33 or 40.

In one embodiment the humanised VL variable domain comprises a sequence independently selected from SEQ ID NO: 33, 40, 341, 342 and 343.

In one embodiment there is provided an antibody molecule comprising a VH independently selected from SEQ ID NO: 34 and 35 and a VL with a sequence shown in SEQ ID NO: 33.

In one embodiment there is provided an antibody molecule comprising a VH independently selected from SEQ ID NO: 34 and 35 and a VL with a sequence shown in SEQ ID NO: 250.

In one embodiment there is provided an antibody molecule comprising a VH independently selected from SEQ ID NO: 41 and 42 and a VL with a sequence shown in SEQ ID NO: 40.

In one embodiment there is provided an antibody molecule comprising a VH independently selected from SEQ ID NO: 41 and 42 and a VL independently selected from SEQ ID NO: 40, 341, 342 and 343.

It will be appreciated that these humanised grafted variable regions (SEQ ID NOs 41, 42, 40, 341, 342 and 343) may be modified to reduce the number of donor residues and to replace these with the original human residue (s).

In one example therefore there is provided an antibody molecule comprising a VL independently selected from SEQ ID NO: 40, 341, 342 and 343 in which the residue at position 3 has been replaced by glutamine (Q) and/or the residue at position 70 has been replaced by Aspartic acid (D).

In one example there is provided an antibody molecule comprising a VH comprising the sequence given in SEQ ID NO: 41 in which the residue at position 24 is has been replaced by glutamine (Q) and/or the residue at position 48 has been replaced by Aspartic acid (D), and/or the residue at position 49 has been replaced by Serine (S) and/or the residue at position 73 has been replaced by Asparagine (N) and/or the residue at position 78 has been replaced by Leucine (L).

In one example there is provided an antibody molecule comprising a VH comprising the sequence given in SEQ ID NO: 42 in which the residue at position 37 is has been replaced by Isoleucine (I) and/or the residue at position 67 has been replaced by Valine (V) and/or the residue at position 71 has been replaced by Valine (V) and/or the residue at position 73 has been replaced by Threonine (T) and/or the residue at position 78 has been replaced by Phenylalanine (F).

In one example there is provided an antibody molecule comprising a VH comprising the sequence given in SEQ ID NO: 41 in which the residue at position 24 is has been replaced by glutamine (Q) and/or the residue at position 48 has been replaced by Aspartic acid (D), and/or the residue at position 49 has been replaced by Serine (S) and/or the residue at position 73 has been replaced by Asparagine (N) and/or the residue at position 78 has been replaced by Leucine (L) and a VL comprising a sequence independently selected from SEQ ID NO: 40, 341, 342 and 343 sequence or a sequence independently selected from SEQ ID NO: 40, 341, 342 and 343 in which the residue at position 3 has been replaced by glutamine (Q) and/or the residue at position 70 has been replaced by Aspartic acid (D).

In one example there is provided an antibody molecule comprising a VH comprising the sequence given in SEQ ID NO: 42 in which the residue at position 37 is has been replaced by Isoleucine (I) and/or the residue at position 67 has been replaced by Valine (V) and/or the residue at position 71 has been replaced by Valine (V) and/or the residue at position 73 has been replaced by Threonine (T)

and/or the residue at position 78 has been replaced by Phenylalanine (F) and a VL comprising a sequence independently selected from SEQ ID NO: 40, 341, 342 and 343 sequence or a sequence independently selected from SEQ ID NO: 40, 341, 342 and 343 in which the residue at position 3 has been replaced by glutamine (Q) and/or the residue at position 70 has been replaced by Aspartic acid (D).

In one embodiment an antibody molecule of the present disclosure is a full length antibody, In one embodiment the antibody molecule of the present disclosure is a Fab or Fab' fragment.

In one embodiment the antibody molecule of the present disclosure is a scFv.

In one embodiment the antibody molecule of the present disclosure is multispecific, for example bispecific or trispecific.

In one embodiment the multispecific antibody molecule (such as a bispecific antibody molecule) of the disclosure in addition to a binding domain specific to CD79 comprises a binding domain specific to another antigen.

In one embodiment the multispecific antibody molecule (such as a bispecific antibody molecule) of the disclosure in addition to a binding domain specific to CD79 comprises a binding domain specific to CD22, for example comprising 1, 2, 3, 4, 5 or 6 anti-CD22 CDRs disclosed herein or variants thereof, such as a variable domain or a variable domain pair, in particular a humanised variable domain or pair of variable domains disclosed herein.

In one embodiment the multispecific antibody molecule (such as the bispecific antibody molecule) of the disclosure comprises a binding domain to CD45, for example comprising 1, 2, 3, 4, 5 or 6 anti-CD45 CDRs disclosed herein or variants, such as a variable domain or a variable domain pair, in particular a humanised variable domain or pair of variable domains disclosed herein.

In one embodiment the binding domain or binding domains of the multispecific molecules of the present invention each independently comprise one or two (such as two) antibody variable domains specific to a relevant antigen (such as at least one binding domain specific to CD79 and a further binding domain specific CD22 or CD45).

In one embodiment the antibody molecule of the present disclosure is specific to CD79a.

In one embodiment the antibody molecule of the present disclosure is specific to CD79b.

In one embodiment the antibody molecule of the present disclosure is specific to the CD79a/CD79b heterodimer.

Also provided is an antibody or binding fragment that binds the same epitope as an antibody or binding fragment explicitly disclosed herein.

In one embodiment there is provided an antibody or binding fragment that cross-blocks an antibody or binding fragment explicitly disclosed herein to human CD79, or is cross-blocked from binding human CD79 by said antibody.

The combination of anti-CD79 together with anti-CD45 or CD22 according to the present disclosure in a bispecific or trispecific format shows interesting biological activity in functional in vitro assays, for example inhibition of B cell signalling as measured by any one of the following: inhibition of phosphorylation of Akt S473, inhibition of phosphorylation of P38 and PLCγ2 Y759 inhibition of IkB, in addition to the inhibition of expression of CD86, CD71 and/or CD40 on B cells. The same level of activity is not apparent for individual components alone and may not be apparent for the components provided in admixture i.e. is only present when the combination is provided a bispecific molecule.

The inhibition observed in these assays is indicative that a multispecific molecule of the invention comprising a binding domain specific to CD45 or CD22 and a binding domain specific to CD79 and that the combination may be used to alter B cell function and provide a therapeutic alternative to depletion of B cells.

The invention also provides novel CD22 antibodies for use in the multispecific molecules of the present invention or for incorporation into any other suitable antibody format.

The invention also provides novel CD45 antibodies for use in the multispecific molecules of the present invention or for incorporation into any other suitable antibody format.

DESCRIPTION OF DRAWINGS

FIG. 10 is a table showing the data for the antigen grid cross specificities. Antigen 2=CD79b and antigen 3=CD22. Values are percentage inhibition (negative value for activation) of phosphorlylation of Syk & represent the mean of multiple V region combinations evaluated.

FIG. 11 is a table showing the data for the antigen grid cross specificities. Antigen 2=CD79b and antigen 3=CD22. Values are percentage inhibition (negative value for activation) of phosphorlylation of PLCγ2 & represent the mean of multiple V-region combinations evaluated.

FIG. 12 is a table showing the data for the antigen grid cross specificities. Antigen 2=CD79b and antigen 3=CD22 and antigen 4=CD4. Values are percentage inhibition (negative value for activation) of phosphorylation of AKT & represent the mean of multiple V region combinations evaluated.

FIG. 13 is a graph showing the percentage inhibition of the phosphorlylation of Syk, PLCγ2 & AKT for each V-region combination for CD79b specificity in Fab-X combined with CD22 specificity in Fab-Y

Figure 1:
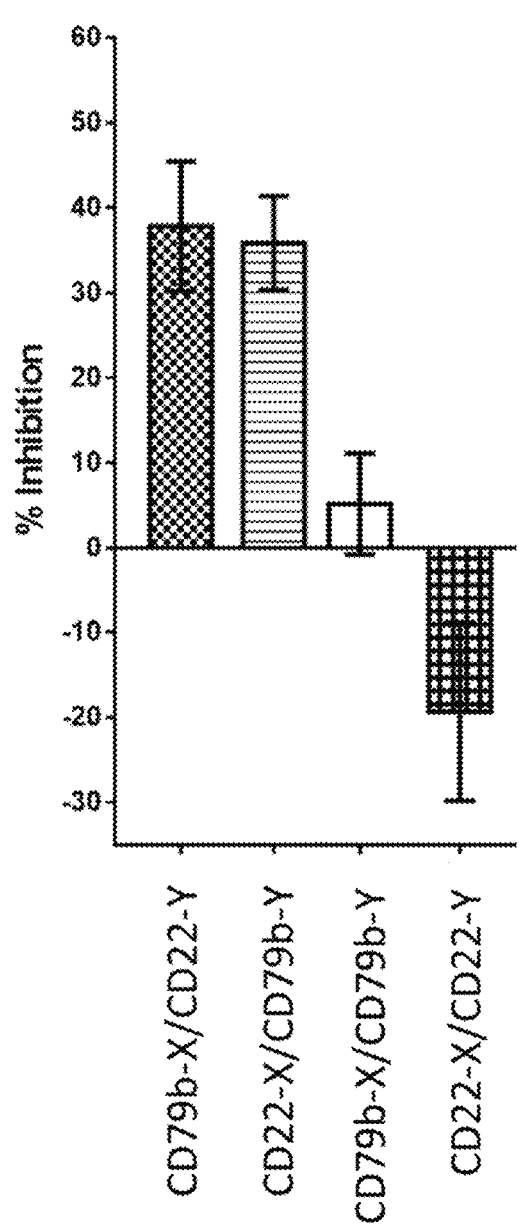
FIG. 1 is a bar chart of the relative potency of inhibition of phosphorylated Akt for bispecific and bivalent combinations of antibodies with specificity for CD22 and CD79b.

Furthermore, inhibition of B cell receptor signalling can lead to inhibition of downstream functions. One such outcome would be the inhibition of co-stimulatory molecules such as CD86 (or reduced expression of the same) which will lead to the inhibition of T cell function, survival and differentiation.

Thus inhibition of B cell receptor signalling can be beneficial in controlling aberrant B cell functions associated with autoimmunity and cancer. B cell receptor signalling is required for B cell proliferation, differentiation, antigen presentation and cytokine release in autoimmune disease. Thus inhibiting BcR activity can regulate B cell functions such as immunoglobulin secretion, T cell activation and control inappropriate B cell activity associated with, for example autoimmune conditions. In addition there are some B cell leukaemias and lymphomas that require B cell receptor signalling for survival and growth which may be controlled by inhibitors of B cell receptor activation.

CD79 as used herein refers to the complex composed of CD79a and CD79b. Accordingly, antibodies or binding domains which bind CD79 may bind to CD79a and/or CD79b. Binds to CD79a and/or CD79b as employed herein refers to specific to CD79a, specific to CD79b, specific to both CD79a and CD79b (i.e. recognises an epitope on CD79a and the same antibody or binding domain also recognises an epitope on CD79b i.e. pan specific) or is specific to the complex of CD79a and CD79b (i.e. recognises an epitope formed from the interaction of CD79a and CD79b in the complex form and this is capable of distinguishing the complex from the individual components).

In one embodiment an antibody or binding fragment thereof employed in the molecules of the present disclosure is specific to CD79a.

In one embodiment an antibody or binding fragment thereof employed in the molecules of the present disclosure is specific to CD79b.

In one embodiment an antibody or binding fragment thereof employed in the molecules of the present disclosure is specific to CD79 complex, i.e. it recognises an epitope present in the complex and is specific thereto, for example an epitope comprising an interaction between CD79a and CD79b.

In one embodiment even where the binding domain is specific to CD79a or CD79b it will be appreciated that the binding domain will preferably still bind to CD79a or CD79b when in the complex form, as the two protein are naturally co-expressed on the cell surface.

Where there are two variable regions in a binding domain and/or in each binding domain, then the two variable regions will generally work co-operatively to provide specificity for the relevant antigen, for example they are a cognate pair or affinity matured to provide adequate affinity such that the domain is specific to a particular antigen. Typically they are a heavy and light chain variable region pair (VH/VL pair).

The antibody molecules of the present invention may comprise a complete antibody molecule having full length heavy and light chains or a fragment thereof and may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

"Multispecific molecule" as employed herein refers to a molecule with the ability to specifically bind at least two distinct antigens, for example different antigens. In one embodiment the multispecific molecule is a bispecific, trispecific or tetraspecific molecule, in particular a bispecific or trispecific molecule.

In one embodiment the antibody molecule of the present disclosure is bispecific.

In one embodiment the antibody molecule of the present disclosure is bispecific, wherein one binding domain binds to CD79.

In one embodiment the antibody molecule of the present disclosure is trispecific.

In one embodiment the antibody molecule of the present disclosure is trispecific, wherein one binding domain binds to CD79.

In one embodiment the antibody molecule of the present disclosure is monospecific for CD79 and monospecific for at least one other antigen i.e. the molecule only comprises one binding domain which binds CD79.

In one embodiment the antibody molecule of the present disclosure is monospecific for CD79 and monospecific for CD22 i.e. the molecule only comprises one binding domain which binds CD79 and one binding domain which binds CD22.

In one embodiment the antibody molecule of the present disclosure is monospecific for CD79 and monospecific for CD45 i.e. the molecule only comprises one binding domain which binds CD79 and one binding domain which binds CD45.

In one embodiment the multispecific molecule of the present disclosure is a single chain.

In one embodiment the multispecific molecule of the present disclosure comprises a heavy chain and also a light chain. In one example, as employed herein a heavy and light chain pairing is not referred to as a dimer, particularly where in one embodiment the molecule of the present disclosure does not comprise multimers, such as dimers of the antibody, unit/fragment or components.

In one aspect the disclosure extends to a molecule of a suitable format specific to at least CD22 and CD79a and to use of antibodies/fragments or combinations thereof specific to CD22 and CD79a in a multispecific molecule, such as a bispecific or trispecific format.

In one aspect the disclosure extends to a molecule of a suitable format specific to at least CD22 and CD79b and to use of antibodies/fragments or combinations thereof specific to CD22 and CD79b in a multispecific molecule, such as a bispecific or trispecific format.

In one aspect the disclosure extends to a molecule of a suitable format specific to at least CD22 and CD79a/b complex and to use of antibodies/fragments or combinations thereof specific to CD22 and CD79a/b complex in a multispecific molecule, such as a bispecific or trispecific format.

In one aspect the disclosure extends to a molecule of a suitable format specific to at least CD45 and CD79a and to use of antibodies/fragments or combinations thereof specific to CD45 and CD79a in a multispecific molecule, such as a bispecific or trispecific format.

In one aspect the disclosure extends to a molecule of a suitable format specific to at least CD45 and CD79b and to use of antibodies/fragments or combinations thereof specific to CD45 and CD79b in a multispecific molecule, such as a bispecific or trispecific format.

In one aspect the disclosure extends to a molecule of a suitable format specific to at least CD45 and CD79a/b complex and to use of antibodies/fragments or combinations thereof specific to CD45 and CD79a/b complex in a multispecific molecule, such as a bispecific or trispecific format.

In one embodiment the molecule of the present disclosure is trispecific, for example where the third binding domain is capable of extending the half-life of the molecule, for example by binding a serum carrier protein.

A variety of proteins exist in plasma and include thyroxine-binding protein, transthyretin, al-acid glycoprotein, transferrin, fibrinogen and albumin, or a fragment of any thereof (Bartalena & Robbins, 1993, Clinics in Lab. Med. 13:583-598; Bree et al., 1986, Clin. Pharmacokin. 11:336-342; Gitlin et al. 1964, J. Clin. Invest. 10:1938-1951; Peters, 1985, Adv Protein Chem. 37:161-245; Waldeman & Strober, 1969, Progr. Allergy, 13:1-110. In on example the third binding domain is specific to serum albumin, for example human serum albumin.

Multispecific Molecule Formats

Examples of suitable multispecific molecules for use in the present invention are known in the art, for example as disclosed in the review "The coming of Age of Engineered Multivalent Antibodies, Nunez-Prado et al Drug Discovery Today Vol 20 Number 5 March 2015, page 588-594, D. Holmes, Nature Rev Drug Disc November 2011:10; 798, Chan and Carter, Nature Reviews Immunology vol 10, May 2010, 301 incorporated herein by reference.

In one embodiment multispecific formats include those known in the art and those described herein, such as wherein the molecule format is selected from the group comprising or consisting of:

tandem sdAb, tandem sdAb-sdAb (three sdAbs);
$(scFv)_2$ (also referred to as tandem scFv), scFv-dsFv, dsscFv-dsFv $(dsFv)_2$;
diabody, dsdiabody, didsdiabody,
scdiabody, dsscdiabody, didsscdiabody;
Dart antibody i.e, $VL_1$ linker $VH_2$ linker and $VH_1$ linker $VL_2$ wherein the C-terminous of $VH_1$ and $VH_2$ are joined by a disulfide bond;
BiTE®, dsBiTE, didsBiTE;
Di-diabody (see Nunez-Prado et al in particular molecule number 25 in FIG. 1 therein), dsdi-diabody, didsdi-diabody;
triabody, dstriabody, didstriabody, tridstriabody;
tetrabodies, dstetrabody, didstetrabody, tridstetrabody, tetradstetrabody;
tandab (see Nunez-Prado et al in particular molecule number 22 in FIG. 1 therein); dstandab, didstandab, tridstandab, tetradstandab;
$[sc(Fv)_2]2$, (see Nunez-Prado et al in particular molecule number 22 in FIG. 1 therein), $ds[sc(Fv)_2]_2$, $dids[sc(Fv)_2]_2$, $trids[sc(Fv)_2]_2$, $tetrads[sc(Fv)_2]_2$,
Pentabody (see Nunez-Prado et al in particular molecule number 27 in FIG. 1 therein);
Fab-scFv (also referred to as a bibody), Fab'scFv, FabdsscFv (or BYbe), Fab'dsscFv;
tribody, dstribody, didstribody (also referred to as Fab-didsscFv or TrYbe or Fab-$(dssFv)_2$), Fab' didsscFv;
Fabdab, FabFv, Fab'dab, Fab'Fv;
Fab single linker Fv (also referred to herein as FabdsFv as disclosed in WO2014/096390), Fab' single linker Fv (also referred to herein as Fab'dsFv);
FabscFv single linker Fv, Fab'scFv single linker Fv;
FabdsscFv single linker Fv, Fab'dsscFv single linker Fv;
FvFabFv, FvFab'Fv, dsFvFabFv, dsFvFab'Fv, FvFabdsFv, FvFab'dsFv, dsFvFabdsFv, dsFvFab'dsFv,
FabFvFv, Fab'FvFv, FabdsFvFv, Fab'dsFvFv, FabFvdsFv, Fab'FvdsFv, FabdsFvdsFv, Fab'dsFvdsFv,
diFab, diFab' including a chemically conjugated diFab', $(FabscFv)_2$, $(Fab)_2scFvdsFv$, $(Fab)_2dsscFvdsFv$, $(FabdscFv)_2$,
$(Fab'scFv)_2$, $(Fab')_2scFvdsFv$, $(Fab')_2dsscFvdsFv$, $(Fab'dscFv)_2$,
$V_HHC_K$ (see Nunez-Prado et al in particular molecule number 6 in FIG. 1 therein);
minibody, dsminibody, didsminibody,
a miniantibody (ZIP) [see Nunez-Prado et al in particular molecule number 7 in FIG. 1 therein], dsminiantibody (ZIP) and didsminiantibody (ZIP);
tribi-minibody [see Nunez-Prado et al in particular molecule number 15 in FIG. 1 therein] dstribi-minibody, didstribi-minibody, tridstribi-minibody;
diabody-$CH_3$, dsdiabody-$CH_3$, didsdiabody-$CH_3$, scdiabody-$CH_3$, dsscdiabody-$CH_3$, didsscdiabody-$CH_3$,
tandemscFv-$CH_3$, tandemdsscFv-$CH_3$, tandemdidsscFv-$CH_3$, tandemtridsscFv-$CH_3$, tandemtetradsscFv-$CH_3$,
scFv-Fc (also referred to herein as a $(scFvCH_2CH_3)_2$), as described in WO2008/012543 and a single chain version thereof, dsscFvscFv-Fc, dsscFv-Fc (also referred to herein as $(dsscFvCH_2CH_3)_2$), scFv-dsFv-Fc, dsscFv-dsFv-Fc, dsFv-Fc (also referred to herein a $(dsFvCH_2CH_3)_2$),
scorpion molecule (Trubion) i.e. a binding domain, linker —$CH_2CH_3$ binding domain as described in U.S. Pat. No. 8,409,577;
SMIP (Trubion) i.e. $(scFv-CH_2CH_3)_2$;
$(dsFvCH_2CH_3)_2$, tandem scFv-Fc, tandem dsscFvscFv-Fc, tandem dsscFv-Fc,
scFv-Fc-scFv, dsscFv-Fc-scFv, scFv-Fc-dsscFv,
diabody-Fc, dsdiabody-Fc, didsdiabody-Fc, triabody-Fc, dstriabody-Fc, didstriabody-Fc, tridstriabody-Fc, tetrabody-Fc, dstetrabody-Fc, didstetrabody-Fc, tridstetrabody-Fc, tetradstetrabody-Fc, dstetrabody-Fc, didstetrabody-Fc, tridstetrabody-Fc, tetradstetrabody-Fc, scdiabody-Fc, dsscdiabody, didsscdiabody;
bi or trifunctional antibody, for example with different heavy chain variable regions and common light chains for example Merus bispecific antibody format (Biclonics®) with common light chains of a fixed sequence and different heavy chains (including different CDRs) and engineered $CH_3$ domain to drive the dimerization o the different heavy chains, Duobody (i.e. wherein one full length chain in the antibody has different specificity to the other full length chain in the antibody);

a full-length antibody wherein Fab arm exchange has been employed to create a bispecific format;

bi or tri functional antibody wherein a full-length antibody has common heavy chain and different light chains also referred to as kappa/lambda body' or 'κ/λ-body see WO2012/023053;

Ig-scFv one, two, three or four from the C terminus of heavy or light chain, scFv-Ig one, two, three or four from the N terminus of heavy or light chain, single linker Ig-Fv, Ig-dsscFv one, two, three or four from the C terminus of heavy or light chain (with one, two, three or four disulfide bonds);

Ig-dsscFv one, two, three or four from the N terminus of heavy or light chain (with one, two, three or four disulfide bonds), Ig single linker Fv (see PCT/EP2015/064450), Ig-dab, dab-Ig, scFv-Ig, V-Ig, Ig-V, scFabFvFc, scFabdsFvFc (single linker version scFavFv), (FabFvFc)$_2$, (FabdsFvFc)$_2$, scFab'FvFc, scFab'dsFvFc, (Fab'FvFc)$_2$, (Fab'dsFvFc)$_2$ and DVDIg, which are discussed in more detail below.

In one embodiment multispecific molecule formats include those known in the art and those described herein, such as wherein the molecule format is selected from the group comprising or consisting of: diabody, scdiabody, triabody, tribody, tetrabodies, tandem scFv, FabFv, Fab'Fv, FabdsFy, Fab-scFv, Fab-dsscFv, Fab-(dsscFv)$_2$, diFab, diFab', tandem scFv-Fc, scFv-Fc-scFv, scdiabody-Fc, scdiabody-CH3, Ig-scFv, scFv-Ig, V-Ig, Ig-V, Duobody and DVDIg, which are discussed in more detail below.

In one embodiment the multispecific antibody molecule of the present disclosure does not comprise an Fc domain i.e. does not comprise a $CH_2$ and a $CH_3$ domain, for example the molecule is selected from the group comprising a tandem scFv, scFv-dsFv, dsscFv-dsFv didsFv, diabody, dsdiabody, didsdiabody, scdiabody (also referred to as an (scFv)$_2$), dsscdiabody, triabody, dstriabody, didstriabody, tridstriabody, tetrabodies, dstetrabody, didstetrabody, tridstetrabody, tetradstetrabody, tribody, dstribody, didstribody, Fabdab, FabFv, Fab'dab, Fab'Fv, Fab single linker Fv (as disclosed in WO2014/096390), Fab' single linker Fv, FabdsFy, Fab'dsFv, Fab-scFv (also referred to as a bibody), Fab'scFv, FabdsscFv, Fab'dsscFv, FabdidsscFv, Fab'didsscFv, FabscFv single linker Fv, Fab'scFv single linker Fv, FabdsscFvs single linker Fv, Fab'dsscFv single linker Fv, FvFabFv, FvFab'Fv, dsFvFabFv, dsFvFab'Fv, FvFabdsFv, FvFab'dsFv, dsFvFabdsFv, dsFvFab'dsFv, FabFvFv, Fab'FvFv, FabdsFvFv, Fab'dsFvFv, FabFvdsFv, Fab'FvdsFv, FabdsFvdsFv, Fab'dsFvdsFv, diFab, diFab' including a chemically conjugated diFab', (FabscFv)$_2$, (Fab)$_2$scFvdsFv, (Fab)$_2$dsscFvdsFv, (FabdscFv)$_2$, minibody, dsminibody, didsminibody, diabody-$CH_3$, dsdiabody-$CH_3$, didsdiabody-$CH_3$, scdiabody-$CH_3$, dsscdiabody-$CH_3$, didsscdiabody-$CH_3$, tandemscFv-$CH_3$, tandemdsscFv-$CH_3$, tandemdidsscFv-$CH_3$, tandemtridsscFv-$CH_3$ and tandemtetradsscFv-$CH_3$.

In one embodiment the molecule of the present disclosure does not comprise an Fc domain.

In one embodiment the molecule of the present disclosure comprises an altered Fc domain as described herein below.

Fc domain as employed herein generally refers to —$(CH_2CH_3)_2$, unless the context clearly indicates otherwise.

In one embodiment the molecule of the present disclosure does not comprise a —$CH_2CH_3$ fragment.

In one embodiment the molecule of the present disclosure does not comprise a $CH_2$ domain. In one embodiment the molecule of the present disclosure does not comprise a $CH_3$ domain.

Molecule as employed herein is used in the biochemistry sense to refer to a group of atoms that form an organic, in particular proteinaceous mass, which includes a complex suitable for handling as a single entity under appropriate conditions once the complex has been formed, for example a complex formed by two or more polypeptide chains.

Molecule and construct are used interchangeably herein, unless the context indicates otherwise. Although, construct may be employed more often to refer to a polynucleotide molecule and molecule may be employed more often to refer an entity primarily comprising an amino acid sequence.

Specificity (or specific) as employed herein refers to where the partners in the interaction only recognise each other or have significantly higher affinity for each other in comparison to non-partners, for example at least 2, 3, 4, 5, 6, 7, 8, 9, 10 times higher affinity, than for example a background level of binding or binding to another unrelated protein.

A 'binding domain' as employed herein refers to a binding region, typically a polypeptide, capable of binding a target antigen, for example with sufficient affinity to characterise the domain as specific for the antigen.

Any suitable binding domains may be used in the multispecific molecules of the present invention. These may be derived from any suitable source.

In one embodiment a biocompatible framework structure is used in a binding domain of the molecules of the present disclosure and such structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See for example, Nygren and Uhlen, 1997, Current Opinion in Structural Biology, 7, 463-469).

The term 'multi-specific molecules' as used herein may also include binding agents based on biological scaffolds including Adnectins, Affibodies, Darpins, Phylomers, Avimers, Aptamers, Anticalins, Tetranectins, Microbodies, Affilins and Kunitz domains. A multispecific molecule of the present invention is typically a multispecific antibody molecule, ie. at least one or more of the binding domains of the multispecific molecule are derived from an antibody or fragment thereof.

Where the binding domain is derived from an antibody, a "binding domain or site" as employed herein is the part of the antibody that contacts the antigen. In one embodiment the binding domain contains at least one variable domain or a derivative thereof, for example a pair of variable domains or derivatives thereof, such as a cognate pair of variable domains or a derivative thereof. Typically this is a VH/VL pair.

Variable regions (also referred to herein as variable domains) generally comprise 3 CDRs and a suitable framework. In one embodiment a binding domain comprises two variable regions, a light chain variable region (VL) and a heavy chain variable region (VH) and together these elements contribute to the specificity of the binding interaction of the antibody or binding fragment.

In one embodiment the variable domains in a binding domain in an antibody molecule of the present disclosure are a cognate pair.

A "cognate pair" as employed herein refers to a heavy and light chain pair of variable domains (or a derivative thereof, such as a humanised version thereof) isolated from a host as a pre-formed couple. This definition does not include variable domains isolated from a library, wherein the original pairing from a host is not retained. Cognate pairs may be advantageous because they are often affinity matured in the host and therefore may have higher affinity for the antigen to which they are specific, than a combination of variable domain pairs selected from a library, such as phage library.

In one embodiment a binding domain in an antibody molecule of the present disclosure is a derivative of a naturally occurring binding domain.

A "derivative of a naturally occurring domain" as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites, GPI anchors, or solvent exposed lysines. These modifications can be achieved by replacing the relevant amino acid residues with a conservative amino acid substitution.

Modification in the CDRs may, for example include replacing one or more cysteines with, for example a serine residue. Asn can be the substrate for deamination and this propensity can be reduced by replacing Asn and/or a neighbouring amino acid with an alternative amino acid, such as a conservative substitution. The amino acid Asp in the CDRs may be subject to isomerization. The latter can be minimized by replacing Asp or a neighbouring amino acid with an alternative amino acid, for example a conservative substitution.

Humanised versions of a variable region are also a derivative thereof, in the context of the present specification. Humanisation may include the replacement of a non-human framework for a human framework and optionally the back-mutation of one or more residues to "donor residues". Donor residues as employed herein refers to residues found in the original variable region isolated from the host, in particular replacing a given amino acid in the human framework with the amino acid in the corresponding location in the donor framework.

In one embodiment, the binding domain or each binding domain is part of (included or incorporated in) an antibody or an antibody fragment.

In one embodiment the binding domains in the molecules of the present disclosure are in immunoglobulin/antibody molecules.

As used herein "antibody molecule" includes antibodies and binding fragments thereof.

In one embodiment the term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site or binding domain herein), located in the variable region of the immunoglobulin molecule.

"Antibody fragments" as employed herein refer to antibody binding fragments including but not limited to Fab, modified Fab, Fab', modified Fab', F(ab')2, Fv, single domain antibodies, scFv, Fv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews-Online 2(3), 209-217).

A "binding fragment" as employed herein refers to a fragment capable of binding a target peptide or antigen with sufficient affinity to characterise the fragment as specific for the peptide or antigen.

The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in WO05/003169, WO05/003170 and WO05/003171. Multi-valent antibodies may comprise multiple specificities e.g. bispecific or may be monospecific (see for example WO92/22853, WO05/113605, WO2009/040562 and WO2010/035012).

The term "Fab fragment" as used herein refers to an antibody fragment comprising a light chain fragment comprising a $V_L$ (variable light) domain and a constant domain of a light chain ($C_L$), and a VH (variable heavy) domain and a first constant domain ($CH_1$) of a heavy chain.

The Fv refers to two variable domains, for example co-operative variable domains, such as a cognate pair or affinity matured variable domains, i.e. a $V_H$ and $V_L$ pair.

Co-operative variable domains as employed herein are variable domains that complement each other and/or both contribute to antigen binding to render the Fv ($V_H/V_L$ pair) specific for the antigen in question.

The following is a list of example antibody formats that may be employed in an antibody molecule of the present disclosue.

"Single domain antibody" (also referred to herein as a dab and sdAb) as used herein refers to an antibody fragment consisting of a single monomeric variable antibody domain. Examples of single domain antibodies include $V_H$ or $V_L$ or $V_H H$.

Tandem-sdAb as employed herein refers to two domain antibodies connected by a linker, for example a peptide linker, in particular where the domain antibodies have specificity for different antigens.

Tandem-sdAb-sdAb as employed herein refers to three domain antibodies connected in series by two linkers, for example peptide linkers, in particular where the domain antibodies have specificity for different antigens.

dsFv as employed herein refers to an Fv with an intra-variable disulfide bond. The dsFv may be a component of a larger molecule, for example the one of the variable domains may be linked, for example via an amino acid linker to another antibody fragment/component.

(dsFv)$_2$ as employed herein refers to a dsFv with one domain linked, for example via a peptide linker or a disulfide bond (for example between, the C-terminus of two VH's) to a domain in a second dsFv, the format resembles a (scFv)$_2$ described below but each pair of variable regions comprise a intra-variable region disulfide bond.

Component as employed herein refers to a building block or portion of a multispecific molecule of the present disclosure, in particular where the component is an antibody fragment such as scFv, Fab or other fragment, in particular as described herein.

Single-chain Fv or abbreviated as "scFv", as used herein refers to an antibody fragment that comprises $V_H$ and $V_L$ antibody domains linked (for example by a peptide linker) to form a single polypeptide chain. The constant regions of the heavy and light chain are omitted in this format.

dsscFv as employed herein refers to scFv with an intra-variable region disulfide bond.

Figure 9:
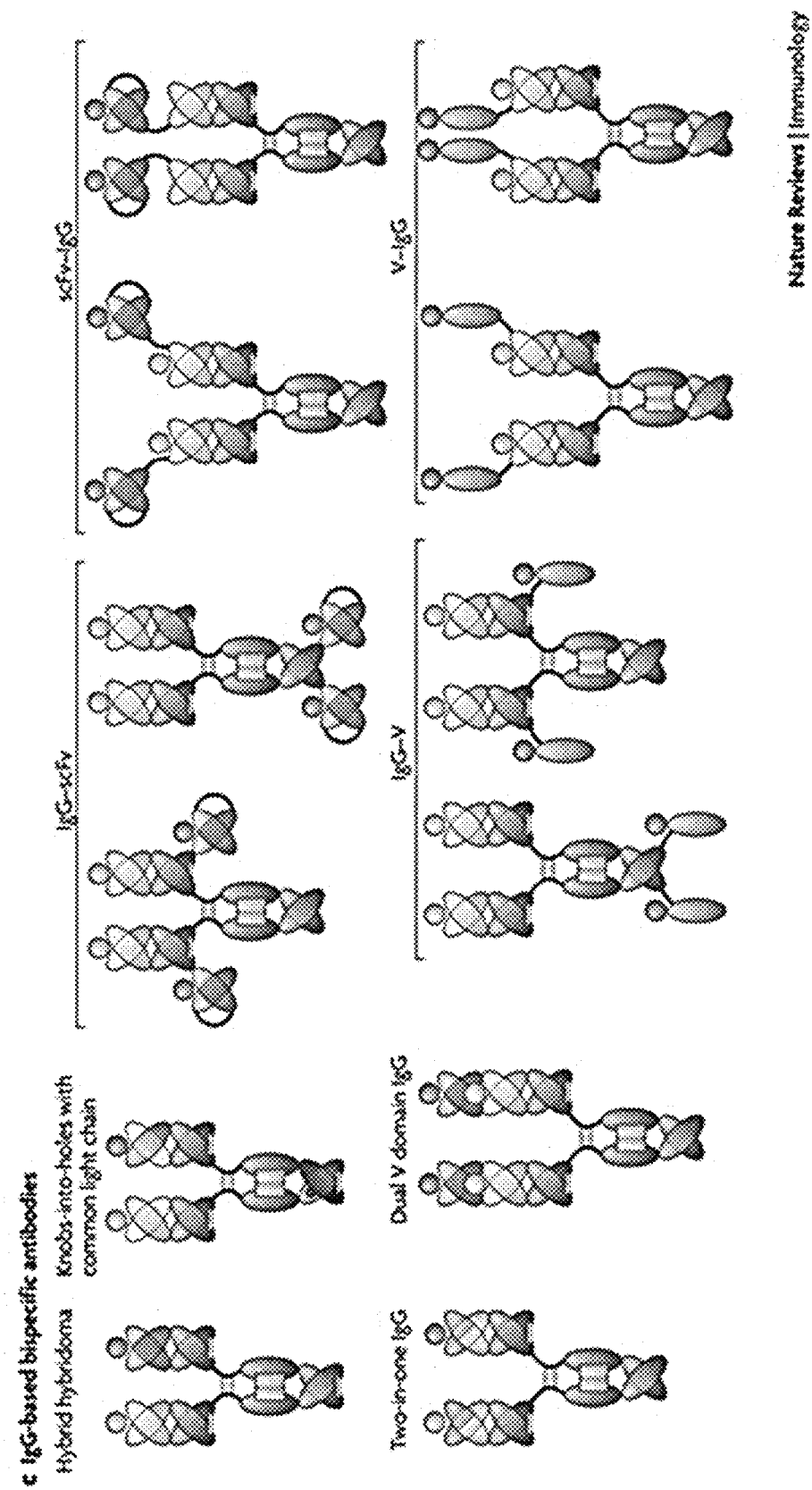
FIG. 9 is an extract from Chan and Carter, Nature Reviews Immunology vol 10, May 2010, 301 showing certain antibody formats

Tandem scFv (also referred to herein as a discFv or (scFv)$_2$) as employed herein refers to two scFvs linked via a single linker such that there is a single inter-Fv linker, for example as shown in FIG. 9b.

Tandem dsscFv (also referred to herein as a scFvdsscFv or dsscFvscFv) as employed herein refers to two scFvs linked via a single linker such that there is a single inter-Fv linker, for example as shown in FIG. 9b, and wherein one of the scFv has an intravariable region disulfide bond.

Tandem didsscFv (also referred to herein as a didsscFv) as employed herein refers to two scFvs linked via a single linker such that there is a single inter-Fv linker, for example as shown in FIG. 9b, and wherein each scFv comprises an intravariable region disulfide bond.

scFv-dsFv as employed herein is a scFv linked, for example by a peptide linker, to an Fv domain which is comprised of two variable domains linked via a disulfide bond to form a dsFv. In this format the VH or VL of the scFv may be linked to the VH or VL of the dsFv.

dsscFv-dsFv as employed herein is a dsscFv linked, for example by a peptide linker, to an Fv domain which is comprised of two variable domains linked via a disulfide bond to form a dsFv. In this format the VH or VL of the dsscFv may be linked to the VH or VL of the dsFv.

Diabody as employed herein refers to two Fv pairs VH/VL which have two inter-Fv linkers, such that the $V_H$ of a first Fv is linked to the $V_L$ of the second Fv and the $V_L$ of the first Fv is linked to the $V_H$ of the second Fv.

dsDiabody as employed herein refers to a diabody comprising an intra-variable region disulfide bond.

didsDiabody as employed herein refers to a diabody comprising two intra-variable region disulfide bonds, i.e. one ds between each pair of variable regions.

Sc-diabody as employed herein refers a diabody comprising an intra-Fv linker, such that the molecule comprises three linkers and forms two normal scFvs, for example $VH_1$linker$VL_1$ linker $VH_2$ linker $V_L2$.

dssc-diabody as employed herein refers to a sc-diabody with an intra-variable region disulfide bond.

didssc-diabody as employed herein refers to a sc-diabody with an intra-variable region disulfide bond between each pair of variable regions.

Dart as employed herein refers to $VL_1$ linker $VH_2$ linker and $VH_1$ linker $VL_2$ wherein the C-terminous of $VH_1$ and $VH_2$ are joined by a disulfide bond Paul A. Moore et al *Blood*, 2011; 117(17):4542-4551.

Bite® as employed herein refers to a molecule comprising two pairs of variable domains in the following format; a domain from pair 1 (eg $VH_1$) connected via a linker to a domain from pair 2 (eg $VH_2$ or $VL_2$) said second domain connected by a linker to the further domain from pair 1 (eg $VL_1$) in turn connected to the remaining domain from pair two (i.e $VL_2$ or $VH_2$).

Di-diabody see Nunez-Prado et al in particular molecule number 25 in FIG. 1 therein.

Dsdi-diabody as employed herein is a di-diabody with an intra-variable region disulfide bond.

Didsdi-diabody as employed herein is a di-diabody with an intra-variable region disulfide bond between each pair of variable regions.

Triabody as employed herein refers to a format similar to the diabody comprising three Fvs and three inter-Fv linkers.

dstriabody as employed herein refers to a triabody comprising an intra-variable region disulfide bond between one of the variable domain pairs.

Didstriabody as employed herein refers to a triabody comprising two intra-variable region disulfide bonds, i.e. one ds between each of two variable domain pairs.

Tridstriabody as employed herein refers to a triabody comprising three intra-variable region disulfide bonds i.e. one ds between each pair of variable regions.

Tetrabody as employed herein refers to a format similar to the diabody comprising four Fvs and four inter-Fv linkers.

dstetrabody as employed herein refers to a tetrabody comprising an intra-variable region disulfide bond between one of the variable domain pairs.

Didstetrabody as employed herein refers to a tetrabody comprising two intra-variable region disulfide bonds, i.e. one ds between each of two variable domain pairs.

Tridstetrabody as employed herein refers to a tetrabody comprising three intra-variable region disulfide bonds i.e. one ds between each of three pairs of variable regions.

Tetradstetrabody as employed herein refers to a tetrabody comprising four intra-variable region disulfide bonds i.e. one ds between each variable domain.

Tribody (also referred to a Fab(scFv)$_2$) as employed herein refers to a Fab fragment with a first scFv appended to the C-terminal of the light chain and a second scFv appended to the C-terminal of the heavy chain.

dstribody as employed herein refers to a tribody comprising a dsscFv in one of the two positions.

didstribody or TrYbe as employed herein refers to a tribody comprising two dsscFvs.

dsFab as employed herein refers to a Fab with an intra-variable region disulfide bond.

dsFab' as employed herein referst to a Fab' with an intra-variable region disulfide bond.

scFab is a single chain Fab fragment.

scFab' is a single chain Fab' fragment.

dsscFab is a dsFab as a single chain.

dsscFab' is a dsFab' as a single chain.

Fabdab as employed herein refers to a Fab fragment with a domain antibody appended to the heavy or light chain thereof, optionally via a linker.

Fab' dab as employed herein refers to a Fab' fragment with a domain antibody appended to the heavy or light chain thereof, optionally via a linker.

FabFv as employed herein refers to a Fab fragment with an additional variable region appended to the C-terminal of each of the following, the $CH_1$ of the heavy chain and CL of the light chain see for example WO2009/040562. The format may be provided as a PEGylated version thereof see for example WO2011/061492, Fab'Fv as employed herein is similar to FabFv, wherein the Fab portion is replaced by a Fab'. The format may be provided as a PEGylated version thereof.

FabdsFv as employed herein refers to a FabFv wherein an intra-Fv disulfide bond stabilises the appended C-terminal variable regions, see for example WO2010/035012. The format may be provided as a PEGylated version thereof.

Fab single linker Fv and Fab' single linker as employed herein refers to a Fab or Fab' fragment linked to a variable domain, for example by a peptide linker, and said variable domain is linked to a second variable domain via an intra-variable domain disulfide bond thereby forming a dsFv, see for example WO2014/096390.

Fab-scFv (also referred to as a bibody) as employed herein is a Fab molecule with a scFv appended on the C-terminal of the light or heavy chain, optionally via a linker.

Fab'-scFv as employed herein is a Fab' molecule with a scFv appended on the C-terminal of the light or heavy chain, optionally via a linker.

FabdsscFv or BYbe as employed herein is a Fab-scFv with a disulfide bond between the variable regions of the single chain Fv.

Fab'dsscFv as employed herein is a Fab'scFv with a disulfide bond between the variable regions of the single chain Fv.

FabscFv-dab as employed herein refers to a Fab with a scFv appended to the C-terminal of one chain and domain antibody appended to the C-terminal of the other chain.

Fab'scFv-dab as employed herein refers to a Fab' with a scFv appended to the C-terminal of one chain and domain antibody appended to the C-terminal of the other chain.

FabdsscFv-dab as employed herein refers to a Fab with a dsscFv appended to the C-terminal of one chain and domain antibody appended to the C-terminal of the other chain.

Fab'dsscFv-dab as employed herein refers to a Fab' with a dsscFv appended to the C-terminal of one chain and domain antibody appended to the C-terminal of the other chain.

FabscFv single linker Fv as employed herein refers to a Fab single linker Fv wherein a domain of the Fv is linked to the heavy or light chain of the Fab and a scFv is linked to the other Fab chain and the domains of the Fv are connected by an intra-variable region disulfide.

FabdsscFv single linker Fv as employed herein refers to a FabscFv single linker Fv wherein the scFv comprises an intra-variable region disulfide bond.

Fab'scFv single linker Fv as employed herein refers to a Fab' single linker Fv wherein a domain of the Fv is linked to the heavy or light chain of the Fab and a scFv is linked to the other Fab chain and the domains of the Fv are connected by an intra-variable region disulfide.

Fab'dsscFv single linker Fv as employed herein refers to a Fab'scFv single linker Fv wherein the scFv comprises an intra-variable region disulfide bond.

FvFabFv as employed herein refers to a Fab with the domains of a first Fv appended to the N-terminus of the heavy and light chain of the Fab and the domains of a second Fv appended to the C-terminus of the heavy and light chain.

FvFab'Fv as employed herein refers to a Fab' with the domains of a first Fv appended to the N-terminus of the heavy and light chain of the Fab' and the domains of a second Fv appended to the C-terminus of the heavy and light chain.

dsFvFabFv as employed herein refers to a Fab with the domains of a first Fv appended to the N-terminus of the heavy and light chain of the Fab wherein the first Fv comprises an intra-variable region disulfide bond and the domains of a second Fv appended to the C-terminus of the heavy and light chain.

FvFabdsFv as employed herein refers to a Fab with the domains of a first Fv appended to the N-terminus of the heavy and light chain of the Fab and the domains of a second Fv appended to the C-terminus of the heavy and light chain and wherein the second Fv comprises an intra-variable region disulfide bond.

dsFvFab'Fv as employed herein refers to a Fab' with the domains of a first Fv appended to the N-terminus of the heavy and light chain of the Fab' wherein the first Fv comprises an intra-variable region disulfide bond and the domains of a second Fv appended to the C-terminus of the heavy and light chain.

FvFab'dsFv as employed herein refers to a Fab' with the domains of a first Fv appended to the N-terminus of the heavy and light chain and the domains of a second Fv appended to the C-terminus of the heavy and light chain of the Fab' and wherein the second Fv comprises an intra-variable region disulfide bond.

dsFvFabdsFv as employed herein refers to a Fab with the domains of a first Fv appended to the N-terminus of the heavy and light chain of the Fab wherein the first Fv comprises an intra-variable region disulfide bond and the domains of a second Fv appended to the C-terminus of the heavy and light chain and wherein the second Fv also comprises an intra-variable region disulfide bond.

dsFvFab'dsFv as employed herein refers to a Fab' with the domains of a first Fv appended to the N-terminus of the heavy and light chain of the Fab' wherein the first Fv comprises an intra-variable region disulfide bond and the domains of a second Fv appended to the C-terminus of the heavy and light chain and wherein the second Fv also comprises an intra-variable region disulfide bond.

FabFvFv as employed herein refers to a Fab fragment with two pairs of Fvs appended in series to the C-terminal of the heavy and light chain, see for example WO2011/086091.

Fab'FvFv as employed herein refers to a Fab' fragment with two pairs of Fvs appended in series to the C-terminal of the heavy and light chain, see for example WO2011/086091.

FabdsFvFv as employed herein refers to a Fab fragment with two pairs of Fvs appended in series to the C-terminal of the heavy and light chain, see for example WO2011/086091, wherein the first Fv pair attached directly to the C-terminal comprise an intra-variable region disulfide bond.

Fab'dsFvFv as employed herein refers to a Fab' fragment with two pairs of Fvs appended in series to the C-terminal of the heavy and light chain, see for example WO2011/086091, wherein the first Fv pair attached directly to the C-terminal comprise an intra-variable region disulfide bond.

FabFvdsFv as employed herein refers to a Fab fragment with two pairs of Fvs appended in series to the C-terminal of the heavy and light chain, wherein the second Fv pair at the "C"-terminal of the molecule comprise an intra-variable region disulfide bond.

Fab'FvdsFv as employed herein refers to a Fab' fragment with two pairs of Fvs appended in series to the C-terminal of the heavy and light chain, wherein the second Fv pair at the "C"-terminal of the molecule comprise an intra-variable region disulfide bond.

FabdsFvdsFv as employed herein refers to a Fab fragment with two pairs of Fvs appended in series to the C-terminal of the heavy and light chain, wherein the first and second Fv pair comprise an intra-variable region disulfide bond.

Fab'dsFvdsFv as employed herein refers to a Fab' fragment with two pairs of Fvs appended in series to the C-terminal of the heavy and light chain, wherein the first and second Fv comprise an intra-variable region disulfide bond.

DiFab as employed herein refers to two Fab molecules linked via their C-terminus of the heavy chains.

DiFab' as employed herein refers to two Fab' molecules linked via one or more disulfide bonds in the hinge region thereof.

DiFab and DiFab' molecules include chemically conjugated forms thereof.

(FabscFv)$_2$ as employed herein refers to a diFab molecule with two scFvs appended thereto, for example appended to the C-terminal of the heavy or light chain, such as the heavy chain.

(Fab'scFv)$_2$ as employed herein refers to a diFab' molecule with two scFvs appended thereto, for example appended to the C-terminal of the heavy or light chain, such as the heavy chain.

(Fab)$_2$scFvdsFv as employed herein refers to a diFab with a scFv and dsFv appended, for example one from each of the heavy chain C-terminal.

(Fab')$_2$scFvdsFv as employed herein refers to a diFab' with a scFv and dsFv appended, for example one from each of the heavy chain C-terminal.

(Fab)$_2$dsscFvdsFv, as employed herein refers to a diFab with a dsscFv and dsFv appended, for example from the heavy chain C-terminal.

(Fab')$_2$dsscFvdsFv as employed herein refers to the a diFab' with a dsscFv and dsFv appended, for example from the heavy chain C-terminal.

Minibody as employed herein refers to (VL/VH-CH$_3$)$_2$.

dsminibody as employed herein refers to (VL/VH-CH$_3$)$_2$ wherein one VL/VH comprises an intra-variable region disulfide bond.

didsminibody as employed herein refers to a (dsFv-CH$_3$)$_2$.

kappa/lambda body' or 'κ/λ-body is in the format of a normal IgG with two heavy chains and two light chains, wherein the two light chains are different to each other, one is a lambda light chain (VL-CL) and the other is a kappa light chain (VK-CK). The heavy chain is identical, even at the CDRs, as described in WO2012/023053.

scFv-Fc as employed herein refers to a scFv appended to the N-terminus of a CH$_2$ domain, for example via a hinge, of constant region fragment —(CH$_2$CH$_3$), such that the molecule has 2 binding domains.

dsscFv-Fc as employed herein refers to a dsscFv appended to the N-terminus of a CH$_2$ domain and a scFv appended to the N-terminus of a second CH$_2$ domain, for example via a hinge, of constant region fragment —(CH$_2$CH$_3$)$_2$, such that the molecule has 2 binding domains.

didsscFv-Fc as employed herein refers to a scFv appended to the N-terminus of a CH$_2$ domain, for example via a hinge, of constant region fragment —(CH$_2$CH$_3$)$_2$, such that the molecule has 2 binding domains Tandem scFv-Fc as employed herein refers to two tandem scFvs, wherein each one is appended in series to the N-terminus of a CH$_2$ domain, for example via a hinge, of constant region fragment —(CH$_2$CH$_3$), such that the molecule has 4 binding domains.

Scdiabody-Fc as employed herein is two scdiabodies, wherein each one is appended to the N-terminus of a CH$_2$ domain, for example via a hinge, of constant region fragment —CH$_2$CH$_3$.

ScFv-Fc-scFv as employed herein refers to four scFvs, wherein one of each is appended to the N-terminus and the C-terminus of both the heavy and light chain of a —CH$_2$CH$_3$ fragment.

Scdiabody-CH$_3$ as employed herein refers to two scdiabody molecules each linked, for example via a hinge to a CH$_3$ domain.

IgG-scFv as employed herein is a full length antibody with a scFv on the C-terminal of each of the heavy chains or each of the light chains.

scFv-IgG as employed herein is a full length antibody with a scFv on the N-terminal of each of the heavy chains or each of the light chains.

V-IgG as employed herein is a full length antibody with a variable domain on the N-terminal of each of the heavy chains or each of the light chains.

IgG-V as employed herein is a full length antibody with a variable domain on the C-terminal of each of the heavy chains or each of the light chains DVD-Ig (also known as dual V domain IgG) is a full length antibody with 4 additional variable domains, one on the N-terminus of each heavy and each light chain.

Duobody or 'Fab-arm exchange' as employed herein is a bispecific IgG format antibody where matched and complementary engineered amino acid changes in the constant domains (typically CH3) of two different monoclonal antibodies lead, upon mixing, to the formation of heterodimers. A heavy:light chain pair from the first antibody will, as a result of the residue engineering, prefer to associate with a heavy:light chain pair of a second antibody. See for example WO2008/119353, WO2011/131746 and WO2013/060867.

In one embodiment an antibody molecule according to the present disclosure is a bispecific protein complex having the formula A-X:Y-B wherein:
A-X is a first fusion protein;
Y-B is a second fusion protein;
X:Y is a heterodimeric-tether;
: is a binding interaction between X and Y;
A is a first protein component of the bispecific selected from a Fab or Fab' fragment;
B is a second protein component of the bispecific selected from a Fab or Fab';
X is a first binding partner of a binding pair independently selected from an antigen or an antibody or binding fragment thereof; and
Y is a second binding partner of the binding pair independently selected from an antigen or an antibody or a binding fragment thereof;
with the proviso that when X is an antigen Y is an antibody or binding fragment thereof specific to the antigen represented by X and when Y is an antigen X is an antibody or binding fragment thereof specific to the antigen represented by Y.

In one aspect, there is provided a multi-specific antibody molecule comprising or consisting of:
a) a polypeptide chain of formula (I):

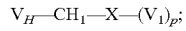

b) a polypeptide chain of formula (II):

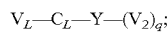

wherein:

$V_H$ represents a heavy chain variable domain;

$CH_1$ represents a domain of a heavy chain constant region, for example domain 1 thereof;

X represents a bond or linker, for example an amino acid linker;

Y represents a bond or linker, for example an amino acid linker;

$V_1$ represents a dab, scFv, dsscFv or dsFv;

$V_L$ represents a variable domain, for example a light chain variable domain;

$C_L$ represents a domain from a constant region, for example a light chain constant region domain, such as Ckappa;

$V_2$ represents a dab, scFv, dsscFv or dsFv;

p is 0 or 1;

q is 0 or 1; and when p is 1 q is 0 or 1 and when q is 1 p is 0 or 1 i.e. p and q do not both represent 0 The format was previously described in WO2015/19772.

In one embodiment the multispecific antibody molecule comprises no more than one binding domain for CD79 selected from VH/VL, V1 or V2.

In one embodiment the multispecific antibody molecule comprises no more than one binding domain for CD45 and no more than one binding domain for CD79.

In one embodiment the multispecific antibody molecule comprises no more than one binding domain for CD22 and no more than one binding domain for CD79.

In one embodiment q is 0 and p is 1.

In one embodiment q is 1 and p is 1.

In one embodiment $V_1$ is a dab and $V_2$ is a dab and together they form a single binding domain of a co-operative pair of variable regions, such as a cognate VH/VL pair, which are optionally linked by a disulphide bond.

In one embodiment $V_H$ and $V_L$ are specific to, CD79, for example CD79a or CD79b.

In one embodiment the $V_1$ is specific to, CD79, for example CD79a or CD79b.

In one embodiment the $V_2$ is specific to, CD79, for example CD79a or CD79b.

In one embodiment the $V_1$ and $V_2$ together (eg as binding domain) are specific to, CD79, for example CD79a or CD79b and $V_H$ and $V_L$ are specific to, CD45 or CD22.

In one embodiment the $V_1$ is specific to, CD45 or CD22.

In one embodiment the $V_2$ is specific to, CD45 or CD22.

In one embodiment the $V_1$ and $V_2$ together (eg as one binding domain) are specific to, CD45 or CD22 and $V_H$ and $V_L$ are specific to CD79.

In one embodiment the $V_1$ is specific to CD45 or CD22, $V_2$ is specific to albumin and $V_H$ and $V_L$ are specific to CD79.

In one embodiment the $V_1$ is specific to albumin, $V_2$ is specific to CD45 and $V_H$ and $V_L$ are specific to CD79.

In one embodiment the $V_1$ is specific to CD79, $V_2$ is specific to albumin and $V_H$ and $V_L$ are specific to CD45 or CD22.

In one embodiment the $V_1$ is specific to albumin, $V_2$ is specific to CD79 and $V_H$ and $V_L$ are specific to CD45 or CD22.

In one embodiment the $V_1$ is a dsscFv specific to CD45 or CD22, $V_2$ is a dsscFv specific to albumin and $V_H$ and $V_L$ are specific to CD79.

In one embodiment the $V_1$ is a dsscFv specific to albumin, $V_2$ is a dscFv specific to CD45 or CD22 and $V_H$ and $V_L$ are specific to CD79.

In one embodiment the $V_1$ is a dsscFv specific to CD79, $V_2$ is a dsscFv specific to albumin and $V_H$ and $V_L$ are specific to CD45 or CD22.

In one embodiment the $V_1$ is a dsscFv specific to albumin, $V_2$ is a dsscFv specific to CD79 and $V_H$ and $V_L$ are specific to CD45 or CD22.

V1, V2, VH and VL in the constructs above may each represent a binding domain and incorporate any of the sequences provided herein.

X and Y represent any suitable linker, for example X and Y may be independently

```
SGGGGSGGGGS                     (SEQ ID NO: 339
or
SGGGGTGGGGS.                    (SEQ ID NO: 340)
```

In one embodiment, when $V_1$ and/or $V_2$ are a dab, dsFv or a dsscFv, the disulfide bond between the variable domains $V_H$ and $V_L$ of $V_1$ and/or $V_2$ is formed between positions $VH_H44$ and $V_L100$.

Where one or more pairs of variable regions in a multispecific antibody molecule comprise a disulphide bond between VH and VL this may be in any suitable position such as between two of the residues listed below (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA.

In one embodiment the disulfide bond is in a position selected from the group comprising:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100b+V_L49$;

$V_H98+VL\ 46$ see for example Protein Science 6, 781-788 Zhu et al (1997);

$V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995) and a position corresponding thereto in variable region pair located in the molecule.

In one embodiment, the disulphide bond is formed between positions $V_H44$ and $V_L100$.

"Monospecific" as employed herein refers to the ability to bind a target antigen only once. Thus is one embodiment the multispecific molecules of the present invention are monospecific for each antigen.

Thus in one embodiment the binding domains of the multispecific molecules according to the present disclosure are monospecific. This is advantageous in some therapeutic applications because the molecules of the disclosure are not able to cross-link antigen via binding the target antigen more than once. Thus in one embodiment bispecific or multispecific molecules of the present-disclosure are not able to cross-link by binding the same target twice in two different locations, for example on the same cell or on two different cells.

Cross-linking, in particular in relation to CD79b on the same cell or different cells can generate signals in vivo, for example which stimulate the activity of the target antigen.

In one example the multispecific molecules of the present invention contain no more than one binding domain for CD22 and no more than one binding domain for CD79. Each binding domain is monospecific.

In one example therefore the multispecific molecule is monovalent for CD22 and monovalent for CD79.

In one example the multispecific molecules of the present invention contain no more than one binding domain for CD45 and no more than one binding domain for CD79. Each binding domain is monospecific.

In one example therefore the multispecific molecule is monovalent for CD45 and monovalent for CD79.

In one embodiment, each antibody or antibody fragment employed in the multi-specific molecules of the present disclosure is monovalent.

Thus in one embodiment the binding domains of the multispecific molecules of the present disclosure are monovalent.

Thus in one embodiment the binding domains of the multispecific molecules of the present disclosure are monovalent and monospecific.

In one embodiment the multispecific molecule of the present disclosure is comprised of two or more monospecific, monovalent binding domains such as Fab, Fab', scFv, VH, VL, VHH, Fv, dsFv, combined or linked in any suitable way to construct a multispecific molecule, for example as described herein above.

In another embodiment, for example where the molecules of the disclosure comprise at least three binding domains then two or three binding domains (for example antibodies, fragments or a combination of an antibody and a fragment) may have different antigen specificities, for example binding to three different target antigens.

The present invention therefore also provides multispecific molecules as set forth in the following paragraphs 1. A multispecific molecule comprising a binding domain specific to the antigen CD22 and a binding domain specific to the antigen CD79a and/or CD79b wherein the binding domain specific to the antigen CD79a and/or CD79b comprises 3 heavy chain CDRs having the sequence given in SEQ ID NO: 8 for CDRH1, SEQ ID NO: 9 for CDRH2 and SEQ ID NO: 4 for CDRH3.
2. A multispecific molecule comprising a binding domain specific to the antigen CD22 and a binding domain specific to the antigen CD79a and/or CD79b wherein the binding domain specific to the antigen CD79b comprises 3 heavy chain CDRs having the sequence given in SEQ ID NO: 11 for CDRH1, SEQ ID NO: 12 for CDRH2 and SEQ ID NO: 3 for CDRH3.
3. A multispecific molecule according to paragraph 1 wherein the binding domain specific for CD79b comprises 3 light chain CDRs having the sequence given in SEQ ID NO: 13 for CDRL1, SEQ ID NO: 14 for CDRL2 and SEQ ID NO: 15, 16, 17 or 18 for CDRL3.
4. A multispecific molecule according to paragraph 2 wherein the binding domain specific for CD79b comprises 3 light chain CDRs having the sequence given in SEQ ID NO: 19 for CDRL1, SEQ ID NO: 20 for CDRL2 and SEQ ID NO: 21, 22, 23 or 24 for CDRL3.
5. A multispecific molecule according to any one of paragraphs 1-4 wherein the binding domain or binding domains comprise an antibody variable region specific to the relevant antigen.
6. A multispecific molecule according to any one of paragraphs 1-5 wherein each binding domain comprises two antibody variable domains.
7. A multispecific molecule according to paragraph 6 wherein the two antibody variable domains are a VH/VL pair.
8. A multispecific molecule according to any one of paragraphs 1 to 7, wherein the molecule is bispecific or trispecific.
9. A multispecific molecule according to any one of paragraphs 1 to 8, wherein the molecule is a fusion protein.
10. A multispecific molecule according to any one of paragraphs 1 to 9, wherein the molecule format is selected from diabody, scdiabody, triabody, tandem scFv, FabFv, Fab'Fv, FabdsFv, Fab-scFv, Fab-dsscFv, Fab-(dsscFv)$_2$ diFab, diFab', tribody, tandem scFv-Fc, scFv-Fc-scFv, scdiabody-Fc, scdiabody-CH$_3$, Ig-scFv, scFv-Ig, V-Ig, Ig-V, Duobody and DVD-Ig.
11. A multispecific molecule according to any one of paragraphs 1 to 10 wherein each binding domain is monospecific.
12. A multispecific molecule according to any one of paragraphs 1 to 11 wherein the multispecific molecule comprises no more than one binding domain which is specific to CD22 and no more than one binding domain which is specific to CD79a and/or CD79b.
13. A multispecific molecule according to any one of paragraphs 1 to 12 wherein the binding domain which is specific to CD22 and the binding domain which is specific to CD79a and/or CD79b are independently selected from a Fab, scFv, Fv, dsFv and dsscFv.
14. A multispecific molecule according to any one of paragraphs 1 to 13, wherein the binding domain specific for CD22 comprises 3 heavy chain CDRs and 3 light chain CDRs from an anti-CD22 antibody provided herein.
15. A multispecific molecule according to any one of paragraphs 1 to 14 in which the binding domains are humanised.
16. A multispecific molecule according to any one of paragraphs 1 to 15 in which one or more amino acids in one or more CDRs have been substituted with another amino acid.
17. A multispecific molecule according to paragraph 16 wherein one or more cysteine residues has been substituted with another amino acid.
18. A multispecific molecule according to paragraph 16 or 17 wherein one or more aspartic acid isomerisation sites and/or asparagine deamidation sites and/or glycosylation sites has been removed by substituting one or more amino acids in one or more CDRs.
19. A multispecific molecule according to any one of paragraphs 1 to 18, which further comprises a binding domain specific to serum albumin, such as human serum albumin.
20. A composition comprising one or more multispecific proteins as defined in any one of paragraphs 1 to 19.

21. A nucleotide sequence encoding a multispecific protein or component thereof as defined in any one of paragraphs 1 to 21.
22. A vector comprising a nucleotide sequence defined in paragraph 21.
23. A multispecific protein according to any one of paragraphs 1 to 22 or a composition according to paragraph 20, for use in therapy.
24. Use of a multispecific protein according to any one of paragraphs 1 to 19 or a composition according to paragraph 20, for the manufacture of a medicament for use in therapy, in particular for the treatment of a condition or disorder described herein.
25. A method of treating a patient, comprising the administration of a therapeutically effective amount of a multispecific protein according to any one of paragraphs 1 to 19 or a composition according to paragraph 20.

The present invention therefore also provides multispecific molecules as set forth in the following paragraphs 26. A multispecific molecule comprising a binding domain specific to the antigen CD45 and a binding domain specific to the antigen CD79a and/or CD79b wherein the binding domain specific to the antigen CD79a and/or CD79b comprises 3 heavy chain CDRs having the sequence given in SEQ ID NO: 8 for CDRH1, SEQ ID NO: 9 for CDRH2 and SEQ ID NO: 4 for CDRH3.
27. A multispecific molecule comprising a binding domain specific to the antigen CD45 and a binding domain specific to the antigen CD79a and/or CD79b wherein the binding domain specific to the antigen CD79b comprises 3 heavy chain CDRs having the sequence given in SEQ ID NO: 11 for CDRH1, SEQ ID NO: 12 for CDRH2 and SEQ ID NO: 3 for CDRH3.
28. A multispecific molecule according to paragraph 1 wherein the binding domain specific for CD79b comprises 3 light chain CDRs having the sequence given in SEQ ID NO: 13 for CDRL1, SEQ ID NO: 14 for CDRL2 and SEQ ID NO: 15, 16, 17 or 18 for CDRL3.
29. A multispecific molecule according to paragraph 2 wherein the binding domain specific for CD79b comprises 3 light chain CDRs having the sequence given in SEQ ID NO: 19 for CDRL1, SEQ ID NO: 20 for CDRL2 and SEQ ID NO: 21, 22, 23 or 24 for CDRL3.
30. A multispecific molecule according to any one of paragraphs 26-29 wherein the binding domain or binding domains comprise an antibody variable region specific to the relevant antigen.
31. A multispecific molecule according to any one of paragraphs 26-30 wherein each binding domain comprises two antibody variable domains.
32. A multispecific molecule according to paragraph 31 wherein the two antibody variable domains are a VH/VL pair.
33. A multispecific molecule according to any one of paragraphs 26 to 32, wherein the molecule is bispecific or trispecific.
34. A multispecific molecule according to any one of paragraphs 26 to 33, wherein the molecule is a fusion protein.
35. A multispecific molecule according to any one of paragraphs 26 to 34, wherein the molecule format is selected from diabody, scdiabody, triabody, tandem scFv, FabFv, Fab'Fv, FabdsFv, Fab-scFv, Fab-dsscFv, Fab-(dsscFv)$_2$ diFab, diFab', tribody, tandem scFv-Fc, scFv-Fc-scFv, scdiabody-Fc, scdiabody-CH3, Ig-scFv, scFv-Ig, V-Ig, Ig-V, Duobody and DVD-Ig.
36. A multispecific molecule according to any one of paragraphs 26 to 35 wherein each binding domain is monospecific.
37. A multispecific molecule according to any one of paragraphs 26 to 36 wherein the multispecific molecule comprises no more than one binding domain which is specific to CD45 and no more than one binding domain which is specific to CD79a and/or CD79b.
38. A multispecific molecule according to any one of paragraphs 26 to 37 wherein the binding domain which is specific to CD45 and the binding domain which is specific to CD79a and/or CD79b are independently selected from a Fab, scFv, Fv, dsFv and dsscFv.
39. A multispecific molecule according to any one of paragraphs 26 to 38, wherein the binding domain specific for CD45 comprises 3 heavy chain CDRs and 3 light chain CDRs from an anti-CD45 antibody provided herein.
40. A multispecific molecule according to any one of paragraphs 26 to 39 in which the binding domains are humanised.
41. A multispecific molecule according to any one of paragraphs 26 to 40 in which one or more amino acids in one or more CDRs have been substituted with another amino acid.
42. A multispecific molecule according to paragraph 41 wherein one or more cysteine residues has been substituted with another amino acid.
43. A multispecific molecule according to paragraph 41 or 42 wherein one or more aspartic acid isomerisation sites and/or asparagine deamidation sites and/or glycosylation sites has been removed by substituting one or more amino acids in one or more CDRs.
44. A multispecific molecule according to any one of paragraphs 26 to 43, which further comprises a binding domain specific to serum albumin, such as human serum albumin.
45. A composition comprising one or more multispecific proteins as defined in any one of paragraphs 26 to 44.
46. A nucleotide sequence encoding a multispecific protein or component thereof as defined in any one of paragraphs 26 to 45.
47. A vector comprising a nucleotide sequence defined in paragraph 46.
48. A multispecific protein according to any one of paragraphs 26 to 44 or a composition according to paragraph 45, for use in therapy.
49. Use of a multispecific protein according to any one of paragraphs 36 to 44 or a composition according to paragraph 45, for the manufacture of a medicament for use in therapy, in particular for the treatment of a condition or disorder described herein.
50. A method of treating a patient, comprising the administration of a therapeutically effective amount of a multispecific protein according to any one of paragraphs 26 to 44 or a composition according to paragraph 45.

Constant Regions

The antibody constant region domains of an antibody molecule of the present disclosure, if present, for example in a full length antibody or multispecific molecule, may be selected having regard to the proposed function of the antibody molecule, and in particular the effector functions which may be required. For example, the constant region domains may be human IgA, IgD, IgE, IgG or IgM domains.

In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

In one embodiment, the antibody heavy chain comprises a $CH_1$ domain and the antibody light chain comprises a CL domain, either kappa or lambda.

In one embodiment, the antibody heavy chain comprises a $CH_1$ domain, a $CH_2$ domain and a $CH_3$ domain and the antibody light chain comprises a CL domain, either kappa or lambda. The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns P. et al., 2009. Specificity and affinity of human Fcgamma receptors and their polymorphic variants for human IgG subclasses. Blood. 113(16):3716-25), see also Jeffrey B. Stavenhagen, et al. Cancer Research 2007 Sep. 15; 67(18):8882-90.

Binding of IgG to the FcγRs or C1q depends on residues located in the hinge region and the $CH_2$ domain. Two regions of the $CH_2$ domain are critical for FcγRs and C1q binding, and have unique sequences in IgG2 and IgG4. Substitutions into human IgG1 of IgG2 residues at positions 233-236 and IgG4 residues at positions 327, 330 and 331 have been shown to greatly reduce ADCC and CDC (Armour K L. et al., 1999. Recombinant human IgG molecules lacking Fcgamma receptor I binding and monocyte triggering activities. Eur J Immunol. 29(8):2613-24 and Shields R L. et al., 2001. High resolution mapping of the binding site on human IgG1 for Fc gamma RI, Fc gamma RII, Fc gamma RIII, and FcRn and design of IgG1 variants with improved binding to the Fc gamma R. J Biol Chem. 276(9):6591-604). Furthermore, Idusogie et al. demonstrated that alanine substitution at different positions, including K322, significantly reduced complement activation (Idusogie E E. et al., 2000. Mapping of the C1q binding site on rituxan, a chimeric antibody with a human IgG1 Fc. J Immunol. 164(8):4178-84). Similarly, mutations in the $CH_2$ domain of murine IgG2A were shown to reduce the binding to FcγRI, and C1q (Steurer W. et al., 1995. Ex vivo coating of islet cell allografts with murine CTLA4/Fc promotes graft tolerance. J Immunol. 155(3): 1165-74).

In one embodiment the Fc region employed is mutated, in particular a mutation described herein. In one embodiment the mutation is to remove binding and/or effector function.

In one embodiment the Fc mutation is selected from the group comprising a mutation to remove binding of the Fc region, a mutation to increase or remove an effector function, a mutation to increase half-life and a combination of the same.

Some antibodies that selectively bind FcRn at pH 6.0, but not pH 7.4, exhibit a higher half-life in a variety of animal models. Several mutations located at the interface between the $CH_2$ and $CH_3$ domains, such as T250Q/M428L (Hinton P R. et al., 2004. Engineered human IgG antibodies with longer serum half-lives in primates. J Biol Chem. 279(8): 6213-6) and M252Y/S254T/T256E+H433K/N434F (Vaccaro C. et al., 2005. Engineering the Fc region of immunoglobulin G to modulate in vivo antibody levels. Nat Biotechnol. 23(10):1283-8), have been shown to increase the binding affinity to FcRn and the half-life of IgG1 in vivo. However, there is not always a direct relationship between increased FcRn binding and improved half-life (Datta-Mannan A. et al., 2007. Humanized IgG1 Variants with Differential Binding Properties to the Neonatal Fc Receptor: Relationship to Pharmacokinetics in Mice and Primates. Drug Metab. Dispos. 35: 86-94).

IgG4 subclass show reduced Fc receptor (FcγRIIIa) binding, antibodies of other IgG subclasses generally show strong binding. Reduced receptor binding in these other IgG subtypes can be effected by altering, for example replacing one or more amino acids selected from the group comprising Pro238, Aps265, Asp270, Asn270 (loss of Fc carbohydrate), Pro329, Leu234, Leu235, Gly236, Gly237, Ile253, Ser254, Lys288, Thr307, Gln311, Asn434 and His435.

In one embodiment a molecule according to the present disclosure has an Fc of IgG subclass, for example IgG1, IgG2 or IgG3 wherein the Fc is mutated in one, two or all following positions S228, L234 and/or D265.

In one embodiment the mutations in the Fc region are independently selected from S228P, L234A, L235A, L235A, L235E and combinations thereof.

It may be desired to either reduce or increase the effector function of an Fc region. Antibodies that target cell-surface molecules, especially those on immune cells, abrogating effector functions is required. In some embodiments, for example for the treatment of autoimmunity, enhanced Fc binding on immune cells by increasing negative Fc receptor binding (FcgRIIb or CD32b) may be desirable see Stavenhagen J B, et al *Advances in Enzyme Regulation* 2007 Dec. 3 and Veri M C, et al. *Arthritis Rheum*, 2010 Mar. 30; 62(7):1933-43. Conversely, for antibodies intended for oncology use, increasing effector functions may improve the therapeutic activity.

Numerous mutations have been made in the $CH_2$ domain of human IgG1 and their effect on ADCC and CDC tested in vitro (Idusogie E E. et al., 2001. Engineered antibodies with increased activity to recruit complement. J Immunol. 166 (4):2571-5). Notably, alanine substitution at position 333 was reported to increase both ADCC and CDC. Lazar et al. described a triple mutant (S239D/I332E/A330L) with a higher affinity for FcγRIIIa and a lower affinity for FcγRIIb resulting in enhanced ADCC (Lazar G A. et al., 2006. Engineered antibody Fc variants with enhanced effector function. PNAS 103(11): 4005-4010). The same mutations were used to generate an antibody with increased ADCC (Ryan M C. et al., 2007. Antibody targeting of B-cell maturation antigen on malignant plasma cells. Mol. Cancer Ther., 6: 3009-3018). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards J O et al 2008. Optimization of antibody binding to Fcgamma RIIa enhances macrophage phagocytosis of tumor cells. Mol Cancer Ther. 7(8):2517-27).

Due to their lack of effector functions, IgG4 antibodies represent a suitable IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation has been shown to prevent this recombination process allowing the design of less unpredictable therapeutic IgG4 antibodies (Labrijn A F. et al., 2009. Therapeutic IgG4 antibodies engage in Fab-arm exchange with endogenous human IgG4 in vivo. Nat Biotechnol. 27(8):767-71). This technology may be employed to create bispecific antibody molecules.

It will also be understood by one skilled in the art that antibodies may undergo a variety of post-translational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

Affinity

The present invention provides anti-CD79 antibody molecules.

In one embodiment a binding domain employed in the molecules of the present disclosure is specific to CD79a.

In one embodiment a binding domain employed in the molecules of the present disclosure is specific to CD79b.

In one embodiment a binding domain employed in the molecules of the present disclosure is specific to CD79 complex, i.e. it recognises an epitope present in the complex and specific thereto, for example an epitope comprising an interaction between CD79a and CD79b.

CD79a (also known as immunoglobulin alpha and B-cell antigen receptor complex-associated protein alpha chain) is a known protein. Expression of CD79a is restricted to B lymphocytes. The human sequence is available in UniProt under entry P11912 (SEQ ID NO: 245 and without signal sequence amino acids 33-226 of SEQ ID NO: 245). The murine version is available in UniProt under entry 11911. The present disclosure relates to all forms of CD79a from any species, in particular human and any natural variants thereof. In one embodiment CD79a refers to the human form of the protein.

CD79b (also known as immunoglobulin associated beta and cluster differentiation 79B) is a known protein. Expression of CD79b is restricted to B lymphocytes. The human sequence is available in UniProt under entry P40259 (SEQ ID NO: 298 and without signal sequence amino acids 29-229 of SEQ ID NO: 298). The murine version in UniProt under entry P15530. The present disclosure relates to all forms of CD79b, from any species, in particular human and any natural variants thereof. In one embodiment CD79b refers to the human form of the protein.

In one embodiment the binding domain specific to CD79 binds CD79a.

In one embodiment the binding domain specific to CD79 binds CD79b.

In one embodiment the binding domain specific to CD79 binds a complex of CD79a and CD79b.

In one embodiment the affinity of the binding domain for CD79 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of the binding domain for CD79a in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of the binding domain for CD79b in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

The multispecific molecules of the present invention may comprise a binding domain specific to the antigen CD22 and a binding domain specific to the antigen CD79a and/or CD79b.

In one embodiment a binding domain employed in the molecules of the present disclosure is specific to CD22.

CD22 (also known as cluster of differentiation-22) is a known protein. CD22 is an inhibitory co-receptor of the B-cell receptor (BCR), and plays a critical role in establishing signalling thresholds for B-cell activation. The human sequence is available in UniProt entry number P20273 (SEQ ID NO:244 and without signal peptide, amino acids 20-847 of SEQ ID NO:244). The murine version in UniProt entry P35329. The present disclosure relates to all forms of CD22, from any species, in particular human and natural variants thereof. In one embodiment CD22 refers to the human form of the protein.

In one embodiment the affinity of the binding domain for CD22 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

The binding domain for CD79 may bind to CD79a and/or CD79b.

It will be appreciated that the affinity of the binding domain for CD22 may be the same or different from the affinity of the binding domain for CD79.

In one embodiment a binding domain employed in the molecules of the present disclosure is specific to CD45.

CD45 (also known as PTPRC) is a known protein. CD45 is a member of the protein tyrosine phosphatase (PTP) family. PTPs are known to be signaling molecules that regulate a variety of cellular processes including cell growth, differentiation, mitotic cycle, and oncogenic transformation. This PTP contains an extracellular domain, a single transmembrane segment and two tandem intracytoplasmic catalytic domains, and thus belongs to receptor type PTP. Various isoforms of CD45 exist: CD45RA, CD45RB, CD45RC, CD45RAB, CD45RAC, CD45RBC, CD45RO, CD45R (ABC). CD45RA is located on naive T cells and CD45RO is located on memory T cells. CD45 splice variant isoforms A, B and C are expressed differentially on human B cells. CD45 is a member of the Protein Tyrosine Phosphatase (PTP) family: Its intracellular (COOH-terminal) region contains two PTP catalytic domains, and the extracellular region is highly variable due to alternative splicing of exons 4, 5, and 6 (designated A, B, and C, respectively), plus differing levels of glycosylation. The CD45 isoforms detected are cell type-, maturation, and activation state-specific. In general the long form of the protein (A, B or C) is expressed on naïve or unactivated B cells and the mature or truncated form of CD45 (RO) is expressed on activated or mature/memory B cells.

The human sequence is available in UniProt entry number P08575, and provided herein in SEQ ID NO: 10, or amino acids 24-1304 of SEQ ID NO: 10, lacking the signal peptide. The murine version in UniProt entry P06800. The present disclosure relates to all forms of CD45, from any species. In one embodiment CD45 refers to the human form of the protein and natural variants and isoforms thereof.

In one embodiment the affinity of the binding domain for CD45 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment, the multi-specific antibody molecules of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al J. Mol. Biol., 250, 359-368, 1996), DNA shuffling (Patten et al Curr. Opin. Biotechnol., 8, 724-733, 1997), phage display (Thompson et al., J. Mol. Biol., 256, 77-88, 1996) and sexual PCR (Crameri et al Nature, 391, 288-291, 1998). Vaughan et al (supra) discusses these methods of affinity maturation.

Antibodies & Generation of Same

Binding domains for use in the present invention may be generated by any suitable method known in the art, for example CDRs may be taken from non-human antibodies including commercially available antibodies and grafted into human frameworks or alternatively chimeric antibodies can be prepared with non-human variable regions and human constant regions etc.

Typically the binding domains for use in the present invention are binding domains derived from antibodies which bind the selected antigen, such as antibodies which bind CD22, CD45, or CD79a and/or CD79b.

Examples of CD22, CD45 and CD79 antibodies are known in the art and these may be employed directly in the molecules of the present invention or screened for suitability using the methods described herein, and subsequently modified if necessary, for example humanised, using the methods described herein. Examples of CD22 antibodies in the clinic include epratuzumab and inotuzumab. Other therapeutic antibodies have been described in the art, for example anti-CD22 antibodies disclosed in US2003202975 and WO14/011520, anti-CD79b antibodies disclosed in WO14011521 and WO15021089. Non-human anti-CD22 antibodies include rabbit monoclonal antibody LS-C2210357 (LSBio) from clone SP104, mouse monoclonal LS-C174778 from clone 4C3, mouse monoclonal LS-C4802, mouse monoclonal LS-B9996 from clone 1B1, mouse monoclonal LS-C340404 from clone 2E6, mouse monoclonal LS-C312263, mouse monoclonal LS-C152867, mouse monoclonal LS-C87523, mouse monoclonal LS-C134333 from clone FRB4, mouse monoclonal LS-C134336, mouse monoclonal LS-C40961 from clone HIB22, mouse monoclonal LS-C134332, the following antibodies from Santa Cruz Biotechnology sc-271579, sc-377304, sc-7032, sc-18909, sc-7932, sc-7323, sc-7307, sc-7031, sc-20053, sc-189000, sc-136440, sc-136507, sc-53031, sc-73363, sc-53032, Abcam rabbit monoclonal Ab33859 (EP498Y), mouse monoclonal antibody AA 1-687 catalog number ABIN1999423, mouse monoclonal from Biolegend workshop number V CD22.14 from clone HIB22.

Commercially available anti-CD79a antibodies include mouse monoclonal LS-B4504 (LSBio) from clone HM57, mouse monoclonal LS-B8330, mouse monoclonal LS-C44954, rabbit monoclonal LS-B9093, mouse monoclonal LS-B8513 from clone JCB117, rabbit monoclonal LS-C210607 from clone SP18, mouse monoclonal LS-C175441 from clone 5E2, mouse monoclonal LS-C338670 from clone 3D3, mouse monoclonal LS-C88120 from clone HM47/A9, mouse monoclonal LS-C191714, mouse monoclonal LS-C87592, mouse monoclonal LS-C44955, mouse monoclonal LS-C95934, mouse monoclonal LS-C121584, mouse monoclonal LS-C121585, mouse monoclonal LS-C204347, mouse monoclonal LS-C88122, Abcam mouse monoclonal ab3121 [HM47/A9], rabbit monoclonal ab79414, and rabbit monoclonal ab133483.

Commercially available CD79b antibodies include mouse monoclonal Abcam antibody ab33295, rat monoclonal ab23826, mouse monoclonal ab103422, rabbit monoclonal ab134103, rabbit monoclonal ab134147, and rabbit monoclonal ab183343.

Examples of CD45 antibodies include rat monoclonal YTH54, YTH25.4, mouse monoclonal from Miltenyi clone 5B1 and clone 30F11, rat monoclonal YAML568, from BD Bioscience mouse monoclonal clone 2D1 catalog No. 347460, from Novus mouse monoclonal antibody 5D3A3 catalog No. NBP2-37293, mouse monoclonal HI30 catalog No. NBP1-79127, mouse monoclonal 4A8A4C7A2 catalog No. NBP1-47428, mouse monoclonal 2B11 catalog No. NBP2-32934, rat monoclonal YTH24.5 catalog No. NB100-63828, rabbit monoclonal Y321 catalog No. NB110-55701, mouse monoclonal PD7/26/16 catalog No. NB120-875, from Santa Cruz mouse monoclonal from clone B8 catalog No. sc-28369, mouse monoclonal from clone F10-89-4 catalog No. sc-52490, rabbit monoclonal from clone H-230 catalog No. sc-25590, goat monoclonal from clone N-19 catalog No. sc-1123, mouse monoclonal from clone OX1 catalog No. sc-53045, rat monoclonal (T29/33) catalog No sc-18901, rat monoclonal (YAML 501.4) catalog No. sc65344, rat monoclonal (YTH80.103) catalog No sc-59071, mouse monoclonal (35105) catalog No. sc-53201, mouse monoclonal (35-Z6) catalog No. sc-1178, mouse monoclonal (158-4D3) catalog No. sc-52386, mouse monoclonal to CD45RO (UCH-L1) catalog No. sc-1183, mouse monoclonal to CD45RO (2Q1392) catalog No. sc-70712.

CD45 antibodies are also disclosed in WO2005/026210, WO02/072832 and WO2003/048327 incorporated herein by reference.

Such commercially available antibodies may be useful tools in the discovery of futher therapeutic antibodies.

The skilled person may generate antibodies for use in the multi-specific molecules of the invention using any suitable method known in the art.

Antigen polypeptides, for use in generating antibodies for example for use to immunize a host or for use in panning, such as in phage display, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The antigen polypeptide may in some instances be part of a larger protein such as a fusion protein for example fused to an affinity tag or similar. In one embodiment the host may be immunised with a cell, such as a fibroblast, transfected with the relevant protein or polypeptide, for example co-transfected with CD79a and CD79b.

Antibodies generated against an antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al 1983, Immunology Today, 4:72) and the EBV-hybridoma technique (Cole et al Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by, for example, the methods described by Babcook, J. et al 1996, Proc. Natl. Acad. Sci. USA 93(15):7843-78481; WO92/02551; WO2004/051268 and WO2004/106377.

The antibodies for use in the present disclosure can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO90/02809; WO91/10737; WO92/01047; WO92/18619; WO93/11236; WO95/15982; WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; 5,969,108, and WO20011/30305.

In one example the multi-specific molecules of the present disclosure are fully human, in particular one or more of the variable domains are fully human.

Fully human molecules are those in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP0546073, U.S. Pat. Nos. 5,545,806, 5,569,825, 5,625,126, 5,633,425, 5,661,016, 5,770,429, EP 0438474 and EP0463151.

In one example the binding domains of the multi-specific molecules according to the disclosure are humanised.

Humanised (which include CDR-grafted antibodies) as employed herein refers to molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

As used herein, the term "humanised antibody molecule" refers to an antibody molecule wherein the heavy and/or light chain contains one or more CDRs (including, if desired, one or more modified CDRs) from a donor antibody (e.g. a murine or rabbit monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

Examples of human frameworks which can be used in the present disclosure are KOL, NEWM, REI, EU, TUR, TEI, LAY and POM (Kabat et al supra). For example, KOL and NEWM can be used for the heavy chain, REI can be used for the light chain and EU, LAY and POM can be used for both the heavy chain and the light chain. Alternatively, human germline sequences may be used; these are available at: http//www2mre-lmb.cam.ac.uk/vbase/list2.php.

In a humanised antibody molecule of the present disclosure, the acceptor heavy and light chains do not necessarily need to be derived from the same antibody and may, if desired, comprise composite chains having framework regions derived from different chains.

The framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al 1998, Nature, 332, 323-324). Such changes should be kept to the minimum necessary to recover the affinity of the donor antibody. A protocol for selecting residues in the acceptor framework regions which may need to be changed is set forth in WO91/09967.

Derivatives of frameworks may have 1, 2, 3, 4, 5, 6, 7, 8, 9 or 10 amino acids replaced with an alternative amino acid, for example with a donor residue.

Donor residues are residues from the donor antibody, i.e. the antibody from which the CDRs were originally derived, in particular the residue in a corresponding location from the donor sequence is adopted. Donor residues may be replaced by a suitable residue derived from a human receptor framework (acceptor residues).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one example there is provided a binding domain comprising a heavy chain variable region (for example, VH), specific for CD79 which comprises three CDRs, wherein CDR H1 has the sequence given in SEQ ID NO: 11, CDR H2 has the sequence given in SEQ ID NO: 12, and CDR H3 has the sequence given in SEQ ID NO:3.

In one embodiment there is provided a binding domain comprising a heavy chain variable region (for example, VH), specific for CD79 comprising 3 heavy chain CDRs SEQ ID NO: 8 for CDRH1, SEQ ID NO: 9 for CDRH2 and SEQ ID NO: 4 for CDRH3.

In one embodiment there is provided a binding domain comprising a light chain variable region (for example VL) specific for CD79 comprising 3 light chain CDRs SEQ ID NO: 19 for CDRL1, SEQ ID NO: 20 for CDRL2 and SEQ ID NO: 21 for CDRL3.

In one embodiment there is provided a binding domain comprising a light chain variable region (for example VL) specific for CD79 comprising 3 light chain CDRs SEQ ID NO: 13 for CDRL1, SEQ ID NO: 14 for CDRL2 and SEQ ID NO: 15 for CDRL3.

In one example there is provided a binding domain comprising a heavy chain variable region (VH), specific for CD79 which comprises three CDRs, wherein CDR H1 has the sequence given in SEQ ID NO: 11, CDR H2 has the sequence given in SEQ ID NO: 12, and CDR H3 has the sequence given in SEQ ID NO:3 and a light chain variable region (VL) which comprises three CDRs, wherein CDR L1 has the sequence given in SEQ ID NO: 19, CDR L2 has the sequence given in SEQ ID NO: 20 and CDR L3 has the sequence given in SEQ ID NO: 21, 22, 23 or 24.

In one example there is provided a binding domain specific for CD79 comprising a heavy chain variable region (VH) which comprises three CDRs, wherein CDR H1 has the sequence given in SEQ ID NO: 11, CDR H2 has the sequence given in SEQ ID NO: 12, and CDR H3 has the sequence given in SEQ ID NO:3 and a light chain variable region (VL) which comprises three CDRs, wherein CDR L1 has the sequence given in SEQ ID NO: 19, CDR L2 has the sequence given in SEQ ID NO: 20 and CDR L3 has the sequence given in SEQ ID NO: 21.

In one example there is provided an anti-CD79 antibody or fragment thereof containing one or more binding domains comprising the CDRs given in SEQ ID NOs 11, 12, 3, 19, 20 and 21.

In one example there is provided a binding domain comprising a heavy chain variable region (VH), specific for CD79 which comprises three CDRs, wherein CDR H1 has the sequence given in SEQ ID NO: 8, CDR H2 has the sequence given in SEQ ID NO: 9, and CDR H3 has the sequence given in SEQ ID NO:4 and a light chain variable region (VL) which comprises three CDRs, wherein CDR L1 has the sequence given in SEQ ID NO: 13, CDR L2 has the sequence given in SEQ ID NO: 14 and CDR L3 has the sequence given in SEQ ID NO: 15.

In one example there is provided an anti-CD79 antibody or fragment thereof containing one or more binding domains comprising the CDRs given in SEQ ID NOs 8, 9, 4, 13, 14 and 15.

In one example there is provided a binding domain comprising a heavy chain variable region (VH), specific for CD79 which comprises three CDRs, wherein CDR H1 has the sequence given in SEQ ID NO: 8, CDR H2 has the sequence given in SEQ ID NO: 9, and CDR H3 has the sequence given in SEQ ID NO:4 and a light chain variable region (VL) which comprises three CDRs, wherein CDR L1 has the sequence given in SEQ ID NO: 13, CDR L2 has the sequence given in SEQ ID NO: 14 and CDR L3 has the sequence given in SEQ ID NO: 15, 16, 17 or 18.

In one embodiment an antibody molecule according to the present disclosure is humanised and incorporates CDRs described herein or variants therof In one embodiment the heavy chain variable region human framework employed in the antibody molecule of the present disclosure is selected from the group comprising IGHV3-48, IGHV4-59, IGHV3-66 and a variant of any one of the same wherein one, two, three, four, five, six, seven, eight, nine, ten or more amino acids are substituted with an amino acid other than cysteine, for example substituted with a residue in the corresponding location in the original donor antibody, for example from the donor VH sequences provided in SEQ ID NO:31 or 38. Typically the human framework further comprises a suitable J region sequence, such as the JH4 or JH2 J region.

In one embodiment substitutions in the VH framework (particularly for use with heavy chain anti-CD79 CDRs described herein above) may be made in one or more, such as at 1, 2, 3, 4, 5, 6, 7 or 8 positions selected from 24, 37, 48, 49, 67, 71, 73 and 78 (such as at least substitution at position 73 and 78), for example substitution in all of the positions 24, 48, 49, 73, and 78 (particularly suitable for IGHV3-66) or all of the positions 24, 48, 49, 71, 73, and 78 (particularly suitable for IGHV3-48) or all the positions 37, 49, 67, 71, 73, 76 and 78 or all of the positions 37, 67, 71, 73, 76 and 78 (particularly suitable for IGHV4-59).

In one embodiment after substitution position 24 of the VH framework is valine.

In one embodiment after substitution position 37 of the VH framework is valine.

In one embodiment after substitution position 48 of the VH framework is isoleucine.

In one embodiment after substitution position 49 of the VH framework is glycine.

In one embodiment after substitution position 67 of the VH framework is phenylalanine.

In one embodiment after substitution position 71 of the VH framework is lysine.

In one embodiment after substitution position 71 of the VH framework is arginine.

In one embodiment after substitution position 73 of the VH framework is serine.

In one embodiment after substitution position 78 of the VH framework is valine.

It will be appreciated that one or more of these substitutions may be combined to generate a humanised VH region for use in an antibody molecule of the invention.

In one embodiment the humanised VH variable domain comprises a sequence independently selected from SEQ ID NO: 34, 35, 41 and 42.

In one embodiment residue 1 of the VH is changed to glutamic acid to facilitate processing of the sequence.

In one embodiment the light chain variable region human framework employed in the humanised antibody molecule of the present disclosure is selected from the group comprising IGKV1-6, IGKV1D-13 and a variant of any one of the same wherein one, two, three, four, five or six amino acids are substituted with an amino acid other than cysteine, for example substituted with a donor residue in the corresponding location in the original donor antibody for example from the donor VL sequences provided in SEQ ID NO:29 or 36. Typically the human framework further comprises a suitable J region such as a JK4 J region.

In one embodiment a human VL framework employed (for example to accept light chain anti-CD79 CDRs) in an antibody molecule of the present disclosure comprises an amino acid substituted in at least one position, such as 1, 2, 3, 4, 5 or 6 selected from the group comprising 2, 3, 36, 46, 49 and 70, for example wherein the original amino acid in the framework is substituted for another amino acid other than cysteine, in particular substituted for a residue in the corresponding location in the framework of the donor antibody.

In one embodiment the human VL framework employed is an IGKV1 framework and has substitutions in at least positions 3 and 70.

In one embodiment the human VL framework employed (such as an IGKV1 framework) has substitutions in positions 2, 3, 36, 46, 49 and 70 (particularly suitable for IGKV1D-13) or positions 3 and 70 (particularly suitable for IGKV1-6).

In one embodiment after susbstitution position 2 of the VL framework is glutamine.

In one embodiment after susbstitution position 3 of the VL framework is valine or aspartic acid.

In one embodiment after substitution position 36 of the VL framework is leucine.

In one embodiment after substitution position 46 of the VL framework is glutamine.

In one embodiment after substitution position 49 of the VL framework is histidine.

In one embodiment after substitution position 70 of the VL framework is glutamine.

It will be appreciated that one or more of these substitutions may be combined to generate a humanised VL region for use in an antibody of the invention.

In one embodiment the humanised VL variable domain comprises a sequence independently selected from SEQ ID NO: 33 or 40.

In one embodiment the humanised VL variable domain comprises a sequence independently selected from SEQ ID NO: 33, 40, 341, 342 and 343.

In one embodiment there is provided an antibody molecule comprising a VH independently selected from SEQ ID NO: 34 and 35 and a VL with a sequence shown in SEQ ID NO: 33.

In one embodiment there is provided an antibody molecule comprising a VH independently selected from SEQ ID NO: 34 and 35 and a VL with a sequence shown in SEQ ID NO: 250.

In one embodiment there is provided an antibody molecule comprising a VH independently selected from SEQ ID NO: 41 and 42 and a VL with a sequence shown in SEQ ID NO: 40.

In one embodiment there is provided an antibody molecule comprising a VH independently selected from SEQ ID NO: 41 and 42 and a VL independently selected from SEQ ID NO: 40, 341, 342 and 343.

It will be appreciated that these humanised grafted variable regions (SEQ ID NOs 41, 42, 40, 341, 342 and 343) may be further modified to reduce the number of donor residues and to replace these with the original human residue (s).

In one example therefore there is provided an antibody molecule comprising a VL independently selected from SEQ ID NO: 40, 341, 342 and 343 in which the residue at position 3 has been replaced by glutamine (Q) and/or the residue at position 70 has been replaced by Aspartic acid (D).

In one example there is provided an antibody molecule comprising a VH comprising the sequence given in SEQ ID NO: 41 in which the residue at position 24 is has been replaced by glutamine (Q) and/or the residue at position 48 has been replaced by Aspartic acid (D), and/or the residue at position 49 has been replaced by Serine (S) and/or the residue at position 73 has been replaced by Asparagine (N) and/or the residue at position 78 has been replaced by Leucine (L).

In one example there is provided an antibody molecule comprising a VH comprising the sequence given in SEQ ID NO: 42 in which the residue at position 37 is has been replaced by Isoleucine (I) and/or the residue at position 67 has been replaced by Valine (V) and/or the residue at position 71 has been replaced by Valine (V) and/or the residue at position 73 has been replaced by Threonine (T) and/or the residue at position 78 has been replaced by Phenylalanine (F).

In one example there is provided an antibody molecule comprising a VH comprising the sequence given in SEQ ID NO: 41 in which the residue at position 24 is has been replaced by glutamine (Q) and/or the residue at position 48 has been replaced by Aspartic acid (D), and/or the residue at position 49 has been replaced by Serine (S) and/or the residue at position 73 has been replaced by Asparagine (N) and/or the residue at position 78 has been replaced by Leucine (L) and a VL comprising a sequence independently selected from SEQ ID NO: 40, 341, 342 and 343 sequence or a sequence independently selected from SEQ ID NO: 40, 341, 342 and 343 in which the residue at position 3 has been replaced by glutamine (Q) and/or the residue at position 70 has been replaced by Aspartic acid (D).

In one example there is provided an antibody molecule comprising a VH comprising the sequence given in SEQ ID NO: 42 in which the residue at position 37 is has been replaced by Isoleucine (I) and/or the residue at position 67 has been replaced by Valine (V) and/or the residue at position 71 has been replaced by Valine (V) and/or the residue at position 73 has been replaced by Threonine (T) and/or the residue at position 78 has been replaced by Phenylalanine (F) and a VL comprising a sequence independently selected from SEQ ID NO: 40, 341, 342 and 343 sequence or a sequence independently selected from SEQ ID NO: 40, 341, 342 and 343 in which the residue at position 3 has been replaced by glutamine (Q) and/or the residue at position 70 has been replaced by Aspartic acid (D).

In one embodiment the present invention provides a multispecific molecule comprising a CD79 binding domain as described herein above and a CD22 binding domain, such as a binding domain described herein below or a variant thereof.

In one embodiment a multispecific molecule according to the present disclosure comprises a binding domain specific to CD22 which comprises 3 heavy chain CDRS selected from the group comprising SEQ ID NO: 43, 44, 45, 46, 47, 60, 61, 62, 63, 64, 65, 72, 73, 74, 75, 76, 101, 102, 103, 104, 105, 116, 117, 118, 119, 120, 121, 122, 123, 124, 125, 136, 137, 138, 139, 140, 141, 142, 143 and 144.

In one embodiment a multispecific molecule according to the present disclosure comprises a binding domain specific to CD22 which comprises 3 light chain CDRS selected from the group comprising SEQ ID NO: 48, 49, 50, 66, 67, 68, 77, 78, 79, 80, 81, 82, 83, 84, 85, 86, 87, 88, 89, 90, 91, 92, 93, 94, 106, 107, 108, 126, 127, 128, 145, 146 and 147.

In one embodiment a multispecific molecule according to the present disclosure comprises a binding domain specific to CD22 which comprises 3 heavy chain CDRS selected from the group comprising SEQ ID NO: 43, 44, 45, 46, 47, 60, 61, 62, 63, 64, 65, 72, 73, 74, 75, 76, 101, 102, 103, 104, 105, 116, 117, 118, 119, 120, 121, 122, 123, 124, 125, 136, 137, 138, 139, 140, 141, 142, 143 and 144 and 3 light chain CDRS selected from the group comprising SEQ ID NO: 48, 49, 50, 66, 67, 68, 77, 78, 79, 80, 81, 82, 83, 84, 85, 86, 87, 88, 89, 90, 91, 92, 93, 94, 106, 107, 108, 126, 127, 128, 145, 146 and 147.

In one embodiment there is provided a binding domain comprising a heavy chain variable region (VH), specific for CD22 comprising 3 heavy chain CDRs SEQ ID NO: 43 or 44 for CDRH1, SEQ ID NO: 45 or 46 for CDRH2 and SEQ ID NO: 47 for CDRH3.

In one embodiment there is provided a binding domain comprising a heavy chain variable region (VH), specific for CD22 comprising 3 heavy chain CDRs SEQ ID NO: 60 or 61 for CDRH1, SEQ ID NO: 62 or 63 for CDRH2 and SEQ ID NO: 64 or 65 for CDRH3.

In one embodiment there is provided a binding domain comprising a heavy chain variable region (VH), specific for CD22 comprising 3 heavy chain CDRs SEQ ID NO: 72 or 73 for CDRH1, SEQ ID NO: 74 or 75 for CDRH2 and SEQ ID NO: 76 for CDRH3.

In one embodiment there is provided a binding domain comprising a heavy chain variable region (VH), specific for CD22 comprising 3 heavy chain CDRs SEQ ID NO: 101 or 102 for CDRH1, SEQ ID NO: 103 or 104 for CDRH2 and SEQ ID NO: 105 for CDRH3.

In one embodiment there is provided a binding domain comprising a heavy chain variable region (VH), specific for CD22 comprising 3 heavy chain CDRs SEQ ID NO: 116 for CDRH1, SEQ ID NO: 117, 118, 119, 120, 121 or 122 for CDRH2 and SEQ ID NO: 123, 124 or 125 for CDRH3.

In one embodiment there is provided a binding domain comprising a heavy chain variable region (VH), specific for CD22 comprising 3 heavy chain CDRs SEQ ID NO: 136 or 137 for CDRH1, SEQ ID NO: 138, 139, 140, 141, 142 and 143 for CDRH2 and SEQ ID NO: 144 for CDRH3.

In one embodiment there is provided a binding domain comprising a light chain variable region specific for CD22 comprising 3 light chain CDRs SEQ ID NO: 48 for CDRL1, SEQ ID NO: 49 for CDRL2 and SEQ ID NO: 50 for CDRL3.

In one embodiment there is provided a binding domain comprising a light chain variable region specific for CD22 comprising 3 light chain CDRs SEQ ID NO: 66 for CDRL1, SEQ ID NO: 67 for CDRL2 and SEQ ID NO: 68 for CDRL3.

In one embodiment there is provided a binding domain comprising a light chain variable region specific for CD22 comprising 3 light chain CDRs SEQ ID NO: 77 for CDRL1, SEQ ID NO: 78 for CDRL2 and SEQ ID NO: 79, 80, 81, 82, 83, 84, 85, 86, 87, 88, 89, 90, 91, 92, 93 or 94 for CDRL3.

In one embodiment there is provided a binding domain comprising a light chain variable region specific for CD22 comprising 3 light chain CDRs SEQ ID NO: 106 for CDRL1, SEQ ID NO: 107 for CDRL2 and SEQ ID NO: 108 for CDRL3.

In one embodiment there is provided a binding domain comprising a light chain variable region specific for CD22 comprising 3 light chain CDRs SEQ ID NO: 126 for CDRL1, SEQ ID NO: 127 for CDRL2 and SEQ ID NO: 128 for CDRL3.

In one embodiment there is provided a binding domain comprising a light chain variable region specific for CD22 comprising 3 light chain CDRs SEQ ID NO: 145 for CDRL1, SEQ ID NO: 146 for CDRL2 and SEQ ID NO: 147 for CDRL3.

In one example there is provided a binding domain specific to CD22 comprising a heavy chain variable region (VH), which comprises three CDRs, wherein CDR H1 has the sequence given in SEQ ID NO: 43 or 44, CDR H2 has the sequence given in SEQ ID NO: 45 or 46, and CDR H3 has the sequence given in SEQ ID NO: 47 and a light chain variable region (VL) which comprises three CDRs, wherein CDR L1 has the sequence given in SEQ ID NO: 48, CDR L2 has the sequence given in SEQ ID NO: 49 and CDR L3 has the sequence given in SEQ ID NO: 50.

In one example there is provided a binding domain specific to CD22 comprising a heavy chain variable region (VH), which comprises three CDRs, wherein CDR H1 has the sequence given in SEQ ID NO: 60 or 61, CDR H2 has the sequence given in SEQ ID NO: 62 or 63, and CDR H3 has the sequence given in SEQ ID NO: 64 or 65 and a light chain variable region (VL) which comprises three CDRs, wherein CDR L1 has the sequence given in SEQ ID NO: 66, CDR L2 has the sequence given in SEQ ID NO: 67 and CDR L3 has the sequence given in SEQ ID NO: 68.

In one example there is provided a binding domain specific to CD22 comprising a heavy chain variable region (VH), which comprises three CDRs, wherein CDR H1 has the sequence given in SEQ ID NO: 72 or 73, CDR H2 has the sequence given in SEQ ID NO: 74 or 75, and CDR H3 has the sequence given in SEQ ID NO: 76 and a light chain variable region (VL) which comprises three CDRs, wherein CDR L1 has the sequence given in SEQ ID NO: 77, CDR L2 has the sequence given in SEQ ID NO: 78 and CDR L3 has the sequence given in SEQ ID NO: 79, 80, 81, 82, 83, 84, 85, 86, 87, 88, 89, 90, 91, 92, 93 or 94.

In one example there is provided a binding domain specific to CD22 comprising a heavy chain variable region (VH), which comprises three CDRs, wherein CDR H1 has the sequence given in SEQ ID NO: 101 or 102, CDR H2 has the sequence given in SEQ ID NO: 103 or 104, and CDR H3 has the sequence given in SEQ ID NO: 105 and a light chain variable region (VL) which comprises three CDRs, wherein CDR L1 has the sequence given in SEQ ID NO: 106, CDR L2 has the sequence given in SEQ ID NO: 107 and CDR L3 has the sequence given in SEQ ID NO: 108.

In one example there is provided a binding domain specific to CD22 comprising a heavy chain variable region (VH), which comprises three CDRs, wherein CDR H1 has the sequence given in SEQ ID NO: 116, CDR H2 has the sequence given in SEQ ID NO: 117, 118, 119, 120, 121 or 122 and CDR H3 has the sequence given in SEQ ID NO: 123, 124 or 125 and a light chain variable region (VL) which comprises three CDRs, wherein CDR L1 has the sequence given in SEQ ID NO: 126, CDR L2 has the sequence given in SEQ ID NO: 127 and CDR L3 has the sequence given in SEQ ID NO: 128.

In one example there is provided a binding domain specific to CD22 comprising a heavy chain variable region (VH), which comprises three CDRs, wherein CDR H1 has the sequence given in SEQ ID NO: 136 or 137, CDR H2 has the sequence given in SEQ ID NO: 138, 139, 140, 141, 142 or 143, and CDR H3 has the sequence given in SEQ ID NO: 144 and a light chain variable region (VL) which comprises three CDRs, wherein CDR L1 has the sequence given in SEQ ID NO: 145, CDR L2 has the sequence given in SEQ ID NO: 146 and CDR L3 has the sequence given in SEQ ID NO: 147.

In one embodiment the present invention provides a multispecific molecule comprising a CD79 binding domain as described herein above and a CD45 binding domain, such as a binding domain described herein below.

In one embodiment there is provided a binding domain comprising a heavy chain variable region (VH), specific for CD45 comprising 3 heavy chain CDRs SEQ ID NO: 155 or 156 for CDRH1, SEQ ID NO: 157, 158, 159, 160, 161, 162, 163 or 164 for CDRH2 and SEQ ID NO: 165 for CDRH3.

In one embodiment there is provided a binding domain comprising a heavy chain variable region (VH), specific for CD45 comprising 3 heavy chain CDRs SEQ ID NO: 178 or 179 for CDRH1, SEQ ID NO: 180 or 181 for CDRH2 and SEQ ID NO: 182 for CDRH3.

In one embodiment there is provided a binding domain comprising a heavy chain variable region (VH), specific for CD45 comprising 3 heavy chain CDRs SEQ ID NO: 195 for CDRH1, SEQ ID NO: 196 or 197 for CDRH2 and SEQ ID NO: 198 for CDRH3.

In one embodiment there is provided a binding domain comprising a heavy chain variable region (VH), specific for CD45 comprising 3 heavy chain CDRs SEQ ID NO: 212 or 213 for CDRH1, SEQ ID NO: 214 or 215 for CDRH2 and SEQ ID NO: 216, 217, 218 or 219 for CDRH3.

In one embodiment there is provided binding domain comprising a light chain variable region specific for CD45 comprising 3 light chain CDRs SEQ ID NO: 166 for CDRL1, SEQ ID NO: 167 for CDRL2 and SEQ ID NO: 168, 169 or 170 for CDRL3.

In one embodiment there is provided a binding domain comprising a light chain variable region specific for CD45 comprising 3 light chain CDRs SEQ ID NO: 183 for CDRL1, SEQ ID NO: 184 for CDRL2 and SEQ ID NO: 185, 186 or 187 for CDRL3.

In one embodiment there is provided a binding domain comprising a light chain variable region specific for CD45 comprising 3 light chain CDRs SEQ ID NO: 199 for CDRL1, SEQ ID NO: 200 for CDRL2 and SEQ ID NO: 201, 202, 203 or 204 for CDRL3.

In one embodiment there is provided binding domain comprising a light chain variable region specific for CD45 comprising 3 light chain CDRs SEQ ID NO: 220, 221, 222 or 223 for CDRL1, SEQ ID NO: 224 for CDRL2 and SEQ ID NO: 225 for CDRL3.

In one example there is provided a binding domain specific to CD45 comprising a heavy chain variable region (VH), which comprises three CDRs, wherein CDR H1 has the sequence given in SEQ ID NO: 155 or 156, CDR H2 has the sequence given in SEQ ID NO: 157, 158, 159, 160, 161, 162, 163 or 164 and CDR H3 has the sequence given in SEQ ID NO: 165 and a light chain variable region (VL) which comprises three CDRs, wherein CDR L1 has the sequence given in SEQ ID NO: 166, CDR L2 has the sequence given in SEQ ID NO: 167 and CDR L3 has the sequence given in SEQ ID NO: 168, 169 or 170.

In one example there is provided a binding domain specific to CD45 comprising a heavy chain variable region (VH), which comprises three CDRs, wherein CDR H1 has the sequence given in SEQ ID NO: 178 or 179, CDR H2 has the sequence given in SEQ ID NO: 180 or 181 and CDR H3 has the sequence given in SEQ ID NO: 182 and a light chain variable region (VL) which comprises three CDRs, wherein CDR L1 has the sequence given in SEQ ID NO: 183, CDR L2 has the sequence given in SEQ ID NO: 184 and CDR L3 has the sequence given in SEQ ID NO: 185, 186 or 187.

In one example there is provided a binding domain specific to CD45 comprising a heavy chain variable region (VH), which comprises three CDRs, wherein CDR H1 has the sequence given in SEQ ID NO: 195, CDR H2 has the sequence given in SEQ ID NO: 196 or 197 and CDR H3 has the sequence given in SEQ ID NO: 198 and a light chain variable region (VL) which comprises three CDRs, wherein CDR L1 has the sequence given in SEQ ID NO: 199, CDR L2 has the sequence given in SEQ ID NO: 200 and CDR L3 has the sequence given in SEQ ID NO: 201, 202, 203 or 204.

In one example there is provided a binding domain specific to CD45 comprising a heavy chain variable region (VH), which comprises three CDRs, wherein CDR H1 has the sequence given in SEQ ID NO: 212 or 213, CDR H2 has the sequence given in SEQ ID NO: 214 or 215, and CDR H3 has the sequence given in SEQ ID NO: 216, 217, 218 or 219 and a light chain variable region (VL) which comprises three CDRs, wherein CDR L1 has the sequence given in SEQ ID NO: 220, 221, 222 or 223 CDR L2 has the sequence given in SEQ ID NO: 224 and CDR L3 has the sequence given in SEQ ID NO: 225.

In one embodiment there is provided an antibody molecule comprising a VL and VH pair specific to CD79b selected from SEQ ID NO: 33 and 34, 33 and 35, 250 and 34, 250 and 35, 40 and 41, and 40 and 42.

In one embodiment there is provided an antibody molecule comprising a VL and VH pair specific to CD79b selected from SEQ ID NO: 341 and 41, 341 and 42, 342 and 41, 342 and 42, 343 and 41, and 343 and 42.

In one embodiment there is provided an antibody molecule comprising a VL and VH pair specific to CD22 selected from SEQ ID NO: 55 and 56, 55 and 246, 55 and 247, 55 and 248, 69 and 70, 69 and 71, 69 and 251, 69 and 252, 69 and 253, 69 and 254, 98 and 99, 98 and 100, 98 and 255, 98 and 256, 113 and 114, 113 and 115, 113 and 257, 113 and 258, 133 and 134, 133 and 135, 133 and 259, 133 and 260, 152 and 153, 152 and 154, 152 and 261, and 152 and 262.

In one embodiment there is provided an antibody molecule comprising a VL and VH pair specific to CD45 selected from SEQ ID NO: 175 and 176, 175 and 177, 175 and 263, 175 and 264, 192 and 193, 192 and 194, 192 and 265, 192 and 266, 209 and 211, 209 and 267, 209 and 268, 209 and 269, 210 and 211, 210 and 267, 210 and 268, 210 and 269, 230 and 232, 230 and 270, 230 and 271, 230 and 272, 231 and 232, 231 and 270, 231 and 271, and 231 and 272.

In one example the present invention provides a multispecific molecule comprising a binding domain specific to the antigen CD79 and a binding domain specific to the antigen CD22 wherein this pair of binding domains comprise 6 CDRs from a CD79 antibody and 6 CDRs from a CD22 antibody said pair of antibodies being selected from the following list of pairs of CD79 and CD22 antibodies; 4447 and 4120, 4447 and 4126, 4447 and 4127, 4447 and 4128, 4447 and 4130, 4447 and 4132, 4450 and 4120, 4450 and 4126, 4450 and 4127, 4450 and 4128, 4450 and 4130, and 4450 and 4132.

In one example the present invention provides a multi-specific molecule comprising a binding domain specific to the antigen CD79 and a binding domain specific to the antigen CD45 wherein this pair of binding domains comprise 6 CDRs from a CD79 antibody and 6 CDRs from a CD45 antibody said pair of antibodies being selected from the following list of pairs of CD79 and CD45 antibodies; 4447 and 4122, 4447 and 4129, 4447 and 4131, 4447 and 4133, 4450 and 4122, 4450 and 4129, 4450 and 4131, and 4450 and 4133.

The sequences of these CD79 antibodies (antibody 4447 and antibody 4450), including VH, VL and CDR sequences are provided herein and in FIG. 51. The sequences of these CD22 antibodies (antibodies 4120, 4126, 4127, 4128, 4130, 4132) including VH, VL and CDR sequences are provided herein and may be combined as binding domains in molecules of the present invention. The sequences of these CD45 antibodies (antibodies 4122, 4129, 4131 and 4133) including VH, VL and CDR sequences are provided herein and may be combined as binding domains in molecules of the present invention.

In one embodiment there is provided a variable domain or a binding domain comprising a pair of variable domains with a sequence disclosed herein.

In one example there is provided a binding domain specific to albumin comprising a heavy chain variable region (VH) having the sequence given in SEQ ID NO: 240 and a light chain variable region (VL) having the sequence given in SEQ ID NO: 242.

In one embodiment a binding domain or domains are humanised.

In one example one or more CDRs provided herein may be modified to remove undesirable residues or sites, such as cysteine residues or aspartic acid (D) isomerisation sites or asparagine (N) deamidation sites.

For example one or more cysteine residues in any one of the CDRs may be substituted with another amino acid, such as serine.

In one example an Asparagine deamidation site may be removed from one or more CDRs by mutating the asparagine residue (N) and/or a neighbouring residue to any other suitable amino acid. In one example an asparagine deamidation site such as NG or NS may be mutated, for example to NA or NT.

In one example an Aspartic acid isomerisation site may be removed from one or more CDRs by mutating the aspartic acid residue (D) and/or a neighbouring residue to any other suitable amino acid. In one example an aspartic acid isomerisation site such as DG or DS may be mutated, for example to EG, DA or DT.

In one example an N-glycosylation site such as NLS may be removed by mutating the asparagine residue (N) to any other suitable amino acid, for example to SLS or QLS. In one example an N-glycosylation site such as NLS may be removed by mutating the serine residue (S) to any other residue with the exception of threonine (T).

The skilled person is able to test variants of CDRs or humanised sequences in any suitable assay such as those described herein to confirm activity is maintained.

Specific binding to antigen may be tested using any suitable assay including for example ELISA or surface plasmon resonance methods such as BIAcore where binding to antigen (CD22 or CD79) may be measured. Such assays may use isolated natural or recombinant CD22 or CD79 (a and/or b) or a suitable fusion protein/polypeptide. In one example binding is measured using recombinant CD22 (such as the sequence provided in SEQ ID NO: 244 or amino acids 20-847 of SEQ ID NO: 244) or CD79 (such as the sequence provided in SEQ ID NO: 245 and SEQ ID NO:298 (CD79b) and amino acids 33-226 of SEQ ID NO:245 and amino acids 29-229 of SEQ ID NO: 298) or CD45 (such as the sequence provided herein in SEQ ID NO: 10, or amino acids 24-1304 of SEQ ID NO: 10, lacking the signal peptide) by for example surface plasmon resonance, such as BIAcore. Alternatively the proteins may be expressed on a cell, such as a HEK cell and affinity measured employing a flow cytometry based affinity determination.

The antibody sequences provided by the present invention may be used to identify further antibodies and hence binding domains suitable for use in the antibody molecules of the present invention such as the multispecific molecules of the present invention. Antibodies which cross-block the binding of an antibody molecule according to the present invention to CD79 in particular, an antibody molecule comprising the heavy chain sequence given in SEQ ID NO: 38, 41 or 42 and the light chain sequence given in SEQ ID NO: 36 or 40 or an antibody molecule comprising the heavy chain sequence given in SEQ ID NO: 31, 34 or 35 and the light chain sequence given in SEQ ID NO: 29 or 33 may be similarly useful in binding CD79 and therefore be similarly useful antibodies for example in the multispecific molecules of the present invention. Accordingly, the present invention also provides an antibody molecule comprising a binding domain specific to the antigen CD79b wherein the binding domain for CD79b cross-blocks the binding of any one of the antibody molecules described herein above to CD79 and/or is cross-blocked from binding CD79 by any one of those antibodies, optionally further comprising a binding domain specific to the antigen CD22 or CD45. In one embodiment, such an antibody binds to the same epitope as an anti-CD79 antibody described herein above. In another embodiment the cross-blocking antibody binds to an epitope which borders and/or overlaps with the epitope bound by an anti-CD79 antibody described herein above.

Similarly antibodies which cross-block the binding of an antibody molecule according to the present invention to CD22, in particular, an antibody molecule comprising a heavy chains and corresponding light chain shown in Table 1:

| Light Chain SEQ ID NO: | Corresponding Heavy Chain SEQ ID NO: |
|---|---|
| 51 | 53 |
| 95 | 97 |
| 109 | 111 |
| 129 | 131 |
| 148 | 150 |
| 249 | 58 |
| 55 | 56 |
| 55 | 246 |
| 55 | 247 |
| 55 | 248 |
| 69 | 70 |
| 69 | 71 |
| 69 | 251 |
| 69 | 252 |
| 69 | 253 |
| 69 | 254 |
| 98 | 99 |
| 98 | 100 |
| 98 | 255 |
| 98 | 256 |

-continued

| Light Chain SEQ ID NO: | Corresponding Heavy Chain SEQ ID NO: |
|---|---|
| 113 | 114 |
| 113 | 115 |
| 113 | 257 |
| 113 | 258 |
| 133 | 134 |
| 133 | 135 |
| 133 | 259 |
| 133 | 260 |
| 152 | 153 |
| 152 | 154 |
| 152 | 261 |
| 152 | 262 |

Accordingly, the present invention also provides a multi-specific molecule comprising a binding domain specific to the antigen CD22 and a binding domain specific to the antigen CD79 wherein the binding domain for CD22 cross-blocks the binding of any one of the antibody molecules described herein above to CD22 and/or is cross-blocked from binding CD22 by any one of those antibodies. In one embodiment, such an antibody binds to the same epitope as an antibody described herein above. In another embodiment the cross-blocking antibody binds to an epitope which borders and/or overlaps with the epitope bound by an antibody described herein above.

Similarly antibodies which cross-block the binding of an antibody molecule according to the present invention to CD45, in particular, an antibody molecule comprising a heavy chains and corresponding light chain shown in Table 2:

| Light Chain SEQ ID NO: | Corresponding Heavy Chain SEQ ID NO: |
|---|---|
| 171 | 173 |
| 188 | 190 |
| 205 | 207 |
| 226 | 228 |
| 175 | 176 |
| 175 | 177 |
| 175 | 263 |
| 175 | 264 |
| 192 | 193 |
| 192 | 194 |
| 192 | 265 |
| 192 | 266 |
| 209 | 211 |
| 209 | 267 |
| 209 | 268 |
| 209 | 269 |
| 210 | 211 |
| 210 | 267 |
| 210 | 268 |
| 210 | 269 |
| 230 | 232 |
| 230 | 270 |
| 230 | 271 |
| 230 | 272 |
| 231 | 232 |
| 231 | 270 |
| 231 | 271 |
| 231 | 271 |

Accordingly, in one example the present invention also provides a multi-specific molecule comprising a binding domain specific to the antigen CD45 and a binding domain specific to the antigen CD79 wherein the binding domain for CD45 cross-blocks the binding of any one of the antibody molecules described herein above to CD45 and/or is cross-blocked from binding CD45 by any one of those antibodies. In one embodiment, such an antibody binds to the same epitope as an antibody described herein above. In another embodiment the cross-blocking antibody binds to an epitope which borders and/or overlaps with the epitope bound by an antibody described herein above.

Cross-blocking antibodies can be identified using any suitable method in the art, for example by using competition ELISA or BIAcore assays where binding of the cross blocking antibody to antigen (CD22 and/or CD45 and/or CD79) prevents the binding of an antibody of the present invention or vice versa. Such cross blocking assays may use, cell expressed, isolated natural or recombinant CD22, CD45 or CD79 (a and/or b) or a suitable fusion protein/polypeptide. In one example binding and cross-blocking is measured using recombinant CD22 or a suitable fragment or natural variant thereof (such as the sequence provided in SEQ ID NO: 244 or the sequence provided in amino acids 20-847 of SEQ ID NO: 244) or CD79 such as the sequence provided in SEQ ID NO:245 or the sequence provided in amino acids 33-226 of SEQ ID NO: 245 (CD79a) and/or the sequence provided in SEQ ID NO:298(CD79b) or the sequence provided in amino acids 29-229 of SEQ ID NO: 298.

In one example binding and cross-blocking is measured using recombinant CD45 or a suitable fragment or natural variant thereof (such as the sequence provided in SEQ ID NO: 10, or amino acids 24-1304 of SEQ ID NO: 10, lacking the signal peptide).

Alternatively or in addition, the antibodies according to this aspect of the invention may be cross-blocked from binding to antigen (CD22 or CD79) by an a binding domain disclosed herein, for example comprising the CDRs derived from the heavy chain variable sequence given in and the light chain sequence given in Table 1.

Alternatively or in addition, the antibodies according to this aspect of the invention may be cross-blocked from binding to antigen (CD45 or CD79) by an a binding domain disclosed herein, for example comprising the CDRs derived from the heavy chain variable sequence given in and the light chain sequence given in Table 2.

Also provided therefore is a multi-specific molecule comprising a binding domain specific to the antigen CD22 and a binding domain specific to the antigen CD79b wherein the binding domain for CD79b cross-blocks the binding of any one of the antibody molecules described herein above to CD79b and/or is cross-blocked from binding CD79b by any one of those antibodies by greater than 80%, for example by greater than 85%, such as by greater than 90%, in particular by greater than 95% and optionally wherein the binding domain for CD22 cross-blocks the binding of any one of the antibody molecules described herein above to CD22 and/or is cross-blocked from binding CD22 by any one of those antibodies by greater than 80%, for example by greater than 85%, such as by greater than 90%, in particular by greater than 95%.

Such cross-blocking antibodies may have comparable activity in functional assays as the multi-specific antibody molecules described herein below.

Also provided therefore is a multi-specific molecule comprising a binding domain specific to the antigen CD45 and a binding domain specific to the antigen CD79b wherein the binding domain for CD79b cross-blocks the binding of any one of the antibody molecules described herein above to CD79b and/or is cross-blocked from binding CD79b by any one of those antibodies by greater than 80%, for example by greater than 85%, such as by greater than 90%, in particular by greater than 95% and optionally wherein the binding domain for CD45 cross-blocks the binding of any one of the antibody molecules described herein above to CD45 and/or is cross-blocked from binding CD45 by any one of those antibodies by greater than 80%, for example by greater than 85%, such as by greater than 90%, in particular by greater than 95%.

Such cross-blocking antibodies may have comparable activity in functional assays as the multi-specific antibody molecules described herein below.

The present disclosure also extends to novel polypeptide sequences disclosed herein and sequences at least 80% similar or identical thereto, for example 85% or greater, such 90% or greater, in particular 95%, 96%, 97%, 98% or 99% or greater similarity or identity.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

Accordingly in one example, the present invention provides an antibody molecule wherein the variable domain of the light chain comprises a sequence having at least 80% identity or similarity to the light chain variable domain of SEQ ID NO:36, 29, 33, 40 or 250.

The present invention also provides an antibody molecule wherein the variable domain of the heavy chain comprises a sequence having at least 80% identity or similarity to the heavy chain variable domain of SEQ ID NO:38, 31, 34, 35, 41 or 42.

In one example, the present invention provides an antibody molecule wherein the variable domain of the light chain comprises a sequence having at least 80% identity or similarity to the light chain variable domain of SEQ ID NO:36, 29, 33, 40 or 250 and the variable domain of the heavy chain comprises a sequence having at least 80% identity or similarity to the heavy chain variable domain of SEQ ID NO:38, 31, 34, 35, 41 or 42.

Such sequences are at least 80% similar or identical, for example 85% or greater, such as 90% or greater, in particular 95%, 96%, 97%, 98% or 99% or greater similarity or identity to the reference sequence.

It will be appreciated that the antibody molecule of the present invention, may be incorporated into other molecular formats or constructs, wherein the binding domains provided by the present invention bind to and thereby target CD79. For example, binding regions of the present invention, for example fragments such as a Fab or scFv may be used to re-direct cells in vivo, for example via the transduction of T cells with chimeric antigen receptors (CAR-T cells) and then transferring these cells into the patient (Nat. Revs. Drug Disc. 2015. 14. 499-509). Accordingly, the present invention also provides a chimeric antigen receptor comprising one or more binding domains as described herein.

Linkers

The teaching herein of linkers in one context can equally be applied to linkers in different contexts where a linker is employed, such as in any multispecific molecule of the present invention.

In one embodiment, the linker employed in a molecule of the disclosure is an amino acid linker 50 residues or less in length, for example selected from a sequence shown in sequence 273 to 336.

TABLE 3

Hinge linker sequences

| SEQ ID NO: | SEQUENCE |
|---|---|
| 273 | DKTHTCAA |
| 274 | DKTHTCPPCPA |
| 275 | DKTHTCPPCPATCPPCPA |
| 276 | DKTHTCPPCPATCPPCPATCPPCPA |
| 277 | DKTHTCPPCPAGKPTLYNSLVMSDTAGTCY |
| 278 | DKTHTCPPCPAGKPTHVNVSVVMAEVDGTCY |
| 279 | DKTHTCCVECPPCPA |
| 280 | DKTHTCPRCPEPKSCDTPPPCPRCPA |
| 281 | DKTHTCPSCPA |

TABLE 4

Flexible linker sequences

| SEQ ID NO: | SEQUENCE |
|---|---|
| 282 | SGGGGSE |
| 283 | DKTHTS |
| 284 | (S)GGGGS |
| 285 | (S)GGGGSGGGGS |
| 286 | (S)GGGGSGGGGSGGGGS |
| 287 | (S)GGGGSGGGGSGGGGSGGGGS |
| 288 | (S)GGGGSGGGGSGGGGSGGGGSGGGGS |
| 289 | AAAGSG-GASAS |
| 290 | AAAGSG-XGGGS-GASAS |

TABLE 4-continued

Flexible linker sequences

| SEQ ID NO: | SEQUENCE |
|---|---|
| 291 | AAAGSG-XGGGSXGGGS-GASAS |
| 292 | AAAGSG-XGGGSXGGGSXGGGS-GASAS |
| 293 | AAAGSG-XGGGSXGGGSXGGGSXGGGS-GASAS |
| 294 | AAAGSG-XS-GASAS |
| 295 | PGGNRGTTTTRRPATTTGSSPGPTQSHY |
| 296 | ATTTGSSPGPT |
| 297 | ATTTGS |
| 298 | GS |
| 299 | EPSGPISTINSPPSKESHKSP |
| 300 | GTVAAPSVFIFPPSD |
| 301 | GGGGIAPSMVGGGGS |
| 302 | GGGGKVEGAGGGGGS |
| 303 | GGGGSMKSHDGGGGS |
| 304 | GGGGNLITIVGGGGS |
| 305 | GGGGVVPSLPGGGGS |
| 306 | GGEKSIPGGGGS |
| 307 | RPLSYRPPFPFGFPSVRP |
| 308 | YPRSIYIRRRHPSPSLTT |
| 309 | TPSHLSHILPSFGLPTFN |
| 310 | RPVSPFTFPRLSNSWLPA |
| 311 | SPAAHFPRSIPRPGPIRT |
| 312 | APGPSAPSHRSLPSRAFG |
| 313 | PRNSIHFLHPLLVAPLGA |
| 314 | MPSLSGVLQVRYLSPPDL |
| 315 | SPQYPSPLTLTLPPHPSL |
| 316 | NPSLNPPSYLHRAPSRIS |
| 317 | LPWRTSLLPSLPLRRRP |
| 318 | PPLFAKGPVGLLSRSFPP |
| 319 | VPPAPVVSLRSAHARPPY |
| 320 | LRPTPPRVRSYTCCPTP- |
| 321 | PNVAHVLPLLTVPWDNLR |
| 322 | CNPLLPLCARSPAVRTFP |

(S) is optional in sequences 284 to 288.

Examples of rigid linkers include the peptide sequences GAPAPAAPAPA (SEQ ID NO:337), PPPP (SEQ ID NO:338) and PPP.

Other linkers are shown in Table 5:

| SEQ ID NO: | SEQUENCE |
|---|---|
| 323 | DLCLRDWGCLW |
| 324 | DICLPRWGCLW |
| 325 | MEDICLPRWGCLWGD |
| 326 | QRLMEDICLPRWGCLWEDDE |
| 327 | QGLIGDICLPRWGCLWGRSV |
| 328 | QGLIGDICLPRWGCLWGRSVK |
| 329 | EDICLPRWGCLWEDD |
| 330 | RLMEDICLPRWGCLWEDD |
| 331 | MEDICLPRWGCLWEDD |
| 332 | MEDICLPRWGCLWED |
| 333 | RLMEDICLARWGCLWEDD |
| 334 | EVRSFCTRWPAEKSCKPLRG |
| 335 | RAPESFVCYWETICFERSEQ |
| 336 | EMCYFPGICWM |

Effector Molecules

If desired a multispecific molecule for use in the present invention may be conjugated to one or more effector molecule(s). It will be appreciated that the effector molecule may comprise a single effector molecule or two or more such molecules so linked as to form a single moiety that can be attached to the multispecific molecules of the present invention. Where it is desired to obtain an antibody or multispecific molecule according to the present disclosure linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

In one embodiment the multispecific molecules of the present disclosure may comprise an effector molecule.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracindione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$; Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Functional Assays

Typically suitable binding domains for use in the present invention can be identified by testing one or more binding domain pairs in a functional assay. For example an anti-CD79 antibody molecule such as a multi specific molecule comprising a binding domain specific to the antigen CD22 and a binding domain specific to the antigen CD79a and/or CD79b may be tested in one or more functional assays.

A "functional assay," as used herein, is an assay that can be used to determine one or more desired properties or activities of the protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, cytokine production assays, antibody production and isotype switching, and cellular differentiation assays.

The efficacy of multispecific antibodies according to the present disclosure can be compared to individual antibodies or mixtures of antibodies (or fragments) in such models by methods generally known to one of ordinary skill in the art.

The functional assays may be repeated a number of times as necessary to enhance the reliability of the results. Various statistical tests known to the skilled person can be employed to identify statistically significant results and thus identify multispecific molecules with biological functions.

Examples of suitable functional assays are described in the Examples herein and include measuring the ability of a multispecific molecule of the present invention to inhibit B cell activation following stimulation with anti-IgM, as measured by detecting the inhibition of markers of B cell activation such as phosphorylated Akt expression, phosphorylated P38 expression, PLCγ signalling, CD40 expression, CD71 expression and/or CD86 expression. When establishing a functional assay for screening the skilled person can set a suitable threshold over which an identified activity is deemed a 'hit'. Where more than one functional assay is used the threshold for each assay may be set at a suitable level to establish a manageable hit rate. In one example the hit rate may be 3-5%. In one example the criteria set when searching for pairs of binding domains that inhibit B cell function may be at least 30% inhibition of at least two phospho-readouts, as described above and in the examples herein, in a B cell activation assay.

In one example an antibody molecule, such as a multispecific molecule, of the present invention has an IC50 of less than 1 nM for inhibition of phosphorylated P38 in anti-IgM stimulated B cells, preferably an IC50 of less than 0.5 nM. In one example the IC50 of the multispecific molecule in this assay is less than 0.05 nM.

In one example an antibody molecule, such as a multispecific molecule, of the present invention has an IC50 of less than 1 nM for inhibition of phosphorylated Akt in anti-IgM stimulated B cells, preferably an IC50 of less than 0.1 nM. In one example the IC50 of the multispecific molecule in this assay is less than 0.05 nM.

In one example an antibody molecule, such as a multispecific molecule, of the present invention has an IC50 of less than 1 nM for inhibition of phosphorylated PLCγ2 in anti-IgM stimulated B cells, preferably an IC50 of less than 0.8 nM. In one example the IC50 of the multispecific molecule in this assay is less than 0.05 nM.

In one example a multispecific molecule of the present invention has an IC50 of less than 5 nM for inhibition of CD71 expression in anti-IgM stimulated B cells, preferably an IC50 of less than 3 nM. In one example the IC50 of the multispecific molecule in this assay is less than 0.5 nM.

In one example an antibody molecule, such as a multispecific molecule, of the present invention has an IC50 of less than 5 nM for inhibition of CD40 expression in anti-IgM stimulated B cells. In one example the IC50 of the multispecific molecule in this assay is less than 0.5 nM.

In one example an antibody molecule, such as a multispecific molecule, of the present invention has an IC50 of less than 5 nM for inhibition of CD86 expression in anti-IgM stimulated B cells, preferably an IC50 of less than 2 nM. In one example the IC50 of the multispecific molecule in this assay is less than 0.5 nM.

In one example an antibody molecule, such as a multispecific molecule, of the present invention has an IC50 of less than 5 nM for inhibition of CD71, CD40 and CD86 expression in anti-IgM stimulated B cells and/or an IC50 of less than 1 nM for inhibition of phosphorylated PLCγ2, P38 and AKT in anti-IgM stimulated B cells.

In one embodiment in vivo assays, such as animal models, including mouse tumor models, models of auto-immune disease, virus-infected or bacteria-infected rodent or primate models, and the like, may be employed to test molecules of the present disclosure.

An example of a suitable format for screening and discovery of binding domains is described herein below.

The term "biological function" as used herein refers to an activity that is natural to or the purpose of the biological entity being tested, for example a natural activity of a cell, protein or similar. Ideally the presence of the function can be tested using an in vitro functional assay, including assays utilizing living mammalian cells. Natural function as employed herein includes aberrant function, such as functions associated with cancers.

The term "synergistic function" as used herein refers to biological activity that is not observed or higher than observed when the first and second proteins of a bispecific protein complex of the present disclosure are not employed together, for example activity which is only observed in a bispecific form. Therefore, "synergistic" includes novel biological function.

The present disclosure provides a molecule with at least specificity to CD22 and CD79 with a novel biological function.

Novel biological function as employed herein refers to function which is not apparent or absent until the two or more synergistic entities [protein A and protein B] are brought together (as a bispecific or otherwise) or a previously unidentified function.

Higher as employed herein refers to an increase in activity including an increase from zero i.e. some activity in the bispecific where the individual uncomplexed bispecific component or components has/have no activity in the relevant functional assay, also referred to herein as new activity or novel biological function. Higher as employed herein also includes a greater than additive function in the bispecific in a relevant functional assay in comparison to the individual uncomplexed bispecific components or bivalent binding domains, for example 10, 20, 30, 40, 50, 60, 70, 80, 90, 100, 200, 300% or more increase in a relevant activity.

In one embodiment the novel synergistic function is a higher inhibitory activity.

In one embodiment the multispecific antibody molecule of the present invention has a higher inhibitory activity than the sum of the activity of a bivalent binding domain to CD22 and a bivalent binding domain to CD79a provided alone or in admixture The term "peptide" as used herein refers to a short polymer of amino acids linked by peptide bonds, wherein the peptide contains in the range of 2 to 100 amino acids, for example 5 to 99, such as 6 to 98, 7 to 97 or 8 to 96. In one embodiment a peptide employed in the present disclosure is an amino acid sequence of 50 amino acid residues or less, for example 40, 30, 10 or less. The peptides used in the present disclosure are of a sufficient length to be fit for purpose, for example if the peptide is a linker, it needs to be suitably long to allow the fragment which it links to perform its biological function; alternatively if the peptide is a binding partner, it must be capable of binding specifically to another entity such as an antibody.

A "functional assay," as used herein, is an assay that can be used to determine one or more desired properties or activities of the protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, cytokine production assays, antibody production and isotype switching, and cellular differentiation assays, In one embodiment in vivo assays, such as animal models, including mouse tumor models, models of auto-immune disease, virus-infected or bacteria-infected rodent or primate models, and the like, may be employed to test molecules of the present disclosure.

In the context of bispecific antibody complexes, the efficacy of bispecific antibody molecules according to the present disclosure can be compared to individual antibodies or mixtures of antibodies (or fragments) in such models by methods generally known to one of ordinary skill in the art.

The functional assays may be repeated a number of times as necessary with or without different samples of a particular bispecific antibody complex to enhance the reliability of the results. Various statistical tests known to the skilled person can be employed to identify statistically significant results and thus identify bispecific antibody complexes with biological functions, and in particular to identify optimal variable region pairs for use in multspecific molecule of the present invention.

Compositions and Medical Uses

In one aspect there is provided a molecule according to the present disclosure or a component, such as a fusion protein, a heterodimerically-tethered bispecific protein complex, a composition comprising a molecule of the invention, including a fusion protein or said bispecific protein complex, a multiplex, array, library as defined herein.

In one embodiment the molecules of the present disclosure, for example an antibody described herein, a multispecific molecule and a bispecific protein complex are suitable for therapeutic applications and may provide novel therapies for treating diseases. Thus in a further aspect, there is provided a molecule of the present disclosure, for example a bispecific protein complex as described above, for use in therapy. The molecules of the present disclosure including the bispecific protein complexes described herein are suitable for treating a range of diseases, such as cancer.

The molecules of the present disclosure, including the multispecific molecules and bispecific protein complexes described herein are also particularly suited for inhibiting B cell function in order to control immune and autoimmune reactions in various autoimmune diseases.

Thus, the present disclosure extends to a method of treating a disease in a patient, comprising the administration of a therapeutically effect amount of a molecule of the present disclosure, for example a multispecific molecule or bispecific protein complex of the present disclosure. In one aspect, there is provided a pharmaceutical composition comprising one or more molecules of the present disclosure, for example a multispecific molecule of the present disclosure.

Various different components can be included in the composition, including pharmaceutically acceptable carriers, excipients and/or diluents. The composition may, optionally, comprise further molecules capable of altering the characteristics of the population of multispecific molecules of the invention thereby, for example, reducing, stabilizing, delaying, modulating and/or activating the function of the antibodies. The composition may be in solid, or liquid form and may be, inter alia, be in the form of a powder, a tablet, a solution or an aerosol.

The present invention also provides a pharmaceutical or diagnostic composition comprising an antibody molecule or a multispecific molecule of the present invention in combination with one or more of a pharmaceutically acceptable excipient, diluent or carrier. Accordingly, provided is the use of a multispecific molecule of the invention for use in the treatment and for the manufacture of a medicament for the treatment of a pathological condition or disorder.

Pathological Conditions

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

In one embodiment the disorder is cancer, for example leukemia, including lyphocytic leukemia, such as acute lymphoblastic leukemia or chronic lymphocytic leukemia; or myelogenus leukemia, such as acture myelogenous leukemia or chronic myelogenous leukemia.

In one embodiment autoimmune disease includes:—
Acute disseminated encephalomyelitis (adem), acute necrotizing hemorrhagic leukoencephalitis, Addison's disease, adrenal insufficiency, hypocortisolism, alopecia areata, amyloidosis, ankylosing spondylitis, spondyloarthritis, Strumpell-marie disease, anti-GBM/anti-TBM nephritis, antiphospholipid syndrome (aps), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune lymphoproliferative syndrome (ALPS), Canale-Smith syndrome, autoimmune myocarditis, autoimmune oophoritis, autoimmune pancreatitis (AIP), autoimmune polyglandular syndromes (types I, II & III), autoimmune retinopathy (AR), autoimmune thrombocytopenic purpura (ATP), autoimmune thyroid disease, autoimmune urticaria, axonal/neuronal neuropathies, balo disease, Behcet's disease, bullous pemphigoid, cardiomyopathy, Castleman disease, coeliac disease, chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid (CP), Crohn's disease, inflammatory bowel disease, colitis, enteritis, ileitis, Cogans syndrome, cold agglutinin disease, congenital heart block, Coxsackie myocarditis, crest disease, cryoglobulinemia, demyelinating neuropathies, dermatitis herpetiformis, Duhring's disease, dermatomyositis, diabetes, type I, discoid lupus erythematosus (DLE), Dressler's syndrome, endometriosis, epidermolysis bullosa (EB) and eb acquisita (EBA), eosinophilic gastroenteritis, esophagitis, eosinophilic fasciitis, schulman's syndrome, erythema nodosum, experimental allergic encephalomyelitis, Evans syndrome, fibrosing alveolitis, giant cell arteritis (temporal arteritis), giant cell myocarditis, glomerulonephritis (non-proliferative: focal segmental glomerulosclerosis and membranous glomerulonephritis. proliferative: IgA nephropathy), goodpasture's syndrome, granulomatosis with polyangiitis (GPA) (formerly called Wegener's granulomatosis), Graves' disease, Guillain-Barré syndrome, Miller Fisher syndrome, acute motor axonal neuropathy, acute motor sensory axonal neuropathy, acute panautonomic neuropathy, Bickerstaff's brainstem encephalitis, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy (IGAN), berger's syndrome, synpharyngitic glomerulonephritis, IgA pemphigus, IgG4-related sclerosing disease, immune-regulated infertility, inclusion body myositis, insulin-dependent diabetes mellitus, interstitial cystitis, Isaac's syndrome, neuromyotonia, juvenile arthritis, juvenile myositis, Kawasaki syndrome, Lambert-Eaton syndrome, leukocytoclastic vasculitis, lichen planus, lichen sclerosus, ligneous conjunctivitis, linear IgA dermatosis (LAD), pemphigoid, lupus (SLE), Lyme disease, Meniere's disease, microscopic polyangiitis (MPA), mixed connective tissue disease (MCTD), monoclonal gammaopathy, Mooren's ulcer, Mucha-Habermann disease, multiple sclerosis, myasthenia gravis, myositis, narcolepsy, neuromyelitis optica (devic's), neuromyotonia, Isaac's syndrome (acquired, paraneoplastic, hereditary), neutropenia, ocular cicatricial pemphigoid, optic neuritis, oophoritis, opsoclonus-myoclonus syndrome, orchitis, palindromic rheumatism, pandas (pediatric autoimmune neuropsychiatric disorders associated with streptococcus), paraneoplastic autoimmune multiorgan syndrome (PAMS), paraneoplastic cerebellar degeneration, paraneoplastic pemphigus (PNP), paroxysmal nocturnal hemoglobinuria (PNH), Parry Romberg syndrome, Parsonnage-Turner syndrome, pars planitis (peripheral uveitis), pempgigoid gestationis (PG), pemphigus vulgaris (PV), pemphigus folliaceus (PF), peripheral neuropathy, perivenous encephalomyelitis, pernicious anemia, Poems syndrome, polyarteritis nodosa (PAN), polymyalgia rheumatic, polymyositis, postmyocardial infarction syndrome, postpericardiotomy syndrome, progesterone dermatitis primary biliary cirrhosis, Hanot syndrome, primary sclerosing cholangitis (PSC), sclerosong cholangitis, psoriasis, psoriatic arthritis, pyoderma gangrenosum, pure red cell aplasia, Rasmussen's encephalitis, chronic focal encephalitis (CFE), Raynauds phenomenon, reactive arthritis, Reiter's syndrome, recoverin-associated retinopathy (RAR), reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, systemic sclerosis, sjogren's syndrome, sperm & testicular autoimmunity, stiff person/man syndrome, subacute bacterial endocarditis (SBE), Susac's syndrome, sympathetic ophthalmia, Takayasu's arteritis, temporal arteritis/giant cell arteritis, thromboangiitis obliterans, Buerger's disease, thrombocytopenic purpura (TTP), Tolosa-Hunt syndrome, transverse myelitis, ulcerative colitis, undifferentiated connective tissue disease (UCTD), uveitis, polymyalgia rheumatica, Takayasu's arteritis, temporal arteritis, Buerger's disease, cutaneous vasculitis, Kawasaki disease, polyarteritis nodosa, Behcet's syndrome, Churg-Strauss syndrome, cutaneous vasculitis, Henoch-Schönlein purpura, microscopic polyangiitis, Wegener's granulomatosis, golfer's vasculitis, vesiculobullous dermatosis, Vitiligowegener's granulomatosis (now termed granulomatosis with polyangiitis (GPA).

In one embodiment the autoimmune disease is selected from the group comprising or consisting of:—ANCA vasculitis, IgA nephropathy (Berger's), pemphigus vulgaris/bullous pemphigoid, ITP, primary biliary cirrhosis, autoimmune thyroiditis (Grave's disease), hashimoto's disease, lupus nephritis, membranous glomerulonephritis (or membranous nephropathy), APS, myasthenia gravis, neuromyelitis optica, primary Sjógren's, autoimmune neutropaenia, autoimmune pancreatitis, dermatosmyositis, autoimmune uveitis, autoimmune retinopathy, Behcet's disease, IPF, systemic sclerosis, liver fibrosis, autoimmune hepatitis, primary sclerosing cholangitis, vitiligo, goodpasture's syndrome, pulmonary alveolar proteinosis, chronic autoimmune urticarial, psoriasis, rheumatoid arthritis, psoriatic arthritis, axial spodyloarthritis, transplantation (including GvHD), asthma, COPD, giant cell arteritis, refractory autoimmune cytopaenias, Evans syndrome (autoimmune haemolytic anaemia), type I diabetes, sarcoidosis, polymyositis, ulcerative colitis, Crohn's disease, coeliac disease, Waldenstrom's macroglobulinaemia, focal segmental glomerulosclerosis, chronic Lyme disease (Lyme borreliosis), lichen planus, Stiff person syndrome, dilated cardiomyopathy, autoimmune (lymphocytic) oophoritis, epidermolysis bullosa acquisita, autoimmune atrophic gastritis, pernicious anaemia, atopic dermatitis, atherosclerosis, multiple sclerosis, Rasmussen's encephalitis, Guillain-Barré syndrome, acquired neuromyotonia, stroke.

In one embodiment the disorder is cancer, for example Leukemia, for example lyphocytic leukemia, such as acute lymphoblastic leukemia or chronic lymphocytic leukemia; or myelogenus leukemia, such as acture myelogenous leukemia or chronic myelogenous leukemia; or lymphoma, such as diffuse large B cell lymphoma or Hodgkin's or non-Hodkin's lymphoma.

The present invention also provides a pharmaceutical or diagnostic composition comprising a molecule of the present disclosure, such as a multispecific molecule described herein in combination with one or more of a pharmaceutically acceptable excipient, diluent or carrier. Accordingly, provided is the use of a molecule of the present disclosure, such as a multispecific molecule as described herein for use in treatment and in the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant. The present invention also provides a process for preparation of a pharmaceutical or diagnostic composition comprising adding and mixing the multispecific molecule of the present invention together with one or more of a pharmaceutically acceptable excipient, diluent or carrier.

The term "pharmaceutically acceptable excipient" as used herein refers to a pharmaceutically acceptable formulation carrier, solution or additive to enhance the desired characteristics of the compositions of the present disclosure. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Such carriers enable the pharmaceutical compositions to be formulated as tablets, pills, dragées, capsules, liquids, gels, syrups, slurries and suspensions, for ingestion by the patient.

The molecules of the disclosure such as a multispecific molecule described herein can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

A thorough discussion of pharmaceutically acceptable carriers is available in Remington's Pharmaceutical Sciences (Mack Publishing Company, N.J. 1991).

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the multispecific molecule of the present disclosure is administered depends on the nature of the condition to be treated, the extent of the inflammation present and on whether the antibody molecule is being used prophylactically or to treat an existing condition.

The frequency of dose will depend on the half-life of the multispecific molecule and the duration of its effect. If the multispecific molecule has a short half-life (e.g. 2 to 10 hours) it may be necessary to give one or more doses per day. Alternatively, if the multispecific molecule has a long half-life (e.g. 2 to 15 days) it may only be necessary to give a dosage once per day, once per week or even once every 1 or 2 months.

In the present disclosure, the pH of the final formulation is not similar to the value of the isoelectric point of the multispecific molecule, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule. Where the product is for injection or infusion, it may take the form of a suspension, solution or emulsion in an oily or aqueous vehicle and it may contain formulatory agents, such as suspending, preservative, stabilising and/or dispersing agents. Alternatively, the multispecific molecule may be in dry form, for reconstitution before use with an appropriate sterile liquid. If the composition is to be administered by a route using the gastrointestinal tract, the composition will need to contain agents which protect the antibody from degradation but which release the bispecific protein complex once it has been absorbed from the gastrointestinal tract.

A nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The term "variant" as used herein refers to peptide or protein that contains at least one amino acid sequence or nucleotide sequence alteration as compared to the amino acid or nucleotide sequence of the corresponding wild-type peptide or protein. A variant may comprise at least 80%, or 85%, or 90%, or 95%, or 98% or 99% sequence identity to the corresponding wild-type peptide or protein. However, it is possible for a variant to comprise less than 80% sequence identity, provided that the variant exhibits substantially similar function to its corresponding wild-type peptide or protein.

In one embodiment the construct of the present disclosure is at least trispecific. In this situation the further specificity may be directed to any antigen of interest, for example antigens to extend half-life such as albumin or Fc neonatal receptor (FcRn); antigens for effector function such as activating or inhibiting Fc receptors or costimulatory molecules; tissue or cell targeting antigens; or antigens to aid blood/brain barrier (BBB) transfer such as transferrin receptor or LRP1.

The disclosure also extends to compositions, such as pharmaceutical compositions comprising said novel formats with the particular antigen specificity.

In a further aspect the disclosure includes use of the formats and the compositions in treatment.

The present invention also provides a process for preparation of a pharmaceutical or diagnostic composition comprising adding and mixing the antibody molecule or multispecific molecule of the present invention together with one or more of a pharmaceutically acceptable excipient, diluent or carrier.

The antibody molecule or multispecific molecule may be the sole active ingredient in the pharmaceutical or diagnostic composition or may be accompanied by other active ingredients including other antibody ingredients or non-antibody ingredients such as steroids or other drug molecules.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg.

Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

Agents as employed herein refers to an entity which when administered has a physiological affect.

Drug as employed herein refers to a chemical entity which at a therapeutic dose has an appropriate physiological affect.

In one embodiment the antibodies or fragments according to the present disclosure are employed with an immunosuppressant therapy, such as a steroid, in particular prednisone.

In one embodiment the antibodies or fragments according to the present disclosure are employed with Rituximab or other B cell therapies.

In one embodiment the antibodies or fragments according to the present disclosure are employed with any B cell or T cell modulating agent or immunomodulator. Examples include methotrexate, microphenyolate and azathioprine.

The dose at which the antibody molecule of the present invention is administered depends on the nature of the condition to be treated, the extent of the inflammation present and on whether the antibody molecule is being used prophylactically or to treat an existing condition. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) and/or long lasting pharmacodynamics (PD) profile it may only be necessary to give a dosage once per day, once per week or even once every 1 or 2 months.

In one embodiment the dose is delivered bi-weekly, i.e. twice a month.

In one embodiment doses are spaced to allow anti-drug (in this case anti-antibody) responses to waine before administration of futher dose.

Half life as employed herein is intended to refer to the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pI of the protein is in the range 8-9 or above then a formulation pH of 7 may be appropriate. Whilst not wishing to be bound by theory it is thought that this may ultimately provide a final formulation with improved stability, for example the antibody or fragment remains in solution.

In one example the pharmaceutical formulation at a pH in the range of 4.0 to 7.0 comprises: 1 to 200 mg/mL of an antibody molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 µm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody or multispecific molecule of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

In one embodiment, the molecule of the present disclosure, such as an antibody molecule described herein may be used to functionally alter the activity of the antigen or antigens of interest. For example, the antibody molecule of the disclosure may neutralize, antagonize or agonise the activity of said antigen or antigens, directly or indirectly.

In one embodiment, molecules of the present disclosure including fusion proteins, bispecific proteins complexes or compositions comprising same are provided for use as a laboratory reagent.

Further Aspects

In a further aspect, there is provided a nucleotide sequence, for example a DNA sequence encoding a construct as described herein including a multispecific molecule or a fusion protein as defined above.

In one embodiment, there is provided a nucleotide sequence, for example a DNA sequence encoding a construct as described herein including a multispecific molecule or a bispecific protein complex or an antibody according to the present disclosure.

The disclosure herein also extends to a vector comprising a nucleotide sequence as defined above.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example. Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example E. coli, and other microbial systems may be used or eukaryotic, for example mammalian, host cell expression systems may also be used. Suitable mammalian host cells include CHO, myeloma or hybridoma cells.

The present disclosure also provides a process for the production of a molecule according to the present disclosure or a component thereof comprising culturing a host cell containing a vector of the present disclosure under conditions suitable for leading to expression of protein from DNA encoding the molecule of the present disclosure, and isolating the molecule.

The molecules of the present disclosure including the bispecific protein complexes described herein may be used in diagnosis/detection kits. The kits may, for example comprise bispecific antibody complexes that are specific for two antigens, both of which are present on the same cell type, and wherein a positive diagnosis can only be made if both antigens are successfully detected. By using a molecule of the present disclosure such as a bispecific antibody complexes described herein rather than two separate antibodies or antibody fragments in a non-complexed form, the specificity of the detection can be greatly enhanced. In one embodiment, the molecules of the present disclosure such as the bispecific antibody complexes are fixed on a solid surface. The solid surface may for example be a chip, or an ELISA plate.

Further provided is the use of a molecule according to the present disclosure, for example a bispecific protein complex described herein for detecting in a sample the presence of a first and a second peptide, whereby the said molecules are used as detection agents.

The molecules of the present disclosure such as the bispecific antibody complexes described herein may for example be conjugated to a fluorescent marker which facilitates the detection of bound antibody-antigen complexes. Such bispecific antibody complexes can be used for immunofluorescence microscopy. Alternatively, the bispecific antibody complexes may also be used for western blotting or ELISA.

In one embodiment, there is provided a process for purifying a molecule according to the present disclosure or a component thereof.

In one embodiment, there is provided a process for purifying a molecule according the present disclosure or a component thereof comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

Sequences of the disclosure are provided herein below and in the Figures.

In the context of this specification "comprising" is to be interpreted as "including".

Aspects of the disclosure comprising certain elements are also intended to extend to alternative embodiments "consisting" or "consisting essentially" of the relevant elements. Positively recited embodiments may be employed herein as a basis for a disclaimer. All references referred to herein are specifically incorporated by reference.

REFERENCES

1. Ribosome display efficiently selects and evolves high-affinity antibodies in vitro from immune libraries. Hanes J, Jermutus L, Weber-Bornhauser S, Bosshard H R, Plückthun A. (1998) Proc. Natl. Acad. Sci. U.S.A. 95, 14130-14135
2. Directed in Vitro Evolution and Crystallographic Analysis of a Peptide-binding Single Chain Antibody Fragment (scFv) with Low Picomolar Affinity. Zhand C, Spinelli S, Luginbuhl B, Amstutz P, Cambillau C, Pluckthun A. (2004) J. Biol. Chem. 279, 18870-18877
3. Antigen recognition by conformational selection. Berger C, Weber-Bornhauser S, Eggenberger Y, Hanes J, Pluckthun A, Bosshard H. R. (1999) F.E.B.S. Letters 450, 149-153

EXAMPLES

The term Fab-Kd-Fab as used in the Examples describes the bispecific protein complex having the formula A-X:Y-B wherein:
- A-X is a first fusion protein;
- Y-B is a second fusion protein;
- X:Y is a heterodimeric-tether;
- A comprises a Fab fragment specific to an antigen such as CD79;
- B comprises a Fab fragment specific to an antigen such as CD45;
- X is a first binding partner of a binding pair such as a scFv;
- Y is a second binding partner of the binding pair such as a peptide; and
- : is an interaction (such as a binding interaction) between X and Y.

Example 1—Production of Fab'-A (Fab-scFv [A-X]) and Fab'-B (Fab-Peptide (B-Y) for Functional Assays Cloning Strategy Antibody variable region DNA was generated by PCR or gene synthesis flanking restriction enzyme sites DNA sequence. These sites were HindIII and XhoI for variable heavy chains and HindIII and BsiWI for variable light chains. This makes the heavy variable region amenable to ligating into the two heavy chain vectors (pNAFH with FabB-Y and pNAFH with FabA-Xds [disulphide stabilised]) as they have complementary restriction sites. This ligates the variable region upstream (or 5') to the murine constant regions and peptide Y (GCN4) or scFv X (52SR4) creating a whole reading frame. The light chains were cloned into standard in house murine constant kappa vectors (pMmCK or pMmCK S171C) which again use the same complimentary restriction sites. The pMmCK S171C vector is used if the variable region is isolated from a rabbit. The cloning events were confirmed by sequencing using primers which flank the whole open reading frame.

Cultivating CHO-S

Suspension CHOS cells were pre-adapted to CDCHO media (Invitrogen) supplemented with 2 mM (100×) glutamx. Cells were maintained in logarithmic growth phase agitated at 140 rpm on a shaker incubator (Kuner A G, Birsfelden, Switzerland) and cultured at 37° C. supplemented with 8% $CO_2$.

Electroporation Transfection

Prior to transfection, the cell numbers and viability were determined using CEDEX cell counter (Innovatis AG. Bielefeld, Germany) and required amount of cells ($2\times10^8$ cells/ml) were transferred into centrifuge conical tubes and were spun at 1400 rpm for 10 minutes. The Pelleted cells were re-suspended in sterile Earls Balanced Salts Solution and spun at 1400 rpm for further 10 minutes. Supernatant was discarded and pellets were re-suspended to desired cell density.

Vector DNA at a final concentration of 400 ug for $2\times10^8$ cells/ml mix and 800 µl was pipetted into Cuvettes (Biorad) and electroporated using in-house electroporation system.

Transfected cells were transferred directly into 1X3L Erlenmeyer Flasks contained ProCHO 5 media enriched with 2 mM glutamx and antibiotic antimitotic (100×) solution (1 in 500) and Cells were cultured in Kuhner shaker incubator set at 37° C., 5% $CO_2$ and 140 rpm shaking. Feed supplement 2 g/L ASF (AJINOMOTO) was added at 24 hr post transfection and temperature dropped to 37° C. for further 13 days culture. At day four 3 mM Sodium buryrate (n-BUTRIC ACID Sodium Salt, Sigma B-5887) was added to the culture.

On day 14, cultures were transferred to tubes and supernatant separated from the cells after centrifugation for 30 minutes at 4000 rpm. Retained supernatants were further filtered through 0.22 um SARTO BRAN P Millipore followed by 0.22 µm Gamma gold filters. Final expression levels were determined by Protein G-HPLC.

Large Scale (1.0 L) Purification

The Fab-A and Fab-B were purified by affinity capture using the AKTA Xpress systems and HisTrap Excel pre-packed nickel columns (GE Healthcare). The culture supernatants were 0.22 µm sterile filtered and pH adjusted to neutral, if necessary, with weak acid or base before loading onto the columns. A secondary wash step, containing 15-25 mM Imidazole, was used to displace any weakly bound host cell proteins/non-specific His binders from the nickel resin. Elution was performed with 10 mM sodium phosphate, pH7.4+1M NaCl+250 mM Imidazole and 2 ml fractions collected. One column volume into the elution system was paused for 10 minutes to tighten the elution peak, and consequently decrease the total elution volume. The cleanest fractions were pooled and buffer exchanged into PBS (Sigma), pH7.4 and 0.22 µm filtered. Final pools were assayed by A280 Scan, SE-HPLC (G3000 method), SDS-PAGE (reduced & non-reduced) and for endotoxin using the PTS Endosafe system.

Example 2—Use of Fab'-A (Fab-scFv [A-X]) and Fab'-b (Fab-peptide [B-Y]) in Heterodimerically-Tether Bispecific Protein Complex Format to Demonstrate that CD79/CD22 Bispecific but Not Bivalent Combinations Inhibit Akt Signaling Human PBMC derived from platelet apheresis cones were banked as frozen aliquots. Prior to an assay being performed, cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-A (Fab-scFv) and Fab'-B (Fab-peptide) with antigen specificity for the cell surface proteins CD22 and CD79b in DMEM containing 10% calf serum and 2 mM glutamine. This grid is shown in Table 4.

TABLE 4

| Possible grid of bispecific and bivalent combinations of antibodies with specificity for CD22 and CD79b. | | |
|---|---|---|
| (A-X) | (B-Y) Fab B | |
| Fab A | CD22-Y | CD79b-Y |
| CD22-X | CD22-X:Y-CD22 | CD22-X:Y-CD79b |
| CD79b-X | CD79b-X:Y-CD22 | CD79b-X:Y-CD79b | where X is a scFv (52SR4) and Y is a peptide (GCN4)

Fab'A-X and Fab'B-Y were incubated together for 90 minutes (in a 37° C./5% $CO_2$ environment) before mixing with $2.5\times10^5$ PBMC in V bottomed 96 well plates. PBMC plus bispecific or bivalent combinations were then incubated together for a further 90 minutes. After this time B cells were activated by the addition of 200 nM of goat F(ab')2 anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+1% BSA+0.01% $NaN_3$) and washed once more. Cells were then resuspended in ice cold Perm Buffer III (BD Biosciences) for 30 minutes before being washed twice in flow buffer. Cells were then stained with a fluorescently labelled anti-CD20 antibody (BD Biosciences) and a fluorescently labelled anti-phospho Akt antibody that recognises a modified serine residue at position 473 on the protein. Plates were then resuspended and incubated for 1 hour at room temperature in the dark. After this time plates were washed a further two times and resuspended in 25 µl of flow buffer. Cellular expression of CD20 and Akt was measured using an Intellicyt HTFC™ flow cytometer.

Using the data analysis software package Forecyt™ (Intellicyt) B cells were identified as distinct from other cell populations and the geometric mean of Akt levels was calculated for each well. All data was then expressed as the percentage inhibition of the maximal response (anti-IgM only) minus the background (cells only). The relative effect of the combinations of CD22 and CD79b is shown in Table 5 (↓=inhibition, ↑=stimulation and ↔=no overall effect).

TABLE 5

Table of the relative potency of inhibition of phosphorylated Akt for bispecific and bivalent combinations of antibodies with specificity for CD22 and CD79b.

| (A-X) | (B-Y) Fab B | |
| --- | --- | --- |
| Fab A | CD22-Y | CD79b-Y |
| CD22-X | ↑↑ | ↓↓↓ |
| CD79b-X | ↓↓↓ | ↔ | where X is a scFv (52SR4) and Y is a peptide (GCN4).

This data is also shown in the form of a bar chart (FIG. 1): the data represents mean values and the error bars are 95% confidence intervals. The data shows that the combinations of CD22 with CD79b can inhibit phospho-Akt expression in B cells stimulated with anti-IgM. In contrast, the combination of CD22 with CD22 exhibited elevated levels of phosho-Akt expression.

Example 3—Use of Fab'-A (Fab-scFv [A-X]) and Fab'-b (Fab-peptide [B-Y]) in Heterodimerically-Tether Bispecific Protein Complex Format to Demonstrate that CD79/CD22 Bispecific but Not Bivalent Combinations InhibitPLCγ2 Signalling Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-a (Fab-scFv [A-X]) and Fab'-B (Fab-peptide [B-Y]) with antigen specificity for the cell surface proteins CD22 and CD79b in DMEM containing 10% calf serum and 2 mM glutamine. This grid is shown in Table 4.

Fab'A-X and Fab'B-Y were incubated together for 90 minutes (in a 37° C./5% $CO_2$ environment) before mixing with 2.5×10$^5$ PBMC in V bottomed 96 well plates. PBMC plus bispecific or bivalent combinations were then incubated together for a further 90 minutes. After this time B cells were activated by the addition of 200 nM of goat F(ab')$_2$ anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and a fluorescently labelled anti-phospho PLCγ2 antibody that recognises a modified tyrosine residue at position 759 on the protein. Plates were then resuspended and incubated for 1 hour at room temperature in the dark. After this time plates were washed a further two times and resuspended in 25 µl of flow buffer. Cellular expression of CD20 and PLCγ2 was measured using an Intellicyt HTFC™ flow cytometer.

Using the data analysis software package Forecyt™ (Intellicyt) B cells were identified as distinct from other cell populations and the geometric mean of PLCγ2 levels was calculated for each well. All data was then expressed as the percentage inhibition of the maximal response (anti-IgM only) minus the background (cells only). The relative effect of the combinations of CD22 and CD79b is shown in Table 6 (↓=inhibition, ↑=stimulation and ↔=no overall effect).

TABLE 6

Table of the relative potency of inhibition of phosphorylated PLCg2 for bispecific and bivalent combinations of antibodies with specificity for CD22 and CD79b.

| (A-X) | (B-Y) Fab B | |
| --- | --- | --- |
| Fab A | CD22-Y | CD79b-Y |
| CD22-X | ↑ | ↓↓↓ |
| CD79b-X | ↓↓↓ | ↔ | where X is a scFv and Y is a peptide

Figure 2:
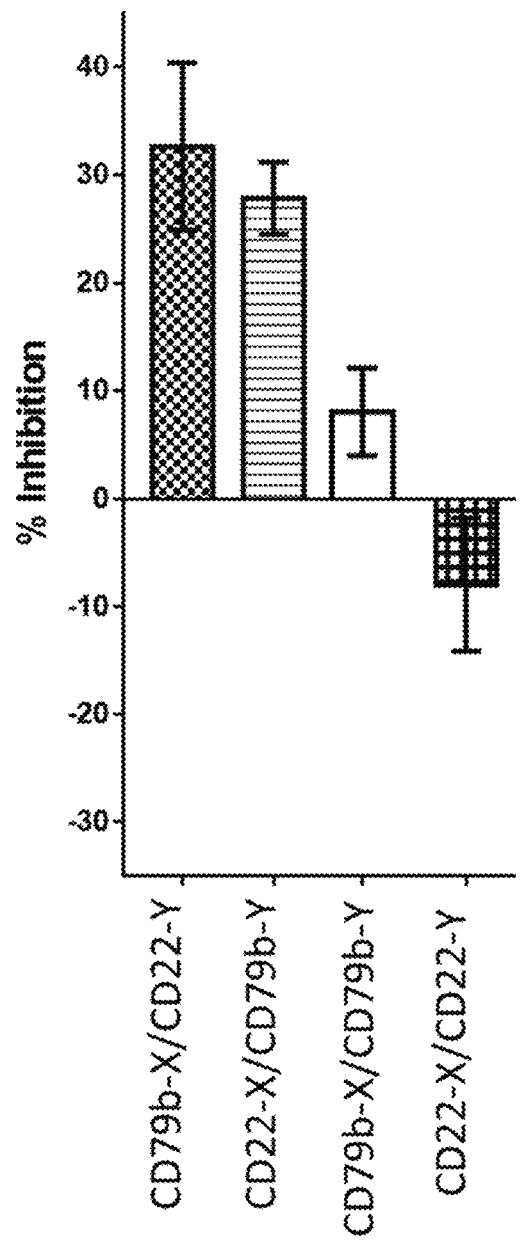
FIG. 2 is a bar chart of the relative potency of inhibition of phosphorylated PLCγ2 for bispecific and bivalent combinations of antibodies with specificity for CD22 and CD79b.

This data can also be expressed as a bar chart (FIG. 2), the data represents mean values and the error bars are 95% confidence intervals. The data shows that the combinations of CD22 with CD79b and CD79b with CD79b can all inhibit phospho-PLCγ2 expression in B cells stimulated with anti-IgM. In contrast, the combination of CD22 with CD22, exhibited elevated levels of phospho-PLCγ2 expression.

Example 4—Use of Fab'-A (Fab-scFv [A-X]) and Fab'-b (Fab-peptide [B-Y]) in Heterodimerically-Tether Bispecific Protein Complex Format to Demonstrate that CD79/CD22 Bispecific Combinations Inhibit CD86 Expression Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-X (Fab-scFv) and Fab'-Y (Fab-peptide) with antigen specificity for the cell surface proteins CD22 and CD79b in DMEM containing 10% calf serum and 2 mM glutamine. This grid is shown in Table 4.

Fab'A-X and Fab'B-Y were incubated together for 90 minutes (in a 37° C./5% $CO_2$ environment) before mixing with 2.5×10$^5$ PBMC in V bottomed 96 well plates. PBMC plus bispecific or bivalent combinations were then incubated together for a further 90 minutes. After this time B cells were activated by the addition of 200 nM of goat F(ab')$_2$ anti-human IgM (Southern Biotechnology) for 24 hours at 37° C. After this time plates were placed on ice and washed once in ice cold flow buffer (PBS+1% BSA+0.01% NaN$_3$). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 μl of flow buffer. Cellular expression of CD19 and CD86 was measured using an Intellicyt HTFC™ flow cytometer.

Using the data analysis software package Forecyt™ (Intellicyt) B cells were identified as distinct from other cell populations and the geometric mean of CD86 levels was calculated for each well. All data was then expressed as the percentage inhibition of the maximal response (anti-IgM only) minus the background (cells only). The relative effect of the combinations of CD22 and CD79b is shown in table 7 (↓=inhibition, ↑=stimulation and ↔=no overall effect).

TABLE 7

Table of the relative potency of inhibition of B Cell CD86 expression for bispecific and bivalent combinations of antibodies with specificity for CD22 and CD79b.

| (A-X) | (B-Y) Fab B | |
|---|---|---|
| Fab A | CD22-Y | CD79b-Y |
| CD22-X | ↑ | ↓↓↓ |
| CD79b-X | ↓↓↓ | ↓↓ | where X is a scFv (52SR4) and Y is a peptide (GCN4)

Figure 3:
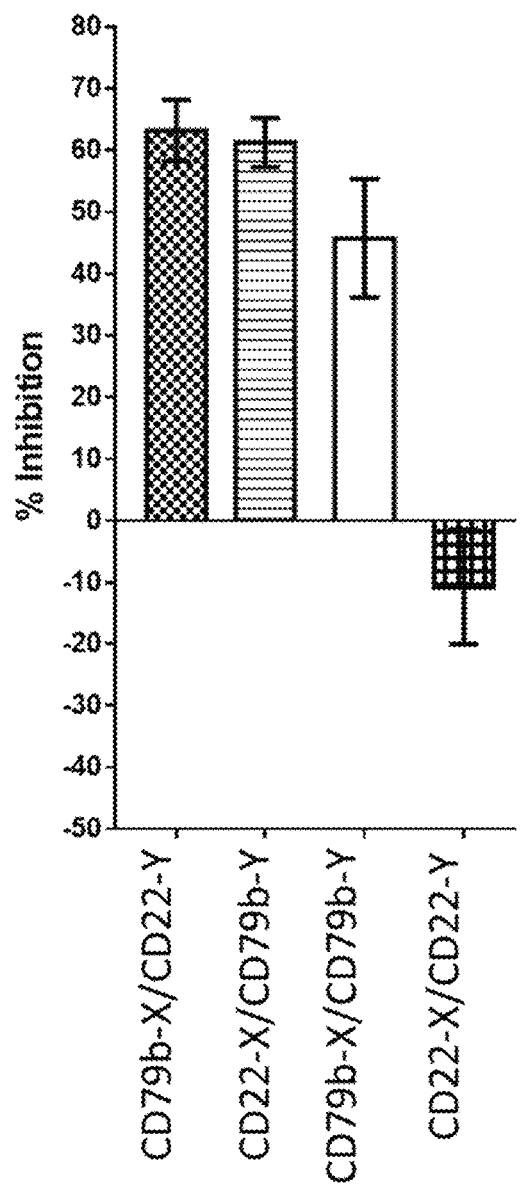
FIG. 3 is a bar chart of the relative potency of inhibition of CD86 expression for bispecific and bivalent combinations of antibodies with specificity for CD22 and CD79b.

This data is also shown in the form of a bar chart (FIG. 3), the data represents mean values and the error bars are 95% confidence intervals. The data shows that the combinations of CD22 with CD79b and CD79b with CD79b can all inhibit CD86 expression on B cells stimulated with anti-IgM. In contrast the combination of CD22 with CD22 exhibited elevated levels of CD86 expression.

Example 5—the Inhibitory Effect of CD22 and CD79b can Only be Reproduced when the Antibodies are Arranged in a Bispecific Orientation Human PBMC derived from platelet apheresis cones were banked as frozen aliquots. Prior to an assay being performed cells were thawed, washed in DMEM (Life Technologies) and allowed to acclimatise to a 37° C./5% CO$_2$ environment. During this period combinations of bispecific, bivalent or mixtures of antibodies were created by diluting equimolar (200 nM) quantities of Fab'-X (Fab-scFv) and/or Fab'-Y (Fab-peptide) with antigen specificity for the cell surface proteins CD22 and CD79b in DMEM containing 10% calf serum and 2 mM glutamine. These combinations are shown in Table 8. For the titration curve experiment these combinations were then diluted in 8 stepwise 1 in 2.5 dilutions to create a dose titration for this combination.

TABLE 8

Grid of bispecific, bivalent or mixtures with specificity for CD22 and CD79b.

| (A-X) | (B-Y) Fab B | | |
|---|---|---|---|
| Fab A | CD22-Y | CD79b-Y | CD79b-X |
| CD22-X | CD22-X:Y-CD22 | CD22-X:Y-CD79b | CD22-X X-CD79 |
| CD79b-X | CD79b-X:Y-CD22 | CD79b-X:Y-CD79b | — |
| CD22-Y | — | CD22-Y Y-CD79b | — | where X is a scFv (52SR4) and Y is a peptide (GCN4)

Fab'A-X and/or Fab'B-Y were incubated together for 90 minutes (in a 37° C./5% CO$_2$ environment) before mixing with 2.5×10$^5$ PBMC in V bottomed 96 well plates. PBMC plus Fab'A-X and/or Fab'B-Y combinations were then incubated together for a further 90 minutes. After this time B cells were activated by the addition of 200 nM of goat F(ab')$_2$ anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+1% BSA+0.01% NaN$_3$) and washed once more. Cells were then resuspended in ice cold Perm Buffer III (BD Biosciences) for 30 minutes before being washed twice in flow buffer. Cells were then stained with a fluorescently labelled anti-CD20 antibody (BD Biosciences), anti-phospho Akt antibody that recognises a modified serine residue at position 473 and an anti-phospho PLCγ2 antibody that recognises a modified tyrosine residue at position 759. Plates were then resuspended and incubated for 1 hour at room temperature in the dark. After this time plates were washed a further two times and resuspended in 25 μl of flow buffer. Cellular expression of CD20, Akt and PLCγ2 was measured using an Intellicyt HTFC™ flow cytometer.

Figure 4:
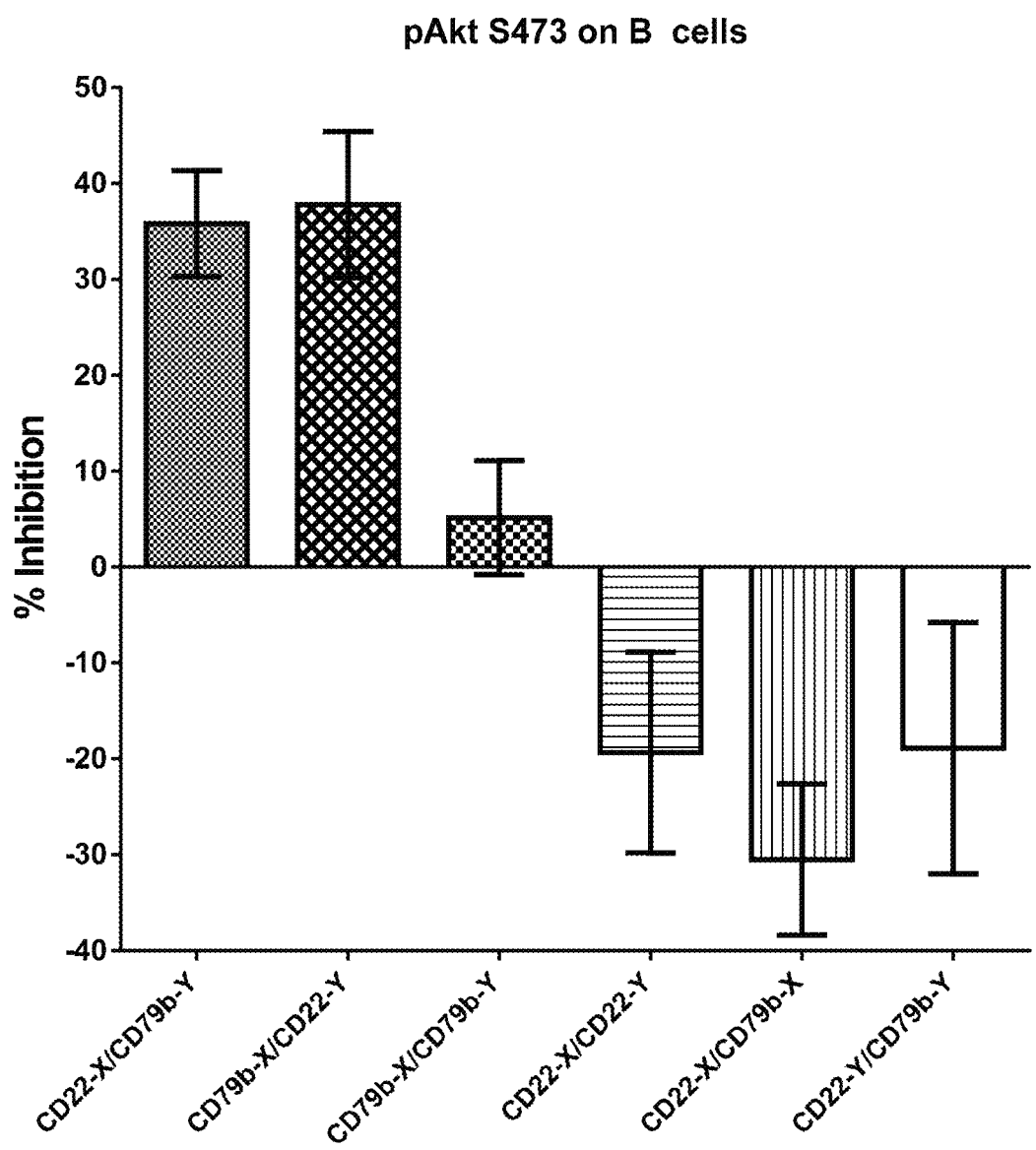
FIG. 4 is a bar chart of the relative potency of inhibition of phosphorylated Akt for bispecific, bivalent or mixtures of antibodies with specificity for CD22 and CD79b.
Figure 5:
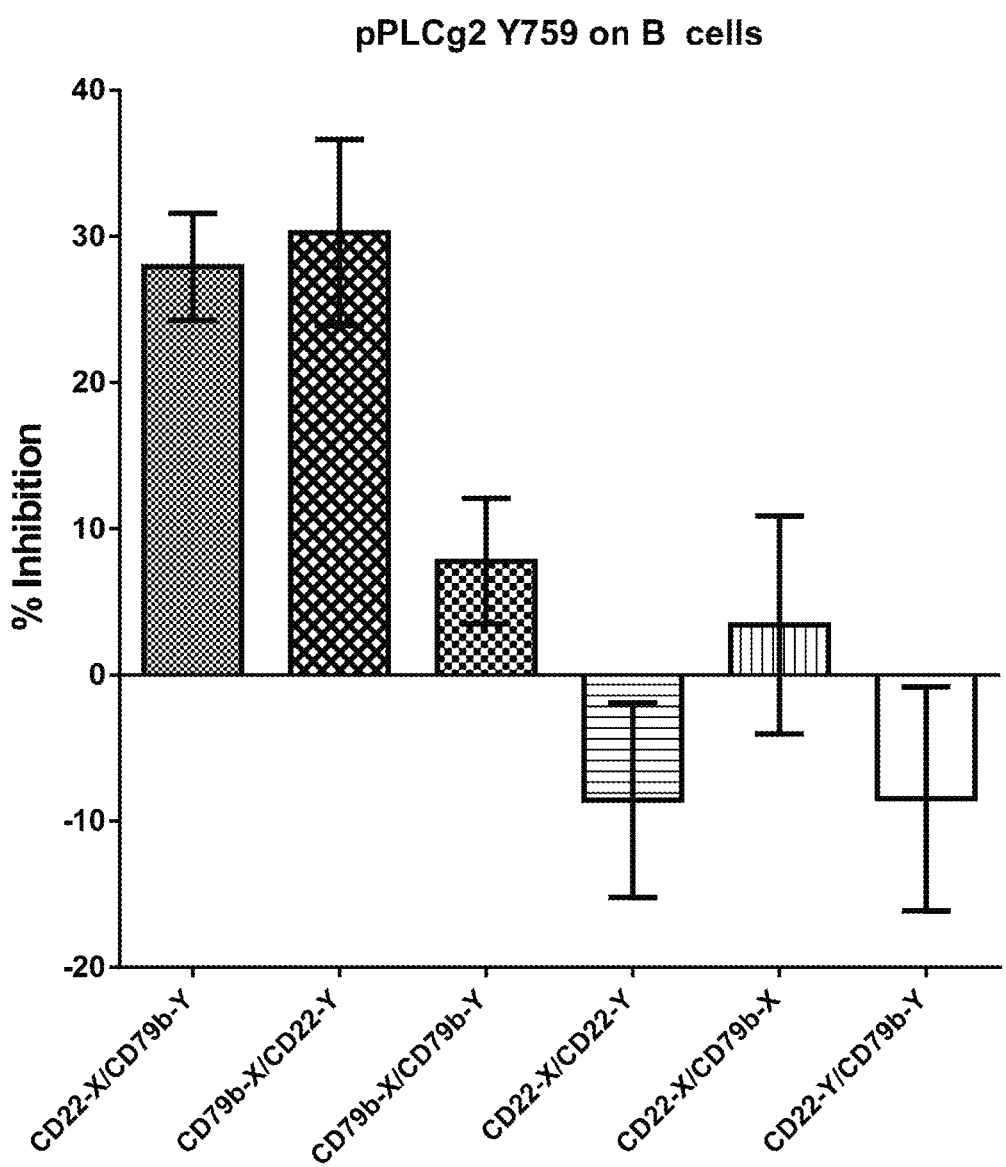
FIG. 5 is a bar chart of the relative potency of inhibition of phosphorylated PLCγ2 for bispecific, bivalent or mixtures of antibodies with specificity for CD22 and CD79b.

Using the data analysis software package Forecyt™ (Intellicyt) B cells were identified as distinct from other cell populations and the geometric mean of Akt and PLCγ2 levels were calculated for each well. All data was then expressed as the percentage inhibition of the maximal response (anti-IgM only) minus the background (cells only). FIGS. 4 and 5 show that only the bispecific combination of CD22 and CD79b but not the mixtures of CD22 and CD79b antibodies inhibited phosphorylated Akt and PLCγ2 expression (the data represents mean values and the error bars are 95% confidence intervals).

In order to validate the inhibition seen with the bispecific combination of CD22 and CD79b this combination along with a mixture of CD22 and CD79b antibodies was titrated and inhibition of total intracellular IkB (signalling readout) and CD86 (activation marker after 24 hours) was measured in B cells.

Figure 6:
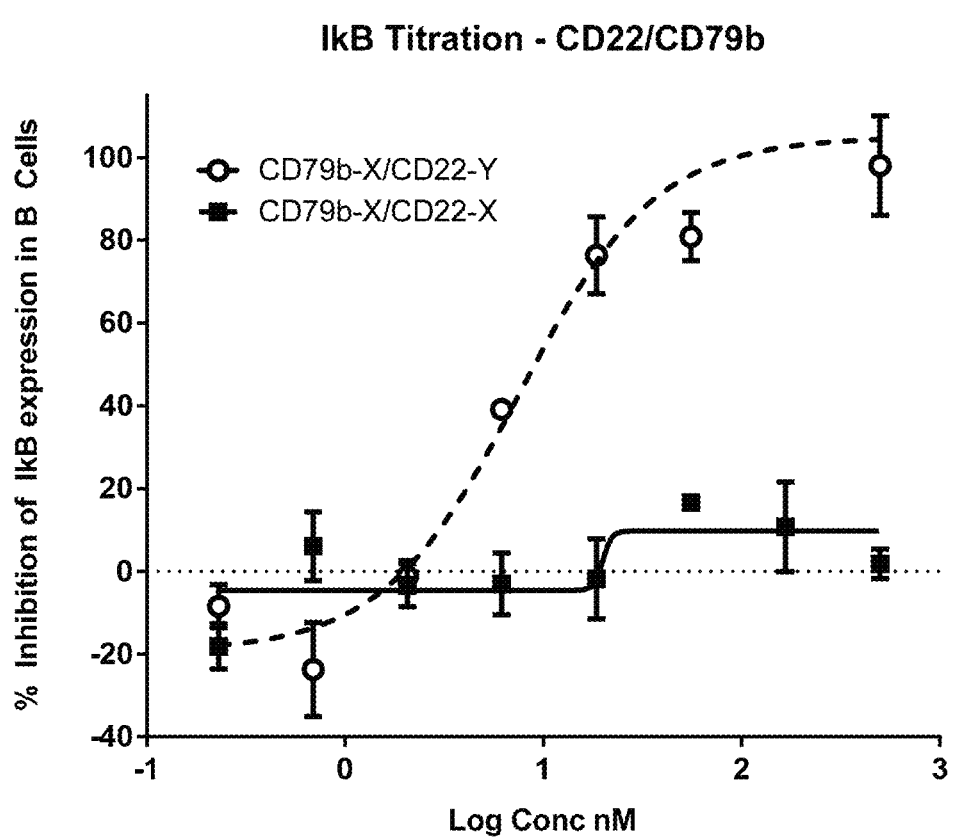
FIG. 6 is a graph showing the titration of the effect of the bispecific combination of CD22 and CD79b on total IkB levels in anti-IgM stimulated B cells.

As can be seen in FIG. 6, a combination of CD22-X/CD79b-Y but not the combination of CD22-X/CD79b-X was able to inhibit NF-kB signal activation after anti-IgM stimulation as measured by the level of total IkB protein. The IC$_{50}$, as extrapolated using a 4 parameter logistic curve fit using Graphpad Prism 6, was 7.5 nM (the data represents mean values and the error bars are standard deviations). Additionally a titration of the combination of CD22-X/CD79b-Y but not the combination of CD22-X/CD79b-X was able to inhibit anti-IgM induced CD86 expression on B cells after 24 hours (see FIG. 7).

Figure 7:
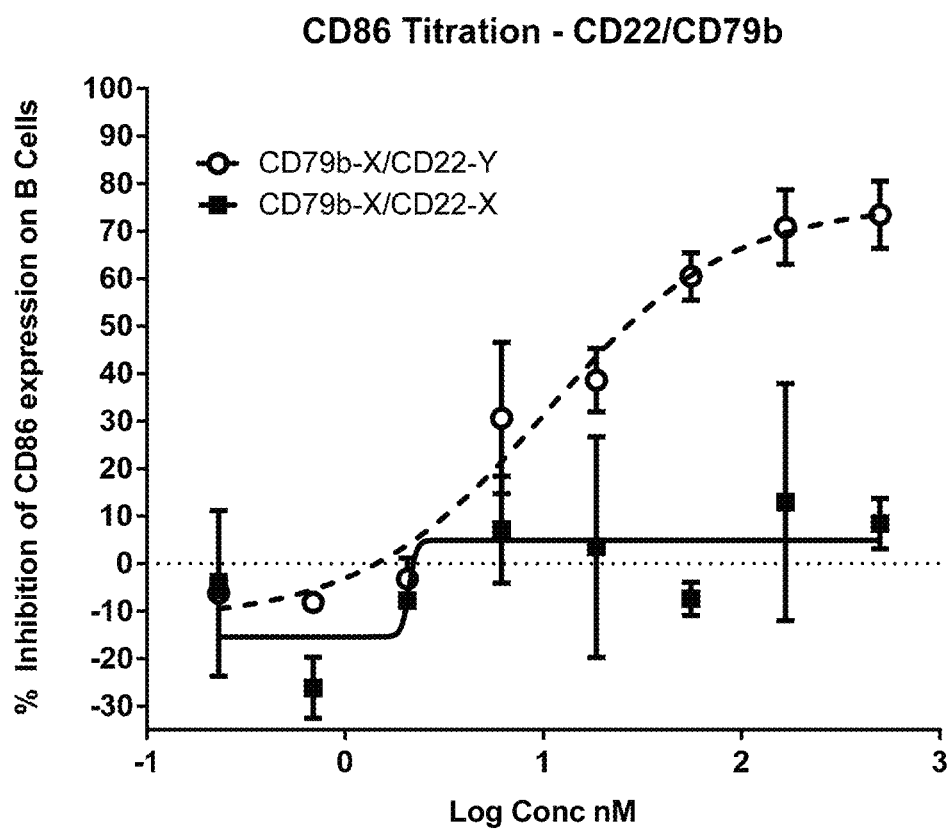
FIG. 7 is a graph showing the titration of the effect of the bispecific combination of CD22 and CD79b on CD86 expression on anti-IgM stimulated B cells.

Human PBMC derived from platelet apheresis cones were banked as frozen aliquots. Prior to an assay being performed cells were thawed, washed in DMEM (Life Technologies) and allowed to acclimatise to a 37 degree C./5% $CO_2$ environment. During this period bispecific combinations were created by diluting equimolar (500 nM) quantities of Fab'-X (Fab-scFv) and Fab'-Y (Fab-peptide) with antigen specificity for the cell surface proteins CD22 and CD79b in DMEM containing 10% calf serum and 2 mM glutamine. These combinations were then diluted in 8 stepwise 1 in 2.5 dilutions to create a dose titration for this combination. Fab'-X and Fab'-Y were incubated together for 90 minutes (in a 37 degree C./5% $CO_2$ environment) before adding $2.5 \times 10^5$ PBMC to V bottomed 96 well plates. PBMC were then added to Fab'-X and Fab'-Y combinations and incubated together for a further 90 minutes. After this time B cells were activated by the addition of 200 nM of goat $F(ab')_2$ anti-human IgM (Southern Biotechnology) for 24 hours at 37 degrees C. To enable detection of cell surface activation markers plates were placed on ice and washed once in ice cold flow buffer (PBS+1% BSA+0.01% $NaN_3$). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 μl of flow buffer. Cellular expression of CD19 and CD86 was measured using an Intellicyt HTFC™ flow cytometer. Using the data analysis software package Forecyt™ (Intellicyt) B cells were identified as distinct from other cell populations and the geometric mean of CD86 levels was calculated for each well. All data was then expressed as the percentage inhibition of the maximal response (anti-IgM only) minus the background (cells only). As can be seen in FIG. 7 a titration of the combination of CD22-X/CD79b-Y was able to inhibit anti-IgM induced CD86 expression on B cells after 24 hours. The IC50, as extrapolated using a 4 parameter logistic curve fit using Graphpad Prism 6, was 10.3 nM (the data represents mean values and the error bars are standard deviations).

Example 6—The Inhibitory Effect of CD22 and CD79b Bispecific Protein can be Reproduced with Different Antibody V Regions Immunisation:
DNA encoding selected antigens was obtained by gene synthesis or commercial sources & cloned into an expression vector with a strong constitutive promoter. Plasmid DNA was then transfected into Rab-9 rabbit fibroblast cells (ATCC® CRL-1414™) using an in-house electroporation system. Twenty four hours later cells were checked for antigen expression by flow cytometry & frozen in aliquots in liquid nitrogen until use. Up to 6 antigens were immunised per rabbit by either co-expression on the same cell or making mixtures of singly or multiple transfected cells. Rabbits were immunised with 3 doses of cells.

Antibody Discovery:
B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 μl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$.

The presence of antigen-specific antibodies in B cell culture supernatants was determined using a homogeneous fluorescence-based binding assay using HEK293 cells co-transfected with the antigens that the rabbits were immunized with. Screening involved the transfer of 10 ul of supernatant from barcoded 96-well tissue culture plates into barcoded 384-well black-walled assay plates containing HEK293 cells transfected with target antigen (approximately 3000 cells/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

Following primary screening, positive supernatants were consolidated on 96-well bar-coded master plates using an Aviso Onyx hit-picking robot and B cells in cell culture plates frozen at −80° C. Master plates were then screened in a homogeneous fluorescence-based binding assay on HEK293 cells transfected with antigens separately and Superavidin™ beads (Bangs Laboratories) coated with recombinant protein as a source of antigen. This was done in order to determine the antigen specificity for each well.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1). Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγfragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and Superavidin™ beads (Bangs Laboratories) coated with recombinant protein or antigen transfected HEK cells. This was done to confirm the specificity of the cloned antibodies.

Production of Small Scale Fab A-X and Fab B-Y (Small Scale (50 mL) Expi293 Transfection)

The Expi293 cells were routinely sub-cultured in Expi293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed Expi293™ Expression Medium for each 50 mL transfection.

To prepare the lipid-DNA complexes for each transfection a total of 50 μg of heavy chain and light chain plasmid DNAs were diluted in Opti-MEM® I medium (LifeTechnologies) to a total volume of 2.5 mL and 135 μL of ExpiFectamine™ 293 Reagent (LifeTechnologies) was diluted in Opti-MEM® I medium to a total volume of 2.5 mL. All dilutions were mixed gently and incubate for no longer than 5 minutes at room temperature before each DNA solution was added to the respective diluted ExpiFectamine™ 293 Reagent to obtain a total volume of 5 mL. The DNA-ExpiFectamine™ 293 Reagent mixtures were mixed gently and incubated for 20-30 minutes at room temperature to allow the DNA-ExpiFectamine™ 293 Reagent complexes to form.

After the DNA-ExpiFectamine™ 293 reagent complex incubation was completed, the 5 mL of DNA-ExpiFectamine™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 μL of ExpiFectamine™ 293 Transfection Enhancer 1 (LifeTechnologies) and 2.5 mL of ExpiFectamine™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Small Scale (50 ml) Purification:

Both Fab-X and Fab-Y were purified separately by affinity capture using a small scale vacuum based purification system. Briefly, the 50 ml of culture supernatants were 0.22 μm sterile filtered before 500 μL, of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+1M NaCl. The eluted fractions buffer exchanged into PBS (Sigma), pH7.4 and 0.22 μm filtered. Final pools were assayed by A280 scan, SE-UPLC (BEH200 method), SDS-PAGE (reduced & non-reduced) and for endotoxin using the PTS Endosafe system.

Human PBMC derived from platelet apheresis cones were banked as frozen aliquots. Prior to an assay being performed cells were thawed, washed in RPMI 1640 (Life Technologies) and allowed to acclimatise to a 37° C./5% $CO_2$ environment. During this period combinations of bispecific, bivalent or mixtures of antibodies were created by diluting equimolar (200 nM) quantities of Fab'-X (Fab-scFv) and/or Fab'-Y (Fab-peptide) with antigen specificity for the cell surface proteins CD22 and CD79b in RPMI 1640 containing 10% fetal bovine serum, 50 units/mL Penicillin, 50 μg/mL Streptomycin and 2 mM glutamine. These combinations of 3 different CD79b Fab-Ys and 3 different CD22 Fab-Xs are shown in Table 9.

TABLE 9

Grid of bispecific proteins with specificity for CD22 and CD79b.

| (A-X) | (B-Y) Fab B | | |
|---|---|---|---|
| Fab A | CD79-Y VR4447 | CD79-Y VR4450 | CD79b-y VR4246 |
| CD22-X VR0982 | CD22-X:Y-CD79b | CD22-X:Y-CD79b | CD22-X:Y-CD79b |
| CD22-X VR4126 | CD22-X:Y-CD79b | CD22-X:Y-CD79b | CD22-X:Y-CD79b |
| CD22-X VR4130 | CD22-X:Y-CD79b | CD22-X:Y-CD79b | CD22-X:Y-CD79b | where X is a scFv (52SR4) and Y is a peptide (GCN4)

Fab'A-X and Fab'B-Y were incubated together for 60 minutes (in a 37° C./5% $CO_2$ environment) before mixing with $2.5 \times 10^5$ PBMC in V bottomed 96 well plates. PBMC plus Fab'A-X and/or Fab'B-Y combinations were then incubated together for a further 90 minutes. After this time B cells were activated by the addition of 12.5 μg/mL of goat F(ab')$_2$ anti-human IgM (Southern Biotechnology) for 10 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+1% BSA+0.1% NaN$_3$+2 mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences), and an anti-phospho PLCγ2 antibody that recognises a modified tyrosine residue at position 759. Plates were then resuspended and incubated for 1 hour at room temperature in the dark. After this time plates were washed a further two times and resuspended in 40 μl of flow buffer. Cellular expression of CD20 and PLCγ2 was measured using an Intellicyt HTFC™ flow cytometer.

Using the data analysis software package Forecyt™ (Intellicyt) B cells were identified as distinct from other cell populations and the geometric mean of PLCγ2 levels were calculated for each well. All data was then expressed as the percentage inhibition of the maximal response (anti-IgM only) minus the background (cells only).

Figure 8:
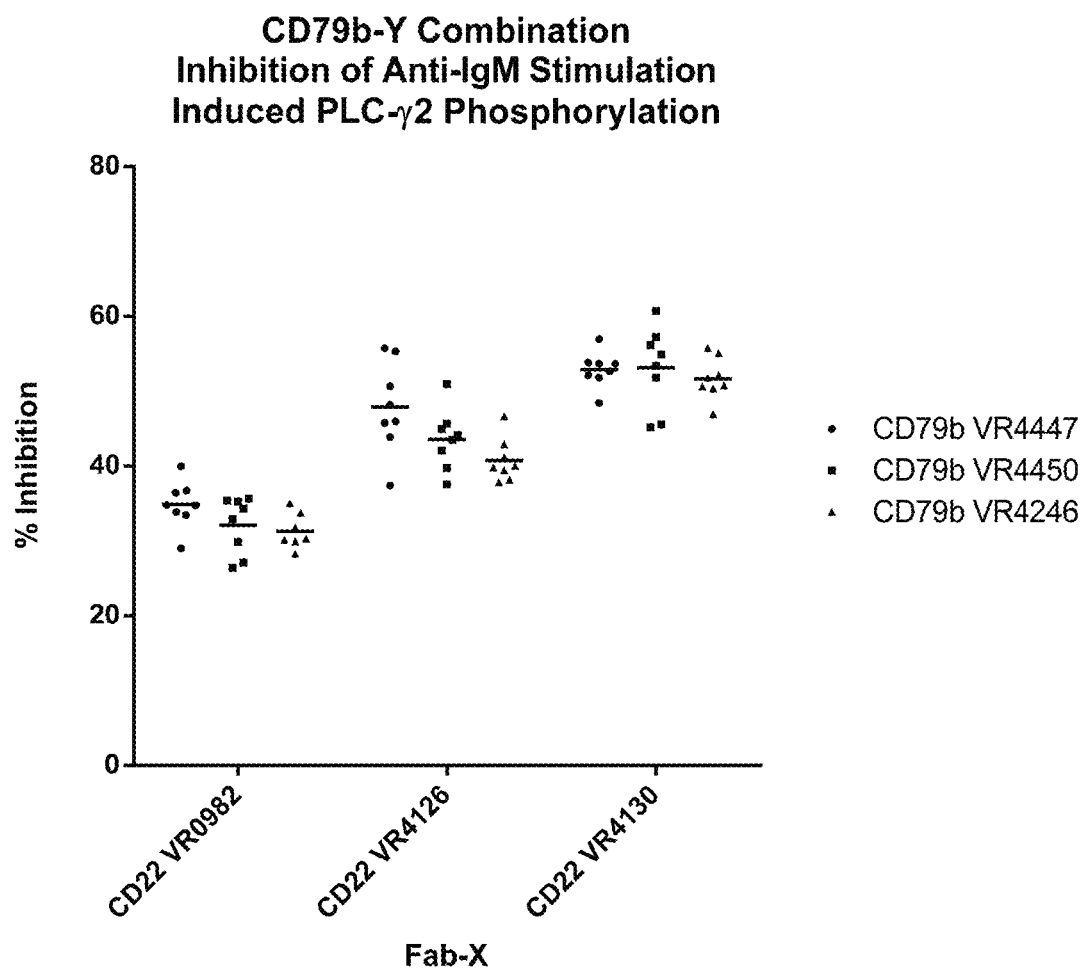
FIG. 8 is a graph of inhibition of phosphorylated PLCγ2 for bispecific proteins with specificity for CD22 and CD79b with different V regions.

As can be seen in FIG. 8 the data shows that the combination of CD22 with CD79b using all the different antibody V regions can inhibit phospho-PLCγ2 expression in B cells stimulated with anti-IgM.

Example 7—Grid Screening of Large Panels of Heterodimerically Tethered Protein Complexes to Identify Novel Bispecific Antibody Targets Introduction:

Following the successful validation of the bispecific format and screening method in the earlier examples the screening was expanded to a larger number of antigen pairs. A panel of antibody variable (V) region pairs to 23 different antigens expressed on B cells was generated. Using the Fab-Kd-Fab [i.e. A-X:Y-B wherein A and B are Fab fragments] format a grid of heterodimerically tethered protein complexes was formed representing multiple V region combinations of each of 315 different antigen pair combinations. These combinations were screened for their ability to modulate BCR (B cell receptor) signalling in a high through-put flow cytometry assay to select novel target pairs for intervention with a bispecific antibody.

Antibodies were Isolated as Described in Example 6.

Screening Assays

Donor PBMCs were rapidly thawed using a water bath set to 37° C., and carefully transferred to a 50 ml Falcon tube. They were then diluted dropwise to 5 ml in assay media to minimise the osmotic shock. The cells were then diluted to 20 ml carefully before adding the final media diluent to make the volume 50 ml. The cells were then spun at 500 g for 5 minutes before removing the supernatant and resuspending the cells in 1 ml media. The cells were then counted and diluted to $1.66 \times 10^6$ cells/ml before dispensing 30 µl per well into a V-bottom TC plate giving a final assay concentration of $5.0 \times 10^4$ cells/well. The cell plate was then stored covered in a 37° C., 5% $CO_2$ incubator until they were required, giving them a minimum of 1 hour to rest.

Fab-X and Fab-Y reagents were mixed in an equimolar ratio at 5× the final assay concentration in assay media and incubated for 90 min at 37° C., 5% $CO_2$. Samples were prepared in a 96-well U-bottom polypropylene plate and covered during the incubation. 10 µl of 5× Fab-KD-Fab mixture was added to the appropriate test wells containing cells and mixed by shaking at 1000 rpm for 30 sec prior to being incubated for 90 min at 37° C., 5% $CO_2$.

The cells were then stimulated with 10 µl of anti-human IgM. The final assay concentration of stimulus varied depending on the assay panel readouts, the three antibody cocktails A, B and C (detailed below) were stimulated at a final assay concentration of either 50 µg/ml (cocktail A & C) or 25 µg/ml (cocktail B). The assay plates were then gently mixed at 1000 rpm for 30 sec prior to incubation at 37° C., 5% $CO_2$ for 5 min (antibody cocktail A & C) or 2 min (antibody cocktail B). The assay was stopped by adding 150 µl ice-cold BD CytoFix to all wells and incubated for 15 min at RT. The fixed cells were then spun at 500 g for 5 min to pellet the cells and allow removal of the supernatant using a BioTek ELx405 plate washer. The pellet was re-suspended by vortexing the plate at 2400 rpm for 30 sec. The cells were then permeabilised at 4° C. by adding 100 µl ice-cold BD Cell Permeabilisation Buffer III for 30 min. The cells were then washed in 100 µl FACS buffer and spun at 500 g for 5 min. Supernatant was again removed by the ELx405 before using it to rapidly dispense 200 µl FACS Buffer to wash away any residual permeabilisation buffer. Cells were again spun at 500 g and the supernatant removed by inversion. During the preceding spin step the antibody cocktail was prepared in FACS Buffer and kept shielded from the light. The cells were then re-suspended by vortexing (2400 RPM, 30 sec) before 20 µl of antibody cocktail was added to all wells and the plate shaken for 30 sec at 1000 rpm. The cells were then incubated for 60 min at RT in the dark.

The cells were then washed twice in 200 µl FACS buffer with a 500 g spin and supernatant removed after each step. Finally the cells were re-suspended by vortexing for 30 sec at 2400 rpm before adding a final 20 µl FACS buffer. The plate(s) were then read on the Intellicyt HTFC/iQue instrument.

FACS Buffer=PBS+1% BSA+0.05% $NaN_3$+2 mM EDTA

Antibody Cocktail A=1:2CD20 PerCp-Cy5.5(BD Biosciences)+1:5PLCγ2AF88+1:10

Akt AF647+1:50ERK1/2PE (diluted in FACS buffer)

Antibody Cocktail B=1:2CD20PerCp-Cy5.5(BD Biosciences)+1:5Syk PE+1:5BLNK AF647 (diluted in FACS buffer)

Antibody Cocktail C=1:5CD20PerCp-Cy5.5(Biolegend)+1:5PLCγ2 AF488+1:10 Akt AF647+1: 5Syk PE (diluted in FACS buffer)

| Reagent | Supplier | Catalogue number |
| --- | --- | --- |
| Anti-human IgM | Southern Biotech | 2022-14 |
| CytoFix | BD Biosciences | 554655 |
| Perm Buffer III | BD Biosciences | 558050 |
| Anti Akt (pS473) AF647 | BD Biosciences | 561670 |
| Anti SYK (pY348) PE | BD Biosciences | 558529 |
| Anti PLCγ2 (pY759) AF488 | BD Biosciences | 558507 |
| Anti-BLNK(pY84) AF647 | BD Biosciences | 558443 |
| Anti ERK1/2 (pT202/pY204) PE | BD Biosciences | 561991 |
| Anti-human CD20 PerCp-Cy5.5 | BD Biosciences | 558021 |
| Anti-human CD20 AF488 | BD Biosciences | 558056 |
| Anti-human CD20 PerCp-Cy5.5 | Biolegend | 340508 |
| Phosphate Buffer Saline (PBS) | Fisher Scientific | 10562765 |
| RPMI 1640 | Life Technologies | 31870 |
| Foetal Calf Serum (FCS) | Life Technologies | 16140 |
| Glutamax | Life Technologies | 35050 |
| Penicillin/Streptomycin (P/S) | Life Technologies | 15070 |
| EDTA | Sigma | 03690 |
| Sodium Azide (NaN3) | Sigma | S2002 |
| Bovine Serum Albumin (BSA) | Sigma | A1470 |

Fab-X+Fab-Y combinations were screened with either antibody cocktail A and B or C alone. All screens were conducted on cone cells from 2 different blood donors. Data was captured and evaluated using commercially available software tools. A total of 2500 Fab-X+Fab-Y combinations were screened to 315 different antigen combinations.

Results

The percentage inhibition of the induction of phosphorylation of BCR signalling cascade proteins by each Fab-Kd-Fab [i.e. A-X:Y-B where A and B are Fab fragments] combination was calculated, in this example looking for new combinations of antigens that inhibit B cell function, the criteria for a positive combination was set as at least 30% inhibition of at least two phospho-readouts by at least one combination of V regions. According to this threshold 11 new antigen pair combinations out of 315 examined met the required criteria. This represents a 3.5% hit rate demonstrating the importance of screening large numbers of combinations to find those of desired activity and how rare the activity of the combination of CC79b and CD22 is.

FIGS. 10-12 show the data for the antigen grid cross specificities. Values are percentage inhibition (negative value for activation) of phosphorlyation of Syk, PLCγ2 & AKT respectively and represent the mean of multiple V-region combinations evaluated. 315 different antigen combinations were tested and as can be seen the effect on BCR signalling by different combinations of antibody varied significantly from strong inhibition e.g. antigen 2 (CD79b) on Fab-X combined with antigen 3 (CD22) on Fab-Y (69.66% inhibition of phospho Syk) and antigen 2 (CD79b) on Fab-Y combined with antigen 3 (CD22) on Fab-X (52.32% inhibition of phospho Syk) shown in FIG. 11) to activation e.g antigen 6 on X and antigen 11 on Y (minus 118.10% phospho Syk FIG. 11).

Figure 14:
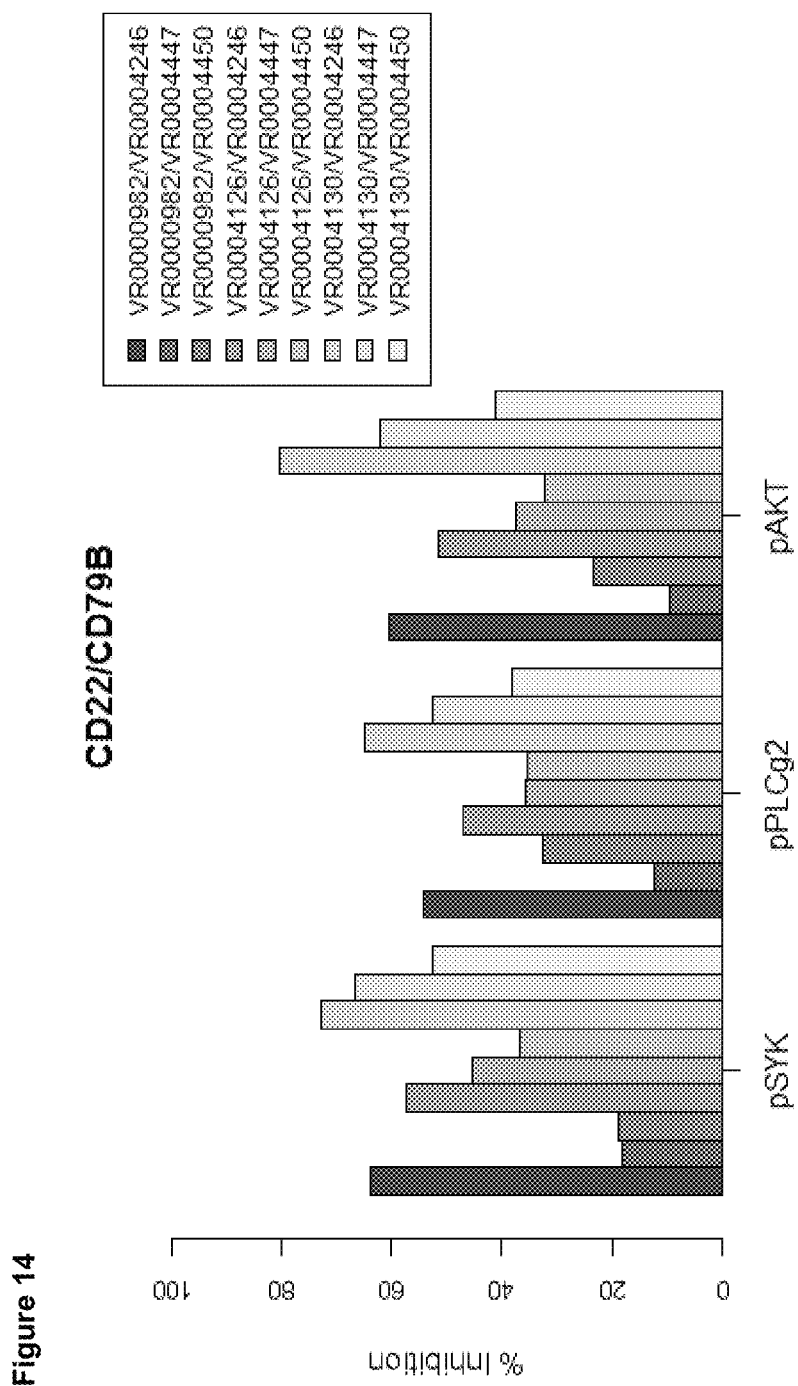
FIG. 14 is a graph showing the percentage inhibition of the phosphorlylation of Syk, PLCγ2 & AKT of the phosphorlylation of Syk, PLCγ2 & AKT for each V-region combination for CD22 specificity in Fab-X comb cell growth, survival and differentiation. This signalling complex can be further regulated by other second signals via signalling through BAFF-R, IL-21R and CD40 and can also be regulated by other signalling molecules such as CD19, CD21, CD83, CD22, CD32b and CD45 amongst others. Upon recognition of antigen by the BcR one of the first responses activated is the upregulation of surface receptors such as the co-stimulatory molecules CD80 and CD86. These molecules bind to corresponding receptors on T cells which deliver further survival and activation signals that allow survival and expansion of T cells that recognise antigen in the context of MHC class II. This response is further amplified by the ability of B cells to present antigen in the context of MHC class II back to the T cell, which releases factors such as IL-2 and IL-21. These cytokines in turn expand B cell number greatly. Thus down regulation of CD86 on the surface of cells may be indicative of inhibition of B cell signalling.

Each data point representing the mean % values represented in FIGS. 10-12 is shown for antigen 2 (CD79b) on Fab-X and antigen 3 (CD22) on Fab-Y in FIG. 13. In this case, 23 different combinations of different antibody V regions were evaluated. The same antigen combination but in alternative orientation, i.e. antigen 2 (CD79b) on Fab-Y and antigen 3 (CD22) on Fab-X is shown in FIG. 14. In this case, 9 different combinations of different antibody V-regions were evaluated. All V regions show inhibition but advantageously this method can also be used in the selection of optimal V-region combinations.

Example 8—Comparison of the Activity of Antigen CD79b Plus Antigen CD22 Co-Targeting in Fab-Kd-Fab Screening Format to a Molecularly Linked Bispecific BYbe Format Introduction:

To check that CD79b/CD22 target pair activity identified in the Fab-Kd-Fab heterodimerically tethered screening complex could translate to similar desired activity in an alternative therapeutic molecularly linked format, Antigen CD79b specificity (VR4447) and antigen CD22 specificity (VR4130) were generated in a BYbe format. This BYbe format consists of the anti-Antigen CD22 V regions (VR4130) as a disulphide stabilised (ds) single chain (sc)-Fv fused to the heavy chain of the anti-Antigen CD79b Fab (VR4447) via a linker SGGGGSGGGGS (SEQ ID NO:17).

Methods:

The purification of BYbes for functional screening was performed as follows:

The functional screening BYbe (Fab-dsscFv [scFv off C-terminus of Fab heavy chain]) formats were purified as follows. Clarified cell culture supernatants from standard expiHEK or CHO expression were 0.22 μm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH2.7. The elution was followed by absorbance at 280 nm, the elution peak collected, and then neutralised with $\frac{1}{25}^{th}$ volume of 2M Tris/HCl pH8.5. The neutralised samples were concentrated using Amicon Ultra-15 concentrators with a 10 kDa (BYbes) molecular weight cut off membrane and centrifugation at 4000×g in a swing out rotor. Concentrated samples were applied to either a XK16/60 or XK26/60 Superdex200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 μm, 7.8×300 mm column developed with an isocratic gradient of 0.2M phosphate, pH7.0 at 1 ml/min, with detection by absorbance at 280 nm. Selected monomer fractions were pooled and concentrated to >1 mg/ml using an Amicon Ultra-15 concentrator with a 10 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 μm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's EndoSafe® Portable Test System with Limulus Amebocyte Lysate (LAL) test cartridges.

Functional Assays

Activation Marker Assay:

Antigen CD79b-specific Fab'-Y and Antigen CD22-specific Fab'-X, were incubated together for 60 minutes (in a 37° C. and 5% $CO_2$ environment) at equimolar concentration. The combinations were titrated from a starting molarity of 100 nM, in 1:4 serial dilutions. Antigen CD79b and CD22-specific BYbe was also titrated from a starting molarity of 100 nM, in 1:4 serial dilutions. In V-bottomed 96 well plates, $1.5 \times 10^5$ PBMC were added to wells, to which were added titrated Fab'-X and Fab'-Y combinations or titrated BYbe. The Fab'-X and Fab'-Y combinations or BYbe were incubated with cells for a further 90 minutes. After this time B cells were activated by the addition of 25 μg/mL of goat $F(ab')_2$ anti-human IgM (Southern Biotechnology) for 24 hours at 37° C. plus 5% $CO_2$. To the wells were added 100 μL, ice-cold FACS buffer (PBS+1% BSA+0.1% $NaN_3$+2 mM EDTA), the plates were sealed and covered with wet-ice for approximately 15 minutes, before centrifuging at 500×g for 5 minutes at 4° C. Excess supernatant was discarded from the cell pellets and the plates shaken at 2000 rpm for 30 seconds.

Cells were then stained with a cocktail of fluorescently labelled anti-CD19, anti-CD20 and anti-CD71, anti-CD40 and anti-CD86 antibodies (BD Biosciences). Plates were shaken briefly and incubated for 1 hour on wet-ice in the dark. After this time plates were washed twice and resuspended in 20 μL of FACS buffer. Cellular expression of CD19, CD20 and CD71, CD40 and CD86 was measured using an Intellicyt iQUE® Screener flow cytometer. Using the data analysis software package Forecyt™ (Intellicyt) B cells were identified as distinct from other cell populations and the geometric mean of CD71, CD40 and CD86 levels were calculated for each well. All data was then expressed as the percentage inhibition of the maximal response (anti-IgM only) minus the background (cells only).

PhosFlow Assay:

Antigen CD79b-specific Fab'-Y and Antigen CD22-specific Fab'-X, were incubated together for 60 minutes (in a 37° C. and 5% $CO_2$ environment) at equimolar concentration. The combinations were titrated from a starting molarity of 100 nM, in 1:4 serial dilutions. Antigen CD79b and Antigen CD22-specific BYbe was also titrated from a starting molarity of 100 nM, in 1:4 serial dilutions. In V-bottomed 96 well plates, $5.0 \times 10^4$ PBMC were added to wells, to which were added titrated Fab'-X and Fab'-Y combinations or titrated BYbe. The Fab'-X and Fab'-Y combinations or BYbe were incubated with cells for a further 90 minutes. After this time B cells were activated by the addition of 25 μg/mL of goat $F(ab')_2$ anti-human IgM (Southern Biotechnology) for 15 minutes at 37° C. plus 5% $CO_2$. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in FACS buffer (PBS+1% BSA+0.01% $NaN_{3+2}$ mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and anti-phosphorylated PLCγ2, anti-phosphorylated Akt and anti-phosphorylated p38 antibodies (BD Biosciences). Plates were then resuspended and incubated for 1 hour at room temperature in the dark. After this time plates were washed a further two times and resuspended in 20 μL of FACS buffer. Cellular expression of CD20 and phospho-PLCγ2, phospho-Akt and phospho-p38 were measured using an Intellicyt iQUE® flow cytometer. Using the data analysis software package Forecyt™ (Intellicyt) B cells were identified as distinct from other cell populations and the geometric mean of PLCγ2, Akt and p38 levels were calculated for each well. All data was then expressed as the percentage inhibition of the maximal response (anti-IgM only) minus the background (cells only).

Results

Figure 15:
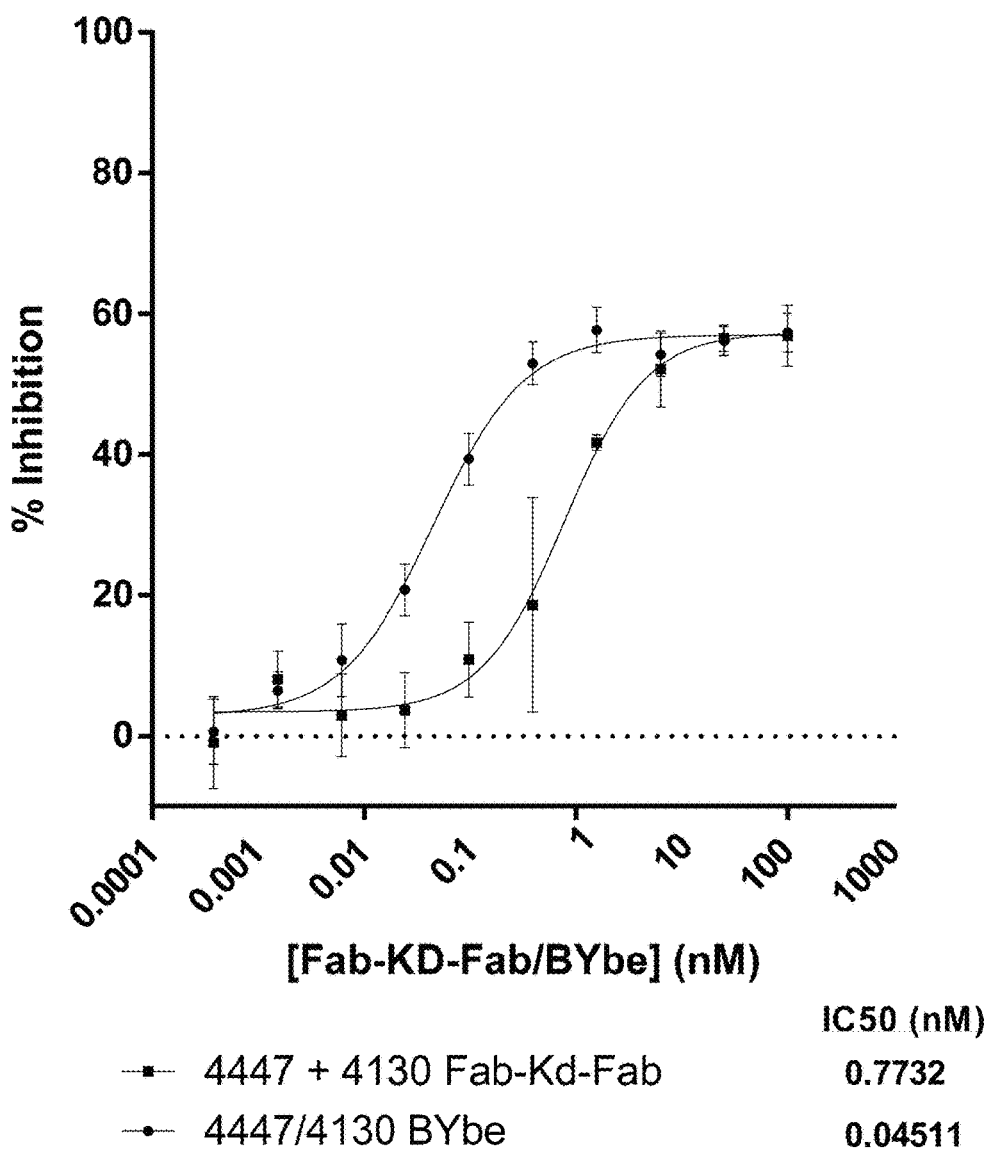
Figure 16:
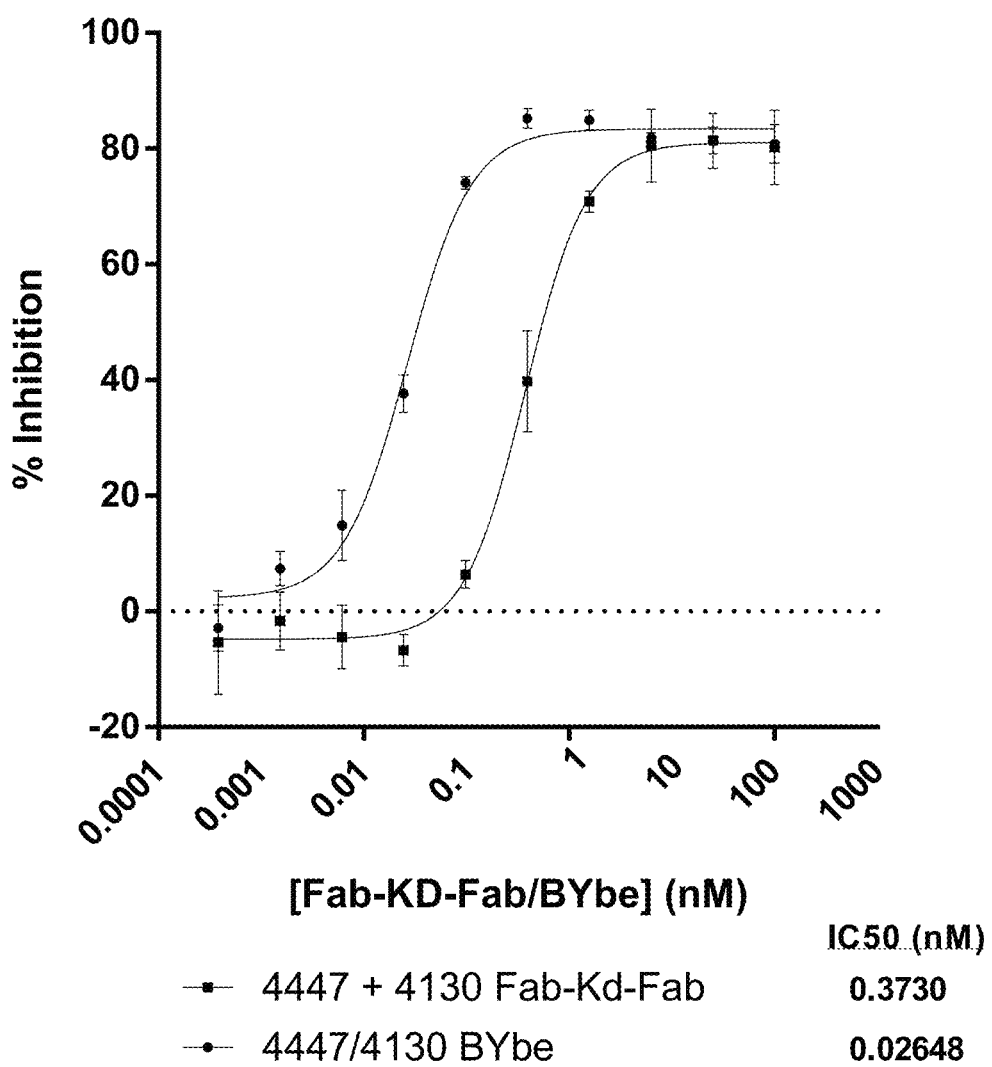
Figure 17:
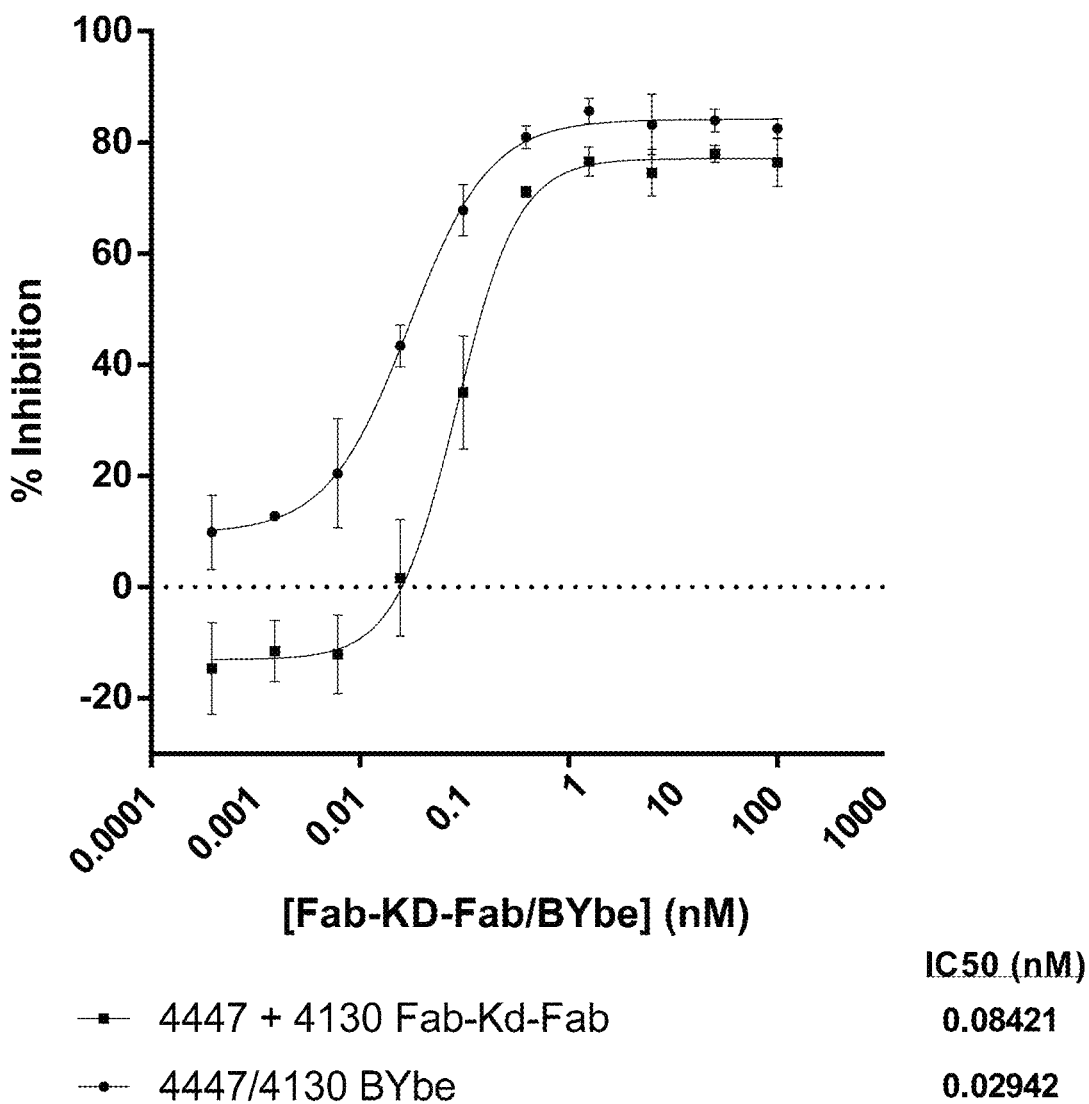

PhosFlow Assay:

The data in FIG. 15 show that targeting antigen CD79b and antigen CD22 either in the Fab-Kd-Fab or BYbe format can inhibit phosphorylated PLCγ2 in B-cells stimulated with anti-IgM. The data in FIG. 16 show that targeting antigen CD79b and antigen CD22 either in the Fab-Kd-Fab or BYbe format can inhibit phosphorylated P38 in B-cells stimulated with anti-IgM. The data in FIG. 17 show that targeting antigen CD79b and antigen CD22 either in the Fab-Kd-Fab or BYbe format can inhibit phosphorylated Akt in B-cells stimulated with anti-IgM.

Figure 18:
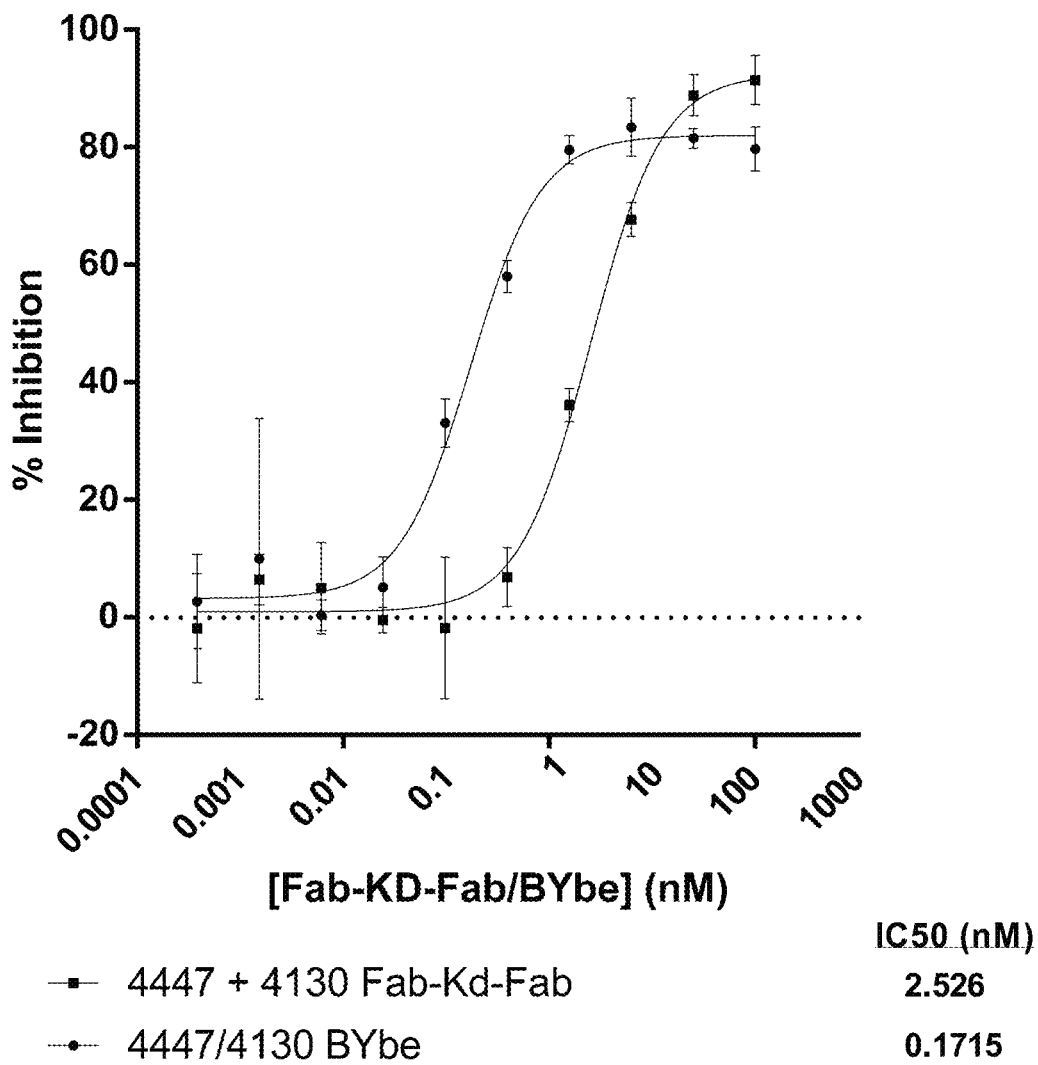
Figure 19:
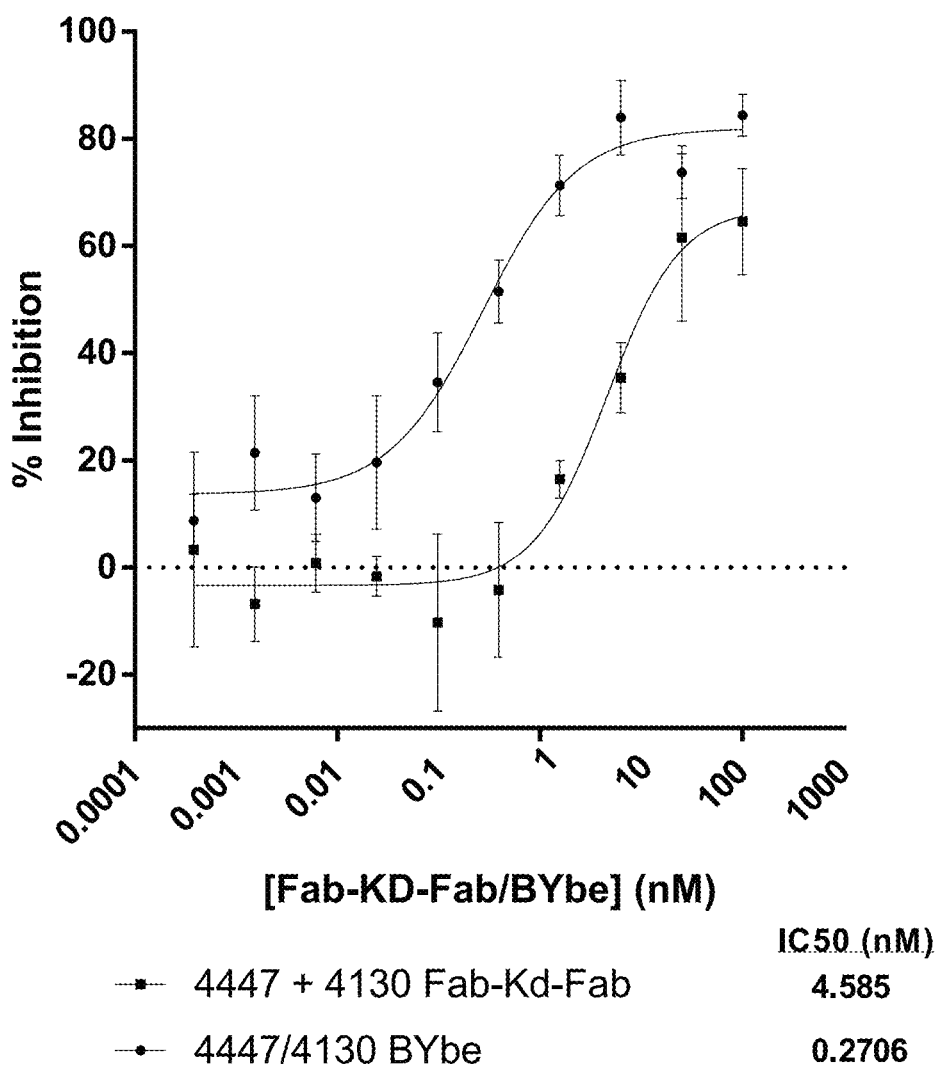
Figure 20:
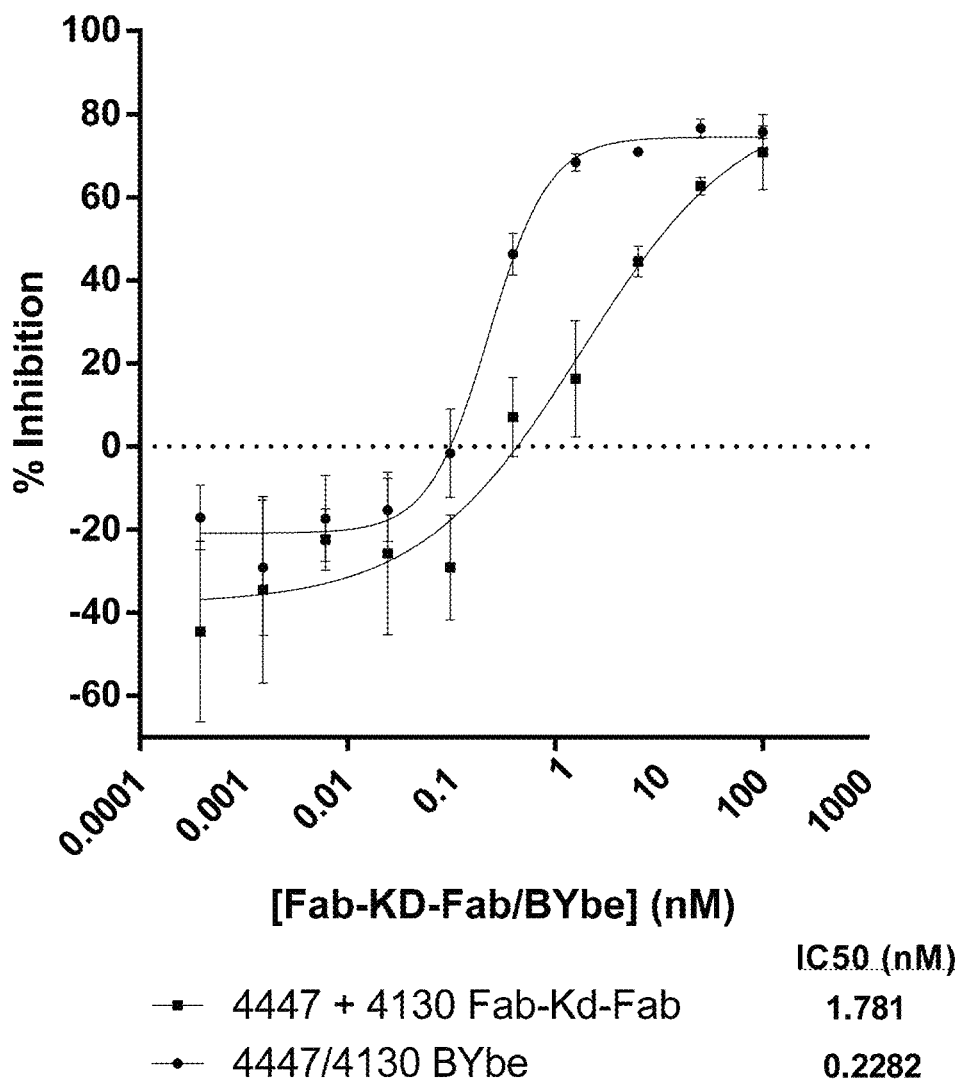

Activation Marker Assay:

As can be seen in FIG. 18, the data show that targeting antigen CD79b and antigen CD22 either in the Fab-Kd-Fab or BYbe format can inhibit CD71 expression on B-cells stimulated with anti-IgM. The data in FIG. 19 show that targeting antigen CD79b and antigen CD22 either in the Fab-Kd-Fab or BYbe format can inhibit CD40 expression on B-cells stimulated with anti-IgM. The data in FIG. 20 show that targeting antigen CD79b and antigen CD22 either in the Fab-Kd-Fab or BYbe format can inhibit CD86 expression on B-cells stimulated with anti-IgM Example 9—Comparison of the Activity of Antigen CD79b Plus Antigen CD22 Co-Targeting in a Molecularly Linked Bispecific Bybe Format with the Further Addition of an Anti-Albumin Binding Domain for Extention of In Vivo Half-Life Introduction:

To check that the CD79b/CD22 target pair activity identified in the Fab-Kd-Fab heterodimerically tethered screening complex could translate to similar desired activity in a potential therapeutic molecularly linked format with an anti-albumin targeted in vivo half-life extension, an anti-albumin antibody fragment was fused to the light chain of the antigen CD22 Fab of the BYbe format described in Example 8 via a linker having the sequence SGGGGSGGGGS (SEQ ID NO:17). Antigen CD79b specificity (VR4447) and antigen CD22 specificity (VR4130 and VR4126) were generated in a Bybe format with and without addition of an anti-albumin fragment (VR0645).

Description of constructs used in this experiment.

| Construct Name | Fab Specificity | Heavy Chain scFv | Light Chain scFv |
|---|---|---|---|
| VR4447/VR4126 BYbe | Antigen CD79b | Antigen CD22 | None |
| VR4447/VR4126/VR645) BYbe/Albumin | Antigen CD79b | Antigen CD22 | Albumin |
| VR4447/VR4130 BYbe | Antigen CD79b | Antigen CD22 | None |
| VR4447/VR4130/VR645) BYbe/Albumin | Antigen CD79b | Antigen CD22 | Albumin |

Methods

Purification of BYbes With/Without Anti-Albumin Additional Specificity

The BYbe (Fab-dsscFv [scFv off C-terminus of Fab heavy chain]) and BYbe with anti-albumin (Fab-2xdsscFv [scFvs off C-terminus of Fab heavy chain and light chain]) formats were purified as follows. Clarified cell culture supernatants from standard expiHEK or CHO expression were 0.22 μm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH 2.7. The elution was followed by absorbance at 280 nm, the elution peak collected, and then neutralised with $\frac{1}{25}^{th}$ volume of 2 M Tris/HCl pH8.5. The neutralised samples were concentrated using Amicon Ultra-15 concentrators with either a 10 kDa or 30 kDa molecular weight cut off membrane and centrifugation at 4000×g in a swing out rotor. Concentrated samples were applied to either a XK16/60 or XK26/60 Superdex 200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 μm, 7.8×300 mm column developed with an isocratic gradient of 0.2 M phosphate, pH 7.0 at 1 ml/min, with detection by absorbance at 280 nm. Selected monomer fractions were pooled and concentrated to >1 mg/ml using an Amicon Ultra-15 concentrator with a 10 kDa or 30 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 μm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's EndoSafe® Portable Test System with Limulus Amebocyte Lysate (LAL) test cartridges.

100 nM of each construct purified protein were pre-incubated with human PBMC derived from five separate donors for 60 min at 37 degree C./5% $CO_2$ in RMPI 1640 media plus 10% foetal bovine serum and 2 mM Glutamax (R10 media). After 60 min cells were stimulated with 25 ug/ml of a goat anti-IgM antibody designed to stimulate B cells only. 24 hours later plates were placed on ice to halt any further cell activation before washing once with ice cold flow cytometry buffer (PBS+1% BSA+0.01% $NaN_3$). All supernatant was removed and cell pellets resuspended. Cells were placed on ice and a cocktail of anti-CD19, -CD20, -CD27, -CD71 and CD86 antibodies added. Cells were incubated for 60 min before washing twice in flow cytometry buffer. Data on the binding of anti-CD27, -CD71 and CD86 to CD19/CD20 positive B cells was generated using an iQUE high throughput flow cytometer. Forecyt software was used to generate histograms and derive geometric mean intensity readings for the binding of anti-CD27, -CD71 and CD86 antibodies to B cells. This data was imported into Excel and percentage inhibition values generated for each combination. The data was then imported into Graphpad Prism and box and whisker charts generated for each combination with the mean indicated by a '+'.

Figure 21:
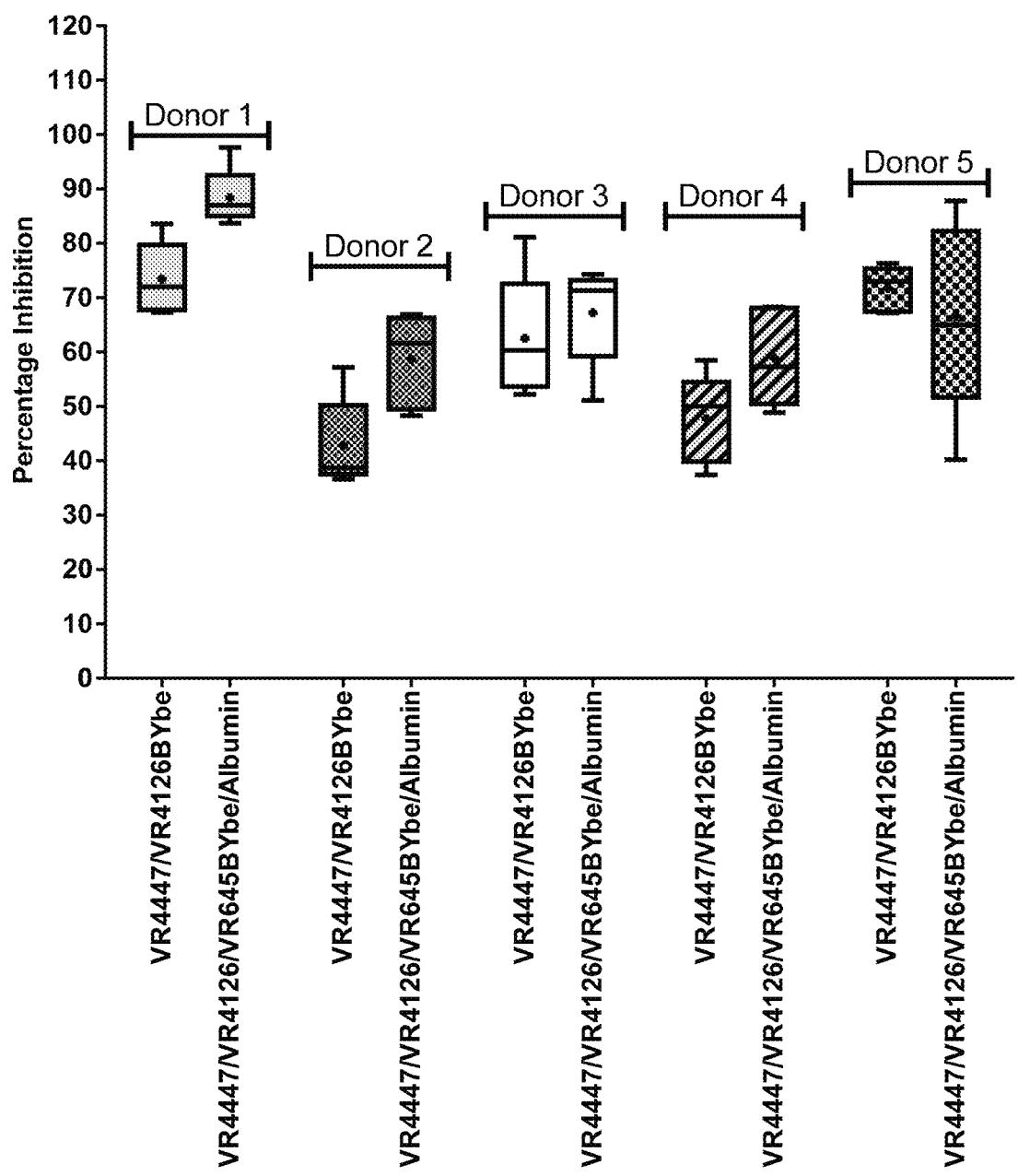

FIG. 21 shows the inhibition of CD27 expression on B cells induced by VR4447/VR4126 BYbe and VR4447/

Figure 22:
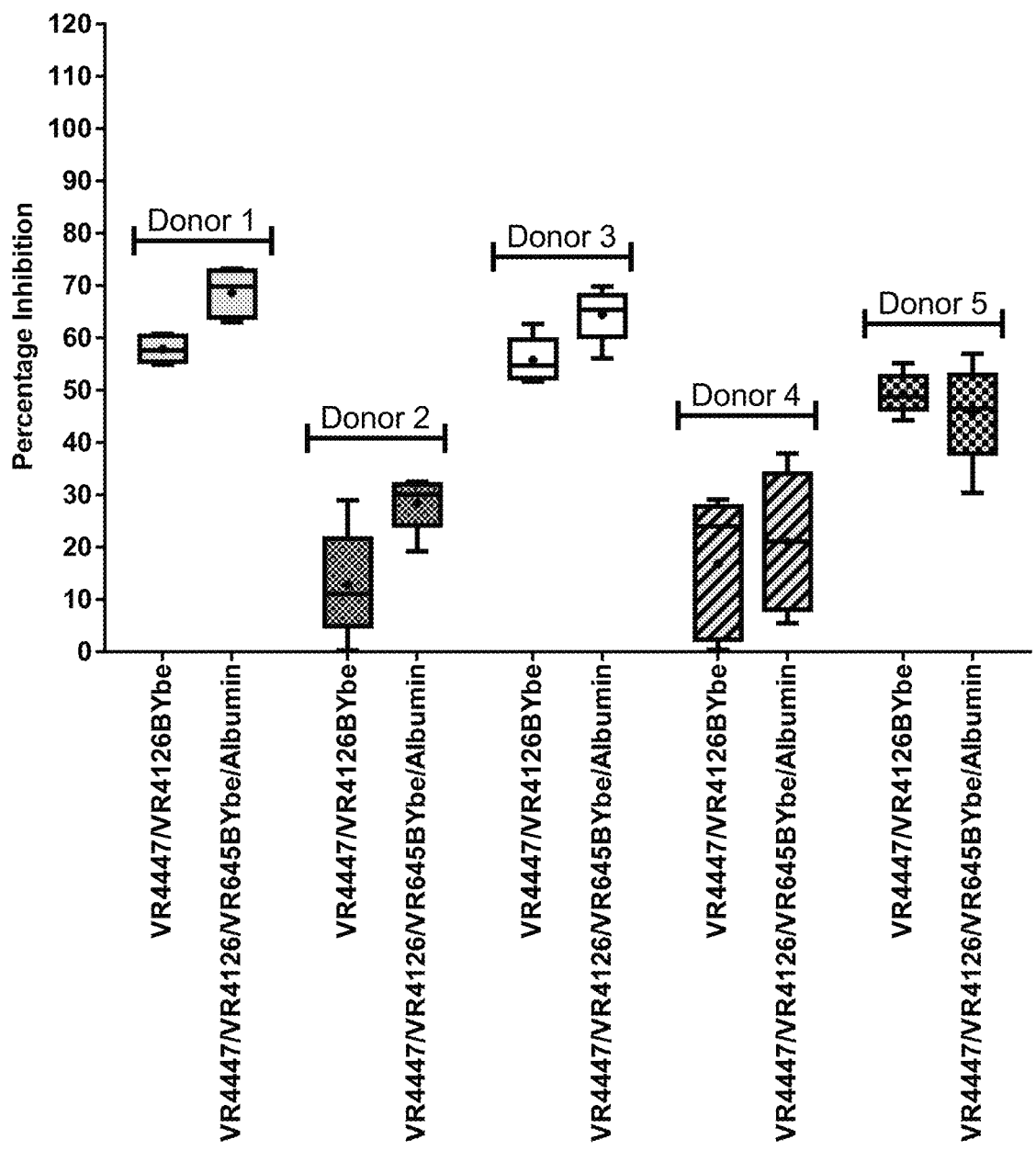
Figure 23:
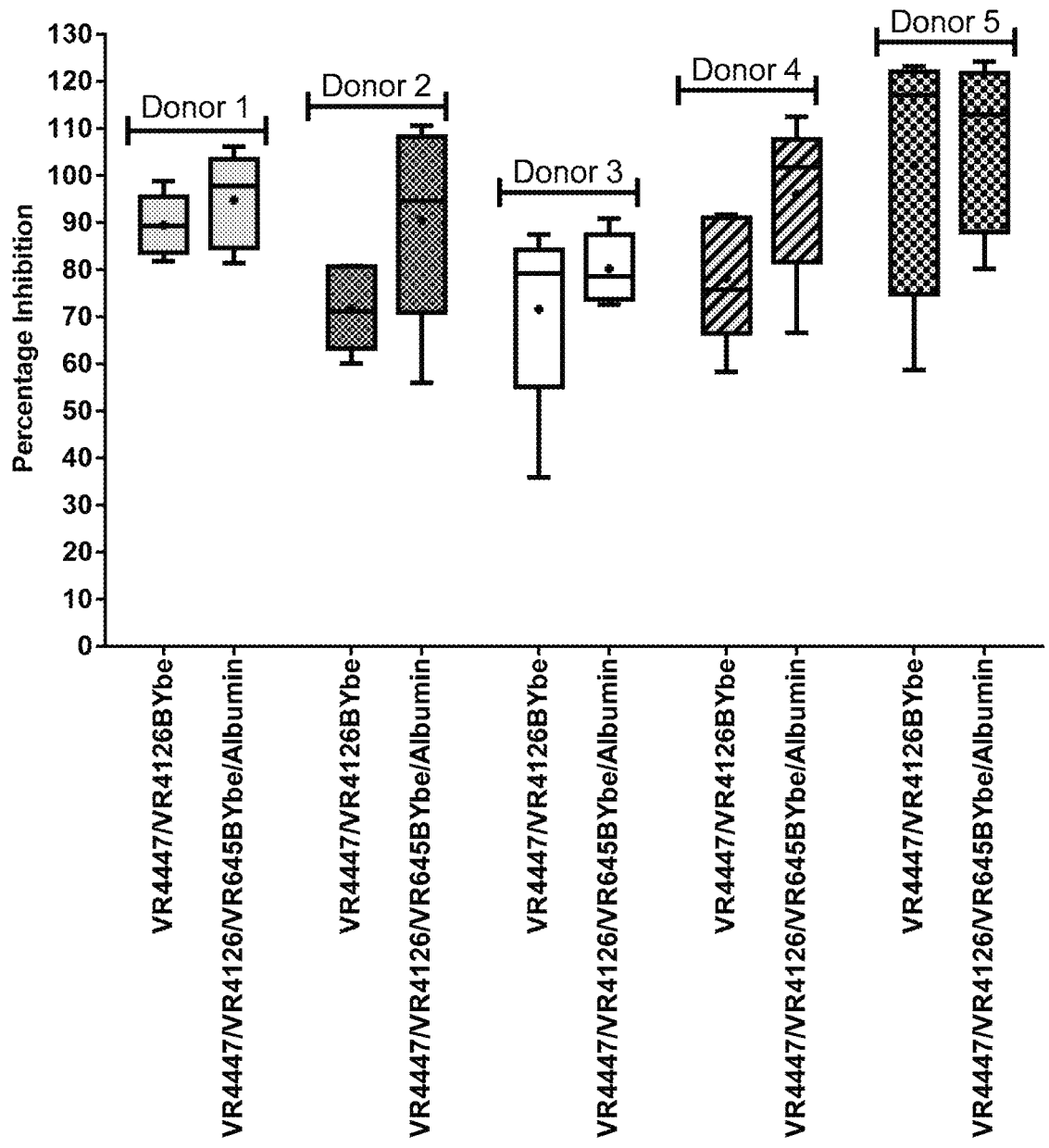

VR4126/VR645 BYbe/Albumin. Across the five donors tested both showed consistently similar levels of inhibition of anti-IgM induced CD27. FIG. 22 shows the inhibition of CD71 expression on B cells induced by VR4447/VR4126 BYbe and VR4447/VR4126/VR645 BYbe/Albumin. Across the five donors both showed consistently similar levels of inhibition of anti-IgM induced CD71. FIG. 23 shows the inhibition of CD86 expression on B cells induced by VR4447/VR4126 BYbe and VR4447/VR4126/VR645 BYbe/Albumin. Across the five donors both showed consistently similar levels of inhibition of anti-IgM induced CD86.

Figure 24:
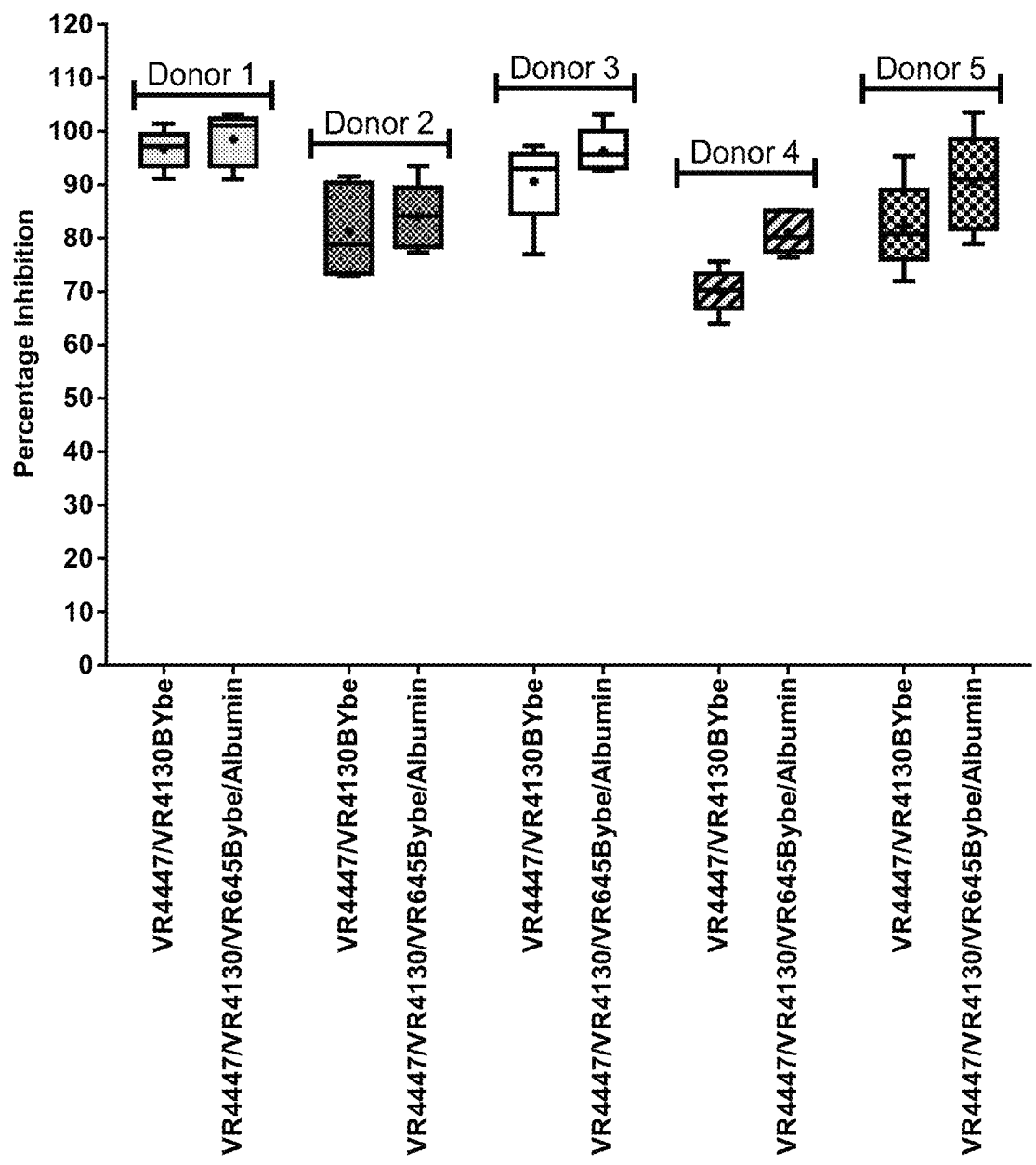
Figure 25:
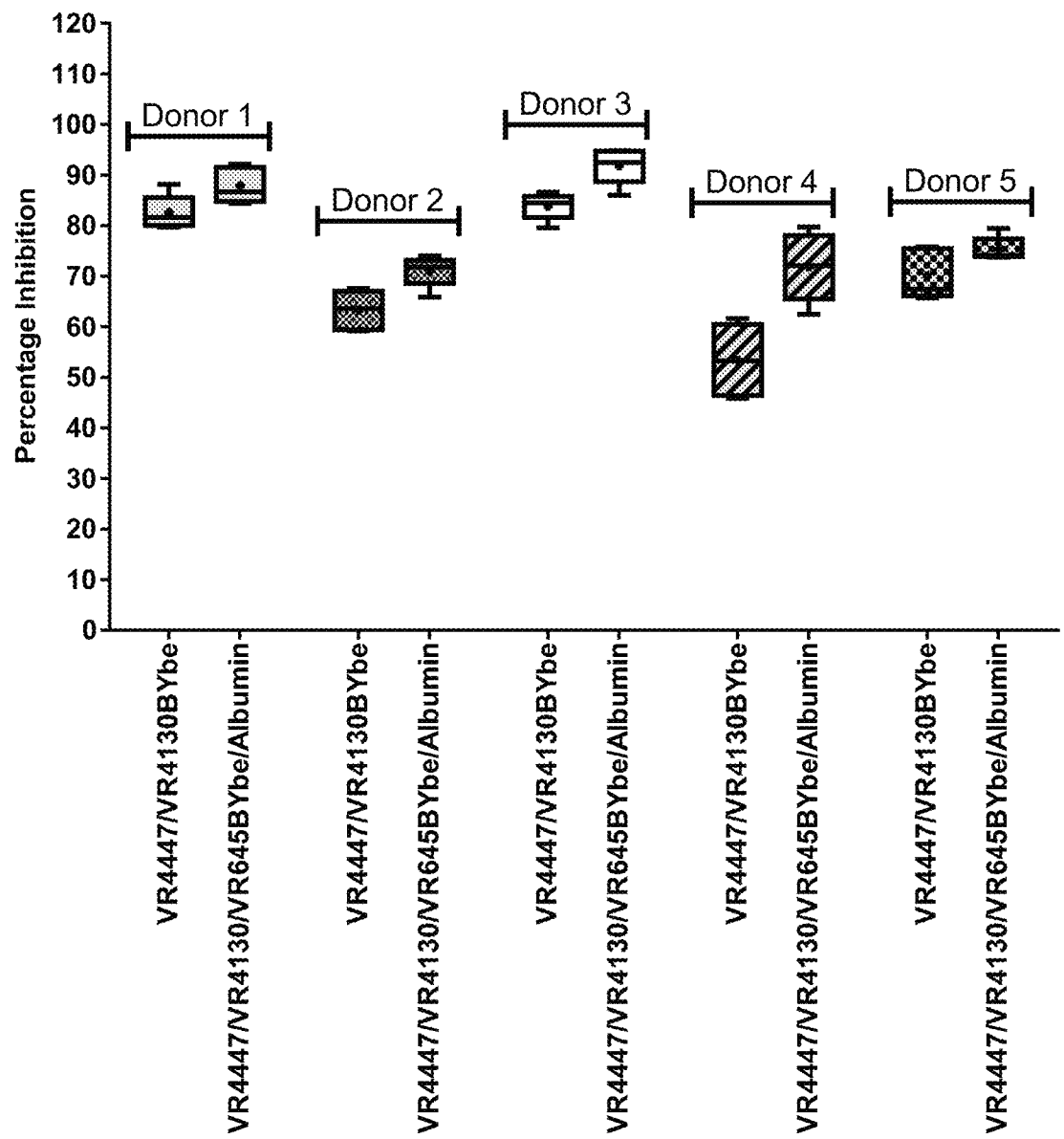
Figure 26:
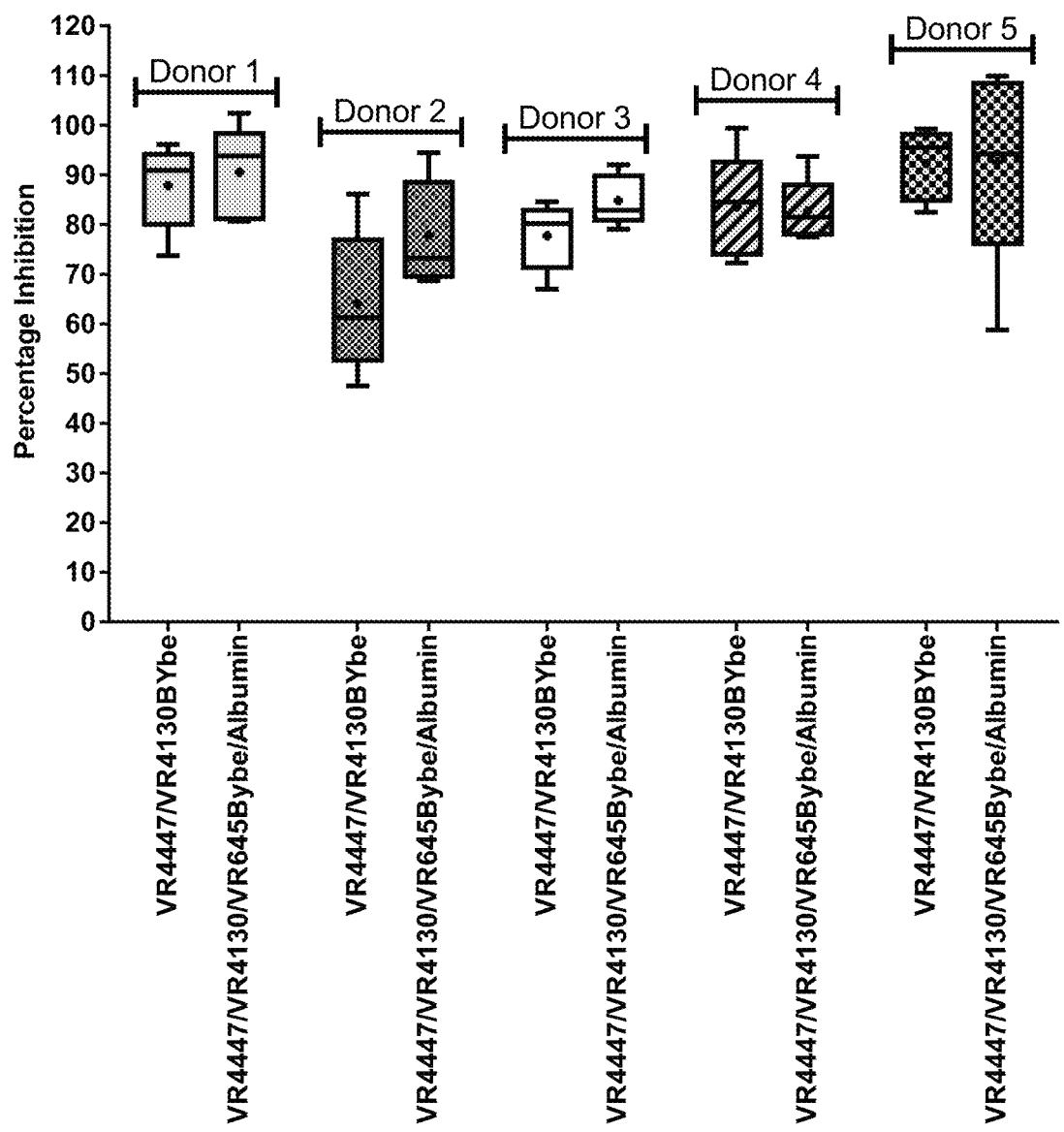

FIG. 24 shows the inhibition of CD27 expression on B cells induced by VR4447/VR4130 BYbe and VR4447/VR4130/VR645 BYbe/Albumin. Across the five donors tested both showed consistently similar levels of inhibition of anti-IgM induced CD27. FIG. 25 shows the inhibition of CD71 expression on B cells induced by VR4447/VR4130 BYbe and VR4447/VR4130/VR645 BYbe/Albumin. Across the five donors both showed consistently similar levels of inhibition of anti-IgM induced CD71. FIG. 26 shows the inhibition of CD86 expression on B cells induced by VR4447/VR4130 BYbe and VR4447/VR4130/VR645 BYbe/Albumin. Across the five donors both showed consistently similar levels of inhibition of anti-IgM induced CD86.

Example 10—Effect of Co-Targeting the Antigen CD79b Plus Antigen CD22 on Memory B Cell Function Using Molecularly Linked Bispecific Bybes With or Without Further Addition of an Anti-Albumin Introduction:

To evaluate whether targeting CD79b/CD22 has a functional effect on B cells in long term culture, IgG production from B cells cultured in isolation or in a mixed PBMC culture was measured. The measurement of specific antibodies to the recall antigen tetanus toxoid provides a read out of memory B cell function.

Antigen CD79b specificity (VR4447) and antigen CD22 specificity (VR4126, VR4127 and VR4130) were generated in a BYbe format with or without addition of an anti-albumin fragment (VR0645). The anti-albumin antibody fragment was fused to the light chain of the antigen CD22 Fab of the BYbe format as described in Example 8 via a linker having the sequence SGGGGSGGGGS (SEQ ID NO:17).

Description of constructs used in this experiment.

| Construct Name | Fab Specificity | Heavy Chain scFv | Light Chain scFv |
|---|---|---|---|
| VR4447/VR4126 BYbe | Antigen CD79b | Antigen CD22 | None |
| VR4447/VR4126/VR645 BYbe/Albumin | Antigen CD79b | Antigen CD22 | Albumin |
| VR4447/VR4127 BYbe | Antigen CD79b | Antigen CD22 | None |
| VR4447/VR4130 BYbe | Antigen CD79b | Antigen CD22 | None |
| VR4447/VR4130/VR645 BYbe/Albumin | Antigen CD79b | Antigen CD22 | Albumin |

Methods

Purification of BYbes With/Without Anti-Albumin Additional Specificity

The BYbe (Fab-dsscFv [scFv off C-terminus of Fab heavy chain]) and BYbe with anti-albumin (Fab-2xdsscFv [scFvs off C-terminus of Fab heavy chain and light chain]) formats were purified as described in example 9.

Activation of B Cells and Measurement of Tetanus Toxoid Specific IgG

Human PBMC or purified B cells derived from up to 3 separate donors were stimulated with 500 ng/ml CD40L, 1 ug/ml CpG and 50 ng/ml IL-21 in 1640 media plus 10% foetal bovine serum and 2 mM Glutamax (R10 medium) for 6 days. Constructs of purified protein were added at a final concentration of 100 nM at day 0 and remained in the culture medium for the duration of the assay. After 6 days the supernatants were harvested and the amount of tetanus toxoid specific IgG was detected by ELISA. Briefly, Maxisorp half-well ELISA plates (Nunc) were coated with 10 ug/ml tetanus toxoid in PBS overnight at 4° C. The plates were then blocked in 5% Milk—in PBS containing 0.05% Tween20 for 2 hours. The supernatants were diluted and then added for 2 hours at room temperature. The plates were washed with PBS-0.05% Tween20 and tetanus bound antibody was detected using a peroxidase-goat anti-human IgG(H+L) diluted to 1 ug/ml in 5% milk-PBS-0.05% Tween20. Plates were developed using TMB substrate solution (KPL) and absorbance was measured at 450 nM using a Synergy 2 micro-plate reader (Biotek). Data was exported to Excel and percentage inhibition was calculated relative to cells cultured without test antibodies. The data was then imported into Graphpad Prism® and plotted as bar charts.

FIG. 27 shows the inhibition of tetanus toxoid IgG production from PBMCs cultured with VR4447/VR4126 BYbe, VR4447/VR4127 BYbe and VR4447/VR4130 BYbe. Data represents pooled data from 3 donors.

FIG. 28 shows the inhibition of tetanus toxoid IgG production from purified B cells cultured with VR4447/VR4126 BYbe, VR4447/VR4127 BYbe and VR4447/VR4130 BYbe. Data represents pooled data from 2 donors.

Figure 29:
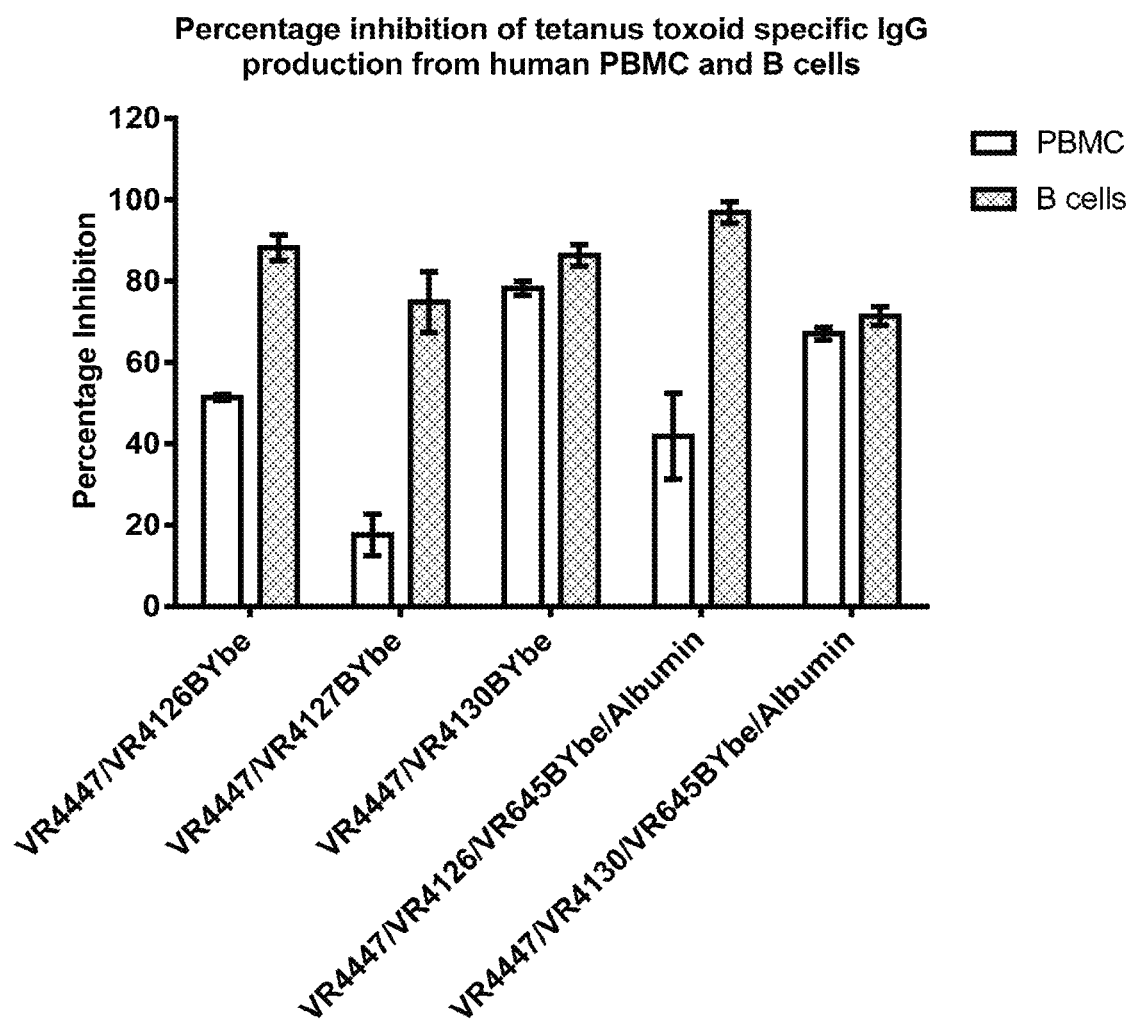

FIG. 29 shows the inhibition of tetanus toxoid IgG production from either PBMC or purified B cells cultured with VR4447/VR4126 BYbe, VR4447/VR4127 BYbe, VR4447/VR4130 BYbe, VR4447/VR4126/VR645 BYbe/Albumin and VR4447/VR4130/VR645 BYbe/Albumin. Data shown from a single donor.

Example 11—Dis-Regulation of BCR Signalling in SLE Patient B Cells & the Effect of Co-Targeting the Antigen CD79b Plus Antigen CD22 on SLE B Cell Function Introduction:

In order to evaluate if the combination of CD79b/CD22 could be used to treat people with autoimmune diseases we used B cells from patients with systemic lupus erythematosus (SLE) as a model system. The impact of the CD79b/CD22 combination (VR4447/VR4130) was tested on the activation status of signalling proteins known to be involved in B cell function but dysregulated in SLE patients compared to healthy volunteers. In this experiment B cells from 12 SLE patients and 12 healthy volunteers were compared for the effect that co-targeting CD79b and CD22 had on their activation status.

Methods:

PhosFlow Assay:

All assays were performed using $2 \times 10^5$ PBMC per well.

In treated samples antigen CD79b and antigen CD22-specific BYbe was tested at a concentration of 100 nM. PBMC from both healthy volunteers and patients with SLE were preincubated with BYbe for 90 minutes at 37° C. In the untreated samples, the BYbe was simply omitted during this incubation period. After this time cells were activated with 25 µg/mL of goat F(ab')$_2$ anti-human IgM (Southern Biotechnology) for 10 minutes at 37° C. plus 5% $CO_2$ and the reaction stopped by the addition of fixative (Cytofix—BD Biosciences). In the unstimulated samples, the anti-human IgM was simply omitted during this incubation period. After 15 minutes at room temperature cells were pelleted (500×g for 5 min) and then resuspended in ice cold perm buffer III (BD Biosciences) before being washed twice in flow buffer (PBS+1% BSA+0.01% $NaN_{3+2}$ mM EDTA). Cells were then stained with anti-CD20, anti-phosphorylated (p) NF-κB, anti-pSyk, anti-pAtk and anti-pErk1&2 and incubated at room temperature in the dark for one hour. Finally plates were washed twice in flow buffer before being measured on an iQUE flow cytometer (Intellicyt). The geometric mean (mean fluorescence intensity, MFI) of pNF-κB, pSyk, pAkt and pErk1&2 expression in B cells was then calculated and expressed in graphical form.

Figure 30:
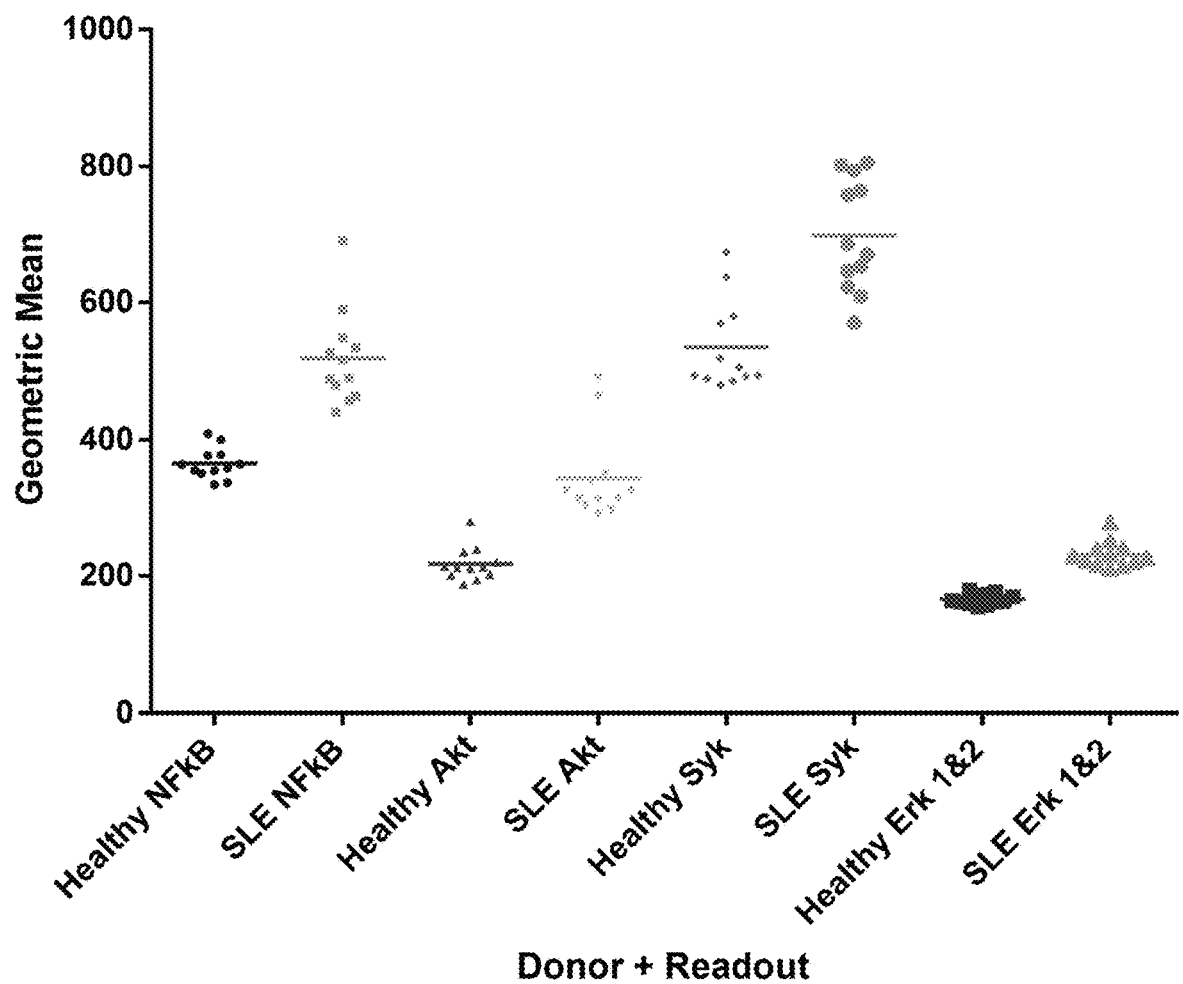
Figure 31:
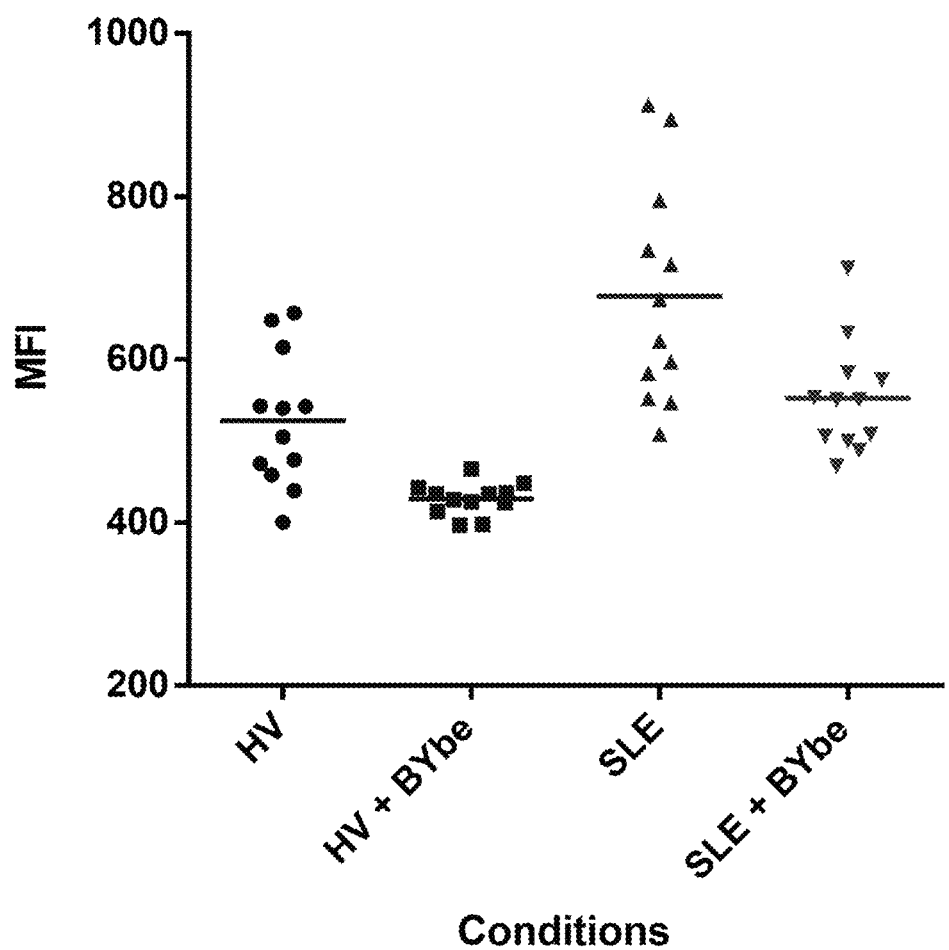
Figure 32:
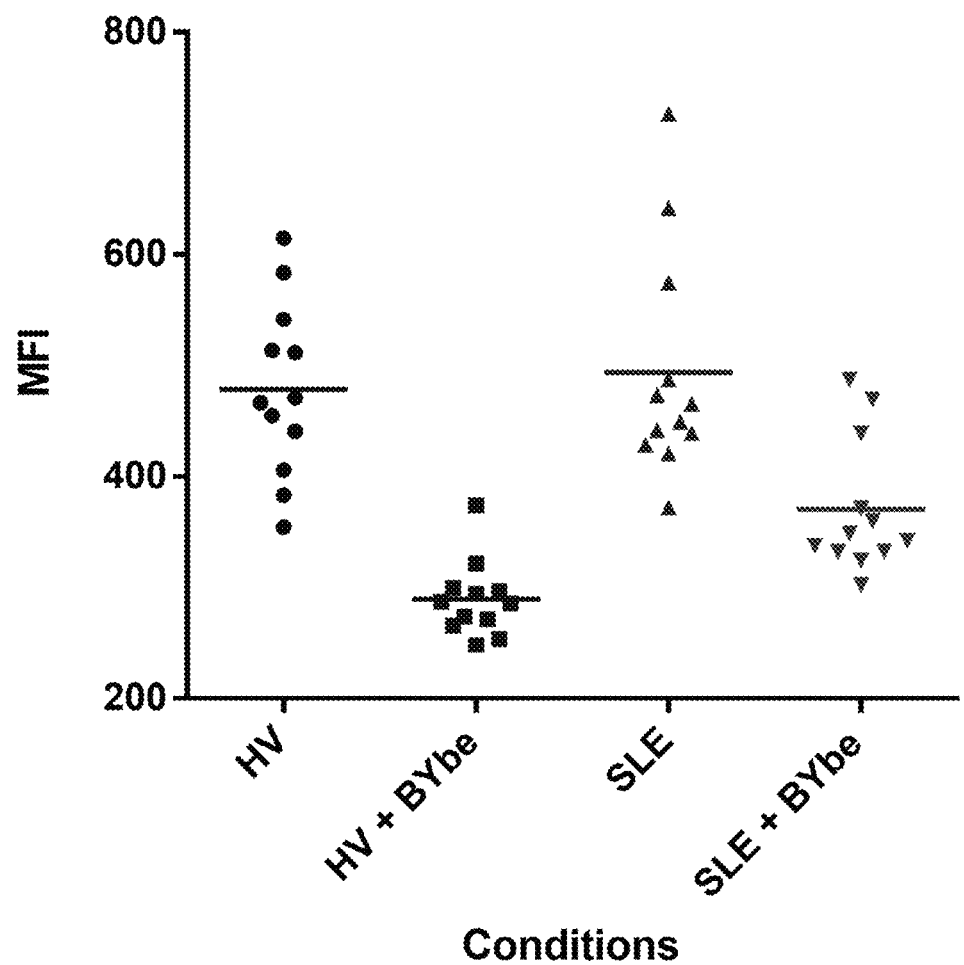
Figure 33:
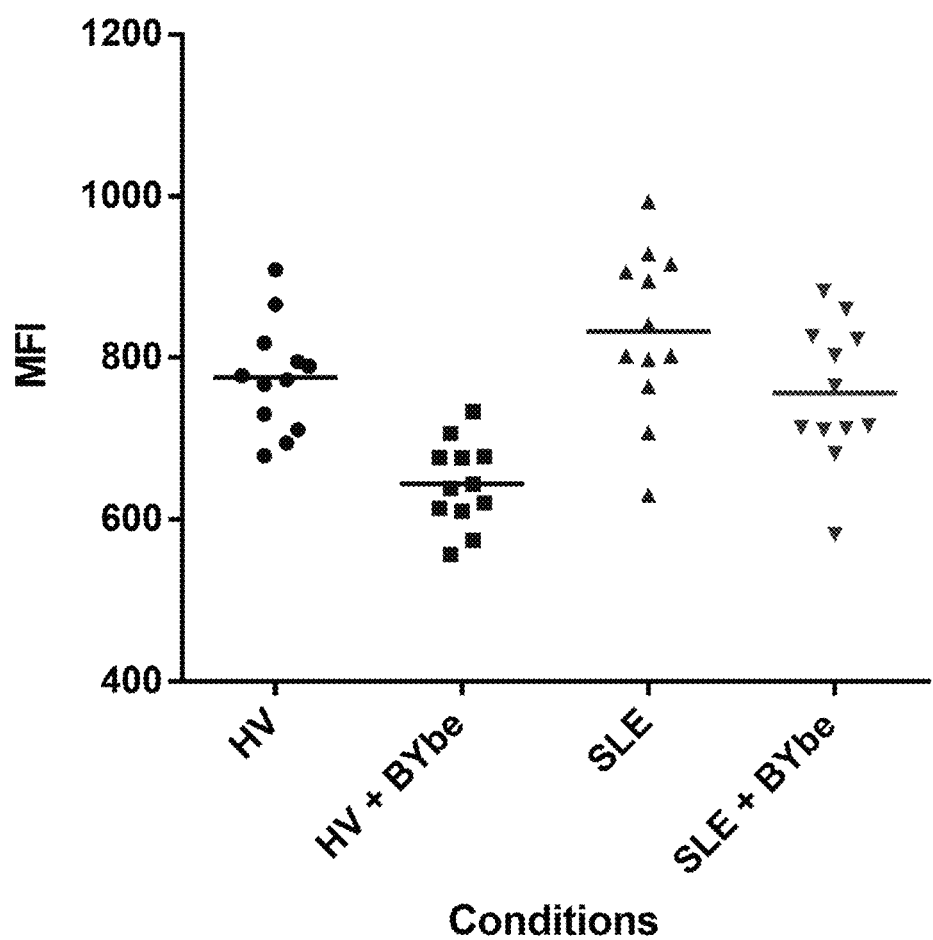
Figure 34:
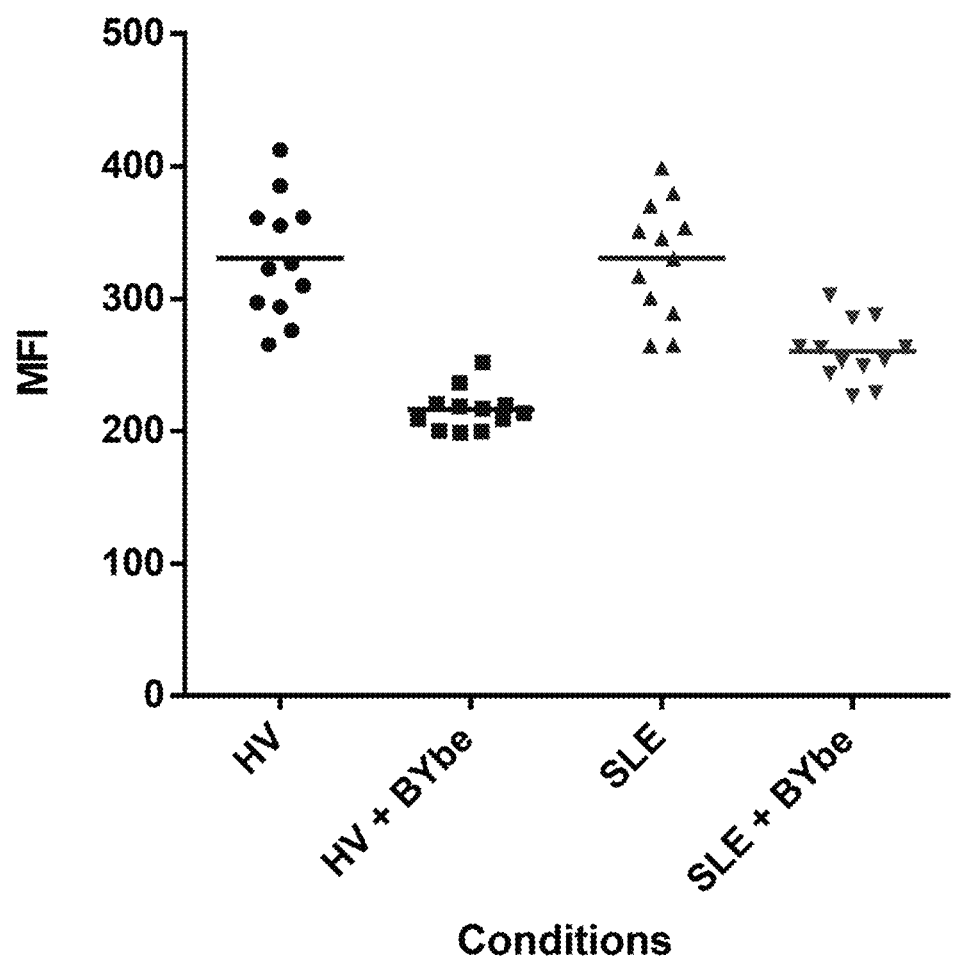

Results:

FIG. 30 shows that the base-line phosphorylation of NF-κB, Syk, Akt and Erk1 &2 (unstimulated & untreated) is elevated in SLE patient B cells as compared to those from healthy volunteers.

FIGS. 31 to 34 shows that the CD79/CD22 BYbe can equally inhibit pNF-κB, pSyk, pAkt and pErk1&2 in healthy volunteers and SLE patients.

Conclusions:

This data shows that B cells from SLE patients are activated before any in vitro stimulation when compared with healthy volunteers. Upon stimulation of the cells via the B cell receptor both healthy volunteers and SLE patients show an enhanced levels of activation compared to the background signal. In both healthy volunteers and SLE patients this signal is substantially blocked by the CD79b/CD22 combination. This data indicates that the CD79b/CD22 combination can inhibit B cell from both healthy volunteers as well as people with an underlying autoimmune disease indicating that this pathway is of fundamental importance to B cell activation.

Example 12—CD45 Fab/CD79Fab Bispecific Complex but not a Mixture of CD45 and CD79 Fab or Bivalent CD79 Fab Complex Inhibits Akt Signalling Human PBMC derived from platelet apheresis cones were banked as frozen aliquots. Prior to an assay being performed, cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-A (Fab-scFv) and Fab-B (Fab-peptide) or Fab-A (Fab-peptide) and Fab-B (Fab-peptide) with antigen specificity for the cell surface proteins CD45 and CD79b in DMEM containing 10% calf serum and 2 mM glutamine. This grid is shown in Table 10.

TABLE 10

Grid of bispecific and bivalent combinations of antibodies with specificity for CD45 and CD79b.

| (A-X or Y) | (B-Y) Fab B | |
|---|---|---|
| Fab A | CD45-Y | CD79b-Y |
| CD45-X | CD45-X:Y-CD45 | CD45-X:Y-CD79b |
| CD79b-X | CD79b-X:Y-CD45 | CD79b-X:Y-CD79b |
| CD45-Y | | CD45-Y:CD79b-Y | where X is a scFv (52SR4) and Y is a peptide (GCN4).

FabA-X and FabB-Y or Fab-A-Y and Fab-B-Y were incubated together for 90 minutes (in a 37° C./5% $CO_2$ environment) before mixing with $2.5×10^5$ PBMC in V bottomed 96 well plates. PBMC plus bispecific or bivalent combinations were then incubated together for a further 90 minutes. After this time B cells were activated by the addition of 200 nM of goat F(ab')$_2$ anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+ 1% BSA+0.01% $NaN_3$) and washed once more. Cells were then resuspended in ice cold Perm Buffer III (BD Biosciences) for 30 minutes before being washed twice in flow buffer. Cells were then stained with a fluorescently labelled anti-CD20 antibody (BD Biosciences) and a fluorescently labelled anti-phospho Akt antibody that recognises a modified serine residue at position 473 on the protein. Plates were then resuspended and incubated for 1 hour at room temperature in the dark. After this time plates were washed a further two times and resuspended in 25 µl of flow buffer. Cellular expression of CD20 and Akt was measured using an Intellicyt HTFC™ flow cytometer.

Using the data analysis software package Forecyt™ (Intellicyt) B cells were identified as distinct from other cell populations and the geometric mean of Akt levels was calculated for each well. All data was then expressed as the percentage inhibition of the maximal response (anti-IgM only) minus the background (cells only). The relative effect of the combinations of CD45 and CD79b is shown in Table 11 (↓=inhibition, ↑=stimulation and ↔=no overall effect).

TABLE 11

Table of the relative potency of inhibition of phosphorylated Akt for bispecific & bivalent combinations of antibodies with specificity for CD45 & CD79b.

| (A-X) | (B-Y) Fab B | |
|---|---|---|
| Fab A | CD45-Y | CD79b-Y |
| CD45-X | Not Tested | Not Tested |
| CD79b-X | ↓↓ | ↔ |
| CD45-Y | Not tested | ↔ | where X is a scFv (52SR4) and Y is a peptide (GCN4).

Figure 35:
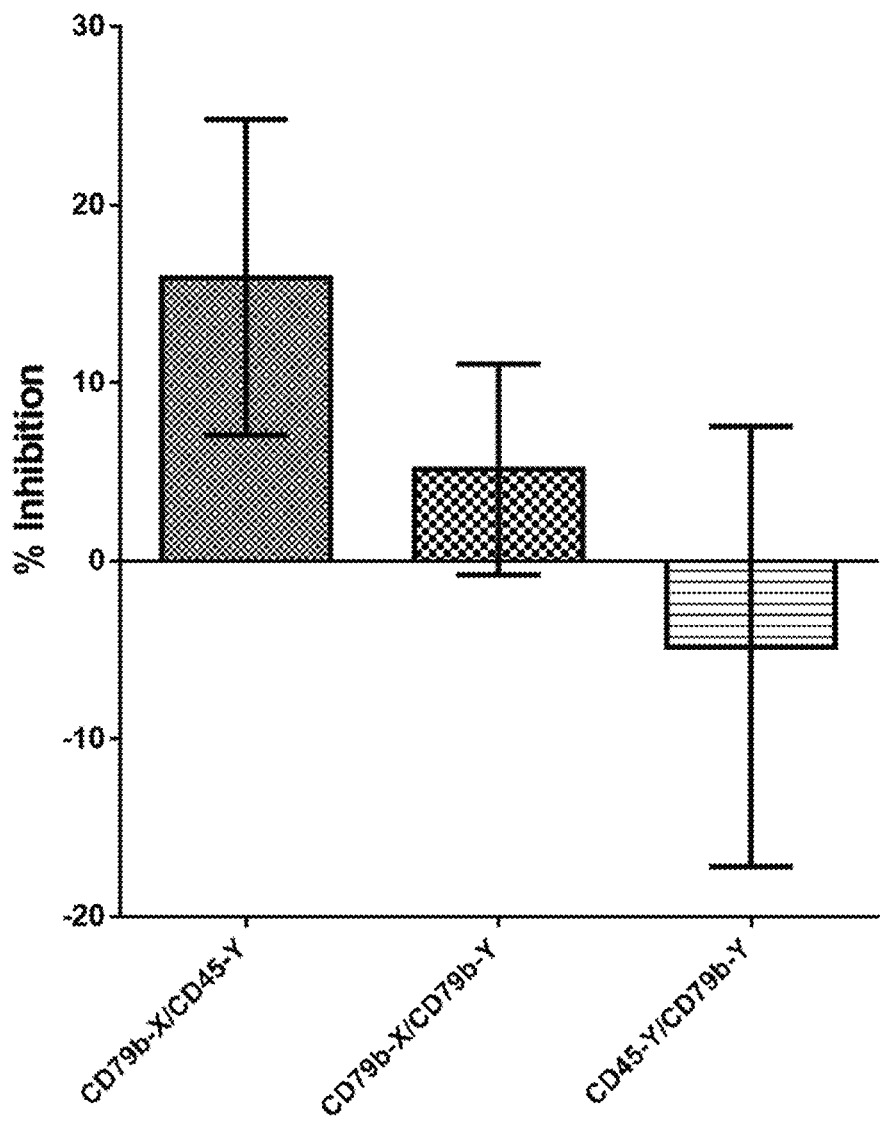

This data is also shown in the form of a bar chart (FIG. 35): the data represents mean values and the error bars are 95% confidence intervals. The data shows that the bispecific combination of CD45 with CD79b can inhibit phospho-Akt expression in B cells stimulated with anti-IgM, whereas combining CD79b-Y with CD79b-Y, which is a mixture which cannot form a bispecific, does not.

Example 13—CD45 Fab/CD79Fab Bispecific Complex but not a Mixture of CD45 and CD79 Fab or Bivalent CD79 Fab' Complex Inhibits PLCγ2 Signalling Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab-a (Fab-scFv [A-X]) and Fab'-B (Fab-peptide [B-Y]) or Fab-A (Fab-peptide) and Fab-B (Fab-peptide with antigen specificity for the cell surface proteins CD45 and CD79b in DMEM containing 10% calf serum and 2 mM glutamine. This grid is shown in Table 10.

Fab'A-X and Fab'B-Y or Fab-A-Y and Fab-B-Y were incubated together for 90 minutes (in a 37° C./5% $CO_2$ environment) before mixing with $2.5 \times 10^5$ PBMC in V bottomed 96 well plates. PBMC plus bispecific or bivalent combinations were then incubated together for a further 90 minutes. After this time B cells were activated by the addition of 200 nM of goat $F(ab')_2$ anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and a fluorescently labelled anti-phospho PLCγ2 antibody that recognises a modified tyrosine residue at position 759 on the protein. Plates were then resuspended and incubated for 1 hour at room temperature in the dark. After this time plates were washed a further two times and resuspended in 25 μl of flow buffer. Cellular expression of CD20 and PLCg2 was measured using an Intellicyt HTFC™ flow cytometer.

Using the data analysis software package Forecyt™ (Intellicyt) B cells were identified as distinct from other cell populations and the geometric mean of PLCγ2 levels was calculated for each well. All data was then expressed as the percentage inhibition of the maximal response (anti-IgM only) minus the background (cells only). The relative effect of the combination of CD45 and CD79b is shown in Table 12 (↓=inhibition, ↑=stimulation and ↔=no overall effect).

TABLE 12

Table of the relative potency of inhibition of phosphorylated PLCg2 for bispecific and bivalent combinations of antibodies with specificity for CD45 and CD79b.

| (A-X or Y) | (B-Y) Fab B | |
| --- | --- | --- |
| Fab A | CD45-Y | CD79b-Y |
| CD45-X | | Not Tested |
| CD79b-X | ↓↓↓ | ↔ |
| CD45-Y | Not tested | ↔ | where X is a scFv and Y is a peptide

This data can also be expressed as a bar chart (FIG. 36), the data represents mean values and the error bars are 95% confidence intervals. The data shows that the bispecific combination of CD45 with CD79b, inhibit phospho-PLCγ2 expression in B cells stimulated with anti-IgM, whereas combining CD79b-Y with CD79b-Y, which is a mixture which cannot form a bispecific, does not.

Example 14—The Bispecific CD45 and CD79b Complex can Potently Inhibit the Expression of CD86 on B Cells Human PBMC derived from platelet apheresis cones were banked as frozen aliquots. Prior to an assay being performed cells were thawed, washed in DMEM (Life Technologies) and allowed to acclimatise to a 37 degree C./5% $CO_2$ environment. During this period bispecific combinations were created by diluting equimolar (500 nM) quantities of Fab-X (Fab-scFv) and Fab-Y (Fab-peptide) with antigen specificity for the cell surface proteins CD45 and CD79b in DMEM containing 10% calf serum and 2 mM glutamine. These combinations were then diluted in 8 stepwise 1 in 2.5 dilutions to create a dose titration for this combination. Fab-X and Fab-Y were incubated together for 90 minutes (in a 37 degree C./5% $CO_2$ environment) before adding $2.5 \times 10^5$ PBMC to V bottomed 96 well plates. PBMC were then added to Fab'-X and Fab'-Y combinations and incubated together for a further 90 minutes. After this time B cells were activated by the addition of 200 nM of goat $F(ab')_2$ anti-human IgM (Southern Biotechnology) for 24 hours at 37 degrees C. To enable detection of cell surface activation markers plates were placed on ice and washed once in ice cold flow buffer (PBS+1% BSA+0.01% $NaN_3$). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 ul of flow buffer. Cellular expression of CD19 and CD86 was measured using an Intellicyt HTFC™ flow cytometer. Using the data analysis software package Forecyt™ (Intellicyt) B cells were identified as distinct from other cell populations and the geometric mean of CD86 levels was calculated for each well. All data was then expressed as the percentage inhibition of the maximal response (anti-IgM only) minus the background (cells only). As can be seen in FIG. 37 a titration of the combination of CD45-X/CD79b-Y was able to inhibit anti-IgM induced CD86 expression on B cells after 24 hours. The $IC_{50}$, as extrapolated using a 4 parameter logistic curve fit using Graphpad Prism 6, was 4.7 nM (the data represents mean values and the error bars are standard deviations).

Example 15—The Inhibitory Effect of CD45 and CD79b Bispecific Protein can be Reproduced with Different Antibody V Regions Immunisation:

DNA encoding antigens CD79a and CD79b and CD45 was obtained by gene synthesis or commercial sources & cloned into an expression vector with a strong constitutive promoter. Plasmid DNA was then transfected into Rab-9 rabbit fibroblast cells (ATCC® CRL1414™) using an in-house electroporation system. For CD79 immunisations, both CD79a and CD79b were co-transfected. Twenty four hours later cells were checked for antigen expression by flow cytometry & frozen in aliquots in liquid nitrogen until use. Up to 6 antigens were immunised per rabbit by either co-expression on the same cell or making mixtures of singly or multiple transfected cells. Rabbits were immunised with 3 doses of cells.

Antibody Discovery:

B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 μl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$. The presence of antigen-specific antibodies in B cell culture supernatants was determined using a homogeneous fluorescence-based binding assay using HEK293 cells co-transfected with CD79a and CD79b or CD45. Screening involved the transfer of 10 ul of supernatant from barcoded 96-well tissue culture plates into barcoded 384-well black-walled assay plates containing HEK293 cells transfected with target antigen (approximately 3000 cells/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

Following primary screening, positive supernatants were consolidated on 96-well bar-coded master plates using an Aviso Onyx hit-picking robot and B cells in cell culture plates frozen at −80° C. Master plates were then screened in a homogeneous fluorescence-based binding assay on HEK293 cells transfected with CD79a and CD79b or CD45 antigens or Superavidin™ beads (Bangs Laboratories) coated with recombinant CD45 protein as a source of antigen. This was done in order to determine the antigen specificity for each well.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1). Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγfragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and Superavidin™ beads (Bangs Laboratories) coated with recombinant protein or antigen transfected HEK cells. This was done to confirm the specificity of the cloned antibodies.

Production of Small Scale Fab A-X and Fab B-Y (Small Scale (30 ml) Expl293 Transfection)

The Expi293 cells were routinely sub-cultured in Expi293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed Expi293™ Expression Medium for each 50 mL transfection.

To prepare the lipid-DNA complexes for each transfection a total of 50 µg of heavy chain and light chain plasmid DNAs were diluted in Opti-MEM® I medium (LifeTechnologies) to a total volume of 2.5 mL and 135 µL of ExpiFectamine™ 293 Reagent (LifeTechnologies) was diluted in Opti-MEM® I medium to a total volume of 2.5 mL. All dilutions were mixed gently and incubate for no longer than 5 minutes at room temperature before each DNA solution was added to the respective diluted ExpiFectamine™ 293 Reagent to obtain a total volume of 5 mL. The DNA-ExpiFectamine™ 293 Reagent mixtures were mixed gently and incubated for 20-30 minutes at room temperature to allow the DNA-ExpiFectamine™ 293 Reagent complexes to form.

After the DNA-ExpiFectamine™ 293 reagent complex incubation was completed, the 5 mL of DNA-ExpiFectamine™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 µL of ExpiFectamine™ 293 Transfection Enhancer 1 (LifeTechnologies) and 2.5 mL of ExpiFectamine™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Small Scale (50 ml) Purification:

Both Fab-X and Fab-Y were purified separately by affinity capture using a small scale vacuum based purification system. Briefly, the 50 ml of culture supernatants were 0.22 µm sterile filtered before 500 µL, of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+1M NaCl. The eluted fractions buffer exchanged into PBS (Sigma), pH7.4 and 0.22 µm filtered. Final pools were assayed by A280 scan, SE-UPLC (BEH200 method), SDS-PAGE (reduced & non-reduced) and for endotoxin using the PTS Endosafe system.

Human PBMC derived from platelet apheresis cones were banked as frozen aliquots. Prior to an assay being performed cells were thawed, washed in RPMI 1640 (Life Technologies) and allowed to acclimatise to a 37° C./5% $CO_2$ environment. During this period combinations of bispecific, bivalent or mixtures of antibodies were created by diluting equimolar (200 nM) quantities of Fab'-X (Fab-scFv) and Fab'-Y (Fab-peptide) with antigen specificity for the cell surface proteins CD45 and CD79b in RPMI 1640 containing 10% fetal bovine serum, 50 units/mL Penicillin, 50 µg/mL Streptomycin and 2 mM L-glutamine. These combinations of 3 different CD79b Fab-Ys and 2 different CD45 Fab-Xs are shown in Table 13.

TABLE 13

Grid of bispecific proteins with specificity for CD45 and CD79b.

| (A-X) | (B-Y) Fab B | | |
|---|---|---|---|
| Fab A | CD79-Y VR4447 | CD79-Y VR4450 | CD79b-y VR4246 |
| CD45-X VR4131 | CD45-X:Y-CD79b | CD45-X:Y-CD79b | CD45-X:Y-CD79b |
| CD45X VR4248 | CD45-X:Y-CD79b | CD45-X:Y-CD79b | CD45-X:Y-CD79b | where X is a scFv (52SR4) and Y is a peptide (GCN4)

FabA-X and FabB-Y were incubated together for 60 minutes (in a 37° C./5% $CO_2$ environment) before mixing with $2.5 \times 10^5$ PBMC in V bottomed 96 well plates. PBMC plus FabA-X and/or FabB-Y combinations were then incubated together for a further 90 minutes. After this time B cells were activated by the addition of 12.5 μg/mL of goat $F(ab')_2$ anti-human IgM (Southern Biotechnology) for 10 minutes at 37° C. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in flow buffer (PBS+1% BSA+0.1% $NaN_{3+2}$ mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences), and an anti-phospho PLCγ2 antibody that recognises a modified tyrosine residue at position 759. Plates were then resuspended and incubated for 1 hour at room temperature in the dark. After this time plates were washed a further two times and resuspended in 40 μl of flow buffer. Cellular expression of CD20 and PLCγ2 was measured using an Intellicyt HTFC™ flow cytometer.

Using the data analysis software package Forecyt™ (Intellicyt) B cells were identified as distinct from other cell populations and the geometric mean of PLCγ2 levels were calculated for each well. All data was then expressed as the percentage inhibition of the maximal response (anti-IgM only) minus the background (cells only).

As can be seen in FIG. 38 the data shows that the combination of CD45 with CD79b with different antibody V regions can inhibit phospho-PLCγ2 expression in B cells stimulated with anti-IgM.

Example 16—Grid Screening of Large Panels as Previously Described in Example 7 Results The percentage inhibition of the induction of phosphorylation of BCR signalling cascade proteins by each Fab-Kd-Fab [i.e. A-X:Y-B where A and B are Fab fragments] combination was calculated, in this example looking for new combinations of antigens that inhibit B cell function, the criteria for a positive combination was set as at least 30% inhibition of at least two phospho-readouts by at least one combination of V regions. According to this threshold 11 new antigen pair combinations out of 315 examined met the required criteria. This represents a 3.5% hit rate demonstrating the importance of screening large numbers of combinations to find those of desired activity and how rare the activity of the combination of CD79b and CD45 is.

FIGS. 10-12 show the data for the antigen grid cross specificities. Values are percentage inhibition (negative value for activation) of phosphorlyation of Syk, PLCγ2 & AKT respectively and represent the mean of multiple V-region combinations evaluated. 315 different antigen combinations were tested and as can be seen the effect on BCR signalling by different combinations of antibody varied significantly from strong inhibition e.g. antigen 2 (CD79b) on Fab-X combined with antigen 4 (CD45) on Fab-Y (70.4% inhibition of phospho Syk FIG. 10) to activation e.g antigen 6 on X and antigen 11 on Y (minus 118.10% phospho Syk FIG. 10).

Figure 39:
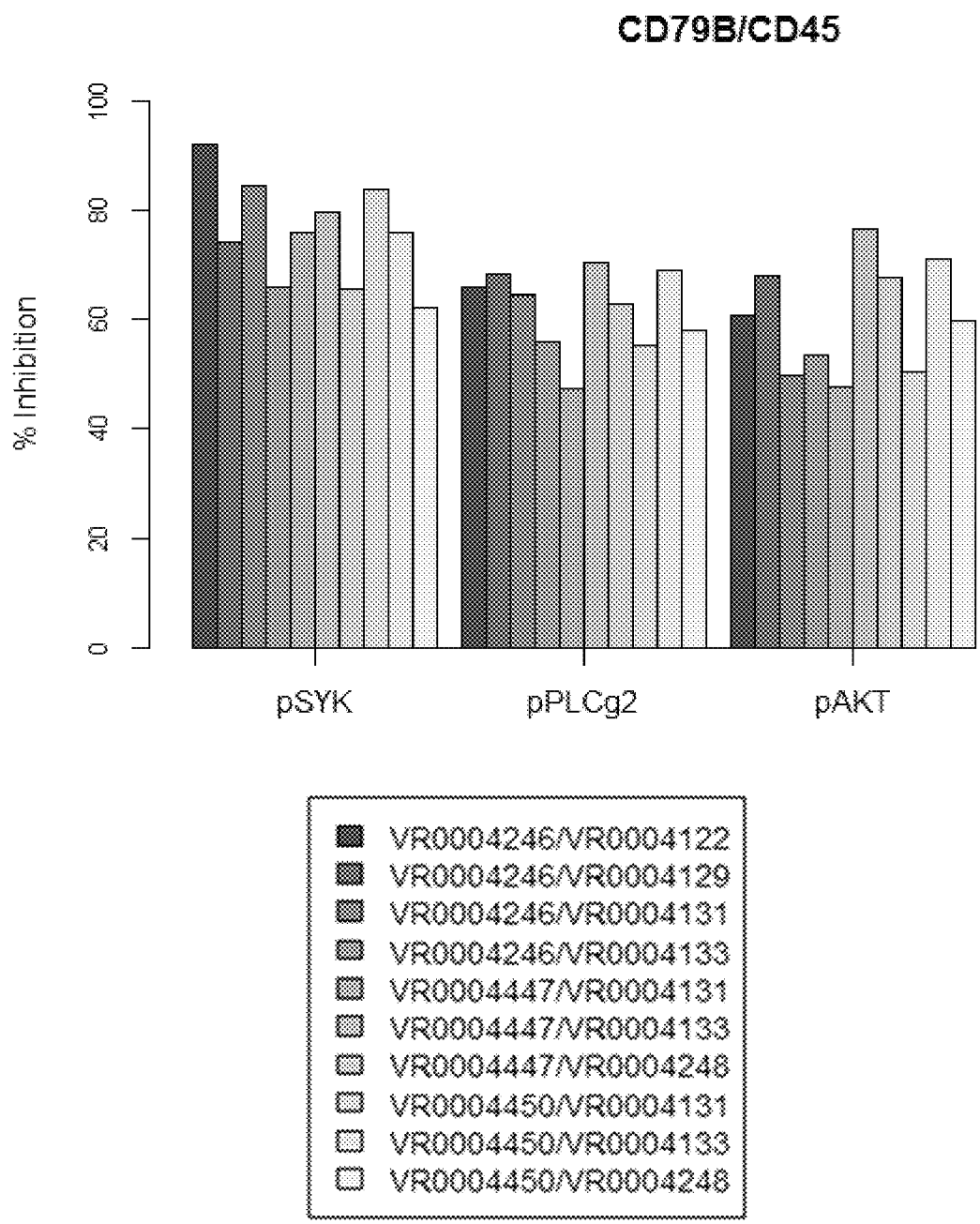
Figure 40:
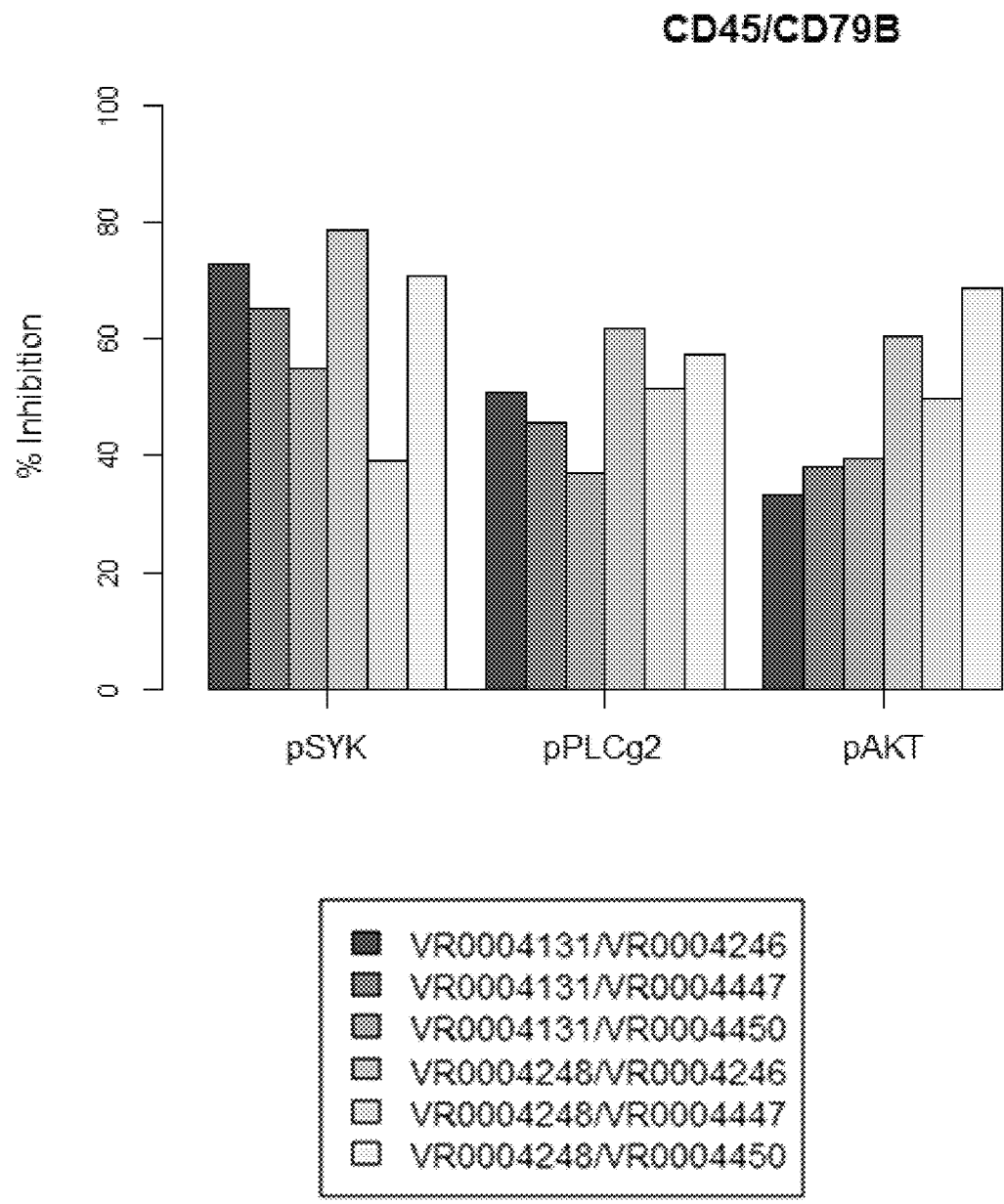
Figure 41:
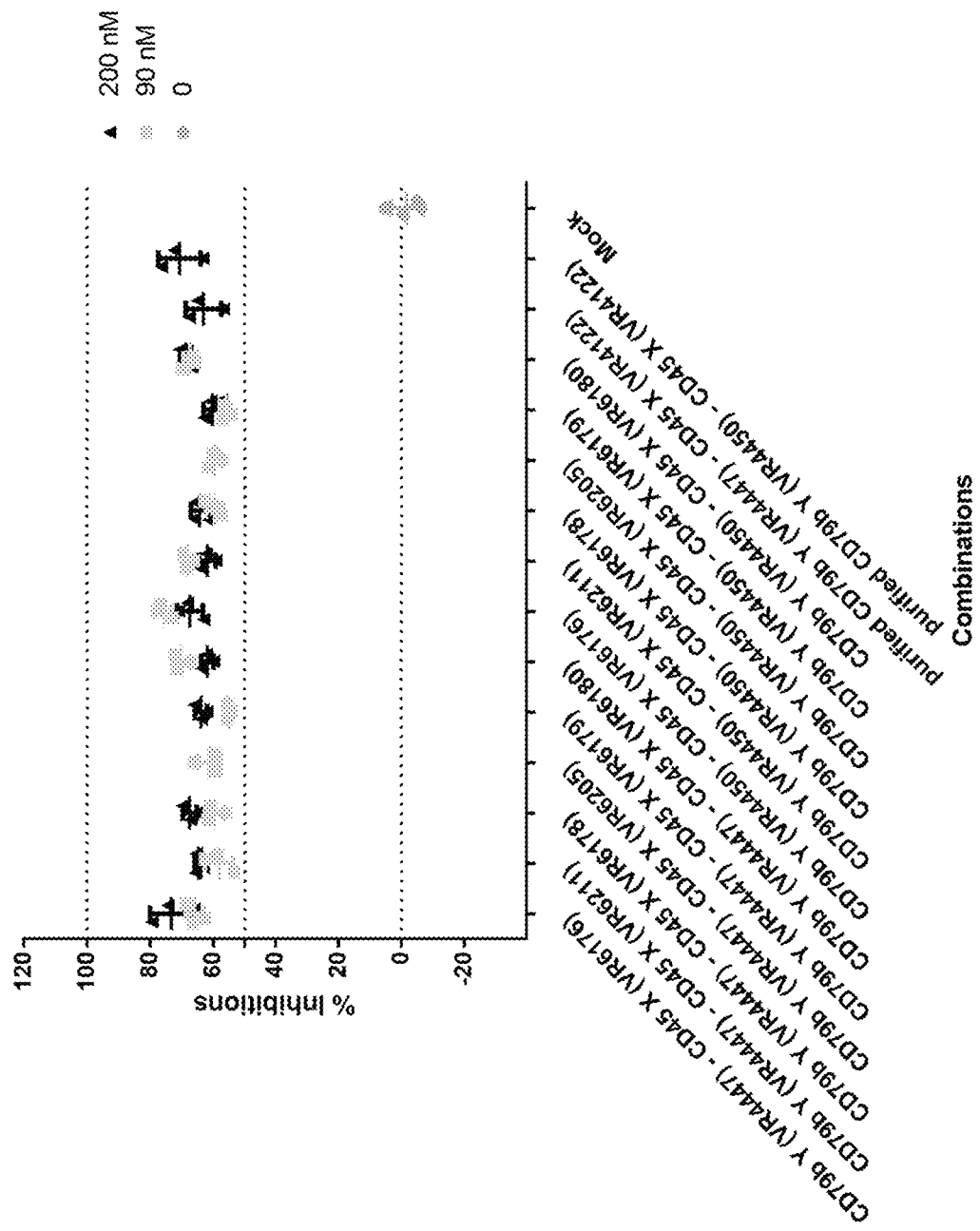
Figure 42:
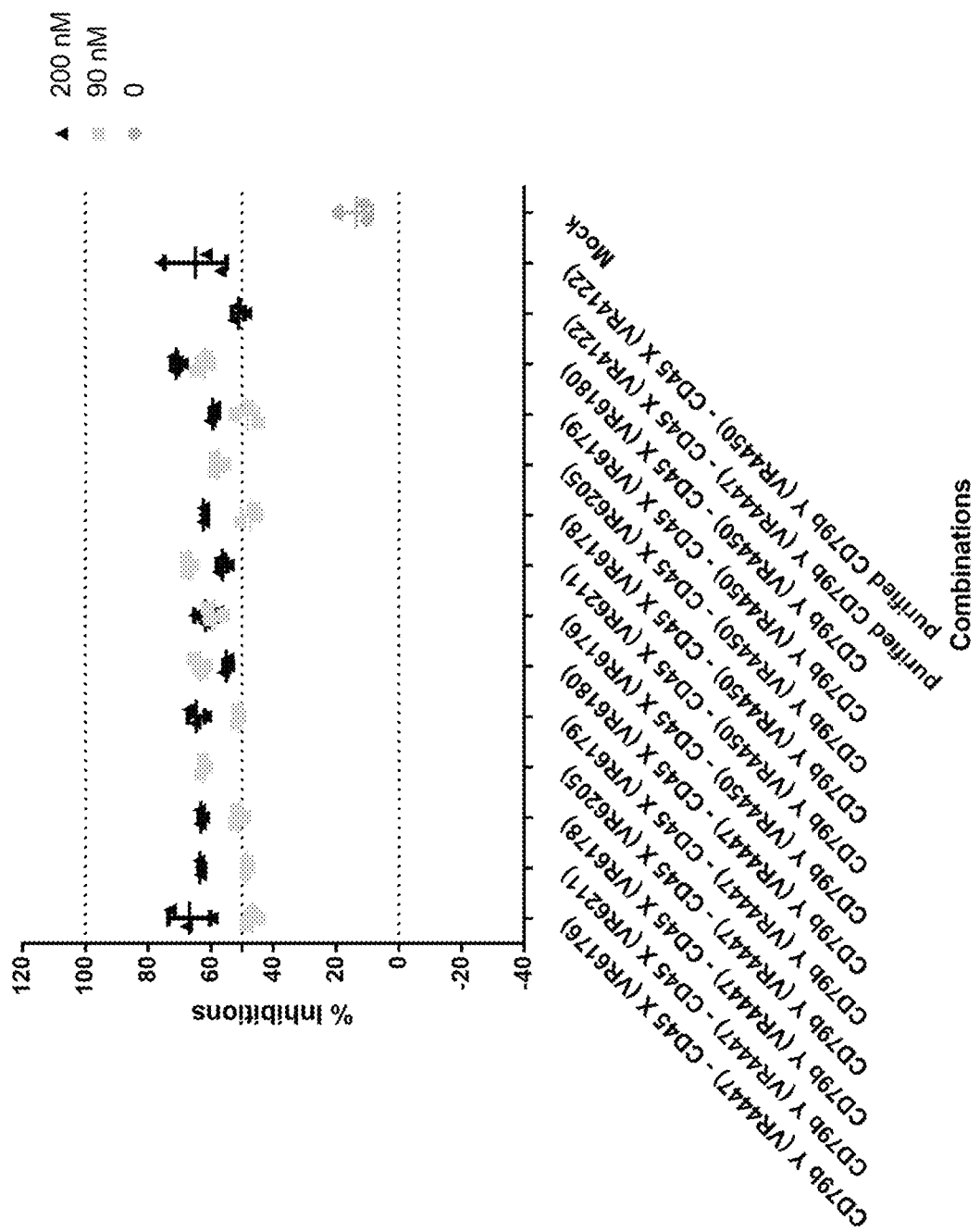
Figure 43:
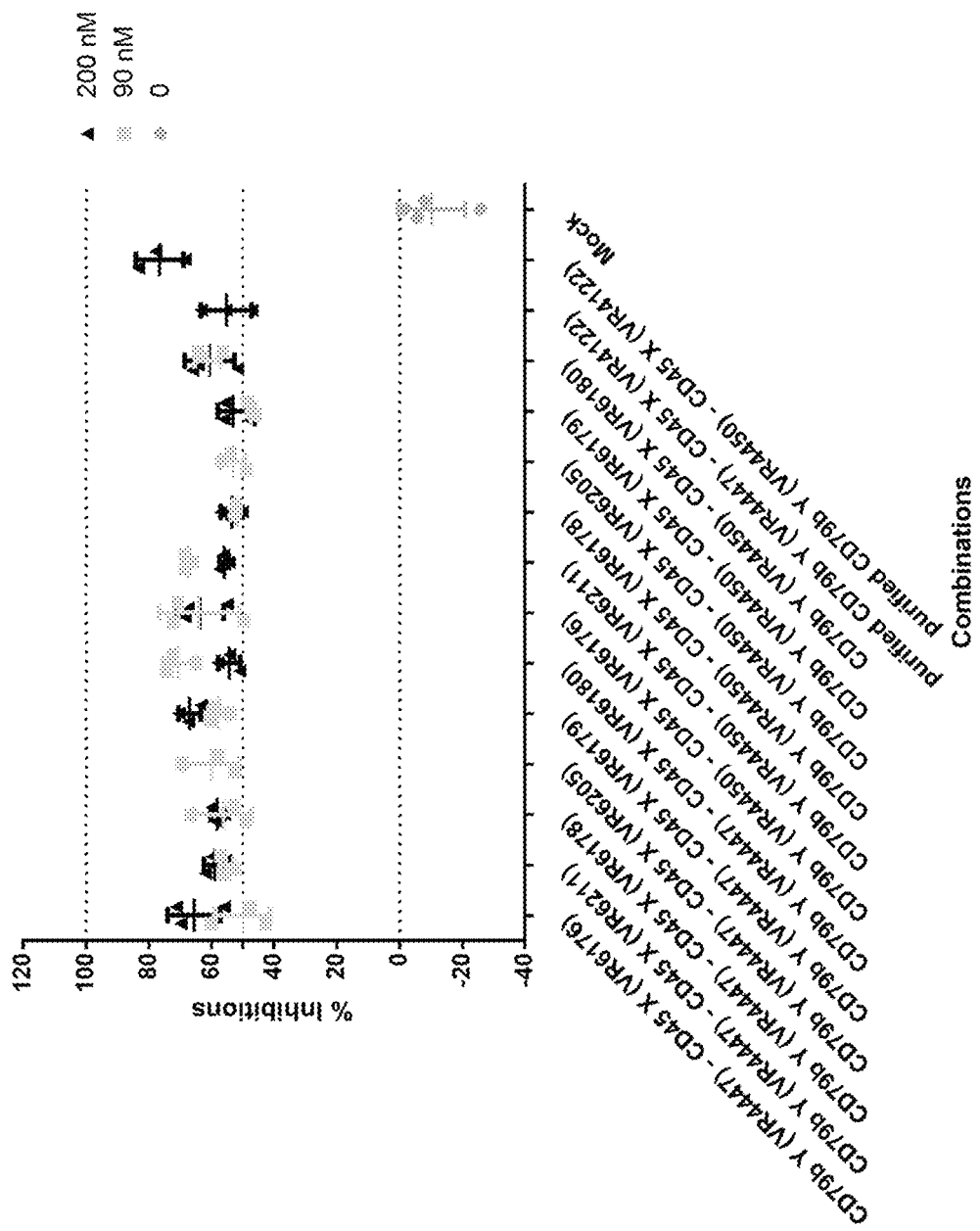
Figure 44:
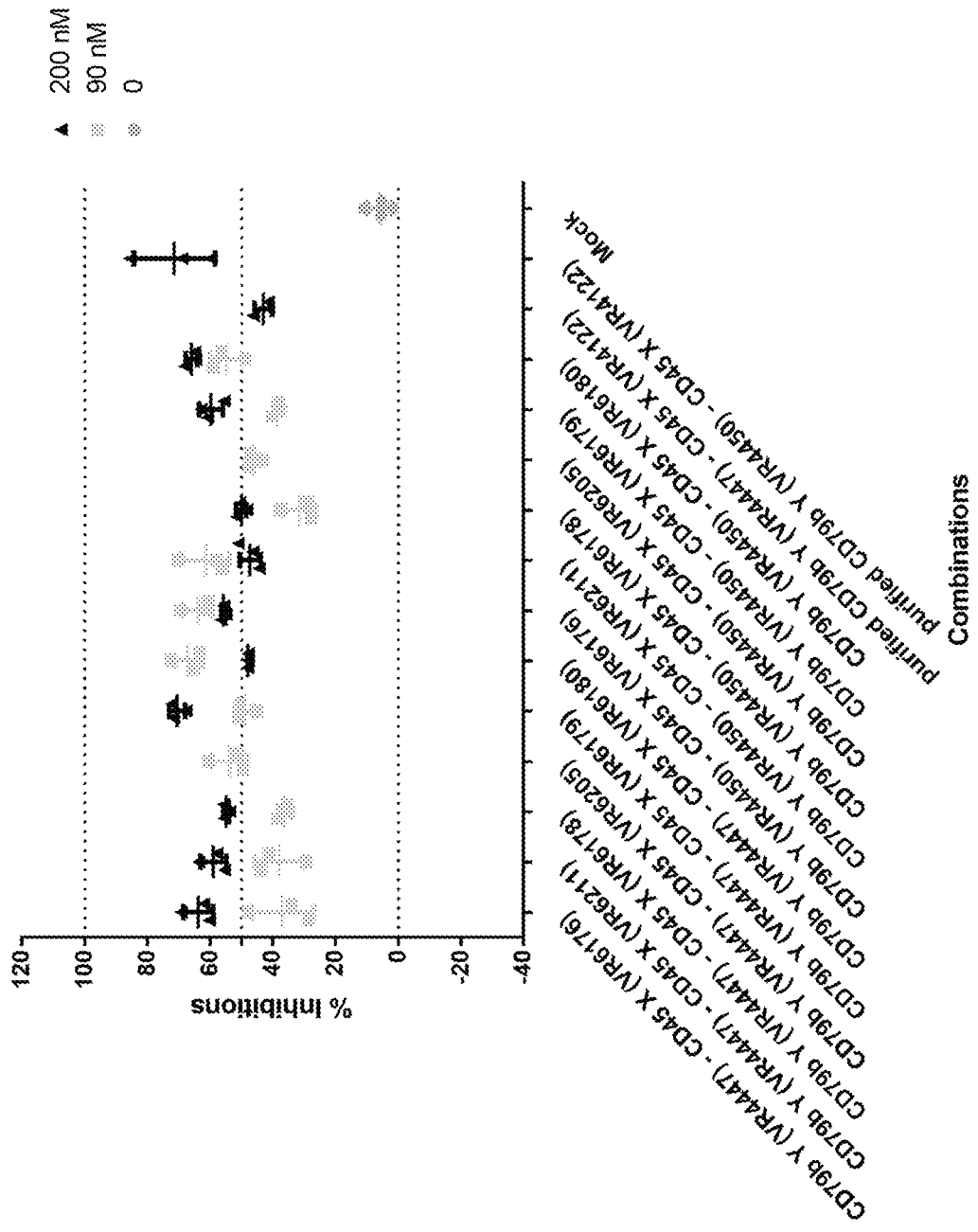
Figure 45:
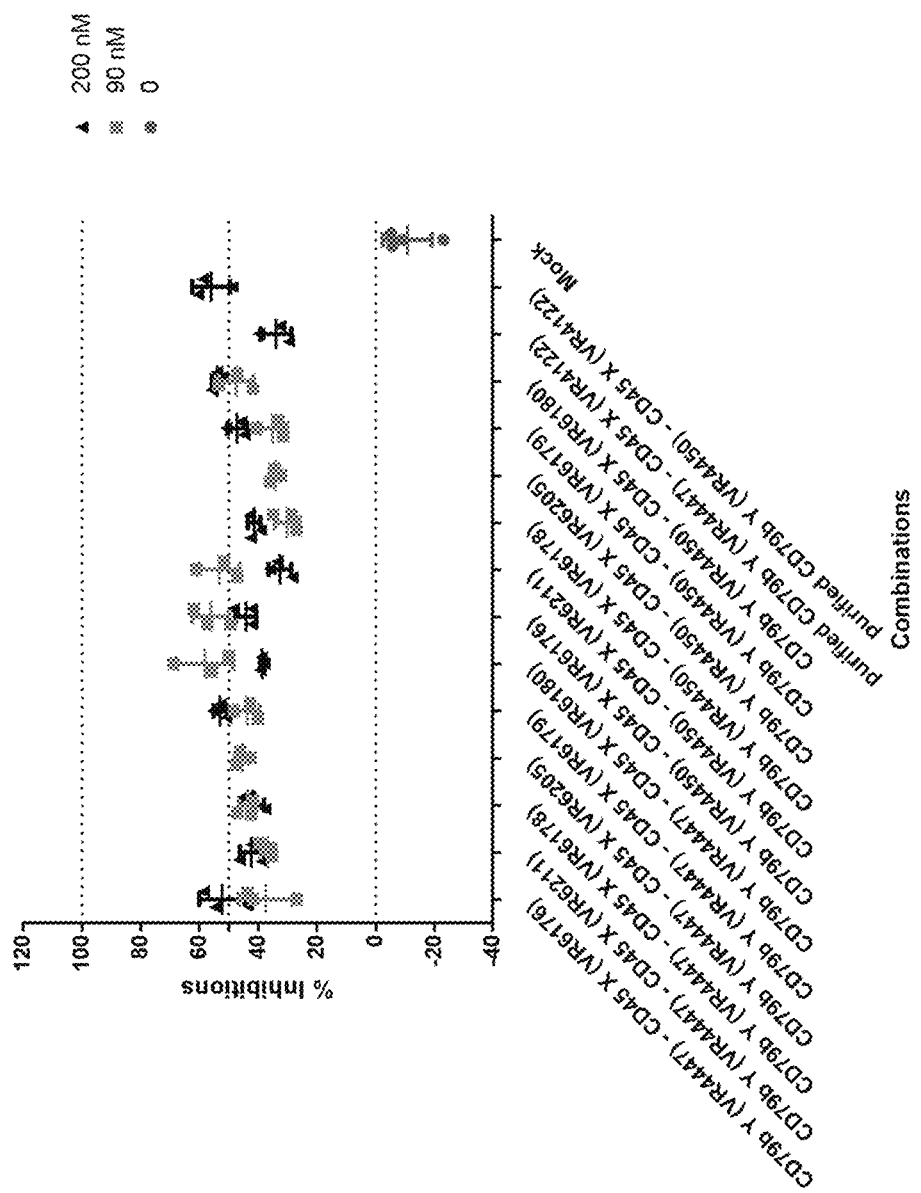
Figure 46:
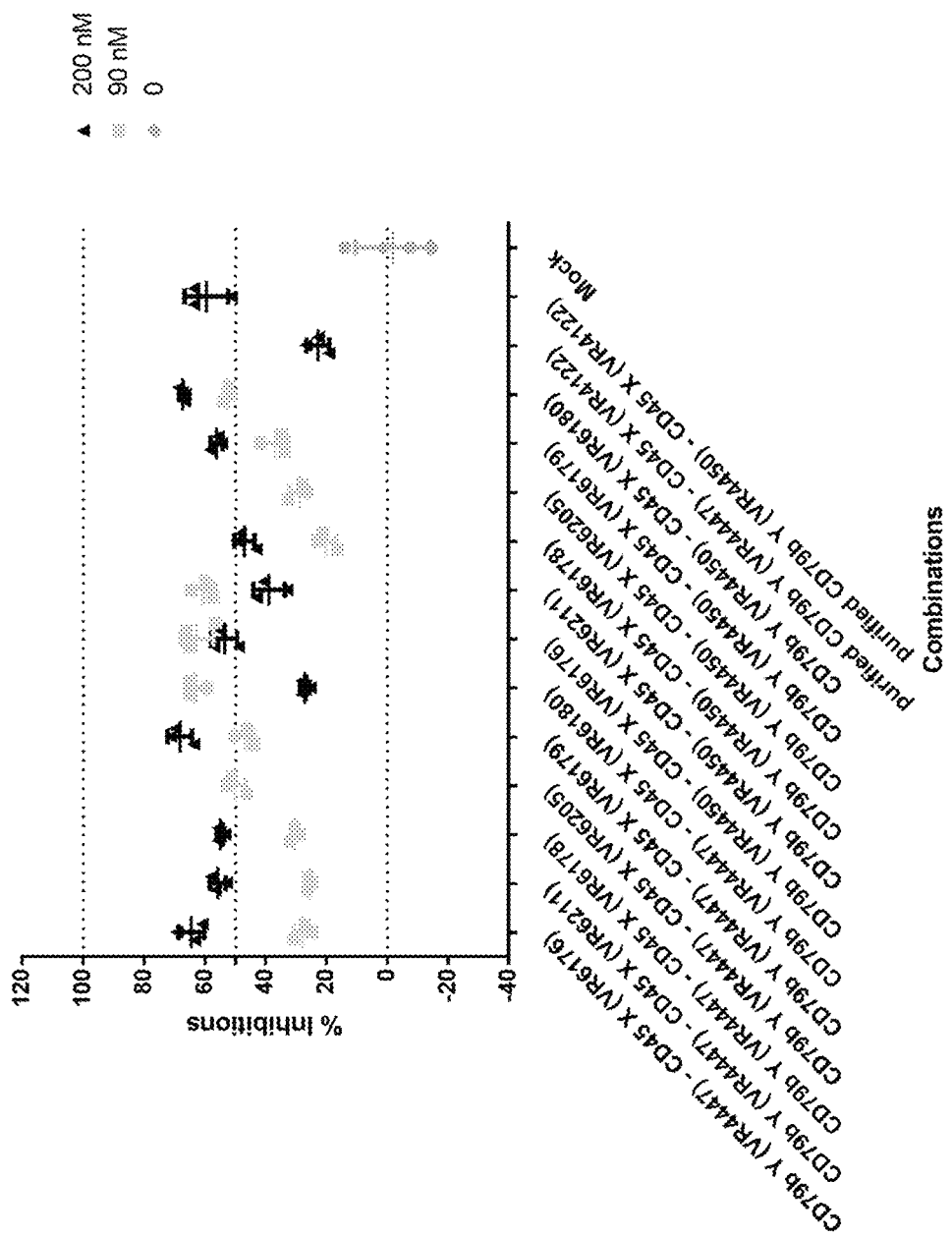

Each data point representing the mean % values represented in FIGS. 10-12 is shown for antigen combination 2 (CD79b) on Fab-X and antigen 4 (CD45) on Fab-Y in FIG. 39. In this case, 10 different combinations of different antibody V regions were evaluated. The same antigen combination but in alternative orientation, i.e. antigen 2 (CD79b) on Fab-Y and antigen 4 (CD45) on Fab-X is shown in FIG. 40. In this case, 6 different combinations of different antibody V regions were evaluated. Again, all V regions show inhibition but optimal V region combinations can be identified and selected using the method.

Example 17—Screening of Transiently Expressed V-Regions to Antigen CD45 as Fab-X with Purified Anti-CD79b Fab-Y in Heterodimerically Tethered Protein Complexes to Select Optimal Anti-CD45 Antibody V-Regions Introduction:

New V-regions to CD45 that inhibit B cell signalling as a bispecific antibody in combination with CD79b specific V regions were identified using grid screening of heterodimerically tethered protein complexes. The CD45 V regions were expressed transiently as Fab-X and combined with purified anti-CD79b Fab-Y. The inhibition of activation of B cell signalling was measured to select the most potent anti-CD45 and anti-CD79b V regions.

The preparation of antigen expressing cells and immunisation of rabbits was carried out in the same way as described in Example 6.

Antibody Discovery:

B cell cultures were prepared in the same way as described in Example 6.

The screening of antigen-specific antibodies in B cell culture supernatants and the deconvolution step for identification of antigen specific B cells was determined in the same way as Example 6.

Antibody variable region genes were recovered from single cells by reverse transcription (RT)-PCR using heavy and light chain variable region-specific primers. Two rounds of PCR were performed, with the nested 2° PCR incorporating restriction sites at the 3' and 5' ends allowing cloning of the variable region into mouse Fab-X and mouse kappa (VL) mammalian expression vector. These vectors were then co-transfected in HEK-293 cells using 293Fectin (Life Technologies) or in Expi293 cells using Expifectamine (Life Technologies) and left to express for 6 days. Supernatants were tested in a homogeneous fluorescence-based binding assay on HEK293 cells transfected with antigen and Superavidin™ beads (Bangs Laboratories) coated with recombinant protein or antigen transfected HEK cells. This was done to confirm the specificity of the cloned antibodies.

In addition to the Fab-X transient supernatants, negative control Mock supernatants were prepared in the same way using an irrelevant control DNA.

The expression levels of Fab-X were determined by Protein G-HPLC.

Production of Purified Fab-X and Fab-Y:

Purified Fab-X and Fab-Y was prepared using the same method described in Example 6.

PhosFlow Assay:

CD79b-specific Fab-Y and CD45-specific Fab-X, either purified or in transient supernatant, were incubated together for 60 minutes (in a 37° C. & 5% $CO_2$ environment) at equimolar concentration of 200 nM and 90 nM. A mock supernatant was also included neat. In V-bottomed 96 well plates, $5.0 \times 10^4$ PBMC were added to wells, to which were added titrated Fab-X and Fab-Y combinations or mock supernatant. The combinations and cells were then incubated together for a further 90 minutes. After this time B cells were activated by the addition of 25 µg/mL of goat F(ab')$_2$ anti-human IgM (Southern Biotechnology) for 15 minutes at 37° C. plus 5% $CO_2$. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in FACS buffer (PBS+1% BSA+0.01% $NaN_{3+2}$ mM EDTA) and washed once more. Cells were then resuspended in ice cold Perm Buffer III (BD Biosciences) for 30 minutes before being washed twice in flow buffer. Cells were then stained as described in Example 6, except that instead of 3 different antibody cocktails, only one cocktail was used with the same assay concentrations and incubation conditions as described for antibody cocktail A in Example 6.

Antibody Cocktail=1:3CD20PerCp-Cy5.5+1: 5PLCγ2AF88+1:10Akt AF647+1:5p38MAPK PE (diluted in FACS buffer).

Results

As can be seen in FIGS. 41 to 46, the data shows that the combination of different transiently expressed antigen CD45 V regions in Fab-X with 2 different purified antigen CD79b V regions (VR447 and VR4450) in Fab-Y can inhibit B cell activation (as measured by inhibition of PLCγ2, p38 and Akt) to different levels and screening in a bispecific format therefore facilitates selection of optimal V region combinations. Combinations with transient Fab-X are compared to a reference combination with a purified CD45 Fab-X (VR4122).

Example 18—Effect of Co-Targeting the Antigen CD79b Plus Antigen CD45 on Memory B Cell Function Using Molecularly Linked Bispecific Bybes with or without Further Addition of an Anti-Albumin Introduction:

To check that targeting CD79b/CD45 has a functional effect on B cells in long term culture, IgG production from B cells in a mixed PBMC culture was measured. The measurement of specific antibodies to the recall antigen tetanus toxoid provides a read out of memory B cell function.

Antigen CD79b specificity (VR4447) and antigen CD45 specificity (VR4248 and VR4133) were generated in a BYbe format with or without addition of an anti-albumin fragment (VR0645). The anti-albumin antibody fragment was fused to the light chain of the antigen CD45 Fab of the BYbe format as described in Example 8.

Description of constructs used in this experiment.

| Construct Name | Fab Specificity | Heavy Chain scFv | Light Chain sFv |
|---|---|---|---|
| VR4447/VR4248 BYbe | Antigen CD79b | Antigen CD45 | None |
| VR4447/VR4248/VR645 BYbe/Albumin | Antigen CD79b | Antigen CD45 | Albumin |
| VR4447/VR4133 BYbe | Antigen CD79b | Antigen CD45 | None |
| VR4447/VR4133/VR645 BYbe/Albumin | Antigen CD79b | Antigen CD45 | Albumin |

Methods

Purification of BYbes With/Without Anti-Albumin Additional Specificity

The BYbe (Fab-dsscFv [scFv off C-terminus of Fab heavy chain]) and BYbe with anti-albimin (Fab-2xdsscFv [scFvs off C-terminus of Fab heavy chain and light chain]) formats were purified as follows. Clarified cell culture supernatants from standard expiHEK or CHO expression were 0.22 µm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH 2.7. The elution was followed by absorbance at 280 nm, the elution peak collected, and then neutralised with $\frac{1}{25}^{th}$ volume of 2 M Tris/HCl pH8.5. The neutralised samples were concentrated using Amicon Ultra-15 concentrators with either a 10 kDa or 30 kDa molecular weight cut off membrane and centrifugation at 4000×g in a swing out rotor. Concentrated samples were applied to either a XK16/60 or XK26/60 Superdex 200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 µm, 7.8×300 mm column developed with an isocratic gradient of 0.2 M phosphate, pH 7.0 at 1 ml/min, with detection by absorbance at 280 nm. Selected monomer fractions were pooled and concentrated to >1 mg/ml using an Amicon Ultra-15 concentrator with a 10 kDa or 30 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 µm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's EndoSafe® Portable Test System with Limulus Amebocyte Lysate (LAL) test cartridges.

Activation of B Cells and Measurement of Tetanus Toxoid Specific IgG

Human PBMCs were stimulated with 500 ng/ml CD40L, 1 µg/ml CpG and 50 ng/ml IL-21 in 1640 media plus 10% foetal bovine serum and 2 mM Glutamax (R10 medium) for 6 days. Constructs of purified protein were added at a final concentration of 100 nM at day 0 and remained in the culture medium for the duration of the assay. After 6 days the supernatants were harvested and the amount of tetanus toxoid specific IgG was detected by ELISA. Briefly, Maxisorp half-well ELISA plates (Nunc) were coated with 10 ug/ml tetanus toxoid in PBS overnight at 4° C. The plates were then blocked in 5% Milk—in PBS containing 0.05% Tween 20 for 2 hours. The supernatants were diluted and then added for 2 hours at room temperature. The plates were washed with PBS-0.05% Tween20 and tetanus bound antibody was detected using a peroxidase-goat anti-human IgG(H+L) diluted to 1 ug/ml in 5% milk-PBS 0.05% Tween 20. Plates were developed using TMB substrate solution (KPL) and absorbance was measured at 450 nM using a Synergy 2 micro-plate reader (Biotek). Data was exported to Excel and percentage inhibition was calculated relative to cells cultured without test antibodies. The data was then imported into Graphpad Prism® and plotted as bar charts.

Figure 47:
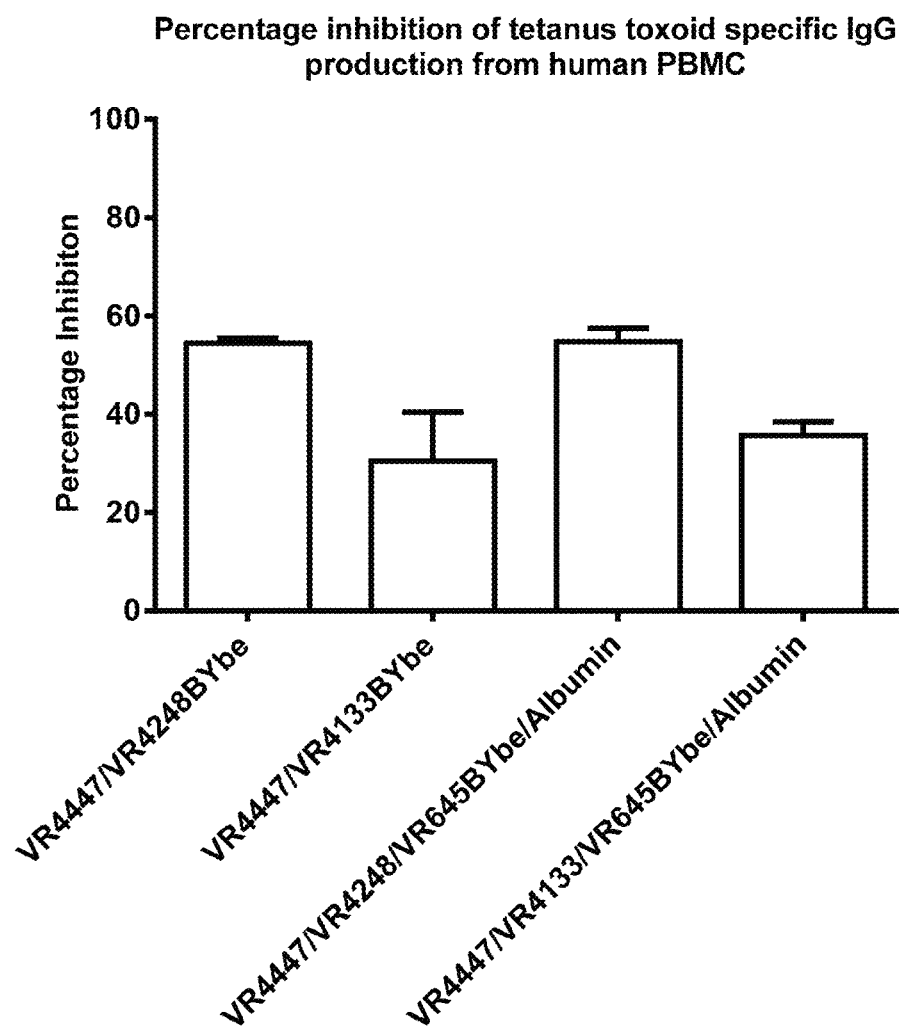

FIG. 47 shows the inhibition of tetanus toxoid IgG production from PBMCs cultured with VR4447/VR4248 BYbe, VR4447/VR4133 BYbe, VR4447/VR4248/VR645 BYbe/Albumin and VR4447/VR4133/VR645 BYbe/Albumin. Data shown is from a single donor.

Example 19—Humanisation Method

Humanised versions of the antibodies obtained in the previous examples and provided in FIG. 51 herein were designed by grafting the CDRs from the rabbit antibody V-regions onto human germline antibody V-region frameworks. In order to improve the likelihood of recovering the activity of the antibody, a number of framework residues from the rabbit V-regions were also retained in the designed humanised sequences. These residues were selected using the protocol outlined by Adair et al. (1991) (Humanised antibodies. WO91/09967). The CDRs grafted from the donor to the acceptor sequence are as defined by Kabat (Kabat et al., 1987), with the exception of CDRH1 where the combined Chothia/Kabat definition is used (see Adair et al., 1991 Humanised antibodies. WO91/09967). Commonly the VH genes of rabbit antibodies are shorter than the selected human VH acceptor genes. When aligned with the human acceptor sequences, framework 1 of the VH regions of rabbit antibodies typically lack the N-terminal residue, which is retained in the humanised antibody. Framework 3 of the rabbit antibody VH regions also typically lack one or two residues (75, or 75 and 76) in the loop between beta sheet strands D and E: in the humanised antibodies the gap is filled with the corresponding residues from the selected human acceptor sequence.

The humanised sequences are provided in FIG. 51 and donor residues indicated in bold and underlined. Variant CDR sequences are also provided.

Certain grafts for antibody 4450 were expressed and tested, see Example 21.

CD79 Ab 4447

Human V-region IGKV1D-13 plus JK4 J-region (IMGT, http://www.imgt.org/) was chosen as the acceptor for antibody 4447 light chain CDRs. In addition to the CDRs, one or more of the following framework residues from the 4447 VK gene (donor residues) may be retained at positions 2, 3, 36, 46, 49 and 70 (Kabat numbering): Glutamine (Q2), Valine (V3), Leucine (L36), Glutamine (Q46), Histidine (H49) and Glutamine (Q70), respectively. In some cases, CDRL3 may be mutated to remove a pair of Cysteine residues (CDRL3 variant 1 or CDRL3 may be mutated to remove only one cysteine residue CDRL3 variants 2 and 3).

Human V-region IGHV3-48 plus JH4 J-region (IMGT, http://www.imgt.org/) was chosen as an acceptor for the heavy chain CDRs of antibody 4447. In addition to the CDRs, one or more of the following framework residues from the 4447 VH gene (donor residues) may be retained at positions 24, 48, 49, 71, 73, and 78 (Kabat numbering): Valine (V24), Isoleucine (I48), Glycine (G49), Lysine (K71), Serine (S73) and Valine (V78), respectively. Human V-region IGHV4-59 plus JH4 J-region (IMGT, http://www.imgt.org/) was chosen as an alternative acceptor for the heavy chain CDRs of antibody 4447. In addition to the CDRs, one or more of the following framework residues from the 4447 VH gene (donor residues) may be retained at positions 37, 67, 71, 73 and 78 (Kabat numbering): Valine (V37), Phenylalanine (F67), Lysine (K71), Serine (S73) and Valine (V78), respectively. The Glutamine residue at position 1 of the human framework was replaced with Glutamic acid (E1) to afford the expression and purification of a homogeneous product: the conversion of Glutamine to pyro-Glutamate at the N-terminus of antibodies and antibody fragments is widely reported.

CD79 Ab 4450

Human V-region IGKV1-6 plus JK4 J-region (IMGT, http://www.imgt.org/) was chosen as the acceptor for antibody 4450 light chain CDRs. In addition to the CDRs, one or more of the following framework residues from the 4450 VK gene (donor residues) may be retained at positions 3 and 70 (Kabat numbering): Aspartic acid (D3) and Glutamine (Q70), respectively. In some cases, CDRL3 may be mutated to modify a potential aspartate isomerisation site (CDRL3 variants 1-3).

Human V-region IGHV3-66 plus JH4 J-region (IMGT, http://www.imgt.org/) was chosen as an acceptor for the heavy chain CDRs of antibody 4450. In addition to the CDRs, one or more of the following framework residues from the 4450 VH gene (donor residues) may be retained at positions 24, 48, 49, 73 and 78 (Kabat numbering): Valine (V24), Isoleucine (I48), Glycine (G49), Serine (S73) and Valine (V78), respectively.

Human V-region IGHV4-59 plus JH4 J-region (IMGT, http://www.imgt.org/) was chosen as an alternative acceptor for the heavy chain CDRs of antibody 4450. In addition to the CDRs, one or more of the following framework residues from the 4450 VH gene (donor residues) may be retained at positions 37, 67, 71, 73 and 78 (Kabat numbering): Valine (V37), Phenylalanine (F67), Arginine (R71), Serine (S73) and Valine (V78), respectively. The Glutamine residue at position 1 of the human framework was replaced with Glutamic acid (E1) to afford the expression and purification of a homogeneous product.

CD22 Ab 4120

Human V-region IGKV1D-13 plus JK4J-region (IMGT, http://www.imgt.org/) was chosen as the acceptor for antibody 4120 light chain CDRs. In addition to the CDRs, one or more of the following framework residues from the 4120 VK gene (donor residues) may be retained at positions 2 and 3 (Kabat numbering): Phenylalanine (F2) and Glutamic acid (E3), respectively.

Human V-region IGHV3-33 plus JH4 J-region (IMGT, http://www.imgt.org/) was chosen as an acceptor for the heavy chain CDRs of antibody 4120. In addition to the CDRs, one or more of the following framework residues from the 4120 VH gene (donor residues) may be retained at positions 11, 48, 71, 73, 76 and 78 (Kabat numbering): Leucine (L11), Isoleucine (I48), Lysine (K71), Serine (S73), Threonine (T76) and Valine (V78), respectively. The Glutamine residue at position 1 of the human framework was replaced with Glutamic acid (E1) to afford the expression and purification of a homogeneous product.

In some cases, CDRH1 and CDRH2 may be mutated to remove Cysteine residues (CDRH1 variant and CDRH2 variant, respectively).

Human V-region IGHV4-38-2 plus JH4 J-region (IMGT, http://www.imgt.org/) was chosen as an alternative acceptor for the heavy chain CDRs of antibody 4120. In addition to the CDRs, one or more of the following framework residues from the 4120 VH gene (donor residues) may be retained at positions 24, 37, 49, 67, 71, 73, 76 and 78 (Kabat numbering): Alanine (A24), Valine (V37), Alanine (A49), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product.

In some cases, CDRH1 and CDRH2 may be mutated to remove Cysteine residues (CDRH1 variant and CDRH2 variant, respectively).

CD22 Ab 4126

Human V-region IGKV1-5 plus JK4 J-region (IMGT, http://www.imgt.org/) was chosen as the acceptor for antibody 4126 light chain CDRs. In addition to the CDRs, one or more of the following framework residues from the 4126 VK gene (donor residues) may be retained at positions 3 and 70 (Kabat numbering): Valine (V3) and Glutamine (Q70), respectively.

Human V-region IGHV3-7 plus JH4 J-region (IMGT, http://www.imgt.org/) was chosen as an acceptor for the heavy chain CDRs of antibody 4126. In addition to the CDRs, one or more of the following framework residues from the 4126 VH gene (donor residues) may be retained at positions 71, 73, 76 and 78 (Kabat numbering): Lysine (K71), Serine (S73), Threonine (T76) and Valine (V78), respectively.

In some cases, CDRH1, CDRH2 and CDRH3 may be mutated to remove Cysteine residues (CDRH1 variant, CDRH2 variant and CDRH3 variant, respectively).

Human V-region IGHV4-4 plus JH4 J-region (IMGT, http://www.imgt.org/) was chosen as an alternative acceptor for the heavy chain CDRs of antibody 4126. In addition to the CDRs, one or more of the following framework residues from the 4126 VH gene (donor residues) may be retained at positions 24, 48, 49, 67, 71, 73, 76 and 78 (Kabat numbering): Alanine (A24), Valine (V48), Alanine (A49), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product.

In some cases, CDRH1, CDRH2 and CDRH3 may be mutated to remove Cysteine residues (CDRH1 variant, CDRH2 variant and CDRH3 variant, respectively).

CD22 Ab 4127

Human V-region IGKV1-5 plus JK4 J-region (IMGT, http://www.imgt.org/) was chosen as the acceptor for antibody 4127 light chain CDRs. In addition to the CDRs, one or more of the following framework residues from the 4127 VK gene (donor residues) may be retained at positions 1, 3 and 70 (Kabat numbering): Alanine (A1), Valine (V3) and Glutamine (Q70), respectively. In some cases, CDRL3 may be mutated to modify potential Aspartic acid isomerisation sites (CDRL3 variants 1-15).

Human V-region IGHV3-9 plus JH4 J-region (IMGT, http://www.imgt.org/) was chosen as an acceptor for the heavy chain CDRs of antibody 4127. In addition to the CDRs, one or more of the following framework residues from the 4127 VH gene (donor residues) may be retained at positions 47, 48, 49, 71, 73, 76, 78 and 94 (Kabat numbering): Leucine (L47), Isoleucine (I48), Glycine (G49), Lysine (K71), Serine (S73), Threonine (T76), Valine (V78) and Arginine (R94), respectively.

In some cases, CDRH1 and CDRH2 may be mutated to remove Cysteine residues (CDRH1 variant and CDRH2 variant, respectively).

Human V-region IGHV4-38-2 plus JH4 J-region (IMGT, http://www.imgt.org/) was chosen as an alternative acceptor for the heavy chain CDRs of antibody 4127. In addition to the CDRs, one or more of the following framework residues from the 4127 VH gene (donor residues) may be retained at positions 24, 37, 47, 67, 71, 73, 76 and 78 (Kabat numbering): Alanine (A24), Valine (V37), Leucine (L47), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

CD22 Ab 4128

Human V-region IGKV1-5 plus JK4 J-region (IMGT, http://www.imgt.org/) was chosen as the acceptor for antibody 4128 light chain CDRs. In addition to the CDRs, one or more of the following framework residues from the 4128 VK gene (donor residues) may be retained at positions 3, 36, 63, 65, 66 and 71 (Kabat numbering): Valine (V3), Phenylalanine (F36), Lysine (K63), Aspartic acid (D65), Arginine (R66) and Tyrosine (Y71), respectively.

Human V-region IGHV3-33 plus JH4 J-region (IMGT, http://www.imgt.org/) was chosen as an acceptor for the heavy chain CDRs of antibody 4128. In addition to the CDRs, one or more of the following framework residues from the 4128 VH gene (donor residues) may be retained at positions 11, 23, 24, 48, 71, 73, 76 and 78 (Kabat numbering): Leucine (L11), Lysine (K23), Glycine (G24), Isoleucine (I48), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

Human V-region IGHV4-59 plus JH4 J-region (IMGT, http://www.imgt.org/) was chosen as an alternative acceptor for the heavy chain CDRs of antibody 4128. In addition to the CDRs, one or more of the following framework residues from the 4128 VH gene (donor residues) may be retained at positions 23, 24, 37, 49, 67, 71, 73, 76 and 78 (Kabat numbering): Lysine (K23), Glycine (G24), Valine (37), Alanine (A49), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

CD22 Ab 4130

Human V-region IGKV1-9 plus JK4 J-region (IMGT, http://www.imgt.org/) was chosen as the acceptor for antibody 4130 light chain CDRs. In addition to the CDRs, one or more of the following framework residues from the 4130 VK gene (donor residues) may be retained at positions 1, 2 and 3 (Kabat numbering): Alanine (A1), Alanine (A2) and Valine (V3), respectively.

Human V-region IGHV3-66 plus JH4 J-region (IMGT, http://www.imgt.org/) was chosen as an acceptor for the heavy chain CDRs of antibody 4130. In addition to the CDRs, one or more of the following framework residues from the 4130 VH gene (donor residues) may be retained at positions 48, 49, 67, 71, 73, 76 and 78 (Kabat numbering): Isoleucine (I48), Glycine (G49), Valine (V67), Lysine (K71), Serine (S73), Threonine (T76) and Valine (V78), respectively. In some cases, CDRH2 may be mutated to remove a Cysteine residue and/or modify a potential Asparagine deamidation site (CDRH2 variants 1-5). CDRH3 may also be mutated to modify a potential Asparagine deamidation site (CDRH3 variants 1-2).

Human V-region IGHV4-4 plus JH4 J-region (IMGT, http://www.imgt.org/) was chosen as an alternative acceptor for the heavy chain CDRs of antibody 4130. In addition to the CDRs, one or more of the following framework residues from the 4130 VH gene (donor residues) may be retained at positions 24, 71, 73, 76 and 78 (Kabat numbering): Alanine (A24), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH2 may be mutated to remove a Cysteine residue and/or modify a potential Asparagine deamidation site (CDRH2 variants 1-5). CDRH3 may also be mutated to modify a potential Asparagine deamidation site (CDRH3 variants 1-2).

CD22 Ab 4132

Human V-region IGKV1-5 plus JK4 J-region (IMGT, http://www.imgt.org/) was chosen as the acceptor for antibody 4132 light chain CDRs. In addition to the CDRs, one or more of the following framework residues from the 4132 VK gene (donor residues) may be retained at positions 3 and 71 (Kabat numbering): Valine (V3) and Tyrosine (Y71), respectively. Human V-region IGHV3-21 plus JH4 J-region (IMGT, http://www.imgt.org/) was chosen as an acceptor for the heavy chain CDRs of antibody 4132. In addition to the CDRs, one or more of the following framework residues from the 4132 VH gene (donor residues) may be retained at positions 48, 49, 71, 73, 76 and 78 (Kabat numbering): Serine (S48), Glycine (G49), Asparagine (N71), Serine (S73), Threonine (T76) and Valine (V78), respectively. In some cases, CDRH1 may be mutated to remove a Cysteine residue (CDRH1 variant). CDRH2 may also be mutated to remove a Cysteine residue and/or modify a potential Asparagine deamidation site (CDRH2 variants 1-5).

Human V-region IGHV4-4 plus JH4 J-region (IMGT, http://www.imgt.org/) was chosen as an alternative acceptor for the heavy chain CDRs of antibody 4132. In addition to the CDRs, one or more of the following framework residues from the 4132 VH gene (donor residues) may be retained at positions 24, 48, 67, 71, 73, 76 and 78 (Kabat numbering): Alanine (A24), Serine (S48), Phenylalanine (F67), Asparagine (N71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 may be mutated to remove a Cysteine residue (CDRH1 variant). CDRH2 may also be mutated to remove a Cysteine residue and/or modify a potential Asparagine deamidation site (CDRH2 variants 1-5).

CD45 Ab 4122

Human V-region IGKV1-5 plus JK4 J-region (IMGT, http://www.imgt.org/) was chosen as the acceptor for antibody 4122 light chain CDRs. In addition to the CDRs, the following framework residue from the 4122 VK gene (donor residue) may be retained at position 71 (Kabat numbering): Tyrosine (Y71). In some cases, CDRL3 may be mutated to modify a potential Aspartic acid isomerisation site (CDRL3 variants 1-2).

Human V-region IGHV3-7 plus JH2 J-region (IMGT, http://www.imgt.org/) was chosen as an acceptor for the heavy chain CDRs of antibody 4122. In addition to the CDRs, one or more of the following framework residues from the 4122 VH gene (donor residues) may be retained at positions 48, 71, 73, 76 and 78 (Kabat numbering): Isoleucine (I48), Lysine (K71), Serine (S73), Threonine (T76) and Valine (V78), respectively.

In some cases, CDRH1 may be mutated to remove a Cysteine residue (CDRH1 variant).

CDRH2 may also be mutated to remove a Cysteine residue and/or modify a potential Asparagine deamidation site (CDRH2 variants 1-7).

Human V-region IGHV2-70 plus JH-2 J-region (IMGT, http://www.imgt.org/) was chosen as an alternative acceptor for the heavy chain CDRs of antibody 4122. In addition to the CDRs, one or more of the following framework residues from the 4122 VH gene (donor residues) may be retained at positions 24, 37, 44, 48, 67, 73 and 76 (Kabat numbering): Alanine (A24), Valine (V37), Glycine (G44), Isoleucine (I48), Phenylalanine (F67), Serine (S73) and Threonine (T76), respectively. The Glutamine residue at position 1 of the human framework was replaced with Glutamic acid (E1) to afford the expression and purification of a homogeneous product. In some cases, CDRH1 may be mutated to remove a Cysteine residue (CDRH1 variant). CDRH2 may also be mutated to remove a Cysteine residue and/or modify a potential Asparagine deamidation site (CDRH2 variants 1-7).

CD45 Ab 4129

Human V-region IGKV1-5 plus JK4 J-region (IMGT, http://www.imgt.org/) was chosen as the acceptor for antibody 4129 light chain CDRs. In addition to the CDRs, the following framework residue from the 4129 VK gene (donor residue) may be retained at position 70 (Kabat numbering): Glutamine (Q70).

In some cases, CDRL3 may be mutated to modify a potential Aspartic acid isomerisation site (CDRL3 variants 1-2).

Human V-region IGHV3-7 plus JH-2 J-region (IMGT, http://www.imgt.org/) was chosen as an acceptor for the heavy chain CDRs of antibody 4129. In addition to the CDRs, one or more of the following framework residues from the 4129 VH gene (donor residues) may be retained at positions 48, 71, 73, 76 and 78 (Kabat numbering): Isoleucine (I48), Lysine (K71), Serine (S73), Threonine (T76) and Valine (V78), respectively.

In some cases, CDRH1 and CDRH2 may be mutated to remove Cysteine residues (CDRH1 variant and CDRH2 variant, respectively).

Human V-region IGHV2-70 plus JH-2 J-region (IMGT, http://www.imgt.org/) was chosen as an alternative acceptor for the heavy chain CDRs of antibody 4129. In addition to the CDRs, one or more of the following framework residues from the 4129 VH gene (donor residues) may be retained at positions 24, 37, 44, 48, 67, 73 and 76 (Kabat numbering): Alanine (A24), Valine (V37), Glycine (G44), Isoleucine (I48), Phenylalanine (F67), Serine (S73) and Threonine (T76), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

CD45 Ab 4131

Human V-region IGKV1-12 plus JK4 J-region (IMGT, http://www.imgt.org/) was chosen as the acceptor for antibody 4131 light chain CDRs. In addition to the CDRs, one or more of the following framework residues from the 4131 VK gene (donor residues) may be retained at positions 3 and 63 (Kabat numbering): Valine (V3) and Lysine (K63), respectively. In some cases, CDRL3 may be mutated to modify a potential Aspartic acid isomerisation site (CDRL3 variants 1-3).

Human V-region IGHV3-7 plus JH-2 J-region (IMGT, http://www.imgt.org/) was chosen as an acceptor for the heavy chain CDRs of antibody 4131. In addition to the CDRs, one or more of the following framework residues from the 4131 VH gene (donor residues) may be retained at positions 48, 69, 71, 73, 76 and 78 (Kabat numbering): Isoleucine (I48), Valine (V69), Glutamic acid (E71), Serine (S73), Threonine (T76), and Valine (V78), respectively. In some cases, CDRH2 may be mutated to remove a Cysteine residue (CDRH2 variant).

Human V-region IGHV4-31 plus JH-2 J-region (IMGT, http://www.imgt.org/) was chosen as an alternative acceptor for the heavy chain CDRs of antibody 4131. In addition to the CDRs, one or more of the following framework residues from the 4131 VH gene (donor residues) may be retained at positions 24, 37, 49, 67, 69, 71, 73, 76 and 78 (Kabat numbering): Alanine (A24), Valine (V37), Alanine (A49), Phenylalanine (F67), Valine (V69), Glutamic acid (E71), Serine (S73), Threonine (T76), and Valine (V78), respectively. The Glutamine residue at position 1 of the human framework was replaced with Glutamic acid (E1) to afford the expression and purification of a homogeneous product.

In some cases, CDRH2 may be mutated to remove a Cysteine residue (CDRH2 variant).

CD45 Ab4133

Human V-region IGKV1D-13 plus JK4 J-region (IMGT, http://www.imgt.org/) was chosen as the acceptor for antibody 4133 light chain CDRs. In addition to the CDRs, one or more of the following framework residues from the 4133 VK gene (donor residues) may be retained at positions 2, 3 and 70 (Kabat numbering): Glutamine (Q2), Valine (V3) and Glutamine (Q70), respectively.

In some cases, CDRL1 may be mutated to remove a potential N-glycosylation site (CDRL1 variant 1-2).

Human V-region IGHV3-21 plus JH-1 J-region (IMGT, http://www.imgt.org/) was chosen as an acceptor for the heavy chain CDRs of antibody 4133. In addition to the CDRs, one or more of the following framework residues from the 4133 VH gene (donor residues) may be retained at positions 48, 49, 71, 73, 76 and 78 (Kabat numbering): Isoleucine (I48), Glycine (G49), Lysine (K71), Serine (S73), Threonine (T76) and Valine (V78), respectively. In some cases, CDRH1 and CDRH2 may be mutated to remove Cysteine residues (CDRH1 variant and CDRH2 variant, respectively). CDRH3 may also be mutated to modify a potential Aspartic acid isomerisation site (CDRH3 variant 1-3).

Human V-region IGHV4-4 plus JH-1 J-region (IMGT, http://www.imgt.org/) was chosen as an alternative acceptor for the heavy chain CDRs of antibody 4133. In addition to the CDRs, one or more of the following framework residues from the 4133 VH gene (donor residues) may be retained at positions 24, 71, 73, 76 and 78 (Kabat numbering): Alanine (A24), Lysine (K71), Serine (S73), Threonine (T76) and Valine (V78), respectively. The Glutamine residue at position 1 of the human framework was replaced with Glutamic acid (E1) to afford the expression and purification of a homogeneous product.

In some cases, CDRH1 and CDRH2 may be mutated to remove Cysteine residues (CDRH1 variant and CDRH2 variant, respectively). CDRH3 may also be mutated to modify a potential Aspartic acid isomerisation site (CDRH3 variant 1-3).

Example 20—Testing Cross Reactivity of Anti-Human CD79 V Regions to Cynomolgus Monkey B Cells Introduction Binding studies were performed on Cynomolgus monkey PBMCs to test if anti-human CD79 V regions cross-react with non-human primate B cells for pre-clinical studies. The CD79 V regions VR4447 and VR4450 were generated as Fab-Y purified molecules and specific binding of these V regions to B cells was detected using an anti-mouse secondary antibody which binds the constant regions of the Fab-Y construct.

Description of constructs used in this experiment.

| Construct Name | Fab Specificity |
| --- | --- |
| VR4447 Fab-Y | Antigen-human CD79b |
| VR4450 Fab-Y | Antigen-human CD79b |

Methods

Generation of Fab-Y Molecules

The parental rabbit V regions for anti-CD79b (VR4447) and (VR4450) were cloned from rabbit B cells as described (WO2016/009030) into Fab-Y construct vectors as previously described.

Transient Expression and Purification Fab-Y

The Expi293 cells were routinely sub-cultured in Expi293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.94 \times 10^6$ viable cells/mL the appropriate volume of cell suspension was added to a sterile 1 L Erlenmeyer shake flask and brought up to the volume of 170 mL by adding fresh, pre-warmed Expi293™ Expression Medium for each 200 mL transfection.

To prepare the lipid-DNA complexes for each transfection a total of 200 µg of heavy chain and light chain plasmid DNAs (2:1 light chain:heavy chain DNA ratio) were diluted in Opti-MEM® I medium (LifeTechnologies) to a total volume of 10 mL and 540 µL of ExpiFectamine™ 293 Reagent (LifeTechnologies) was diluted in Opti-MEM® I medium to a total volume of 10 mL. All dilutions were mixed gently and incubated for no longer than 5 minutes at room temperature before each DNA solution was added to the respective diluted ExpiFectamine™ 293 Reagent to obtain a total volume of 20 mL. The DNA-ExpiFectamine™ 293 Reagent mixtures were mixed gently and incubated for 20-30 minutes at room temperature to allow the DNA-ExpiFectamine™ 293 Reagent complexes to form.

After the DNA-ExpiFectamine™ 293 reagent complex incubation was completed, the 20 mL of DNA-ExpiFectamine™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 1 mL of ExpiFectamine™ 293 Transfection Enhancer 1 (LifeTechnologies) and 10 mL of ExpiFectamine™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Fab-Y was purified by affinity capture using a small scale vacuum based purification system. Briefly, the 200 ml of culture supernatants were 0.22 μm sterile filtered before ~2 mL of Ni Sepharose beads (GE Healthcare) were added. The supernatant beads mixture was then tumbled for about an hour before supernatant was removed by applying vacuum. Beads were then washed with Wash 1 (50 mM Sodium Phosphate 0.5 M NaCl pH 6.2) and Wash 2 (0.5 M NaCl). Elution was performed with 50 mM sodium acetate, pH4.0+ 1M NaCl. The eluted fractions were buffer exchanged into PBS (Sigma), pH7.4 and 0.22 μm filtered. Final pools were assayed by A280 scan, SE-UPLC (BEH200 method), SDS-PAGE (reduced & non-reduced) and for endotoxin using the PTS Endosafe system.

Binding of Anti-Human CD79 V Regions to B Cells from Cynomolgus Monkey

Cynomolgus monkey PBMCs were purified from whole blood using density centrifugation. Briefly, the whole blood was diluted 1:2 in RPMI media and then layered over Lympholyte® Mammal separation medium (CedarLane). The samples were centrifuged at 800 g for 25 minutes without acceleration and brake and the layer of cells at the interface was collected. Contaminating red blood cells were lysed using 5 mls of ACK Lysis buffer (Gibco) for 5 minutes.

The isolated PBMC were plated out into 96 well round bottomed plates and then washed in cold binding buffer (PBS+0.5% BSA+0.1% sodium azide). The VR4447 and VR4450 Fab-Y molecules were added to the cells at a concentration of 50 ug/ml in cold binding buffer. After 30 minutes on ice the cells were washed and binding of the Fab-Y molecules was detected with a FITC-conjugated goat anti-mouse IgG F(ab')$_2$ diluted to 10 ug/ml in cold binding buffer (Jackson ImmunoResearch). Samples were acquired on a BD FACS Canto II instrument and binding was determined using FLOWJO software. B cells were identified using a CD20 antibody. The binding was analysed on the B cells (CD20+) as either geomean of FITC—fluorescence or as percentage positive cells. The data was then imported into Graphpad Prism® and plotted as bar charts.

Results

Figure 48:
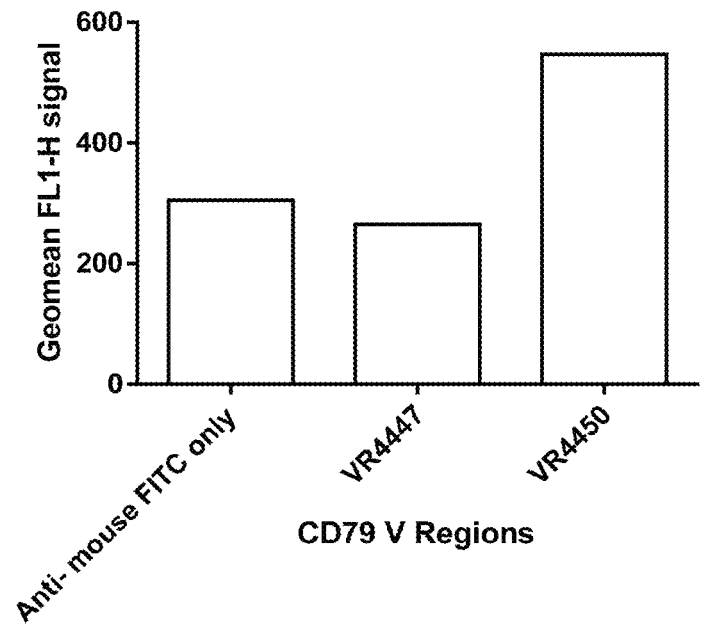
Figure 49:
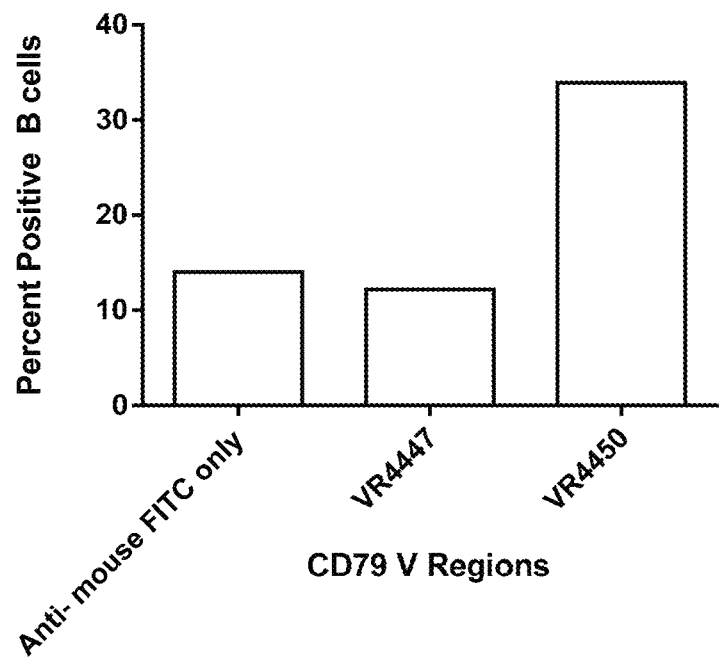

FIG. 48 and FIG. 49 shows binding of the VR4447 and VR4450 Fab-Y molecules to CD20+ B cells. Data is plotted either as the geomean of FITC—fluorescence or as percentage positive cells. Data shown is from a single animal.

Anti-CD79b V region 4450 is cross-reactive with Cynomolgus monkey CD79b on B cells whereas V region 4447 is not.

Example 21—Evaluation of Activity of Different Version of Humanised Anti-CD79b V Region 4450

Introduction

To evaluate the activity of humanised V regions of VR4450, they were cloned into a Fab-Y construct and along with parental rabbit 4450 V regions in Fab-Y expressed transiently and used to generate bispecific antibodies with purified anti-CD22 Fab-X (VR4130) to enable testing of function by measurement inhibition of BCR signalling of B cells in human PBMC.

Methods

The parental rabbit V regions for anti-CD79b (VR4450) and anti-CD22 (VR4130) (FIG. 51) were cloned from rabbit B cells as described (WO2016/009030) into Fab-Y and Fab-X construct vectors respectively. Humanised 4450 V regions were generated by gene synthesis and cloned in to Fab-Y construct vector.

Transient Expression Fab-X and Fab-Y

The Expi293 cells were routinely sub-cultured in Expi293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.94 \times 10^6$ viable cells/mL the appropriate volume of cell suspension was added to a sterile 1 L Erlenmeyer shake flask and brought up to the volume of 170 mL by adding fresh, pre-warmed Expi293™ Expression Medium for each 200 mL transfection.

To prepare the lipid-DNA complexes for each transfection a total of 200 μg of heavy chain and light chain plasmid DNAs (2:1 light chain:heavy chain DNA ratio) were diluted in Opti-MEM® I medium (LifeTechnologies) to a total volume of 10 mL and 540 μL of ExpiFectamine™ 293 Reagent (LifeTechnologies) was diluted in Opti-MEM® I medium to a total volume of 10 mL. All dilutions were mixed gently and incubated for no longer than 5 minutes at room temperature before each DNA solution was added to the respective diluted ExpiFectamine™ 293 Reagent to obtain a total volume of 20 mL. The DNA-ExpiFectamine™ 293 Reagent mixtures were mixed gently and incubated for 20-30 minutes at room temperature to allow the DNA-ExpiFectamine™ 293 Reagent complexes to form. After the DNA-ExpiFectamine™ 293 reagent complex incubation was completed, the 20 mL of DNA-ExpiFectamine™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 1 mL of ExpiFectamine™ 293 Transfection Enhancer 1 (LifeTechnologies) and 10 mL of ExpiFectamine™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Purification

Fab-X was purified by affinity capture using a small scale vacuum based purification system. Briefly, the 200 ml of culture supernatants were 0.22 μm sterile filtered before ~2 mL of Ni Sepharose beads (GE Healthcare) were added. The supernatant beads mixture was then tumbled for about an hour before supernatant was removed by applying vacuum. Beads were then washed with Wash 1 (50 mM Sodium Phosphate 0.5 M NaCl pH 6.2) and Wash 2 (0.5 M NaCl). Elution was performed with 50 mM sodium acetate, pH4.0+ 1M NaCl. The eluted fractions were buffer exchanged into PBS (Sigma), pH7.4 and 0.22 μm filtered. Final pools were assayed by A280 scan, SE-UPLC (BEH200 method), SDS-PAGE (reduced & non-reduced) and for endotoxin using the PTS Endosafe system.

Screening Assay

Donor PBMCs were rapidly thawed using a water bath set to 37° C. then diluted drop wise into assay media (RPMI-1640 media supplemented with 10% FBS, 1% penicillin/streptomycin and 1% Glutamax) to minimise the osmotic shock. The cells were spun at 500 g before removing the supernatant and resuspending the cells in assay media. Cells were then counted and $5.0 \times 10^4$ cells were added to each well of a 96-well V-bottom plate (Nunc) followed by incubation for 1 hour at 37° C., 5% $CO_2$ incubator.

Fab-X and Fab-Y reagents were mixed in an equimolar ratio at 5× the final assay concentration in assay media and incubated for 1 hour at 37° C., 5% $CO_2$ incubator. The appropriate Fab-KD-Fab mixture was added to the test wells containing cells (Table 14) to give a starting concentration of 100 nM and then serially diluted (1:5) in duplicates and mixed by shaking at 1000 rpm for 30 sec prior to being incubated for 1 hour at 37° C., 5% $CO_2$ incubator.

The cells were then stimulated with 12.5 μg/ml final concentration of anti-human IgM (Southern Biotech) while assay media were added to the control unstimulated cells. The assay plate was then gently mixed at 1000 rpm for 30 sec prior to incubation at 37° C., 5% $CO_2$ incubator for 8 min. The assay was stopped by adding ice-cold BD CytoFix to all wells and incubated for 15 min at RT. The fixed cells were then spun at 500 g for 5 min to pellet the cells and allow removal of the supernatant using a BioTek ELx405 plate washer. The pellet was re-suspended by vortexing the plate at 2400 rpm for 30 sec. The cells were then permeabilised at 4° C. by adding ice-cold BD Cell Permeabilisation Buffer III for 30 min. The cells were then washed in FACS buffer (PBS with 1% BSA, 0.05% $NaN_3$ and 2 mM EDTA) and spun at 500 g for 5 min. Supernatant was again removed by the ELx405 before using it to rapidly dispense FACS Buffer to wash away any residual permeabilisation buffer. Cells were again spun at 500 g and the supernatant was removed by the ELx405. The cells were then re-suspended by vortexing (2400 RPM, 30 sec) before antibody cocktail (Anti-Human CD20 (H1FB1) Alexa Fluor 488 (1:10 dilution); Anti-Human Akt Alexa Fluor 647 (1:10 dilution)) was added to all wells. The plate was then shaken for 30 sec at 1000 rpm and the cells were incubated for 45 min at RT in the dark.

The cells were then washed twice in FACS buffer with a 500 g spin and the supernatant was removed after each step. Finally the cells were re-suspended by vortexing for 30 sec at 2400 rpm before adding 20 μl of FACS buffer. The plate was then read on the Intellicyt iQue plus instrument.

TABLE 14

| | | | | | | Plate layout | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | MAX | 100 | | 100 | | 100 | | 100 | | 100 | | MIN |
| B | | 20 | | 20 | | 20 | | 20 | | 20 | | |
| C | | 4 | | 4 | | 4 | | 4 | | 4 | | |
| D | | 0.8 | | 0.8 | | 0.8 | | 0.8 | | 0.8 | | |
| E | | 0.16 | | 0.16 | | 0.16 | | 0.16 | | 0.16 | | |
| F | | 0.032 | | 0.032 | | 0.032 | | 0.032 | | 0.032 | | |
| G | | 0.0064 | | 0.0064 | | 0.0064 | | 0.0064 | | 0.0064 | | |
| H | | 0.00128 | | 0.00128 | | 0.00128 | | 0.00128 | | 0.00128 | | |

Table 14 (Plate layout) - Fab-KD-Fab mixtures were added in duplicates with starting concentration of 100 nM in columns 2-11. Cells were stimulated with 12.5 μg/ml final concentration of anti-human IgM added to columns 1-11. Column 1 (MAX) contained anti-human IgM stimulated cells not treated with a Fab-KD-Fab mixture while column 12 (MIN) contained control unstimulated/untreated cells.

Samples

| Fab-KD-Fab | Purified Fab-X | Transient s/n Fab-Y |
|---|---|---|
| Rabbit 4130 Fab-X/Rabbit 4450 Fab-Y | Rabbit VR4130 | Rabbit VR4450 |
| Rabbit 4130 Fab-X/gL1gH1 4450 Fab-Y | Rabbit VR4130 | gL1gH1 VR4450 |
| Rabbit 4130 Fab-X/gL5gH1 4450 Fab-Y | Rabbit VR4130 | gL5gH1 VR4450 |
| Rabbit 4130 Fab-X/gL6gH1 4450 Fab-Y | Rabbit VR4130 | gL6gH1 VR4450 |
| Rabbit 4130 Fab-X/gL7gH1 4450 Fab-Y | Rabbit VR4130 | gL7gH1 VR4450 |

Results

Figure 50:
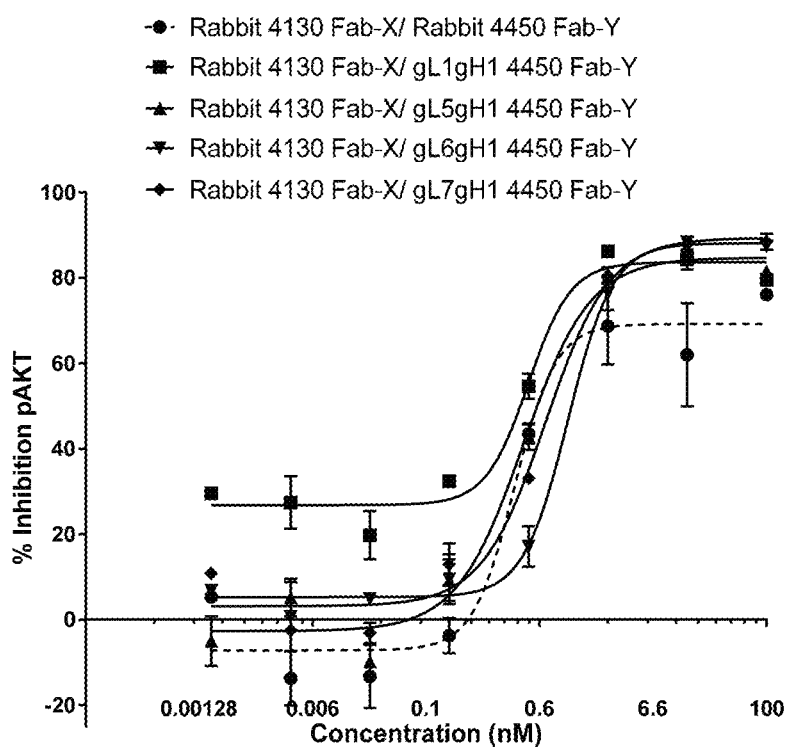

As can be seen in FIG. 50 all four humanised versions of VR4450 have similar activity to the parental rabbit VR4450 V region.

The invention claimed is:

1. An antibody molecule comprising a binding domain specific to human CD79b wherein the binding domain comprises a heavy chain variable domain (VH),
   wherein the VH comprises:
   a CDRH1 of SEQ ID NO:8 or 11,
   a CDRH2 of SEQ ID NO:9 or 12,
   a CDHR3 of EPYEPYDDSNIYYGMDP (SEQ ID NO: 3) or DAGHSDVDVLDI (SEQ ID NO: 4), and
   a light chain variable domain (VL),
   wherein the light chain variable domain (VL) comprises:
   a CDRL1 of SEQ ID NO:13 or 19;
   a CDRL2 of SEQ ID NO:14 or 20;
   a CDRL3 independently selected from the group consisting of SEQ ID NO: 15, 16, 17, 18, 21, 22, 23 and 24.

2. The antibody molecule according to claim 1 wherein CDRH1 is SEQ ID NO:8, CDRH2 is SEQ ID NO:9, CDRH3 is SEQ ID NO:4, CDRL1 is SEQ ID NO:13, CDRL2 is SEQ ID NO:14 and CDRL3 is independently selected from SEQ ID NO:15, 16, 17 and 18.

3. The antibody molecule according claim 1, wherein VH and VL are humanised.

4. The antibody molecule according to claim 3 wherein the variable domain of the heavy chain (VH) comprises a human framework region wherein the residue at at least one of positions 24, 37, 48, 49, 67, 71, 73 and 78 according to Kabat numbering is a donor residue and the variable domain of the light chain (VL) comprises a human framework region wherein the residue at at least one of positions 2, 3, 36, 46, 49 and 70 according to Kabat numbering is a donor residue.

5. The antibody molecule according to claim 3 comprising
   a. a VH having the sequence given in SEQ ID NO:34 or 35 and a VL having the sequence given in SEQ ID NO:33 or 250 or
   b. a VH having the sequence given in SEQ ID NO:41 or 42 and a VL having the sequence given in SEQ ID NO:40, 341, 342 or 343.

6. The antibody molecule according to claim 1, wherein the antibody is:
   a. a full length antibody or
   b. a scFv, Fv, Fab or Fab'fragment.

7. The antibody molecule according to claim 1, wherein the molecule format is selected from diabody, scdiabody, triabody, tandem scFv, FabFv, Fab'Fv, FabdsFv, Fab-scFv, Fab-dsscFv, Fab-(dsscFv)$_2$ diFab, diFab', tribody, tandem scFv-Fc, scFv-Fc-scFv, scdiabody-Fc, scdiabody-CH3, Ig-scFv, scFv-Ig, V-Ig and Ig-V.

8. The antibody molecule according to claim 6 further comprises a binding domain which is specific to CD22.

9. The antibody molecule according to claim 8 wherein each binding domain is monospecific.

10. The antibody molecule according to claim 8 wherein:
    a. the bispecific or trispecific molecule comprises no more than one binding domain which is specific to CD22 and no more than one binding domain which is specific to CD79b; or
    b. the binding domain which is specific to CD22 and the binding domain which is specific to CD79b are independently selected from a Fab, scFv, Fv, dsFv and dsscFv.

11. The antibody molecule according to claim 1 in which one or more binding domains are humanised.

12. The antibody molecule according to claim 1, which further comprises a binding domain specific to serum albumin.

* * * * *